United States Patent
Gampa et al.

(10) Patent No.: US 12,240,910 B2
(45) Date of Patent: Mar. 4, 2025

(54) ANTI-C-C MOTIF CHEMOKINE RECEPTOR 8 (CCR8) ANTIBODIES AND METHODS OF USE

(71) Applicant: GENENTECH, INC., South San Francisco, CA (US)

(72) Inventors: Gautham Gampa, South San Francisco, CA (US); Iraj Hosseini, South San Francisco, CA (US); Mahrukh Huseni, South San Francisco, CA (US); James Thomas Koerber, San Mateo, CA (US); Jian Mehr-Dean Payandeh, Belmont, CA (US); Sascha Rutz, South San Francisco, CA (US); Yonglian Sun, South San Francisco, CA (US); Cecilia P. C. Chiu, Redwood City, CA (US); Teresita Arenzana Delfino, Daly City, CA (US)

(73) Assignee: Genentech, Inc., South San Francisco, CA (US)

( * ) Notice: Subject to any disclaimer, the term of this patent is extended or adjusted under 35 U.S.C. 154(b) by 264 days.

(21) Appl. No.: 17/864,074

(22) Filed: Jul. 13, 2022

(65) Prior Publication Data
US 2023/0049152 A1 Feb. 16, 2023

Related U.S. Application Data

(60) Provisional application No. 63/253,676, filed on Oct. 8, 2021, provisional application No. 63/221,734, filed on Jul. 14, 2021.

(51) Int. Cl.
*C07K 16/28* (2006.01)
*A61K 39/00* (2006.01)
(Continued)

(52) U.S. Cl.
CPC ...... *C07K 16/2866* (2013.01); *A61K 39/3955* (2013.01); *A61K 45/06* (2013.01);
(Continued)

(58) Field of Classification Search
CPC ............ C07K 16/2866; C07K 16/2827; C07K 2317/21; C07K 2317/24; C07K 2317/33;
(Continued)

(56) References Cited

U.S. PATENT DOCUMENTS

| 10,087,259 B1 | 10/2018 | Rudensky et al. |
| 2009/0214533 A1 | 8/2009 | Clynes |
| 2022/0064312 A1 | 3/2022 | Yoshikawa et al. |

FOREIGN PATENT DOCUMENTS

| CN | 110835371 A | 2/2020 |
| EP | 3431105 B1 | 1/2020 |

(Continued)

OTHER PUBLICATIONS

Gutierrez et al., "Analysis of Post-translational CCR8 Modifications and Their Influence on Receptor Activity," J of Bio Chem. 279(15):14726-33, 2004 (8 pages).
(Continued)

*Primary Examiner* — Aurora M Fontainhas
*Assistant Examiner* — Selam Berhane
(74) *Attorney, Agent, or Firm* — Clark & Elbing LLP; Thomas J. Takara

(57) ABSTRACT

The present disclosure provides anti-CCR8 antibodies, and compositions and methods of their preparation and use.

47 Claims, 58 Drawing Sheets

Specification includes a Sequence Listing.

Intratumoral Regulatory T cell Staining versus Conventional CD4 or CD8 T cell Staining

(51) Int. Cl.
  *A61K 39/395* (2006.01)
  *A61K 45/06* (2006.01)
  *A61P 35/00* (2006.01)

(52) U.S. Cl.
  CPC .......... *A61P 35/00* (2018.01); *C07K 16/2827* (2013.01); *A61K 2039/505* (2013.01); *A61K 2039/507* (2013.01); *C07K 2317/21* (2013.01); *C07K 2317/24* (2013.01); *C07K 2317/33* (2013.01); *C07K 2317/34* (2013.01); *C07K 2317/40* (2013.01); *C07K 2317/565* (2013.01); *C07K 2317/732* (2013.01); *C07K 2317/76* (2013.01); *C07K 2317/92* (2013.01)

(58) Field of Classification Search
  CPC ............ C07K 2317/34; C07K 2317/40; C07K 2317/565; C07K 2317/732; C07K 2317/76; C07K 2317/92; A61P 35/00; A61K 39/3955; A61K 45/06; A61K 2039/505; A61K 2039/507
  See application file for complete search history.

(56) References Cited

FOREIGN PATENT DOCUMENTS

| | | |
|---|---|---|
| WO | WO-2007/044756 A2 | 4/2007 |
| WO | WO-2008/073160 A2 | 6/2008 |
| WO | WO-2013/131010 A2 | 9/2013 |
| WO | WO-2015/063187 A1 | 5/2015 |
| WO | WO-2015/179236 A1 | 11/2015 |
| WO | WO-2016/092419 A1 | 6/2016 |
| WO | WO-2017/198631 A1 | 11/2017 |
| WO | WO-2017/205014 A1 | 11/2017 |
| WO | WO-2018/112032 A1 | 6/2018 |
| WO | WO-2018/181425 A1 | 10/2018 |
| WO | WO-2020/138489 A1 | 7/2020 |
| WO | WO-2022/256559 A1 | 12/2022 |

OTHER PUBLICATIONS

International Search Report and Written Opinion for International Patent Application No. PCT/US2022/073671 mailed Dec. 23, 2022 (22 pages).
"Purified anti-human CD198 (CCR8) Antibody," Biolegend. V. 1, Catalog No. 360602, revised Oct. 9, 2013 (2 pages).
International Preliminary Report on Patentability for International Patent Application No. PCT/US2022/073671, dated Jan. 16, 2024 (14 pages).
Ali, S., et al., "An apparent paradox: Chemokine receptor agonists can be used for anti-inflammatory therapy" Mol Immunol 44(7):1477-1482 (Mar. 1, 2007) (6 pgs.).
Angelova, M., et al., "Characterization of the immunophenotypes and antigenomes of colorectal cancers reveals distinct tumor escape mechanisms and novel targets for immunotherapy" Genome Biol 16(1):64 (Mar. 31, 2015) (17 pgs.).
BD Biosciences et al., "BV421 Mouse Anti-Human CCR8 (CD198)" (Human CCR8 Transfected Cell Line; Material No. 566379-Technical Data Sheet),:1-2 ( 2016) (2 pgs.).
Biolegend et al., "PE Anti-Mouse CD279 (PD-1) Antibody" (Technical Data Sheet; Catalog Nos. 114117, 114118; Clone: RMP1-14; Version 2),:1-2 (Feb. 17, 2016) (2 pgs.).
Biolegend, "Purified Anti-Mouse CD198 (CCR8) Antibody" (Technical Data Sheet; Catalog No. 150302; Mouse CD198 (CCR8) transfected cells; Version 1),: (Revised Dec. 16, 2015) available at: <https://www.biolegend.com/de-de/products/purified-anti-mouse-cd198-ccr8-antibody-12025?GroupID=GROUP20> (3 pgs.).
Bos, P., et al., "Transient regulatory T cell ablation deters oncogene-driven breast cancer and enhances radiotherapy" J Exp Med 210(11):2435-2446 (Oct. 21, 2013) (12 pgs.).
Bruhns, P., "Properties of mouse and human IgG receptors and their contribution to disease models" BLOOD 119(24):5640-5649 (Jun. 14, 2012) (10 pgs.).
Campbell, J., et al., "Fc-Optimized Anti-CCR8 Antibody Depletes Regulatory T Cells in Human Tumor Models" Cancer Res 81(11):2983-2994 (Jun. 1, 2021) (12 pgs.).
Chen, L., et al., "Anti-PD-1/PD-L1 therapy of human cancer: past, present, and future" J Clin Invest 125(9):3384-3391 (Sep. 1, 2015) (9 pgs.).
Coghill, J., et al., "CC chemokine receptor 8 potentiates donor Treg survival and is critical for the prevention of murine graft-versus-host disease" Blood 122(5):825-836 (Aug. 1, 2013) (12 pgs.).
Dannull, J., et al., "Enhancement of vaccine-mediated antitumor immunity in cancer patients after depletion of regulatory T cells" J Clin Invest 115(12):3623-3633 (Dec. 1, 2005) (11 pgs.).
Das, S., et al., "Tumor cell entry into the lymph node is controlled by CCL1 chemokine expressed by lymph node lymphatic sinuses" J Exp Med 210(8):1509-1528 (Jul. 29, 2013) (20 pgs.).
Day, C., et al., "Preclinical Mouse Cancer Models: a Maze of Opportunities and Challenges" CELL 163(1):39-53 (Sep. 24, 2015) (15 pgs.).
De Haij, S., et al., "In vivo Cytotoxicity of Type I CD20 Antibodies Critically Depends on Fc Receptor ITAM Signaling" Cancer Res 70(8):3209-3217 (Apr. 15, 2010) (9 pgs.).
De Simone, M., et al., "Transcriptional Landscape of Human Tissue Lymphocytes Unveils Uniqueness of Tumor-Infiltrating T Regulatory Cells" Immunity—Cell Press (w/Suppl. Information), 45(5):1135-1147 (Nov. 15, 2016) (26 pgs.).
Debes, G., et al., "CCL8 and skin T cells-an allergic attraction" Nat Immunol 12(2):111-112 (Jan. 19, 2011).
Dempke, W., et al., "Second-and third-generation drugs for immuno-oncology treatment-The more the better?" Eur J Cancer 74:55-72 (Mar. 1, 2017).
Depis, F., et al., "Preclinical evaluation of JTX-1811, an anti-CCR8 antibody with enhanced ADCC activity, for preferential depletion of tumor-infiltrating regulatory T cells" Abstract (Abstract 4532; Cancer Res 80:Suppl. 16 (Aug. 15, 2020)) AACR Annual Meeting 2020, Philadelphia, PA—US, pp. 1-2 ( Apr. 27-28, 2020).
Dhodapkar, M., et al., "Type II NKT Cells and Their Emerging Role in Health and Disease" J Immunol 198(3):1015-1021 (Feb. 1, 2017).
Dietze, K., et al., "Transient depletion of regulatory T cells in transgenic mice reactivates virus-specific CD8+ T cells and reduces chronic retroviral set points" Proc Natl Acad Sci U S A 108(6):2420-2425 (Feb. 8, 2011).
Eruslanov, E., et al., "Expansion of CCR8+ Inflammatory Myeloid Cells in Cancer Patients with Urothelial and Renal Carcinomas" Clin Cancer Res 19(7):1670-1680 (Apr. 1, 2013).
Finotello, F., et al., "New strategies for cancer immunotherapy: targeting regulatory T cells" Genome Med 9(1):10 (Jan. 27, 2017) (3 pages).
Fu, Q., et al., "Positive intratumoral chemokine (C-C motif) receptor 8 expression predicts high recurrence risk of post-operation clear-cell renal cell carcinoma patients" Oncotarget 7(7):8413-8421 (Feb. 16, 2016).
Ganguly, D., et al., "The role of dendritic cells in autoimmunity" Nat Rev Immunol 13(8):566-577 (Jul. 5, 2013).
Griffith, T., et al., "Inhibition of murine prostate tumor growth and activation of immunoregulatory cells with recombinant canarypox viruses" J Natl Cancer Inst 93(13):998-1007 (Jul. 4, 2001).
Gupta, A., et al., "Antibodies against G-protein coupled receptors: novel uses in screening and drug development" Comb Chem High Throughput Screen 11(6):463-467 (Jul. 1, 2008).
Han, J., "Monoclonal Antibodies as Cancer Therapeutics" N A J Med Sci 3(3):146-151 (Jul. 1, 2010) (6 pages).
Hoelzinger, D., et al., "Blockade of CCL1 Inhibits T Regulatory Cell Suppressive Function Enhancing Tumor Immunity without Affecting T Effector Responses" J Immunol 184(12):6833-6842 (Jun. 15, 2010).
Howard, O., et al., "LEC Induces Chemotaxis and Adhesion by Interacting with CCR1 and CCR8" Blood 96(3):840-845 (Aug. 1, 2000).
Iida, S., et al., "Nonfucosylated Therapeutic IgG1 Antibody Can Evade the Inhibitory Effect of Serum Immunoglobulin G on Antibody-

(56) References Cited

OTHER PUBLICATIONS

Dependent Cellular Cytotoxicity Through its High Binding to FcgammaRIIIa" Clin Cancer Res 12(9):2879-2887 (May 1, 2006).
Iida, S., et al., "Two mechanisms of the enhanced antibody-dependent cellular cytotoxicity (ADCC) efficacy of non-fucosylated therapeutic antibodies in human blood" BMC Cancer 9:58 (Feb. 18, 2009) (12 pages).
Invivogen, "Immunoglobin G" (Technical Product Data Sheet),:1 (Jan. 1, 2011 https://www.invivogen.com/review-antibody-generation (1 page).
Irani, V., et al., "Molecular properties of human IgG subclasses and their implications for designing therapeutic monoclonal antibodies against infectious diseases" Mol Immunol (w/Supplemental Data), 67 (2 Pt. A):171-182 (Oct. 1, 2015) (21 pages).
Ishii, T., et al., "Defucosylated Humanized Anti-CCR4 Monoclonal Antibody KW-0761 as a Novel Immunotherapeutic Agent for Adult T-cell Leukemia/Lymphoma" Clin Cancer Res 16(5):1520-1531 (Mar. 1, 2010).
Islam, S., et al., "Identification of human CCR8 as a CCL18 receptor" J Exp Med 210(10):1889-1898 (Sep. 2, 2013).
Jung, H., et al., "Combination therapy of chemokine receptor inhibition plus PDL-1 blockade potentiates anti-tumor effects in a murine model of breast cancer" J Immunother Cancer 3(SUPPL 2):P227 (Nov. 4, 2015) (1 page).
Kim, E., et al., "Immunopathogenesis and therapy of cutaneous T cell lymphoma" J Clin Invest 115(4):798-812 (Apr. 1, 2005).
Kim, J., et al., "Cutting Edge: Depletion of Foxp3+ Cells Leads to Induction of Autoimmunity by Specific Ablation of Regulatory T Cells in Genetically Targeted Mice" J Immunol (w/Suppl. Information), 183(12):7631-7634 (Dec. 15, 2009) (6 pages).
Kim, J., et al., "Immune escape to PD-L1/PD-1 blockade: seven steps to success (or failure)" Ann Oncol 27(8):1492-1504 (Aug. 1, 2016).
Kipps, T., et al., "Importance of Immunoglobulin Isotype in Human Antibody-Dependent, Cell-Mediated Cytotoxicity Directed by Murine Monoclonal Antibodies" J Exp Med 161(1):1-17 (Jan. 1, 1985).
Klages, K., et al., "Selective Depletion of Foxp3+ Regulatory T Cells Improves Effective Therapeutic Vaccination against Established Melanoma" Cancer Res 70(20):7788-7799 (Oct. 15, 2010).
Klarenbeek, A., et al., "Targeting chemokines and chemokine receptors with antibodies" Drug Discov Today: Technol 9(4):e237-e244 (May 3, 2014).
Kurose, K., et al., "Phase Ia Study of FoxP3+ CD4 Treg Depletion by Infusion of a Humanized Anti-CCR4 Antibody, KW-0761, in Cancer Patients" Clin Cancer Res 21(19):4327-4336 (Oct. 1, 2015).
Larkin, J., et al., "Combined Nivolumab and Ipilimumab or Monotherapy in Untreated Melanoma" New Engl J Med 373(1):23-34 (Jul. 2, 2015).
Laurence, A.,, "Location, movement and survival: the role of chemokines in haematopoiesis and malignancy" Br J Haematol 132(3):255-267 (Feb. 1, 2006).
Li, X., et al., "Efficient Treg depletion induces T-cell infiltration and rejection of large tumors" Eur J Immunol 40(12):3325-3335 (Dec. 1, 2010).
Louahed, J., et al., "CCR8-dependent activation of the RAS/MAPK pathway mediates anti-apoptotic activity of 1-309/ CCL1 and vMIP-I" Eur J Immunol 33(2):494-501 (Feb. 1, 2003).
Mordant, P., et al., "Bioluminescent Orthotopic Mouse Models of Human Localized Non-Small Cell Lung Cancer: Feasibility and Identification of Circulating Tumour Cells" PLOS ONE 6(10):e26073 (Oct. 11, 2011) (9 pages).
Mutalithas, K., et al., "Expression of CCR8 is increased in asthma" Clin Experimental Allergy 40(8):1175-1185 (Aug. 1, 2010).
Nelson, A. "Antibody Fragments: Hope and Hype" MABS 2(1):77-83 (Jan. 31, 2010).
Onishi, H., et al., "Immunotherapy Approaches Targeting Regulatory T-Cells" Anticancer Res 32(3):997-1003 (Mar. 1, 2012).
Onizuka, S., et al., "Tumor Rejection by in Vivo Administration of Anti-CD25 (Interleukin-2 Receptor alpha) Monoclonal Antibody" Cancer Res 59(13):3128-3133 (Jul. 1, 1999).

Penaloza-Macmaster, P., et al., "Interplay between regulatory T cells and PD-1 in modulating T cell exhaustion and viral control during chronic LCMV infection" J Exp Med 211(9):1905-1918 (Aug. 25, 2014).
Pernambuco-Holsten, C.,, "Immunotherapy Combination Nivolumab Plus Ipilimumab Receives FDA Approval for Metastatic Melanoma" Memorial Sloan Kettering Cancer Center: (Oct. 1, 2015) (3 pages).
Plitas, G., et al., "Preferential expression of the chemokine receptor 8 (CCR8) on regulatory T cells (Treg) infiltrating human breast cancers represents a novel immunotherapeutic target" Abstract (Cancer Res 76(4 Suppl): Abstract P4-04-11) San Antonio Breast Cancer Symposium [SABCS], San Antonio, Texas US, (Dec. 8-10, 2015) (2 pages).
Plitas, G., et al., "Regulatory T Cells Exhibit Distinct Features in Human Breast Cancer" IMMUNITY 45(5):1122-1134 (Nov. 15, 2016).
Promega, Inc. et al., "mFcgammaRIV ADCC Reporter Bioassay, Core Kit" (Technical Manual; M1211 and M1215 [TM486]),: (Jan. 1, 2017) (20 pages).
Pyszniak, M., et al., "Percentages of NKT cells in the tissues of patients with non-small cell lung cancer who underwent surgical treatment" Kardiochir Torakochirurgia Pol 11(1):34-39 (Mar. 27, 2014).
R&D Systems et al., "Monoclonal Anti-human CCR8-Flourescein" (Technical Data Sheet; Catalog Number: FAB1429F, Lot No. LCV02),:1-2 (Oct. 1, 2007) https://resources.rndsystems.com/pdfs/datasheets/fab1429f.pdf.
Rajasekaran, N., et al., "Enhancement of antibody-dependent cell mediated cytotoxicity: a new era in cancer treatment" Immunotargets Ther 4:91-100 (May 15, 2015).
Robertson, F., et al., "NKT Cell Networks in the Regulation of Tumor Immunity" Front Immunol 5:543 (Oct. 28, 2014) (12 pages).
Rosenberg, H., et al., "Eosinophils: changing perspectives in health and disease" Nat Rev Immunol 13(1):9-22 (Jan. 1, 2013).
Ruckes, T., et al., "Autocrine antiapoptotic stimulation of cultured adult T-cell leukemia cells by overexpression of the chemokine I-309" Blood 98(4):1150-1159 (Aug. 15, 2001).
Scott, A., et al., "Antibody therapy of cancer" Nat Rev Cancer 12(4):278-287 (Mar. 22, 2012).
Shipman, L., "Interrogating intratumoral Treg cells" Nature Rev Immunol 17(1):4-5 (Jan. 1, 2017) (1 page).
Shuptrine, C., et al., "Monoclonal antibodies for the treatment of cancer" Semi Cancer Biol 22(1):3-13 (Feb. 1, 2012).
Simpson, T., et al., "Fc-dependent depletion of tumor-infiltrating regulatory T cells co-defines the efficacy of anti-CTLA-4 therapy against melanoma" J Exp Med 210(9):1695-1710 (Aug. 26, 2013).
Slauenwhite, D., et al., "Regulation of NKT Cell Localization in Homeostasis and Infection" Front Immunol 6:255 (May 27, 2015) (19 pages).
Spain, L., et al., "Management of toxicities of immune checkpoint inhibitors" Cancer Treat Rev 44:51-60 (Mar. 1, 2016).
Stallard, J., "FDA Approves 'Game Changer' Immunotherapy Drug for Bladder Cancer" Memorial Sloan Kettering Cancer Center: (May 18, 2016) (11 pages).
Stallard, J., "New Approach Could Boost Immunotherapy for Breast Cancer" Memorial Sloan Kettering Cancer Center (Nov. 29, 2016) <https://www.mskcc.org/news/new-approach-could-boost-immunotherapy-for-breast-cancer> (3 pages).
Sugiyama., D., et al., "Anti-CCR4 mAb selectively depletes effector-type FoxP3+CD4+regulatory T cells, evoking antitumor immune responses in humans" PNAS 110(44):17945-17950 (Oct. 14, 2013).
Suzuki, S., et al., "Current status of immunotherapy" JPN J Clin Oncol 46(3):191-203 (Mar. 1, 2016).
Tahir, S., et al., "Loss of IFN-gamma Production by Invariant NK T Cells in Advanced Cancer" J Immunol 167(7):4046-4050 (Oct. 1, 2001).
Takeuchi, Y., et al., "Roles of regulatory T cells in cancer immunity" Int Immunol 28(8):401-409 (Aug. 1, 2016).
Tan, S., et al., "Crystal clear: visualizing the intervention mechanism of the PD-1/PD-L1 interaction by two cancer therapeutic monoclonal antibodies" Protein Cell 7(12):866-877 (Dec. 1, 2016).

(56) References Cited

OTHER PUBLICATIONS

Tanaka, A., et al., "Regulatory T cells in cancer immunotherapy" Cell Res 27(1):109-118 (Jan. 1, 2017).
Tontonoz, M., "Immunotherapy Pioneered at MSK Receives FDA Approval for Advanced Kidney Cancer" Memorial Sloan Kettering Cancer Center (Dec. 4, 2015) (9 pages).
Tontonoz, M., "Combination Immunotherapy Shows New Promise for Lung Cancer" Memorial Sloan Kettering Cancer Center, https://www.mskcc.org/news/new-promise-combination-immunotherapy-lung-cancer (Jun. 1, 2016) (12 pages).
Topalian, S., et al., "Targeting the PD-1/B7-H1(PD-L1) pathway to activate anti-tumor immunity" Curr Opin Immunol 24(2):207-212 (Apr. 1, 2012).
US Clinical TRIALS.gov, "Study of Combination Therapy With Mogamulizumab (KW-0761) and Nivolumab (ONO-4538/BMS-936558) in Subjects With Advanced Solid Tumors" (ClinicalTrials.gov ID: NCT02476123; Study Details, History of Changes; First Posted: Jun. 10, 2015; Last Update Posted: Jun. 30, 2019; Sponsor: Kyowa Hakko Kirin Company, Ltd.-Japan and Ono Pharmaceutical Company, Limited-Japan; Retrieved: Oct. 13, 2021),: (Oct. 1, 2017) (1 page).
US Clinical TRIALS.gov, "Study of Mogamulizumab + MEDI4736 and Mogamulizumab + Tremelimumab in Subjects w/ Advanced Solid Tumors" (Clinical Trial ID No. NCT02301130; Study Details/History Changes; First Posted: Nov. 21, 2014; Last Update Posted: Oct. 13, 2016; Sponsor: Kyowa Hakko Kirin Pharma, Inc. & AstraZeneca: Retrieved: Oct. 13, 2021),: (Oct. 13, 2016) (3 pages).
US Clinical TRIALS.gov, "Study of Mogamulizumab + Nivolumab in Subjects w/Locally Advanced or Metastatic Solid Tumors" (Clinical Trial ID No. NCT02705105; Study Details/History Changes; First Posted: Feb. 24, 2016; Last Update Posted: Nov. 30, 2016; Sponsor: Kyowa Hakko Kirin Pharma, Inc. & Bristol-Myers Squibb; Retrieved: Oct. 13, 2021),; (Nov. 30, 2016) (4 pages).
US ClinicalTrials.gov, "Phase Ia/Ib Multicenter Trial of Mogamulizumab for Advanced or Recurrent Cancer" (Clinical Trial ID No. NCT01929486; Study Details; First Posted: Aug. 28, 2013; Last update Posted: Feb. 17, 2016; Sponsor: Aichi Medical University-Japan; Retrieved: Oct. 14, 2021),: (Feb. 17, 2016) (6 pages).
Van Damme, H., et al., "Therapeutic depletion of CCR8+ tumor-infiltrating regulatory T cells elicits antitumor immunity and synergizes with anti-PD-1 therapy" J Immunother Cancer (w/Suppl. Material), 9(2):e001749 (Feb. 1, 2021) (32 pages).
Vargas, F., et al., "Fc-Optimized Anti-CD25 Depletes Tumor-Infiltrating Regulatory T Cells and Synergizes with PD-1 Blockade to Eradicate Established Tumors" Immunity 46(4):577-586 (Apr. 18, 2017) (11 pages).
Vela, M., et al., "Chemokine Receptor-Specific Antibodies in Cancer Immunotherapy: Achievements and Challenges" Front Immunol 6:12 (Jan. 30, 2015) (15 pages).
Whiteside, S., et al., "CCR8 marks highly suppressive Treg cells within tumours but is dispensable for their accumulation and suppressive function" Immunology 163(4):512-520 (Aug. 1, 2021).
Wilcox, R., "Mogamulizumab: 2 birds, 1 stone" Blood 125(12):1847-1848 (Mar. 19, 2015).
Yamamoto, N., et al., "Anti-CC-chemokine receptor 4 (CCR4) antibody mogamulizumab (Moga) and nivolumab (Nivo) combination phase I study in patients with advanced or metastatic solid tumors" Abstract LBA17; Ann Oncology, 28(Suppl. 5):V611 (Sep. 2017) (1 page).
Zahavi, D., et al., "Enhancing antibody-dependent cell-mediated cytotoxicity: a strategy for improving antibody-based immunotherapy" Antibody Ther 1(1):7-12 (Jul. 24, 2018).
Zelinskyy, G., et al., "The regulatory T-cell response during acute retroviral infection is locally defined and controls the magnitude and duration of the virus-specific cytotoxic T-cell response" Blood 114(15):3199-3207 (Oct. 8, 2009).

FIG. 5A

Heavy Chain Variable Region (Ab4)

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| rb.Ab4 (SEQ ID NO: 8) | Q | Q | S | V | E | E | S | G | G | R | L | V | T | P | G | T | P | L | T | L | T | C | T | V | S | G | F | S | L | S | N | Y | A | M | I | W | V | R | Q | A | P | G |
| hu.Ab4.H1 (SEQ ID NO: 10) | E | V | Q | L | E | E | S | G | G | G | L | V | Q | P | G | G | S | L | R | L | S | C | A | A | S | G | F | S | L | S | N | Y | A | M | I | W | V | R | Q | A | P | G |
| hu.Ab4.H2 (SEQ ID NO: 11) | E | Q | Q | L | E | E | S | G | G | G | L | V | Q | P | G | G | S | L | R | L | S | C | A | A | S | G | F | S | L | S | N | Y | A | M | I | W | V | R | Q | A | P | G |
| hu.Ab4.H3 (SEQ ID NO: 12) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H4 (SEQ ID NO: 13) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H6 (SEQ ID NO: 14) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H7 (SEQ ID NO: 15) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H8 (SEQ ID NO: 16) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H9 (SEQ ID NO: 17) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H10 (SEQ ID NO: 18) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H11 (SEQ ID NO: 19) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H11 (SEQ ID NO: 20) | E | Q | Q | L | E | E | S | G | G | G | L | V | Q | P | G | G | S | L | R | L | S | C | A | V | S | G | F | S | L | S | N | Y | A | M | I | W | V | R | Q | A | P | G |
| hu.Ab4.H12 (SEQ ID NO: 21) | E | V | Q | L | E | E | S | G | G | G | L | V | Q | P | G | G | S | L | R | L | S | C | A | A | S | G | F | S | L | S | N | Y | A | M | I | W | V | R | Q | A | P | G |

CDR H1 - Contact
CDR H1 - Kabat

FIG. 5B

Heavy Chain Variable Region (Ab4), Continued

FIG. 5C

Heavy Chain Variable Region (Ab4), Continued

| Kabat number | 82 | 82A | 82B | 82C | 83 | 84 | 85 | 86 | 87 | 88 | 89 | 90 | 91 | 92 | 93 | 94 | 95 | 96 | 97 | 98 | 99 | 100 | 100A | 100B | 100C | 100D | 100E | 100F | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| rb.Ab4 (SEQ ID NO: 8) | P | T | T | L | E | D | T | A | T | Y | Y | F | C | A | R | W | S | T | D | S | A | I | Y | T | Y | A | F | D | P | W | G | R | G | T | L | V | T | V | S | S |
| hu.Ab4.H1 (SEQ ID NO: 10) | L | R | A | E | E | D | T | A | V | Y | Y | F | C | A | R | W | S | T | D | S | A | I | Y | T | Y | A | F | D | P | W | G | Q | G | T | L | V | T | V | S | S |
| hu.Ab4.H2 (SEQ ID NO: 11) | L | R | A | E | E | D | T | A | V | Y | Y | F | C | A | R | W | S | T | D | S | A | I | Y | T | Y | A | F | D | P | W | G | Q | G | T | L | V | T | V | S | S |
| hu.Ab4.H3 (SEQ ID NO: 12) | L | R | A | E | E | D | T | A | V | Y | Y | F | C | A | R | W | S | T | D | S | A | I | Y | T | Y | A | F | D | P | W | G | Q | G | T | L | V | T | V | S | S |
| hu.Ab4.H4 (SEQ ID NO: 13) | L | R | A | E | E | D | T | A | V | Y | Y | F | C | A | R | W | S | T | D | S | A | I | Y | T | Y | A | F | D | P | W | G | Q | G | T | L | V | T | V | S | S |
| hu.Ab4.H5 (SEQ ID NO: 14) | L | R | A | E | E | D | T | A | V | Y | Y | F | C | A | R | W | S | T | D | S | A | I | Y | T | Y | A | F | D | P | W | G | Q | G | T | L | V | T | V | S | S |
| hu.Ab4.H6 (SEQ ID NO: 15) | L | R | A | E | E | D | T | A | V | Y | Y | F | C | A | R | W | S | T | D | S | A | I | Y | T | Y | A | F | D | P | W | G | Q | G | T | L | V | T | V | S | S |
| hu.Ab4.H7 (SEQ ID NO: 16) | L | R | A | E | E | D | T | A | V | Y | Y | F | C | A | R | W | S | T | D | S | A | I | Y | T | Y | A | F | D | P | W | G | Q | G | T | L | V | T | V | S | S |
| hu.Ab4.H8 (SEQ ID NO: 17) | L | R | A | E | E | D | T | A | V | Y | Y | F | C | A | R | W | S | T | D | S | A | I | Y | T | Y | A | F | D | P | W | G | Q | G | T | L | V | T | V | S | S |
| hu.Ab4.H9 (SEQ ID NO: 18) | L | R | A | E | E | D | T | A | V | Y | Y | Y | C | A | R | W | S | T | D | S | A | I | Y | T | Y | A | F | D | P | W | G | Q | G | T | L | V | T | V | S | S |
| hu.Ab4.H10 (SEQ ID NO: 19) | L | R | A | E | E | D | T | A | V | Y | Y | Y | C | A | R | W | S | T | D | S | A | I | Y | T | Y | A | F | D | P | W | G | Q | G | T | L | V | T | V | S | S |
| hu.Ab4.H11 (SEQ ID NO: 20) | L | R | A | E | E | D | T | A | V | Y | Y | F | C | A | R | W | S | T | D | S | A | I | Y | T | Y | A | F | D | P | W | G | R | G | T | L | V | T | V | S | S |
| hu.Ab4.H12 (SEQ ID NO: 21) | L | R | A | E | E | D | T | A | V | Y | Y | F | C | A | R | W | S | T | D | S | A | I | Y | T | Y | A | F | D | P | W | G | R | G | T | L | V | T | V | S | S |

Heavy Chain Variable Region (Ab5)

FIG. 6B

Heavy Chain Variable Region (Ab5), Continuation

Heavy Chain Variable Region (Ab5), Continuation

FIG. 6D

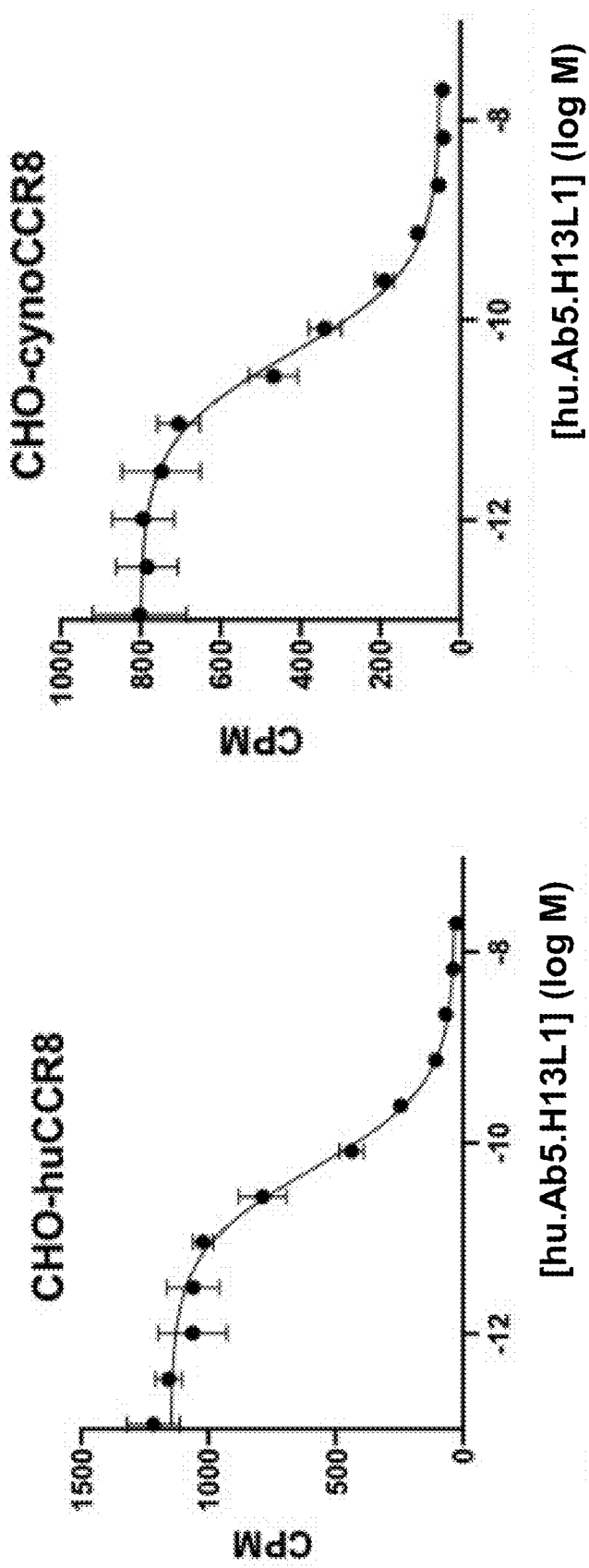

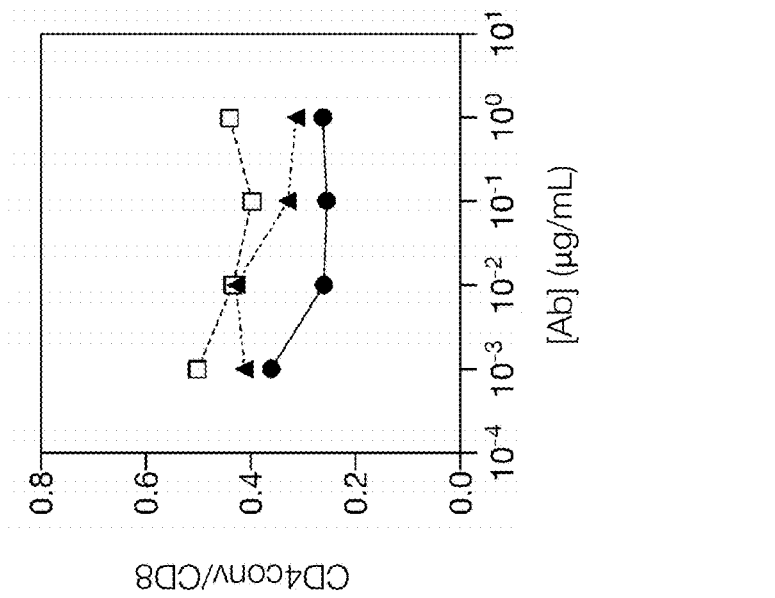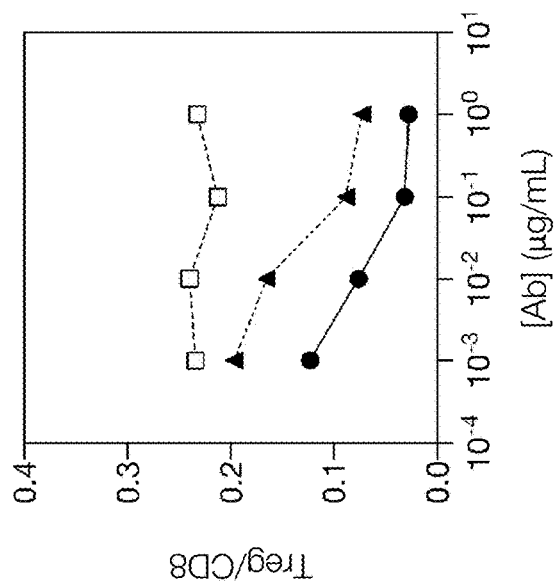
ADCC Activity Against Tregs in MLR-activated Human PBMCs
*hu.Ab4.H12L3 Fucosylated versus Afucosylated Variants*
FIG. 12A
FIG. 12B
- □ gD.Afuc (control)
- ▲ Fucosylated hu.Ab4.H12L3
- ● Afucosylated Afuc.hu.Ab4.H12L3

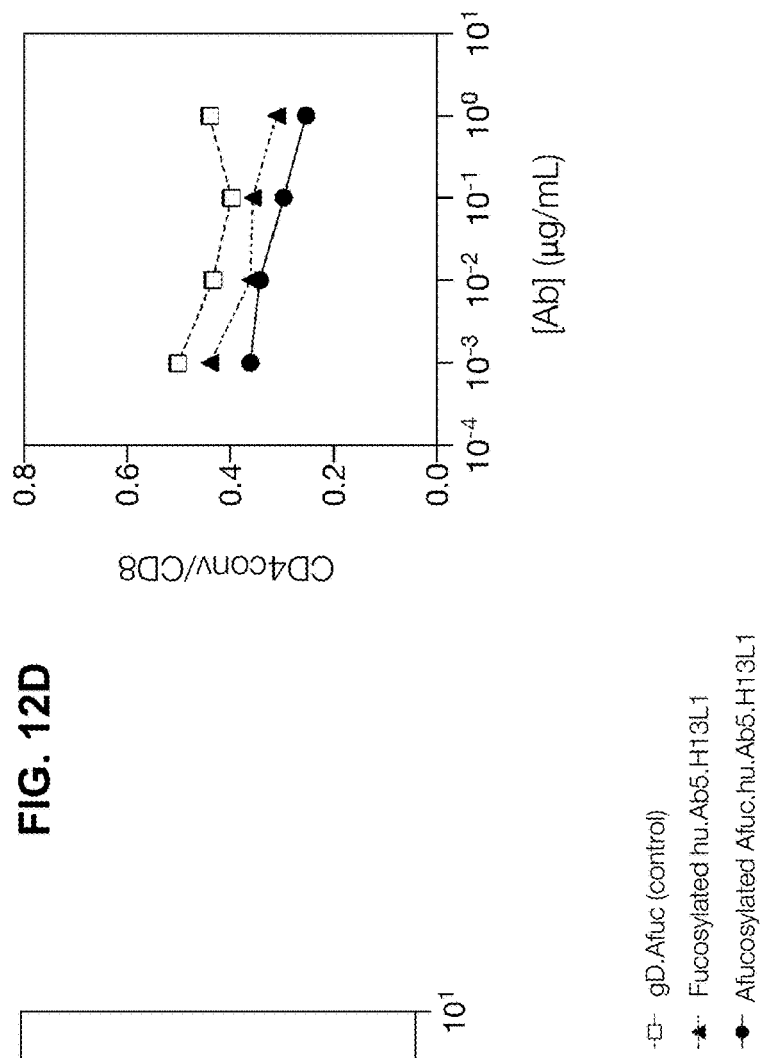
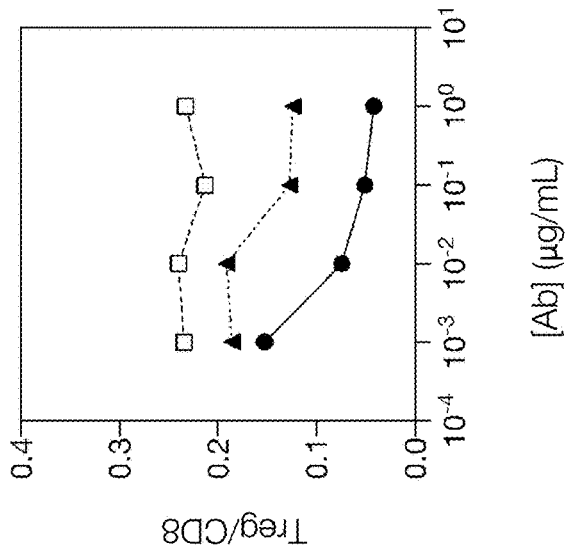
FIG. 12C
FIG. 12D

ADCC Activity Against Tregs in Human RCC Cells
*hu.Ab4.H12L3 Fucosylated versus Afucosylated Variants*

□ gD.Afuc (control)
▲ Fucosylated hu.Ab4.H12L3
● Afucosylated Afuc.hu.Ab4.H12L3

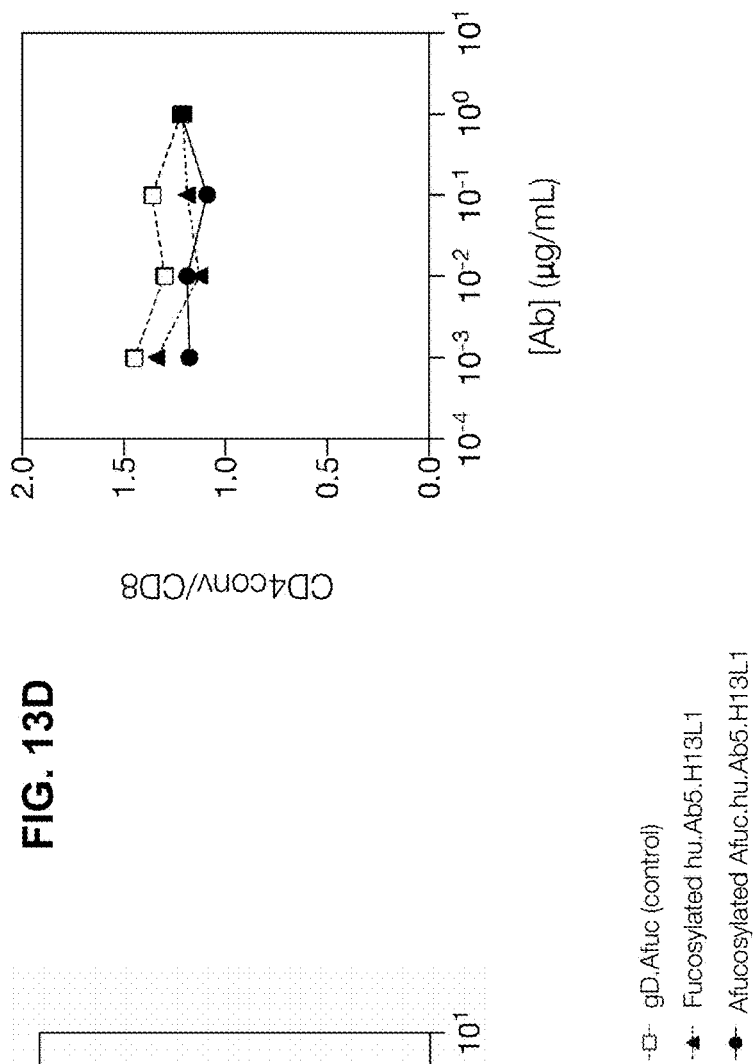
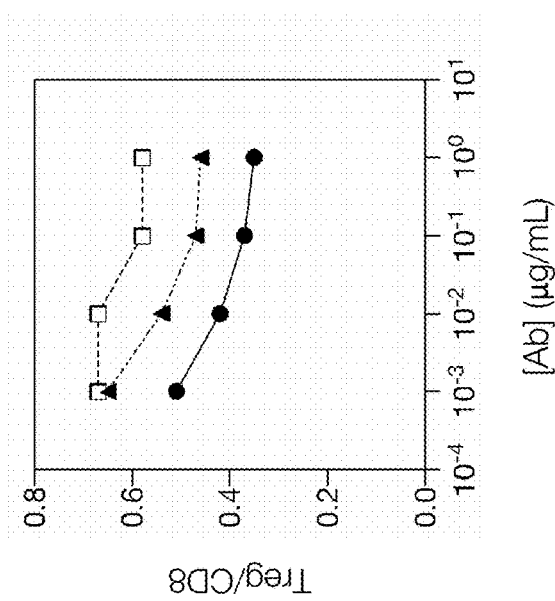
FIG. 13C
FIG. 13D
ADCC Activity Against Tregs in Human RCC Cells
*hu.Ab5.H13L1 Fucosylated versus Afucosylated Variants*
- □ gD.Afuc (control)
- ▲ Fucosylated hu.Ab5.H13L1
- ● Afucosylated Afuc.hu.Ab5.H13L1

Enhanced ADCP activities of Afucosylated Variants in HR/FF and RR/FF genotypes
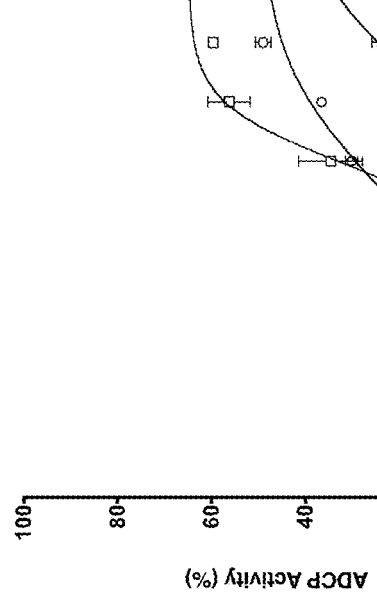
FIG. 14A  HR/FF donor allele
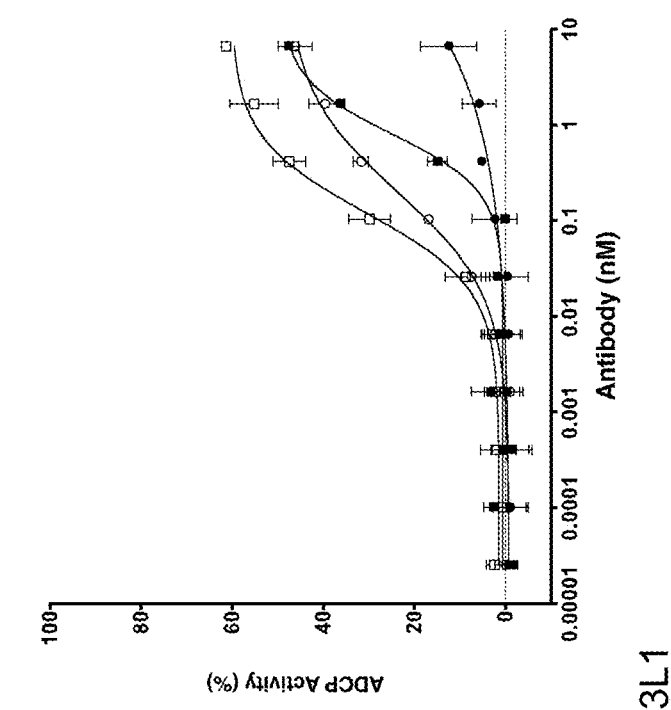
FIG. 14B  RR/FF donor allele
- ● hu.Ab5.H13L1
- ○ Afuc.hu.Ab5.H13L1
- ■ hu.Ab4.H12L3
- □ Afuc.hu.Ab4.H12L3

Enhanced ADCP activities of Afucosylated Variants in HR/VF and RR/VF genotypes
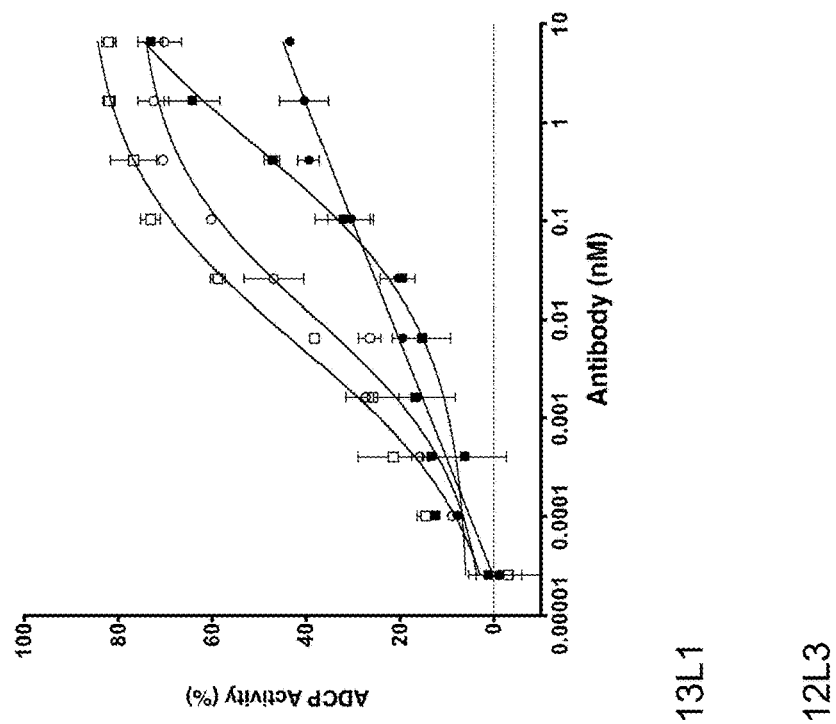
FIG. 14C  HR/VF donor allele Enhanced ADCP activities of Fucosylated Ab5 Variants, including a G236A.I332E mutant, in HR/FF and RR/FF genotypes
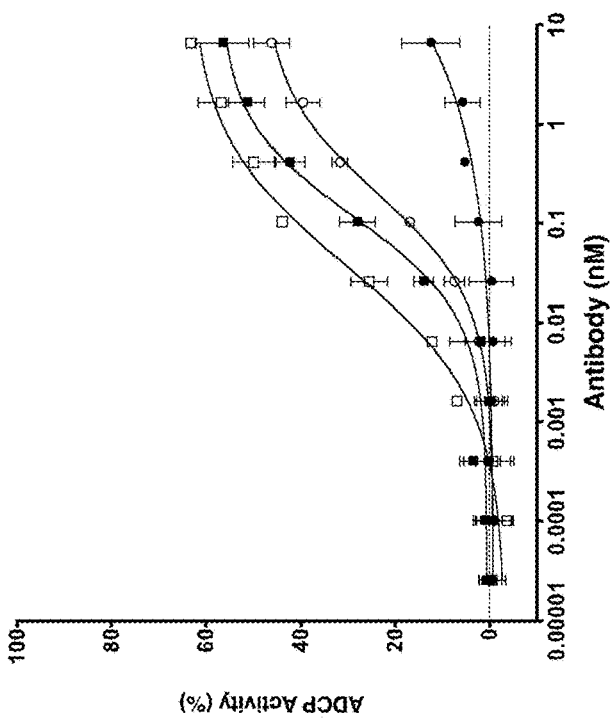
FIG. 15A  HR/FF
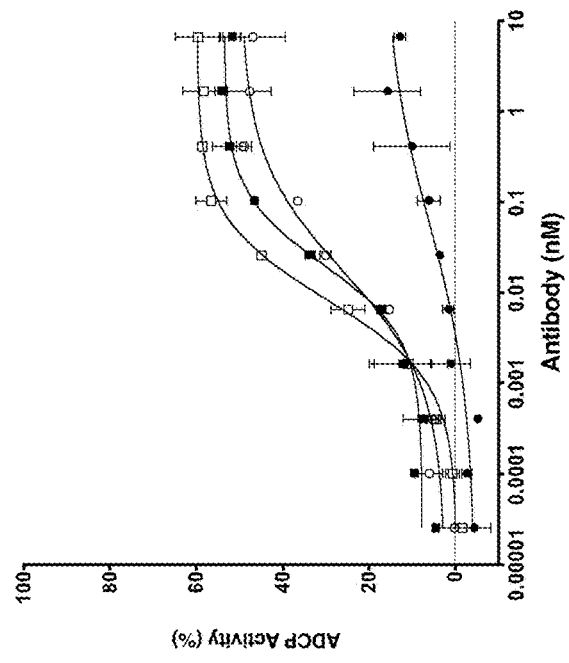
FIG. 15B  RR/FF
● hu.Ab5.H13L1
○ Afu Enhanced ADCP activities of Fucosylated Ab5 Variants, including a G236A.I332E mutant, in HR/VF and RR/VF genotypes
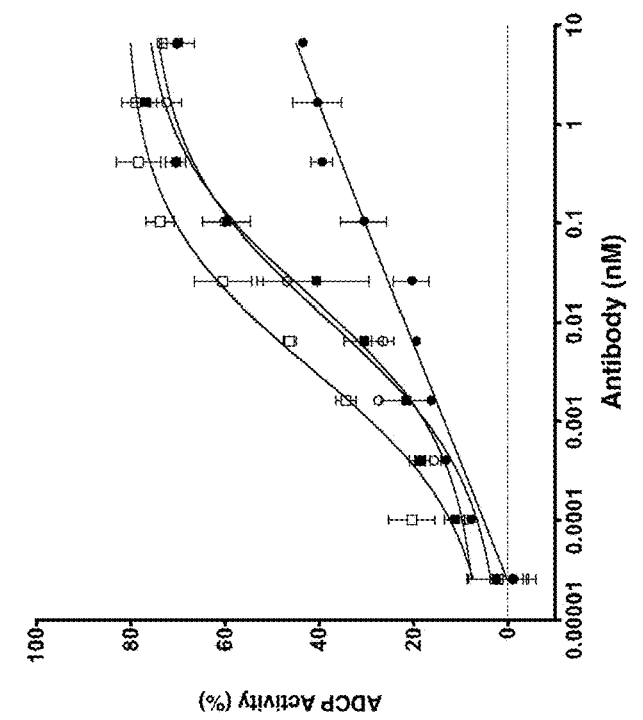
FIG. 15D  RR/VF
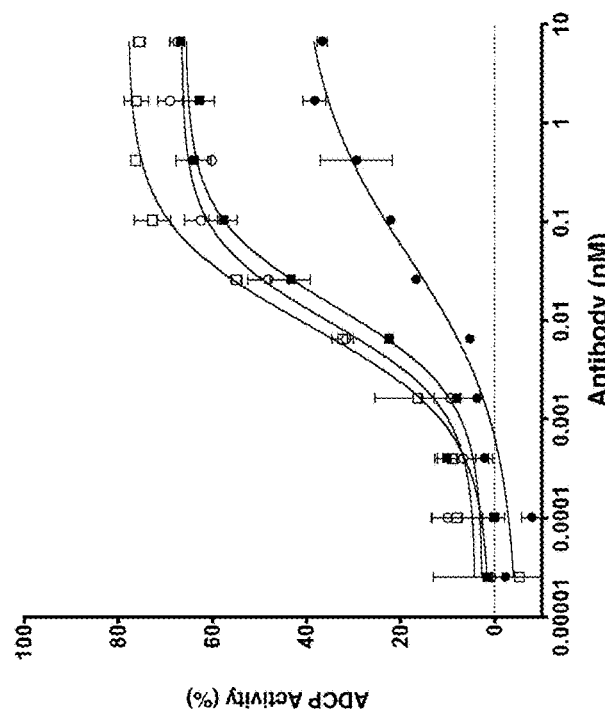
FIG. 15C  HR/VF
● hu.Ab5.H13L1
○ Afu hu.Ab5.H13L1 binds to human CCR8 N-terminus D2 to D6 huCCR8 N-terminus: MDYTLDLSVTTVTDYYYPDIFSSP (SEQ ID NO: 110)

ANTI-C-C MOTIF CHEMOKINE RECEPTOR 8 (CCR8) ANTIBODIES AND METHODS OF USE

CROSS-REFERENCE TO RELATED APPLICATIONS

This application claims priority to U.S. Provisional Application No. 63/253,676 filed on Oct. 8, 2021, and to U.S. Provisional Application No. 63/221,734, filed on Jul. 14, 2021, both of which are hereby incorporated by reference in their entireties, and to which priority is claimed.

SEQUENCE LISTING

The present application contains a Sequence Listing which has been submitted in xml format via EFS-Web and is hereby incorporated by reference in its entirety. Said xml copy, created on Jul. 13, 2022, is named 00B206.1289.xml.

BACKGROUND

Regulatory T (Treg) cells expressing the transcription factor Foxp3 are important for maintaining peripheral immune tolerance and preventing autoimmunity. See, e.g., Sakaguchi et al., *Cell* (2008) 133:775-787. Treg cells also constitute a major component of the immune infiltrate of solid cancers, promoting tumor development and progression by establishing an immunosuppressive tumor microenvironment and dampening anti-tumor immune responses. See, e.g., *Plitas and Rudensky, Annu. Rev. Cancer Biol.* (2020) 4:459-477. Treg cells also hamper the efficacy of immunotherapies. See, e.g., Nishikawa and Sakaguchi, *Curr. Opin. Immunol.* (2014) 27:1-7. An increased proportion of Treg cells among tumor-infiltrating lymphocytes is associated with poorer outcomes in several cancer indications. See, e.g., Fu et al., *Gastroenterology* (2007) 132:2328-2339; Petersen et al., *Cancer* (2006) 107:2866-2872; Shang et al., *Nature—Scientific Reports* (2015) 5:15179 (9 pages); Shen et al., *J. Cancer Res. Clin. Oncol.* (2010) 136:1585-1595; and Tanaka and Sakaguchi, *Eur. J. Immunol.* (2019) 49:1140-1146.

Several strategies directed to Treg cell depletion or inhibition have been shown to enhance anti-tumor immunity and result in tumor growth inhibition in pre-clinical breast, melanoma, and colon cancer models. See, e.g., Bos et al., *J. Exp. Med.* (2013) 2435-2446; Klages et al., *Cancer Res.* (2010) 70:7788-7799; and Pastille et al., *Cancer Res.* (2014) 74:4258-4269. However, strategies targeting surface receptors expressed on both Treg cells and effector T cells, such as CD25, have shown limited efficacy in established tumors likely due to the concomitant depletion of effector T cells critical for anti-tumor immunity. See, e.g., Onizuka et al. *Cancer Res.* (1999) 59:3128-3133.

The chemokine receptor CCR8 is a seven transmembrane G-protein coupled receptor (GPCR) and ligated by human/mouse CCL1 with high affinity, and which is selectively and highly expressed by Treg cells within the tumor microenvironment, but largely absent from peripheral Treg cells or effector T cells. High CCR8 expression on Treg cells is associated with advanced disease stage and decreased overall survival in patients with breast cancer. See, e.g., Plitas et al., *Immunity* (2016) 45:1122-1134. CCR8 therefore represents a promising and safer target for Treg cell depletion in cancer treatment. Therefore, agents that recognize CCR8, and methods of using such agents, are desired.

SUMMARY

The present disclosure provides anti-CCR8 antibodies, composition, and methods of preparation and using the same.

Embodiment 1. In certain non-limiting embodiments, the presently disclosed subject matter provides for a monoclonal antibody that binds to C—C motif chemokine receptor 8 (CCR8), wherein the antibody comprises a heavy chain variable domain (VH) comprising (a) CDR-H1 comprising the amino acid sequence of SEQ ID NO: 29 or SEQ ID NO: 30, (b) CDR-H2 comprising the amino acid sequence of SEQ ID NO: 31, and (c) CDR-H3 comprising the amino acid sequence of SEQ ID NO: 32, and a light chain variable domain (VL) comprising (d) CDR-L1 comprising the amino acid sequence of SEQ ID NO: 26, (e) CDR-L2 comprising the amino acid sequence of SEQ ID NO: 27, and (f) CDR-L3 comprising the amino acid sequence of SEQ ID NO: 28.

Embodiment 2. The foregoing antibody of Embodiment 1, which binds to CCR8 independent of sulfation of CCR8.

Embodiment 3. The foregoing antibody of Embodiment 1 or 2, wherein the antibody binds to an epitope comprised of one or more of amino acid residues 2-6 of SEQ ID NO: 106.

Embodiment 4. The foregoing antibody of any one of Embodiments 1-3, comprising a sequence selected from the group consisting of: (a) a VH sequence having at least about 95%, at least about 96%, at least about 97%, at least about 98%, or at least about 99% identity to an amino acid sequence selected from the group consisting of SEQ ID NOs: 35-47; (b) a VL sequence having at least about 95%, at least about 96%, at least about 97%, at least about 98%, or at least about 99% identity to an amino acid sequence selected from the group consisting of SEQ ID NOs: 48-52; and (c) a VH sequence as defined in (a) and a VL sequence as defined in (b).

Embodiment 5. The foregoing antibody of any one of Embodiments 1-4, comprising a VH sequence selected from the group consisting of SEQ ID NOs: 35-47 and a VL sequence selected from the group consisting of SEQ ID NOs: 48-52.

Embodiment 6. The foregoing antibody of any one of Embodiments 1-5, comprising a sequence selected from the group consisting of: (a) a VH sequence having at least about 95%, at least about 96%, at least about 97%, at least about 98%, or at least about 99% identity to the amino acid sequence of SEQ ID NO: 47; (b) a VL sequence having at least about 95%, at least about 96%, at least about 97%, at least about 98%, or at least about 99% identity to the amino acid sequence of SEQ ID NO: 48; and (c) a VH sequence as defined in (a) and a VL sequence as defined in (b).

Embodiment 7. The foregoing antibody of any one of Embodiments 1-6, comprising a VH sequence having at least about 95%, at least about 96%, at least about 97%, at least about 98%, or at least about 99% identity to an amino acid sequence of SEQ ID NO: 47 and a VL sequence having at least about 95%, at least about 96%, at least about 97%, at least about 98%, or at least about 99% identity to an amino acid sequence of SEQ ID NO: 48.

Embodiment 8. The foregoing antibody of any one of Embodiments 1-7, wherein the VL comprises a V4M mutation, a P43A mutation, a F46L mutation, a C90Q mutation, or a combination thereof.

Embodiment 9. The foregoing antibody of any one of Embodiments 1-8, wherein the VH comprises a G49S mutation, a K71R mutation, a S73N mutation, or a combination thereof.

Embodiment 10. The foregoing antibody of any one of Embodiments 1-9, comprising the heavy chain amino acid sequence of SEQ ID NO: 55, and the light chain amino acid sequence of SEQ ID NO: 56.

Embodiment 11. The foregoing antibody of any one of Embodiments 1-9, comprises the heavy chain amino acid sequence of SEQ ID NO: 60, and the light chain amino acid sequence of SEQ ID NO: 56.

Embodiment 12. The foregoing antibody of any one of Embodiments 1-9, comprises the heavy chain amino acid sequence of SEQ ID NO: 111, and the light chain amino acid sequence of SEQ ID NO: 56.

Embodiment 13. The foregoing antibody of any one of Embodiments 1-9, comprises the heavy chain amino acid sequence of SEQ ID NO: 113, and the light chain amino acid sequence of SEQ ID NO: 56.

Embodiment 14. In certain non-limiting embodiments, the presently disclosed subject matter provides for a monoclonal antibody that binds to CCR8 comprising a VH sequence selected from the group consisting of SEQ ID NOs: 35-47 and a VL sequence selected from the group consisting of SEQ ID NOs: 48-52.

Embodiment 15. In certain non-limiting embodiments, the presently disclosed subject matter provides for a monoclonal antibody that binds to CCR8 comprising a VH sequence of SEQ ID NO: 47 and a VL sequence of SEQ ID NO: 48.

Embodiment 16. In certain non-limiting embodiments, the presently disclosed subject matter provides for a monoclonal antibody that binds to CCR8, wherein the antibody comprises a heavy chain variable domain (VH) comprising (a) CDR-H1 comprising the amino acid sequence of SEQ ID NO: 4 or SEQ ID NO: 5, (b) CDR-H2 comprising the amino acid sequence of SEQ ID NO: 6, and (c) CDR-H3 comprising the amino acid sequence of SEQ ID NO: 7, and a light chain variable domain (VL) comprising (d) CDR-L1 comprising the amino acid sequence of SEQ ID NO: 1, (e) CDR-L2 comprising the amino acid sequence of SEQ ID NO: 2, and (f) CDR-L3 comprising the amino acid sequence of SEQ ID NO: 3.

Embodiment 17. The foregoing antibody of Embodiment 16, which binds to CCR8 independent of sulfation of CCR8.

Embodiment 18. The foregoing antibody of Embodiment 16 or 17, wherein the antibody binds to an epitope comprised of one or more of amino acid residues 91-104 and 172-193 of SEQ ID NO: 106.

Embodiment 19. The foregoing antibody of any one of Embodiments 16-18, comprising a sequence selected from the group consisting of: (a) a VH sequence having at least about 95%, at least about 96%, at least about 97%, at least about 98%, or at least about 99% identity to an amino acid sequence selected from the group consisting of SEQ ID NOs: 10-21; (b) a VL sequence having at least about 95%, at least about 96%, at least about 97%, at least about 98%, or at least about 99% identity to an amino acid sequence selected from the group consisting of SEQ ID NOs: 22-25; and (c) a VH sequence as defined in (a) and a VL sequence as defined in (b).

Embodiment 20. The foregoing antibody of any one of Embodiments 16-19, comprising a VH sequence selected from the group consisting of SEQ ID NOs: 10-21 and a VL sequence selected from the group consisting of SEQ ID NOs: 22-25.

Embodiment 21. The foregoing antibody of any one of Embodiments 16-20, comprising a sequence selected from the group consisting of: (a) a VH sequence having at least about 95%, at least about 96%, at least about 97%, at least about 98%, or at least about 99% identity to the amino acid sequence of SEQ ID NO: 21; (b) a VL sequence having at least about 95%, at least about 96%, at least about 97%, at least about 98%, or at least about 99% identity to the amino acid sequence of SEQ ID NO: 24; and (c) a VH sequence as defined in (a) and a VL sequence as defined in (b).

Embodiment 22. The foregoing antibody of any one of Embodiments 16-21, comprising a VH sequence having at least about 95%, at least about 96%, at least about 97%, at least about 98%, or at least about 99% identity to an amino acid sequence of SEQ ID NO: 21 and a VL sequence having at least about 95%, at least about 96%, at least about 97%, at least about 98%, or at least about 99% identity to an amino acid sequence of SEQ ID NO: 24.

Embodiment 23. The foregoing antibody of any one of Embodiments 16-22, wherein the VL comprises a Y2I mutation.

Embodiment 24. The foregoing antibody of any one of Embodiments 16-23, wherein the VH comprises a S73N mutation, a V78L mutation, a T76N mutation, a F91Y mutation, and a P105Q mutation, or a combination thereof.

Embodiment 25. The foregoing antibody of any one of Embodiments 16-24, comprising the heavy chain amino acid sequence of SEQ ID NO: 57, and the light chain amino acid sequence of SEQ ID NO: 58.

Embodiment 26. The foregoing antibody of any one of Embodiments 16-24, comprises the heavy chain amino acid sequence of SEQ ID NO: 61, and the light chain amino acid sequence of SEQ ID NO: 58.

Embodiment 27. The foregoing antibody of any one of Embodiments 16-24, comprises the heavy chain amino acid sequence of SEQ ID NO: 112, and the light chain amino acid sequence of SEQ ID NO: 58.

Embodiment 28. The foregoing antibody of any one of Embodiments 16-24, comprises the heavy chain amino acid sequence of SEQ ID NO: 114, and the light chain amino acid sequence of SEQ ID NO: 58.

Embodiment 29. In certain non-limiting embodiments, the presently disclosed subject matter provides for a monoclonal antibody that binds to CCR8 comprising a VH sequence selected from the group consisting of SEQ ID NOs: 10-21 and a VL sequence selected from the group consisting of SEQ ID NOs: 22-25.

Embodiment 30. In certain non-limiting embodiments, the presently disclosed subject matter provides for a monoclonal antibody that binds to CCR8 comprising a VH sequence of SEQ ID NO: 21 and a VL sequence of SEQ ID NO: 24.

Embodiment 31. In certain non-limiting embodiments, the presently disclosed subject matter provides for a monoclonal antibody that binds to CCR8, wherein the antibody comprises a heavy chain variable domain (VH) comprising (a) CDR-H1 comprising the amino acid sequence of SEQ ID NO: 82 or SEQ ID NO: 83, (b) CDR-H2 comprising the amino acid sequence of SEQ ID NO: 84, and (c) CDR-H3 comprising the amino acid sequence of SEQ ID NO: 85, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 75.

Embodiment 32. The foregoing antibody of Embodiment 31, comprising a sequence selected from the group consisting of: (a) a VH sequence having at least about 95%, at least about 96%, at least about 97%, at least about 98%, or at least about 99% identity to the amino acid sequence of SEQ ID NO: 95; (b) a VL sequence having at least about 95%, at least about 96%, at least about 97%, at least about 98%, or at least about 99% identity to the amino acid sequence of SEQ ID NO: 94; and (c) a VH sequence as defined in (a) and a VL sequence as defined in (b).

Embodiment 33. The foregoing antibody of Embodiment 31 or 32, comprising a VH sequence of SEQ ID NO: 95 and a VL sequence of SEQ ID NO: 94.

Embodiment 34. The foregoing antibody of any one of Embodiments 31-33, comprising the heavy chain amino acid sequence of SEQ ID NO: 101, and the light chain amino acid sequence of SEQ ID NO: 100.

Embodiment 35. The foregoing antibody of any one of Embodiments 31-33, comprising the heavy chain amino acid sequence of SEQ ID NO: 115, and the light chain amino acid sequence of SEQ ID NO: 100.

Embodiment 36. In certain non-limiting embodiments, the presently disclosed subject matter provides for a monoclonal antibody that binds to CCR8, wherein the antibody comprises a heavy chain variable domain (VH) comprising (a) CDR-H1 comprising the amino acid sequence of SEQ ID NO: 86 or SEQ ID NO: 87, (b) CDR-H2 comprising the amino acid sequence of SEQ ID NO: 88, and (c) CDR-H3 comprising the amino acid sequence of SEQ ID NO: 89, and a light chain variable domain (VL) comprising (d) CDR-L1 comprising the amino acid sequence of SEQ ID NO: 76, (e) CDR-L2 comprising the amino acid sequence of SEQ ID NO: 77, and (f) CDR-L3 comprising the amino acid sequence of SEQ ID NO: 78.

Embodiment 37. The foregoing antibody of Embodiment 36, comprising a sequence selected from the group consisting of: (a) a VH sequence having at least about 95%, at least about 96%, at least about 97%, at least about 98%, or at least about 99% identity to the amino acid sequence of SEQ ID NO: 97; (b) a VL sequence having at least about 95%, at least about 96%, at least about 97%, at least about 98%, or at least about 99% identity to the amino acid sequence of SEQ ID NO: 96; and (c) a VH sequence as defined in (a) and a VL sequence as defined in (b).

Embodiment 38. The foregoing antibody of Embodiment 36 or 37, comprising a VH sequence of SEQ ID NO: 97 and a VL sequence of SEQ ID NO: 96.

Embodiment 39. The foregoing antibody of any one of Embodiments 36-38, comprising the heavy chain amino acid sequence of SEQ ID NO: 103, and the light chain amino acid sequence of SEQ ID NO: 102.

Embodiment 40. The foregoing antibody of any one of Embodiments 36-38, comprising the heavy chain amino acid sequence of SEQ ID NO: 116, and the light chain amino acid sequence of SEQ ID NO: 102.

Embodiment 41. In certain non-limiting embodiments, the presently disclosed subject matter provides for a monoclonal antibody that binds to CCR8, wherein the antibody comprises a heavy chain variable domain (VH) comprising (a) CDR-H1 comprising the amino acid sequence of SEQ ID NO: 90 or SEQ ID NO: 91, (b) CDR-H2 comprising the amino acid sequence of SEQ ID NO: 92, and (c) CDR-H3 comprising the amino acid sequence of SEQ ID NO: 93, and a light chain variable domain (VL) comprising (d) CDR-L1 comprising the amino acid sequence of SEQ ID NO: 79, (e) CDR-L2 comprising the amino acid sequence of SEQ ID NO: 80, and (f) CDR-L3 comprising the amino acid sequence of SEQ ID NO: 81.

Embodiment 42. The foregoing antibody of Embodiment 41, comprising a sequence selected from the group consisting of: (a) a VH sequence having at least about 95%, at least about 96%, at least about 97%, at least about 98%, or at least about 99% identity to the amino acid sequence of SEQ ID NO: 99; (b) a VL sequence having at least about 95%, at least about 96%, at least about 97%, at least about 98%, or at least about 99% identity to the amino acid sequence of SEQ ID NO: 98; and (c) a VH sequence as defined in (a) and a VL sequence as defined in (b).

Embodiment 43. The foregoing antibody of Embodiment 41 or 42, comprising a VH sequence of SEQ ID NO: 99 and a VL sequence of SEQ ID NO: 98.

Embodiment 44. The foregoing antibody of any one of Embodiments 41-43, comprising the heavy chain amino acid sequence of SEQ ID NO: 105, and the light chain amino acid sequence of SEQ ID NO: 104.

Embodiment 45. The foregoing antibody of any one of Embodiments 41-44, comprising the heavy chain amino acid sequence of SEQ ID NO: 117, and the light chain amino acid sequence of SEQ ID NO: 104.

Embodiment 46. In certain non-limiting embodiments, the presently disclosed subject matter provides for a monoclonal antibody that binds to CCR8, wherein the antibody binds to CCR8 independent of sulfation of CCR8.

Embodiment 47. The foregoing antibody of Embodiment 46, wherein the antibody binds to an epitope comprised of one or more of amino acid residues 2-6 of SEQ ID NO: 106.

Embodiment 48. The foregoing antibody of Embodiment 46, wherein the antibody binds to binds to an epitope comprised of one or more of amino acid residues 91-104 and 172-193 of SEQ ID NO: 106.

Embodiment 49. In certain non-limiting embodiments, the presently disclosed subject matter provides for a monoclonal antibody that binds to mouse CCR8, wherein the antibody comprises a heavy chain variable domain (VH) comprising (a) CDR-H1 comprising the amino acid sequence of SEQ ID NO: 65 or SEQ ID NO: 66, (b) CDR-H2 comprising the amino acid sequence of SEQ ID NO: 67 and (c) CDR-H3 comprising the amino acid sequence of SEQ ID NO: 68, and a light chain variable domain (VL) comprising (d) CDR-L1 comprising the amino acid sequence of SEQ ID NO: 62, (e) CDR-L2 comprising the amino acid sequence of SEQ ID NO: 63, and (f) CDR-L3 comprising the amino acid sequence of SEQ ID NO: 64.

Embodiment 50. The foregoing antibody of Embodiment 49, comprising a sequence selected from the group consisting of: (a) a VH sequence having at least about 95%, at least about 96%, at least about 97%, at least about 98%, or at least about 99% identity to the amino acid sequence of SEQ ID NO: 70; (b) a VL sequence having at least about 95%, at least about 96%, at least about 97%, at least about 98%, or at least about 99% identity to the amino acid sequence of SEQ ID NO: 69; and (c) a VH sequence as defined in (a) and a VL sequence as defined in (b).

Embodiment 51. The foregoing antibody of Embodiment 49 or 50, comprising a VH sequence of SEQ ID NO: 70 and a VL sequence of SEQ ID NO: 69.

Embodiment 52. The foregoing antibody of any one of Embodiments 49-51, comprising the heavy chain amino acid sequence of SEQ ID NO: 72, and the light chain amino acid sequence of SEQ ID NO: 71.

Embodiment 53. The foregoing antibody of any one of Embodiments 1 to 48, which is a human antibody.

Embodiment 54. The foregoing antibody of any one of Embodiments 1 to 48, which is a humanized antibody.

Embodiment 55. The foregoing antibody of any one of Embodiments 1 to 52, which is a chimeric antibody.

Embodiment 56. The foregoing antibody of any of Embodiments 1 to 55, which is an antibody fragment that binds to CCR8.

Embodiment 57. The foregoing antibody of any of Embodiments 1 to 56, which is a full-length antibody.

Embodiment 58. The foregoing antibody of Embodiment 57, which is a full-length IgG1 antibody.

Embodiment 59. The foregoing antibody of any of Embodiments 1 to 58, comprising a IgG1 constant domain comprising the amino acid sequence of SEQ ID NO: 53 or SEQ ID NO: 59.

Embodiment 60. The foregoing antibody of any of Embodiments 1 to 59, comprising a kappa constant domain comprising the amino acid sequence of SEQ ID NO: 54.

Embodiment 61. The foregoing antibody of any of Embodiments 1 to 60, wherein the antibody binds to CCR8 with a binding affinity (Kd) of from about 1×10-12 M to about 1×10-11 M.

Embodiment 62. The foregoing antibody of any of Embodiments 1 to 48, wherein the CCR8 is a human CCR8.

Embodiment 63. The foregoing antibody of any of Embodiments 1 to 62, wherein the antibody is afucosylated.

Embodiment 64. In certain non-limiting embodiments, the presently disclosed subject matter provides for an isolated nucleic acid encoding the foregoing antibody of any of Embodiments 1 to 63.

Embodiment 65. In certain non-limiting embodiments, the presently disclosed subject matter provides for a host cell comprising the foregoing nucleic acid of Embodiment 64.

Embodiment 66. In certain non-limiting embodiments, the presently disclosed subject matter provides for a method of producing an antibody that binds to CCR8 comprising culturing the foregoing host cell of Embodiment 65 under conditions suitable for the expression of the antibody.

Embodiment 67. The foregoing method of Embodiment 66, further comprising recovering the antibody from the host cell.

Embodiment 68. In certain non-limiting embodiments, the presently disclosed subject matter provides for an antibody produced by the foregoing method of Embodiment 67.

Embodiment 69. In certain non-limiting embodiments, the presently disclosed subject matter provides for a pharmaceutical composition comprising the foregoing antibody of any of Embodiments 1 to 63 and a pharmaceutically acceptable carrier.

Embodiment 70. The foregoing pharmaceutical composition of Embodiment 69, further comprising an additional therapeutic agent.

Embodiment 71. The foregoing antibody of any one of Embodiments 1 to 63 or the foregoing pharmaceutical composition of any one of Embodiments 69 to 70 for use as a medicament.

Embodiment 72. The foregoing antibody of any one of Embodiments 1 to 63 or the foregoing pharmaceutical composition of any one of Embodiments 69 to 70 for use in treating cancer.

Embodiment 73. In certain non-limiting embodiments, the presently disclosed subject matter provides for use of the foregoing antibody of any one of Embodiments 1 to 63 or the foregoing pharmaceutical composition of any of Embodiments 69 to 70 in the manufacture of a medicament for treating cancer.

Embodiment 74. In certain non-limiting embodiments, the presently disclosed subject matter provides for use of the foregoing antibody of any one of Embodiments 1 to 63 or the foregoing pharmaceutical composition of any of Embodiments 69 to 70 in the manufacture of a medicament for depleting regulatory T cells.

Embodiment 75. In certain non-limiting embodiments, the presently disclosed subject matter provides for a method of treating cancer in a subject in need thereof comprising administering to the subject an effective amount of the foregoing antibody of any one of Embodiments 1 to 63 or the foregoing pharmaceutical composition of any of Embodiments 69 to 70.

Embodiment 76. In certain non-limiting embodiments, the presently disclosed subject matter provides for a method of depleting regulatory T cells in a tumor microenvironment in a subject having cancer comprising administering to the subject an effective amount of the foregoing antibody of any of Embodiments 1 to 63 or the foregoing pharmaceutical composition of any of Embodiments 69 to 70 sufficient to deplete the regulatory T cells in the tumor microenvironment.

Embodiment 77. In certain non-limiting embodiments, the presently disclosed subject matter provides for a method of depleting regulatory T cells outside of a tumor microenvironment in a subject having cancer comprising administering to the subject an effective amount of the foregoing antibody of any of Embodiments 1 to 63 or the foregoing pharmaceutical composition of any of Embodiments 69 to 70 sufficient to deplete the regulatory T cells outside of the tumor microenvironment.

Embodiment 78. In certain non-limiting embodiments, the presently disclosed subject matter provides for an in vitro method of depleting regulatory T cells from a cancer cell population, comprising contacting the cell population with the foregoing antibody of any of Embodiments 1 to 63 or the foregoing pharmaceutical composition of any of Embodiments 69 to 70 in an amount sufficient to deplete the regulatory T cells from the cell population.

Embodiment 79. The foregoing use or method of any one of Embodiments 73-78, wherein the cancer is selected from the group consisting of bladder cancer, blastoma, blood cancer, bone cancer, brain cancer, breast cancer, cervical cancer, colorectal cancer, endometrial cancer, esophageal cancer, gastric cancer, head and neck cancer, kidney cancer, liver cancer, lung cancer, ovarian cancer, pancreatic cancer, prostate cancer, sarcoma, skin cancer, testicular cancer, and uterine cancer.

Embodiment 80. The foregoing use or method of any one of Embodiments 74, 76, 78, and 79, wherein the regulatory T cells present in the tumor microenvironment of the cancer are depleted.

Embodiment 81. The foregoing use or method of any one of Embodiments 74, 77, 78, and 79, wherein the regulatory T cells outside of the tumor microenvironment of the cancer are depleted.

Embodiment 82. The foregoing use or method of any one of Embodiments 73-81, further comprising administering an additional therapeutic agent.

Embodiment 83. The foregoing use or method of Embodiment 82, wherein the additional therapeutic agent is an anti-cancer agent.

Embodiment 84. The foregoing use or method of Embodiment 83, wherein the anti-cancer agent is selected from the group consisting of a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, antiangiogenic agent, an immunomodulatory agent, an inhibitor of cell adhesion, a cytotoxic or cytostatic agent, an activator of cell apoptosis, an agent that increases the sensitivity of cells to apoptotic inducers, a cytokine, an anti-cancer vaccine or oncolytic virus, a toll-like receptor (TLR) agent, a bispecific antibody, a cellular therapy, and immune cell engager.

Embodiment 85. The foregoing use or method of Embodiment 83 or 84, wherein the anti-cancer agent is a PD-L1 binding antagonist.

Embodiment 86. The foregoing use or method of Embodiment 85, wherein the PD-L1 binding antagonist is atezolizumab.

Embodiment 87. The foregoing use or method of any one of Embodiments 73-85, wherein the subject is a human.

Embodiment 88. The foregoing use or method of any one of Embodiments 73-85, wherein the subject is a mouse.

Embodiment 89. In certain non-limiting embodiments, the presently disclosed subject matter provides for a method of treating a disease in a mouse comprising administering an effective amount of a monoclonal antibody of any one of foregoing Embodiments 49-52 to the mouse to treat the disease.

Embodiment 90. The forgoing method of Embodiment 89, wherein the mouse comprises a xenograft.

Embodiment 91. The forgoing antibody of Embodiment 63, wherein the proportion of afucosylation is between about 80% to about 95%.

Embodiment 92. The forgoing antibody of any one of Embodiments 1-15 and 46-48, wherein the mean clearance after a single 10 mg/kg dose administered intravenously on day 1 is between about 3 to about 5 mL/day/kg over a 35 day period.

BRIEF DESCRIPTION OF THE DRAWINGS

As shown in FIG. 3A, CCL1, a known ligand for CCR8, shows agonist activity, but none of the anti-CCR8 test mAbs show agonistic effects. The data in FIG. 3B shows anti-CCR8 mAb hu.Ab4.H1L1 demonstrates antagonistic (neutralizing) activity against the CCR8 ligand CCL1 (20 nM of ligand), whereas anti-CCR8 mAbs hu.Ab5.H1L1 and hu.Ab3.H1L1 demonstrate no ligand blocking (non-neutralizing) activity at the concentration studied. The data in FIG. 3C shows that comparator anti-CCR8 mAbs (the humanized anti-human Yoshida anti-CCR8 antibody, murine anti-human CCR8 mAb 433H (BD Biosciences), and murine anti-human CCR8 mAb L263G8 (Biolegend)) do not show agonistic effects, whereas the CCR8 ligand CCL1 does. The data in FIG. 3D shows comparator anti-CCR8 mAbs (the humanized anti-human Yoshida anti-CCR8 antibody, murine anti-human CCR8 mAb 433H (BD Biosciences), and murine anti-human Biolegend L263G8 (Biolegend)) demonstrate antagonistic (neutralizing) activity against the CCR8 ligand CCL1. The $IC_{50}$ values for the ligand blocking activity are provided in the Examples.

Figure 5A:
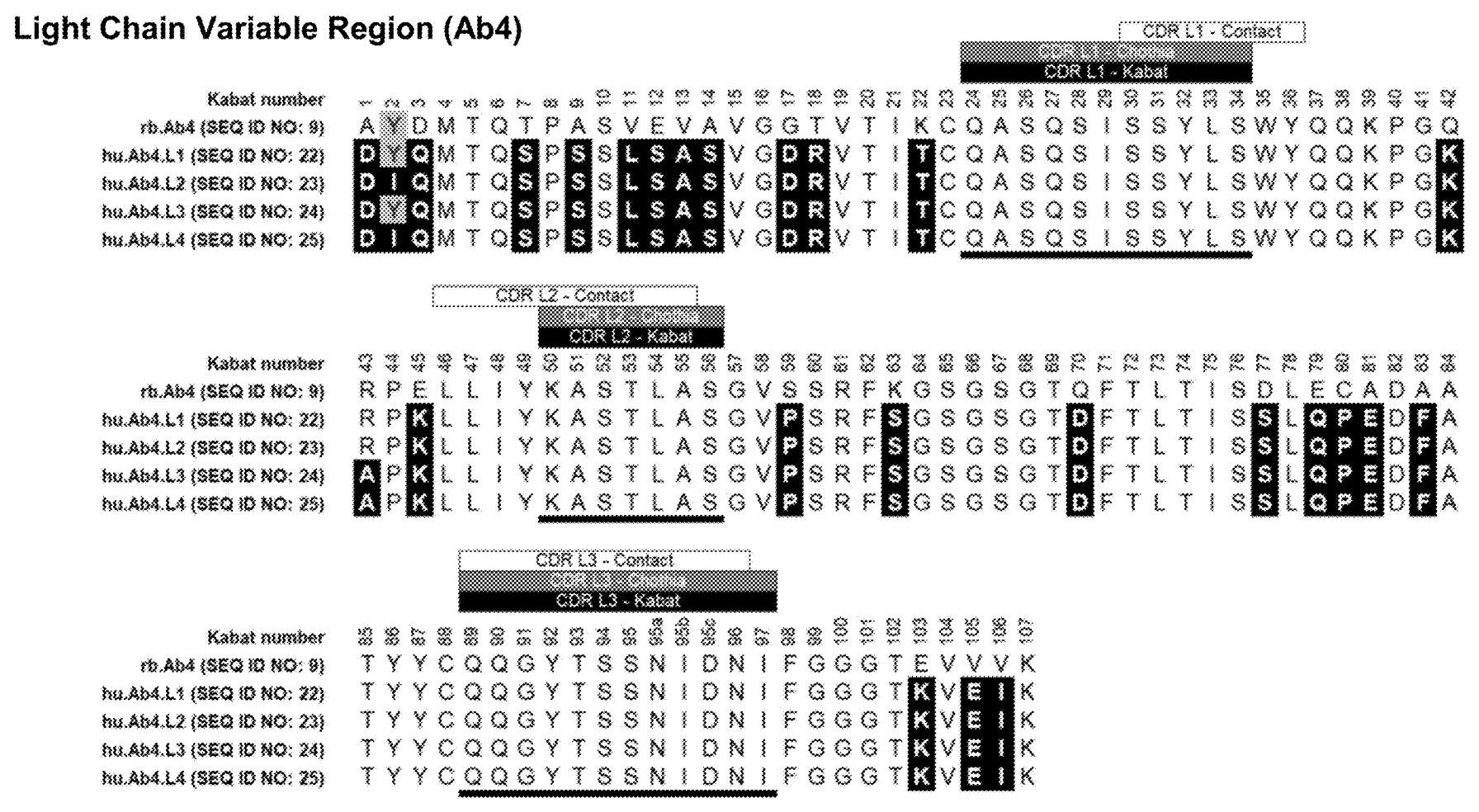
Figure 5C:
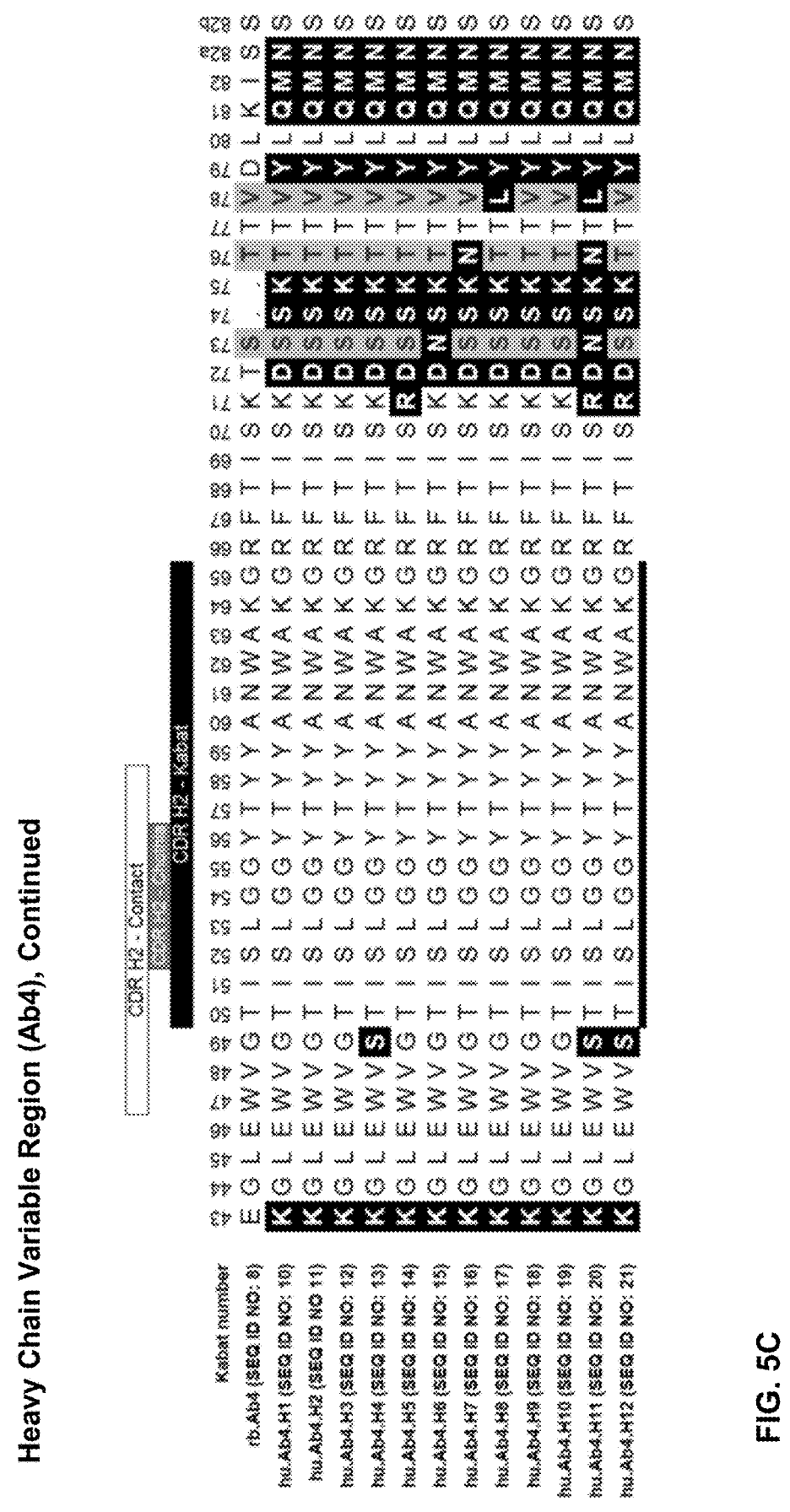

FIGS. 5A-5D depict the light chain variable region (FIG. 5A) and heavy chain variable region (FIGS. 5B-5D) alignment of the sequences for rabbit (rb.Ab4) and humanized Ab4 (L1-L4 and H1-H12) CCR8 mAbs studied. Y2 on light chain (L3) and S73, T76, V78, F91 and P105 on heavy chain (H12) were determined to be the key rabbit Vernier residues based on binding evaluation of the variant antibodies. The CDRs, variable regions, constant regions, and Full-length sequences are provided in the Examples.

Figure 6A:
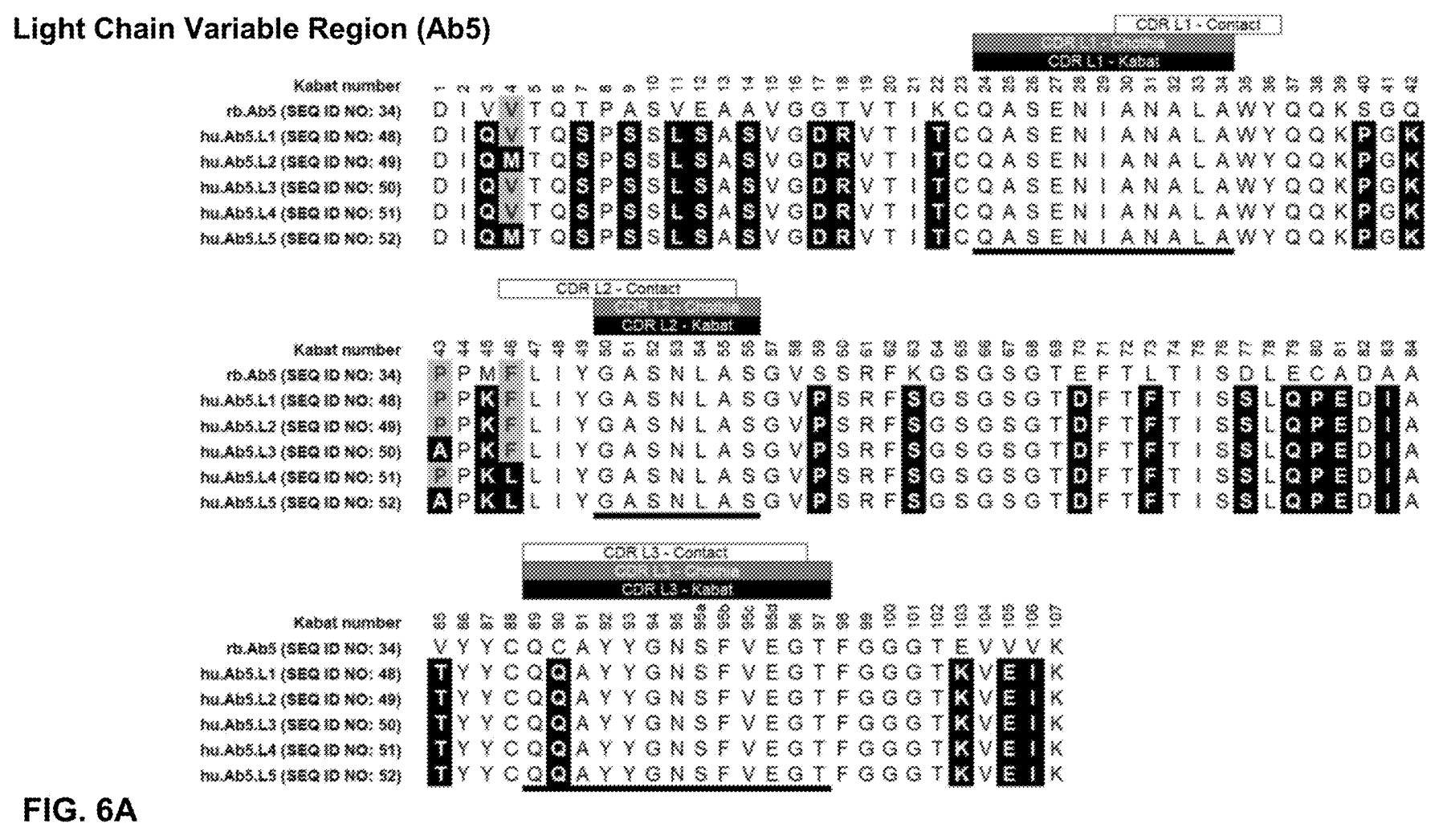
Figure 6B:
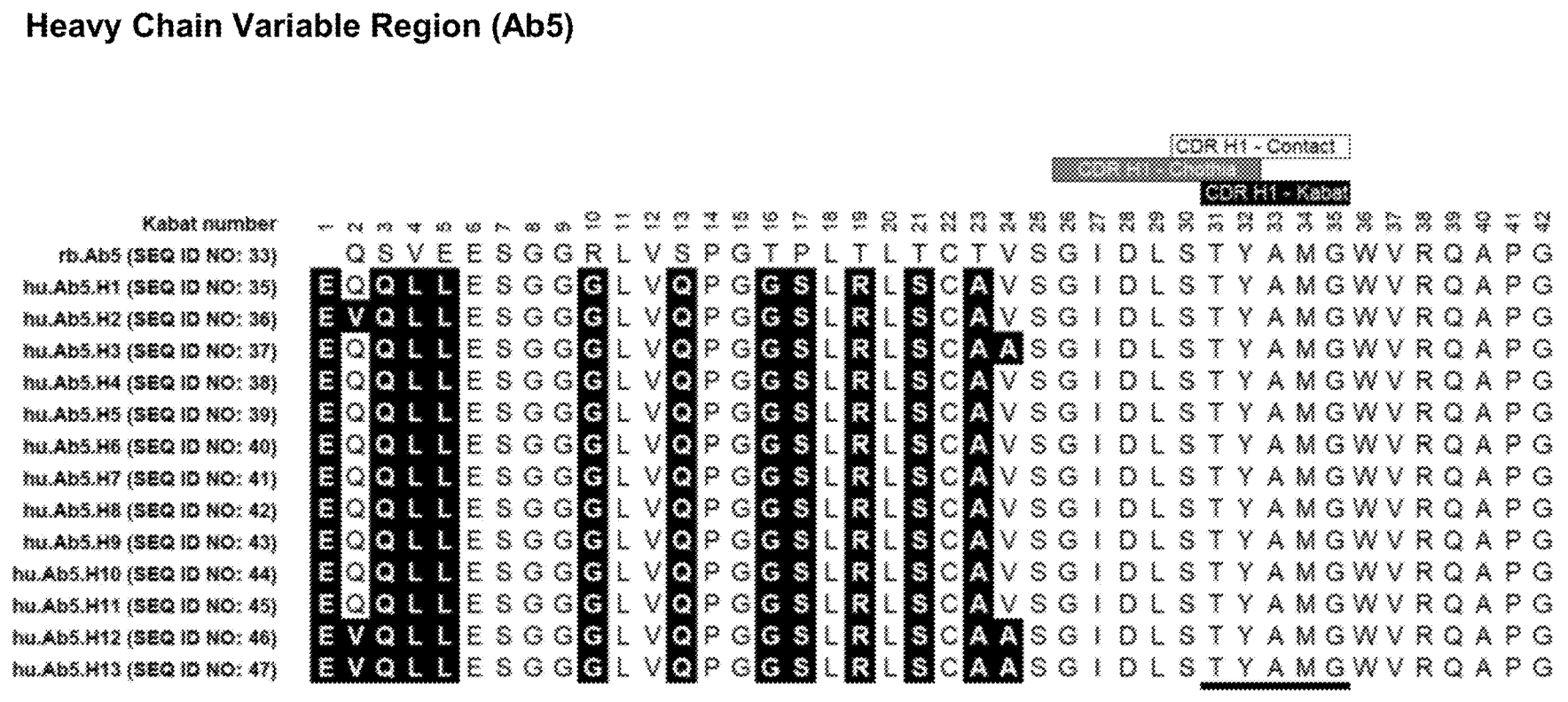
Figure 6D:
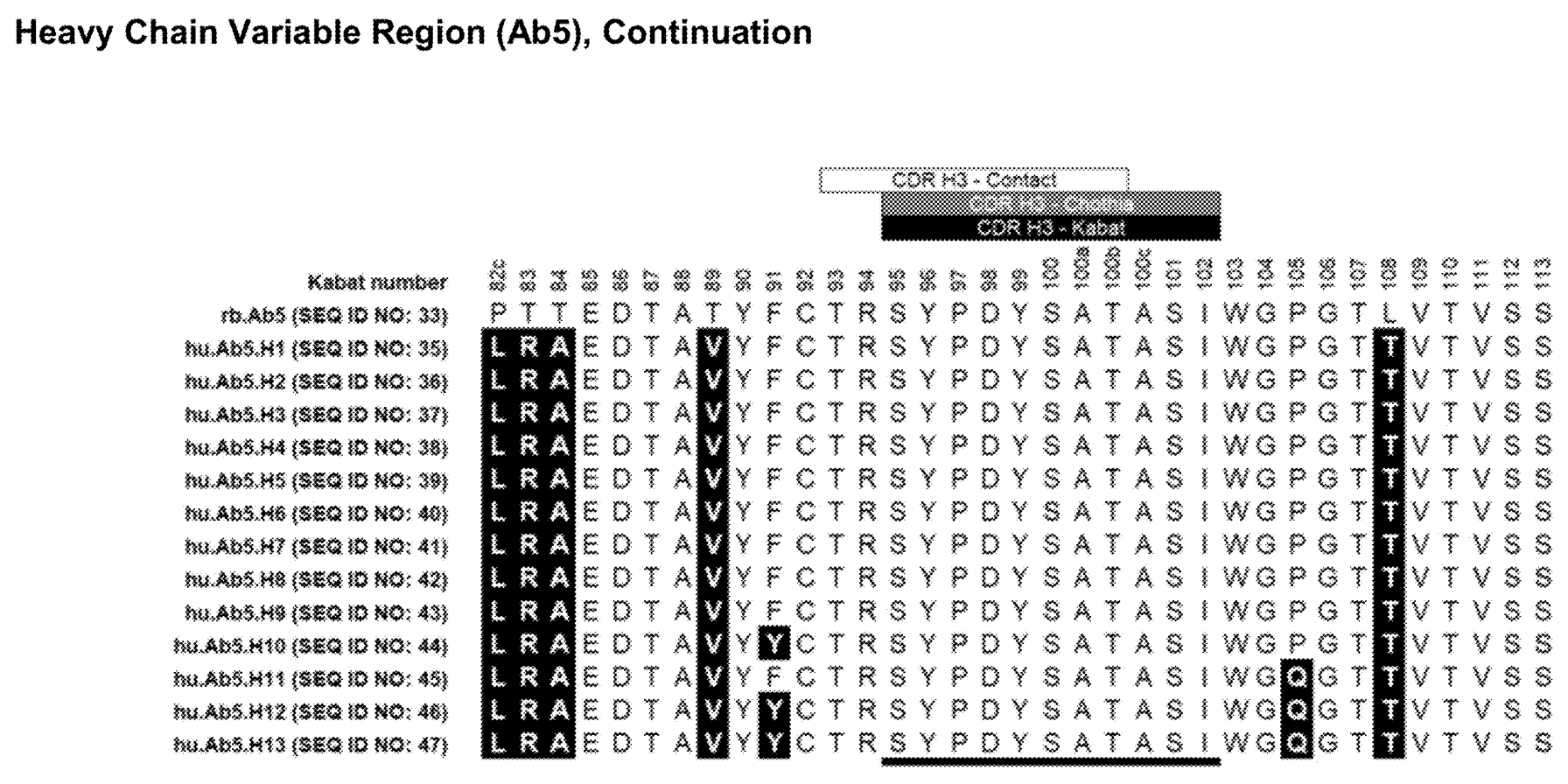

FIGS. 6A-6D depict the light chain variable region (FIG. 6A) and heavy chain variable region (FIGS. 6B-6D) alignment of the sequences for rabbit (rb.Ab5) and humanized Ab5 (L1-L5 and H1-H13) CCR8 mAbs studied. A C90Q mutation in CDR L3 was introduced to remove an unpaired cysteine that would be a liability during manufacturing. V4, P43 and F46 on light chain (L1), and G49, K71 and S73 (H13) on the heavy chain were determined to be the key rabbit Vernier residues based on binding evaluation of the variant antibodies. The CDRs, variable regions, constant regions, and Full-length sequences are provided in the Examples.

FIGS. 7A-7D depicts the results of cell-based affinity measurements for hu.Ab5.H13L1 and hu.Ab4.H12L3 mAbs using radiolabeled IgGs and CHO cell lines stably expressing human CCR8 or cynomolgus monkey ("cyno") CCR8. The data shows hu.Ab4.H12L3 and hu.Ab5.H13L1 mAbs have similar affinity for both human and cyno CCR8, indicating desirable cross-reactivity (Compare FIG. 7A to FIG. 7B, and compare FIG. 7C to FIG. 7D). Kd (nM) affinity data from these studies is provided in the Examples.

Figure 4A:
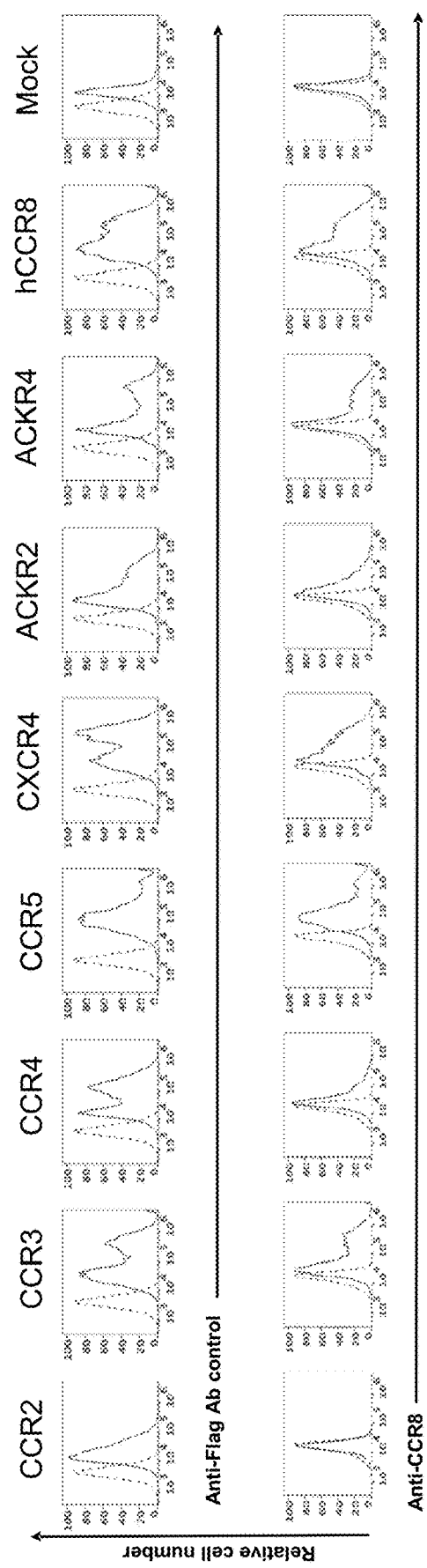
FIGS. 4A-4F depicts the binding data of hu.Ab3.H1L1 (FIG. 4A), hu.Ab4.H1L1 (FIG. 4B), and hu.Ab5.H1L1 (FIG. 4C), as well as the commercial anti-CCR8 mAbs murine anti-human CCR8 mAb 433H (BD Biosciences) (FIG. 4D), and murine anti-human CCR8 mAb L263G8 (Biolegend) (FIG. 4E), and the humanized anti-human Yoshida anti-CCR8 mAb (FIG. 4F), to HEK293 cells that were transiently transfected with N-term FLAG-tagged plasmids encoding for human GPCRs (CCR2, CCR3, CCR4, CCR5, CCR8, CXCR4, ACKR2, and ACKR4), hCCR8 constructs, or with a mock construct using transIT X2 (reagent:DNA=3:1). Cell surface expression of each GPCR was confirmed by staining with an anti-FLAG antibody control (5 ug/mL). mAbs hu.Ab4.H1L1, and hu.Ab5.H1L1 only stained the hCCR8-containing cells, confirming their specificity to hCCR8. mAb hu.Ab3.H1L1 showed staining of multiple other GPCRs, indicating lack of specificity. The CCR8 selective hu.Ab4.H1L1 and hu.Ab5.H1L1 mAbs, which demonstrated the best ADCC activities (as noted in FIG. 2), were carried forward for further study.
Figure 4B:
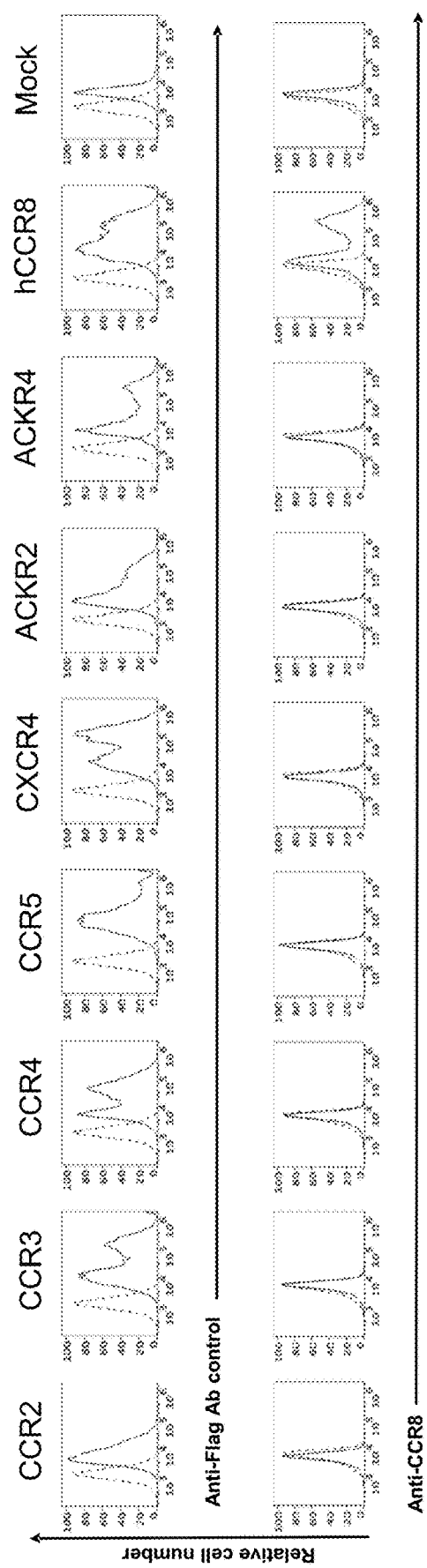
Figure 4C:
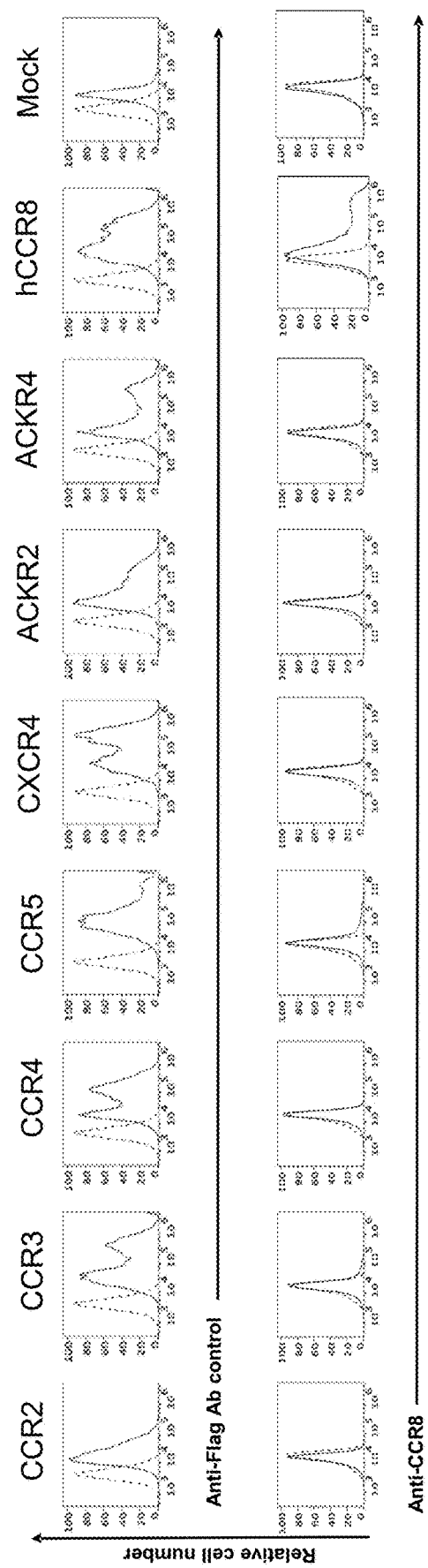
Figure 4D:
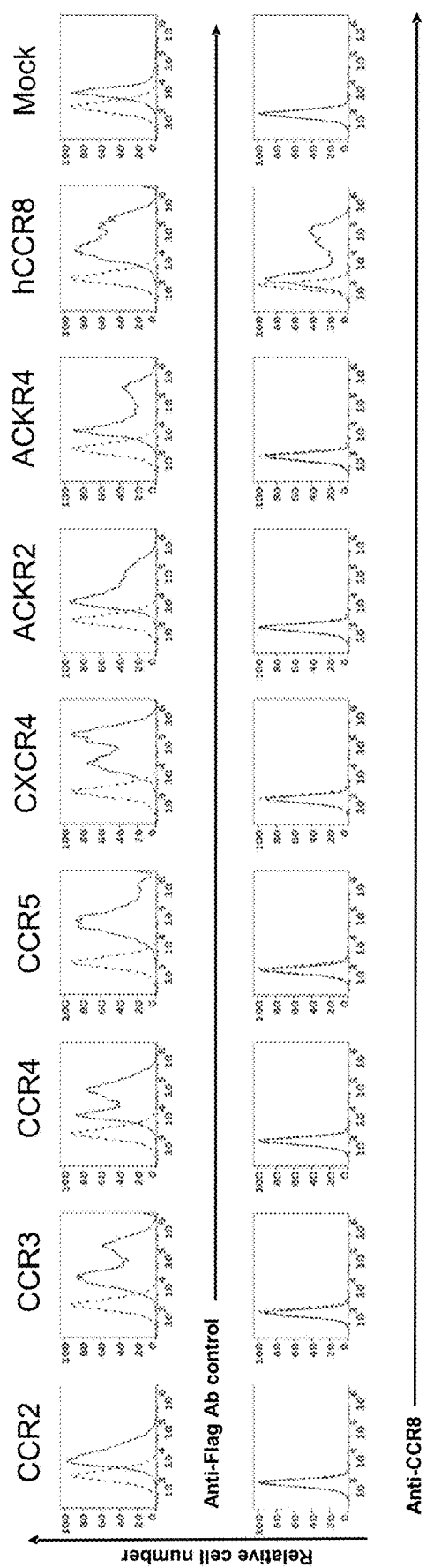
Figure 4E:
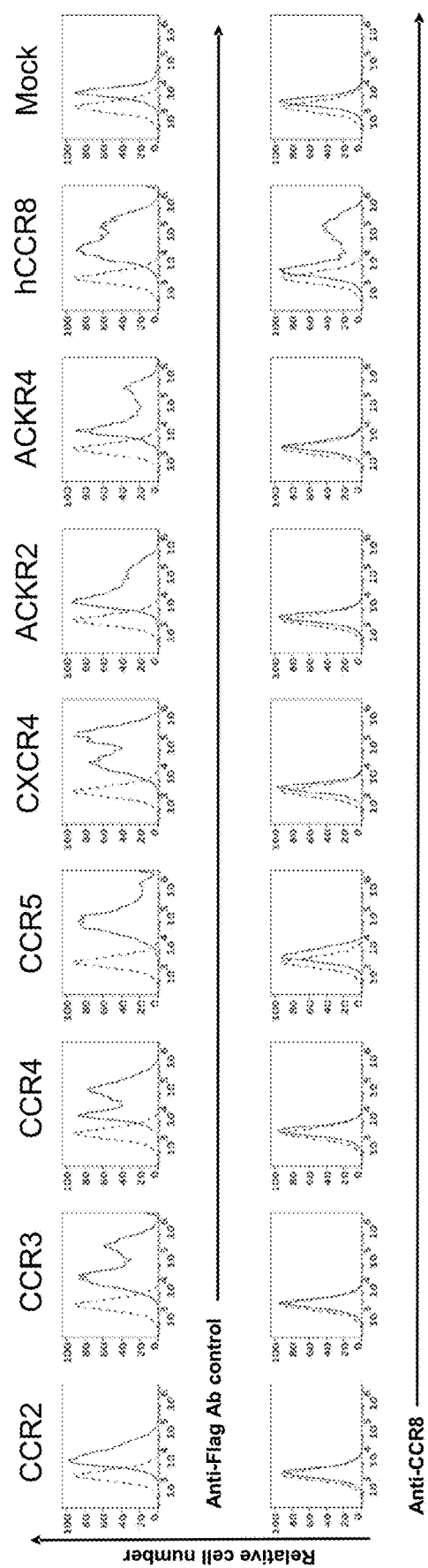
Figure 4F:
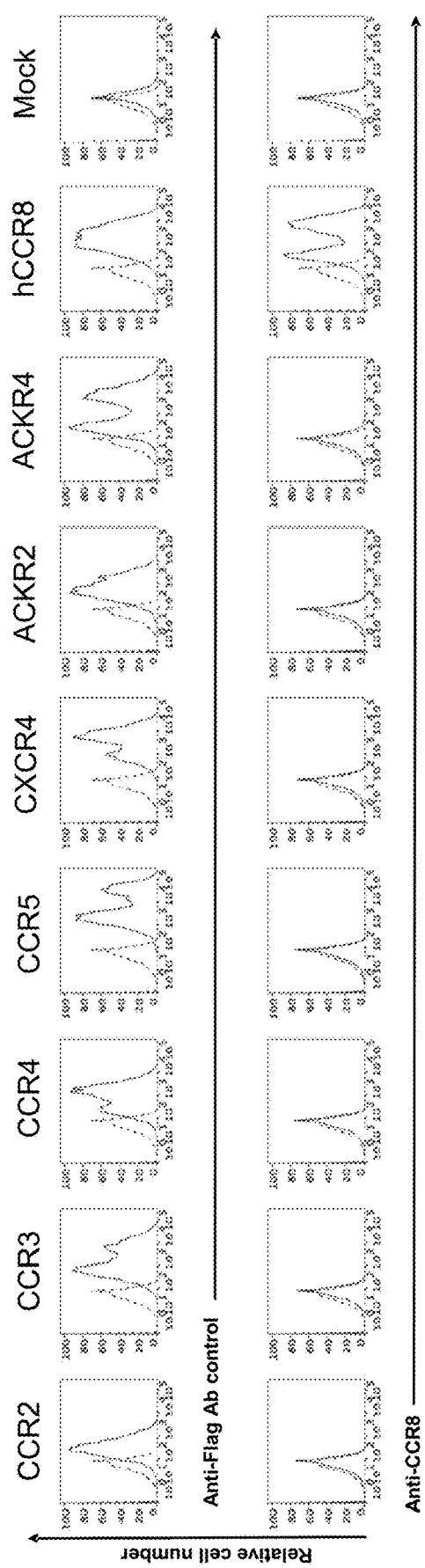
Figure 6C:
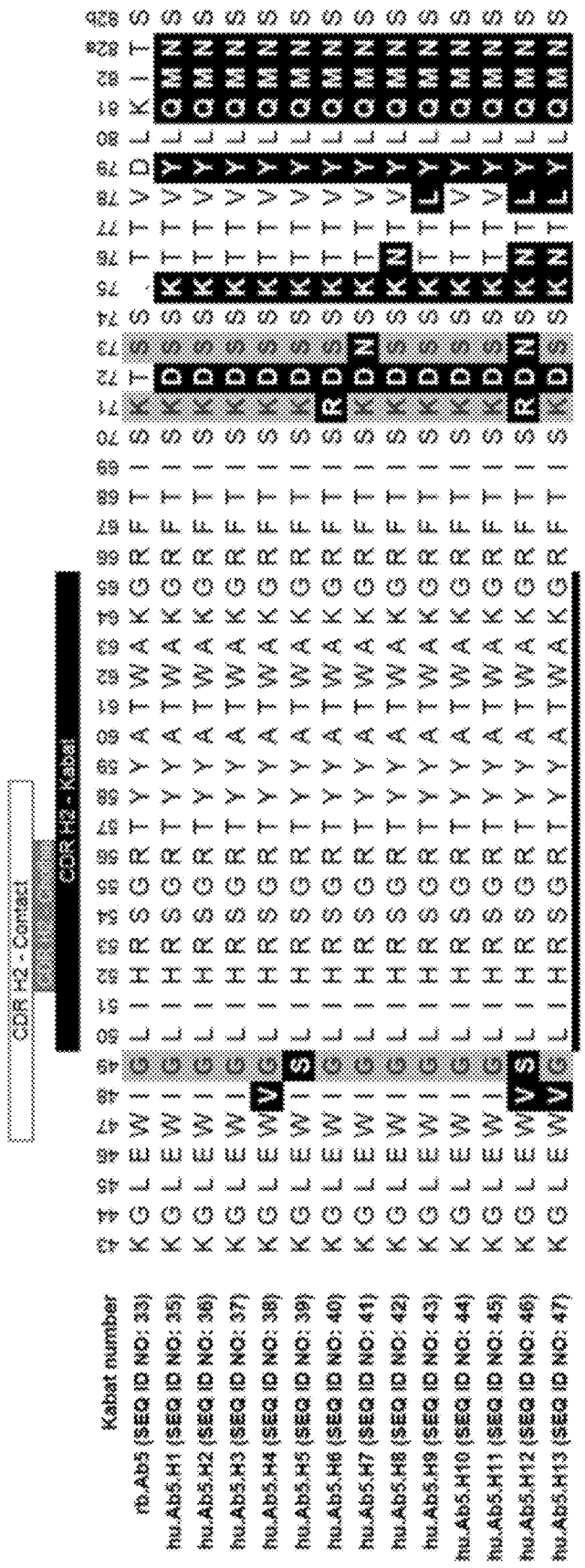
Figure 7B:
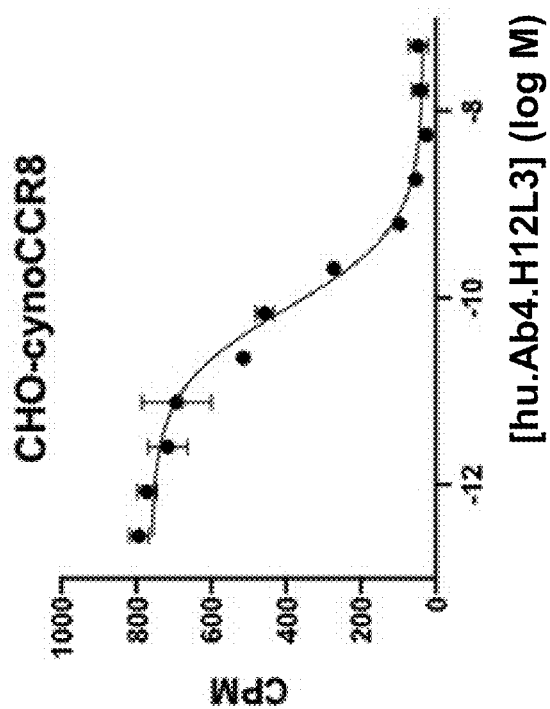
Figure 7A:
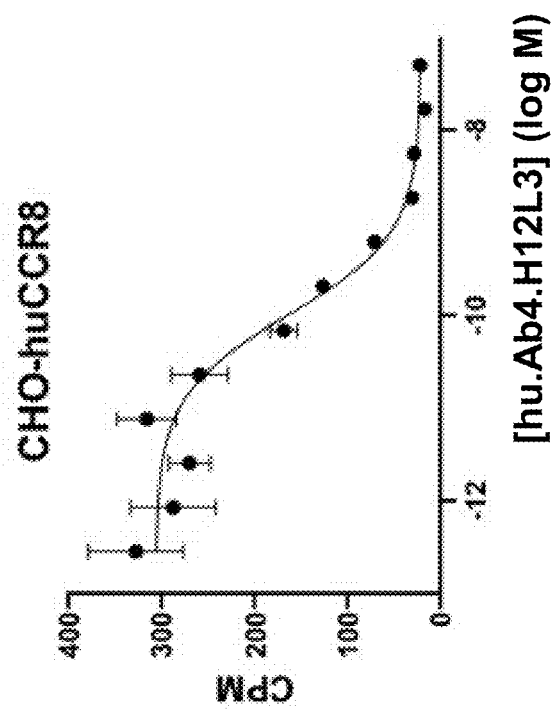

(which impacts binding to the N-terminal epitope for Ab5; see FIG. 16) the CCR8 construct with the C-terminal FLAG is also provided in FIG. 4C.

Figure 9A:
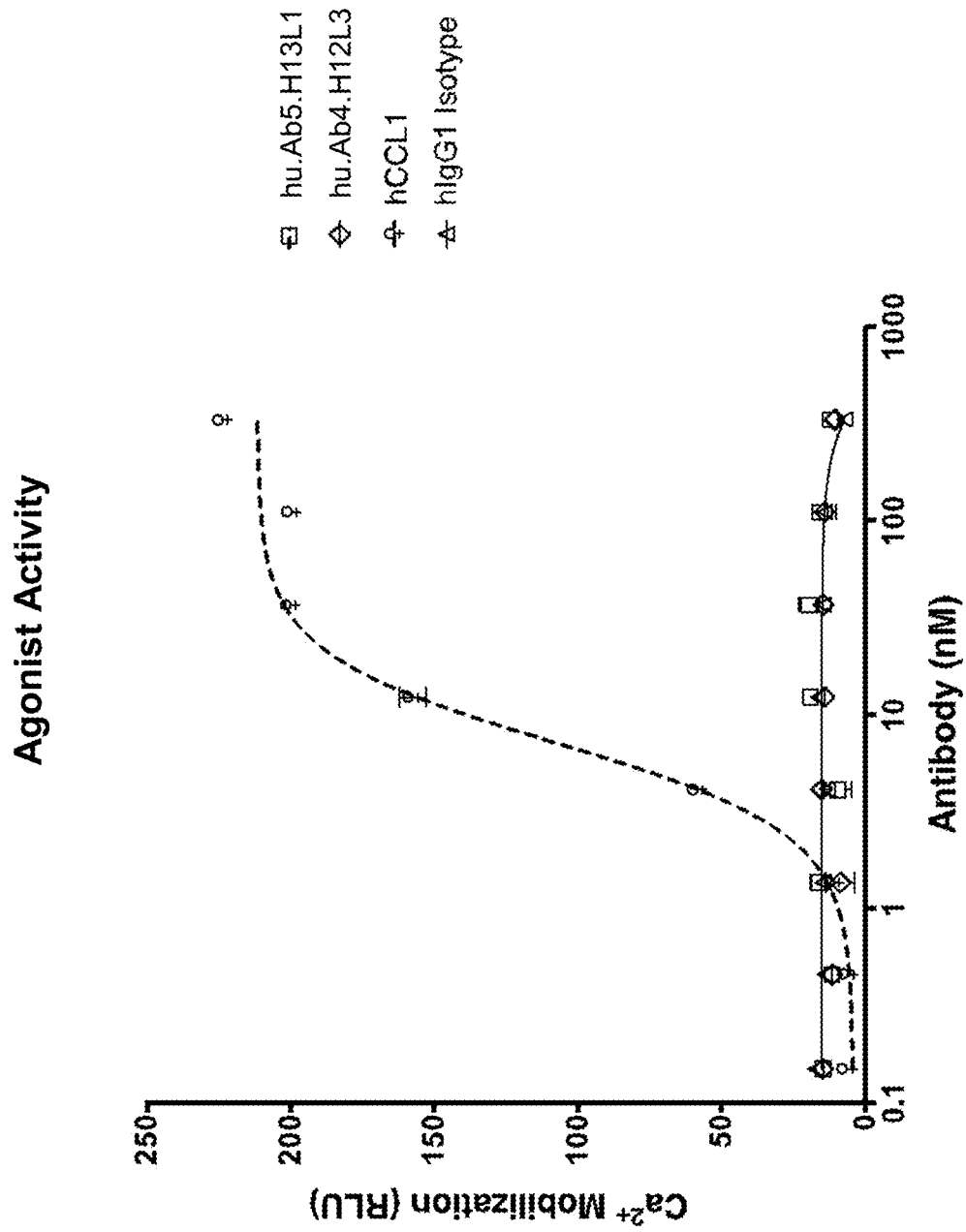
Figure 9B:
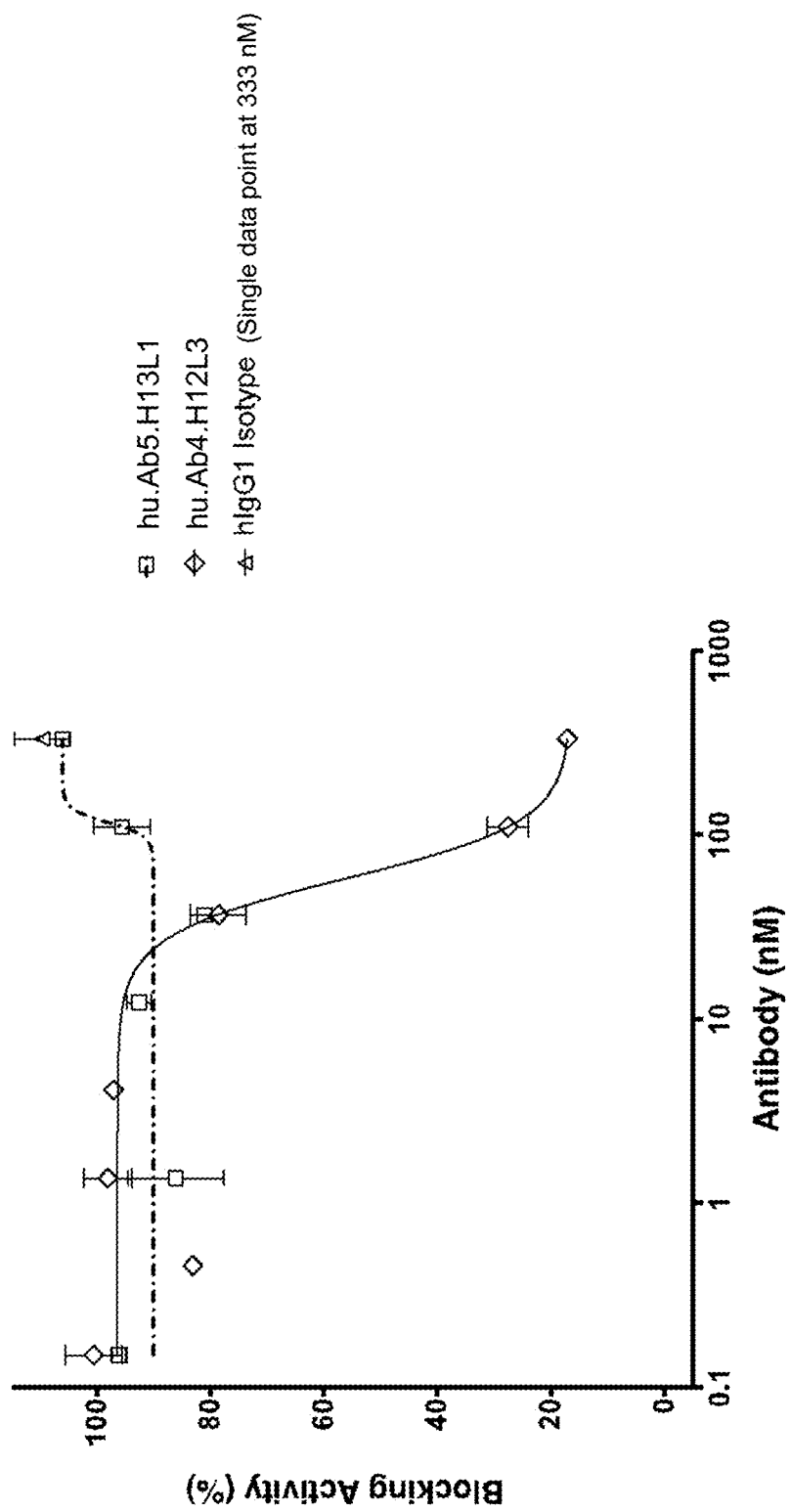
Figure 10A:
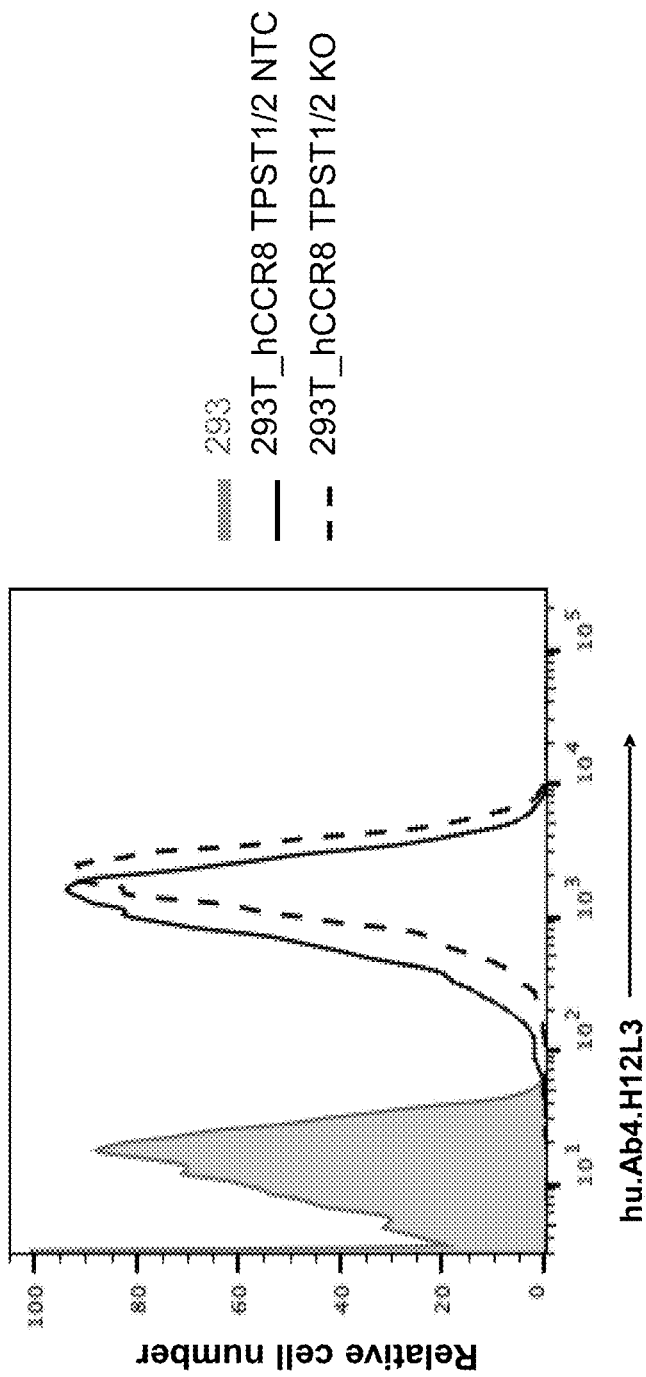
Figure 10B:
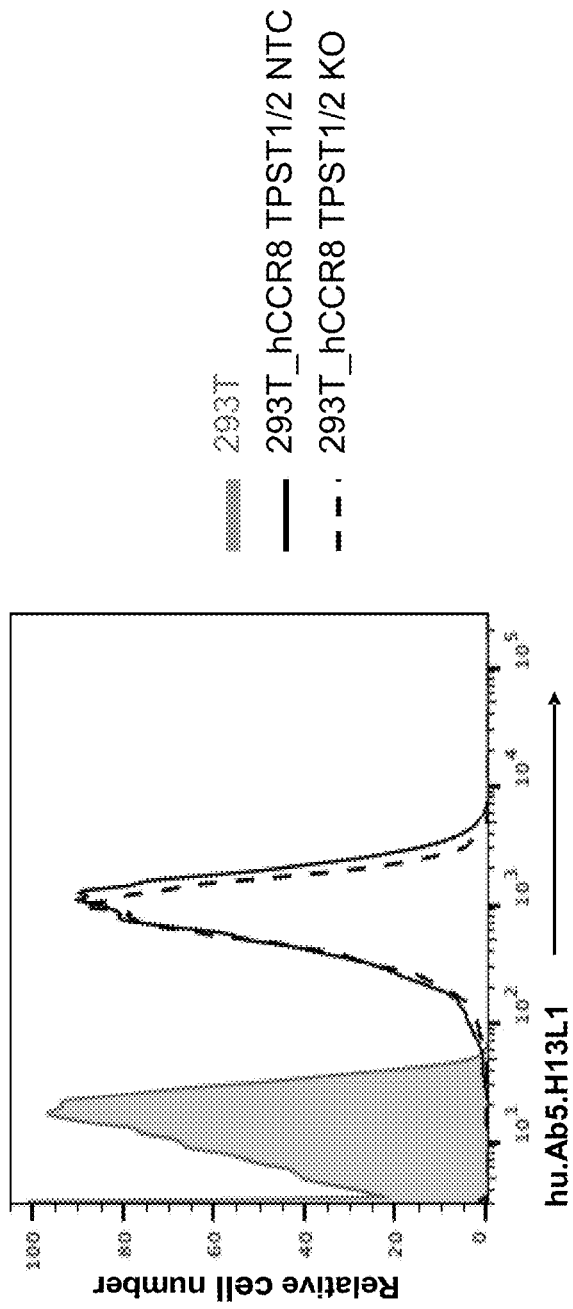
Figure 10C:
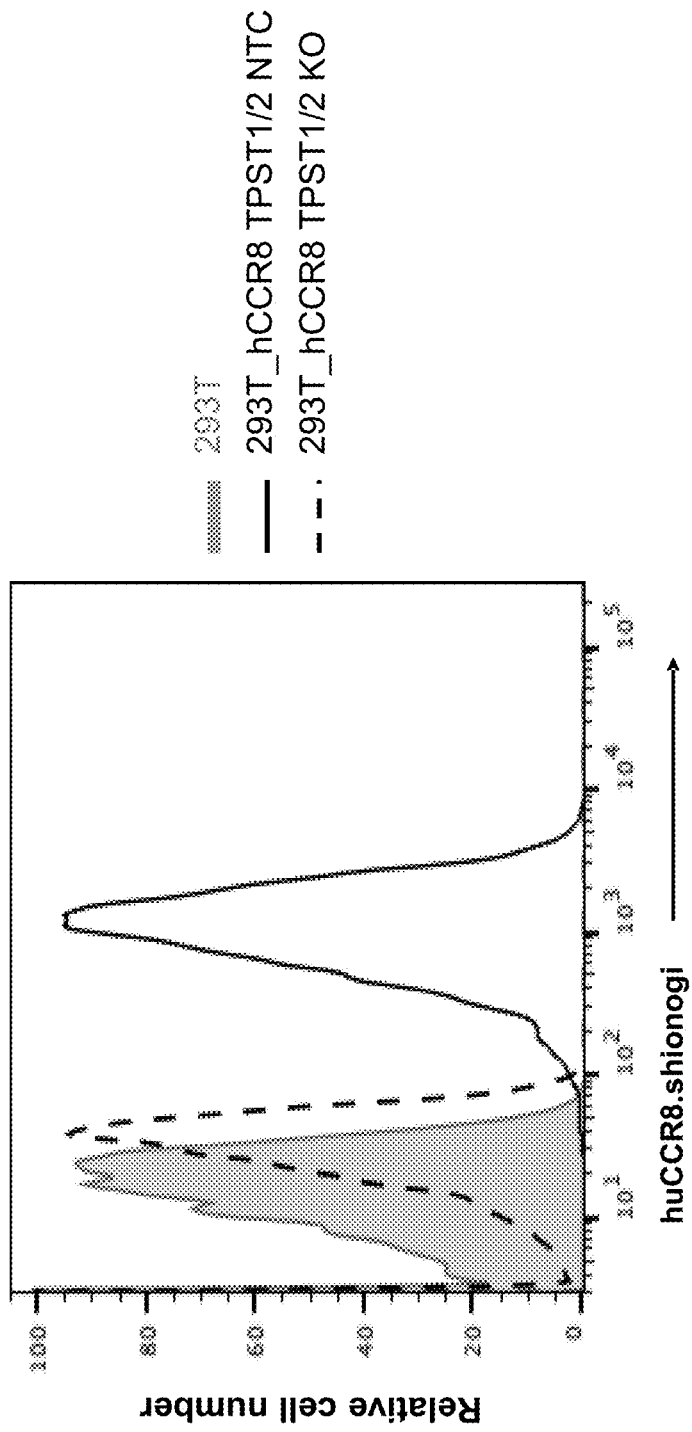
Figure 10D:
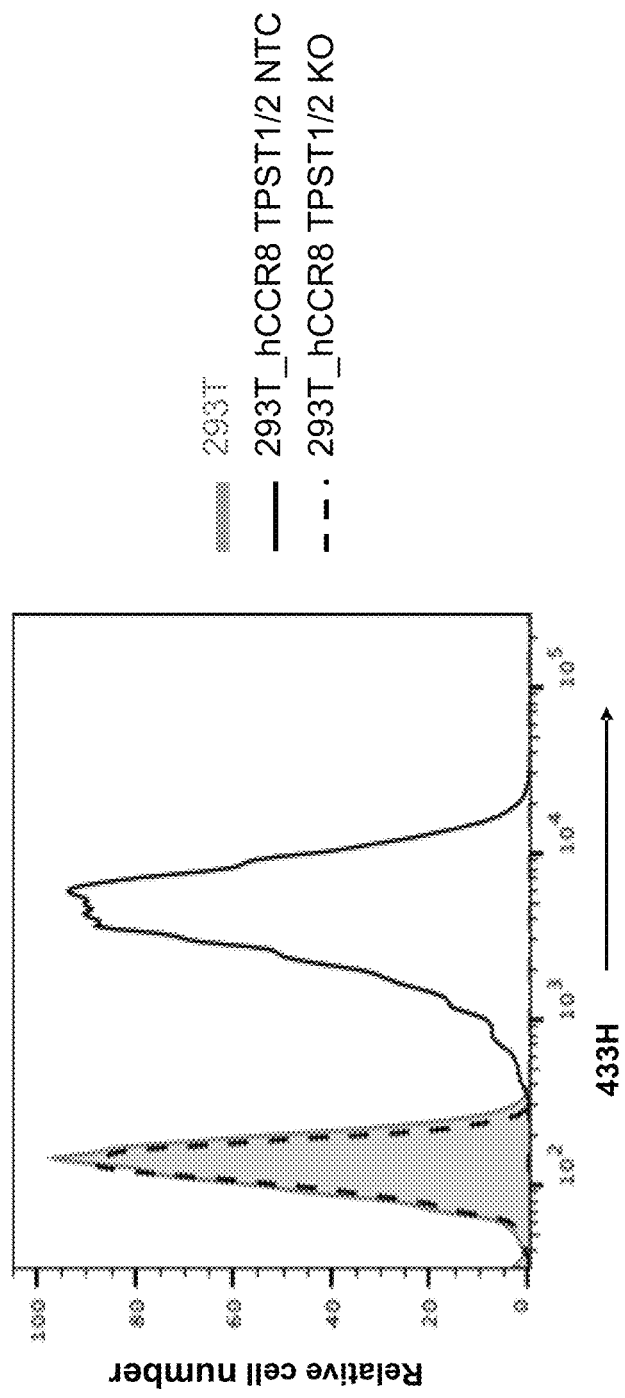
Figure 10E:
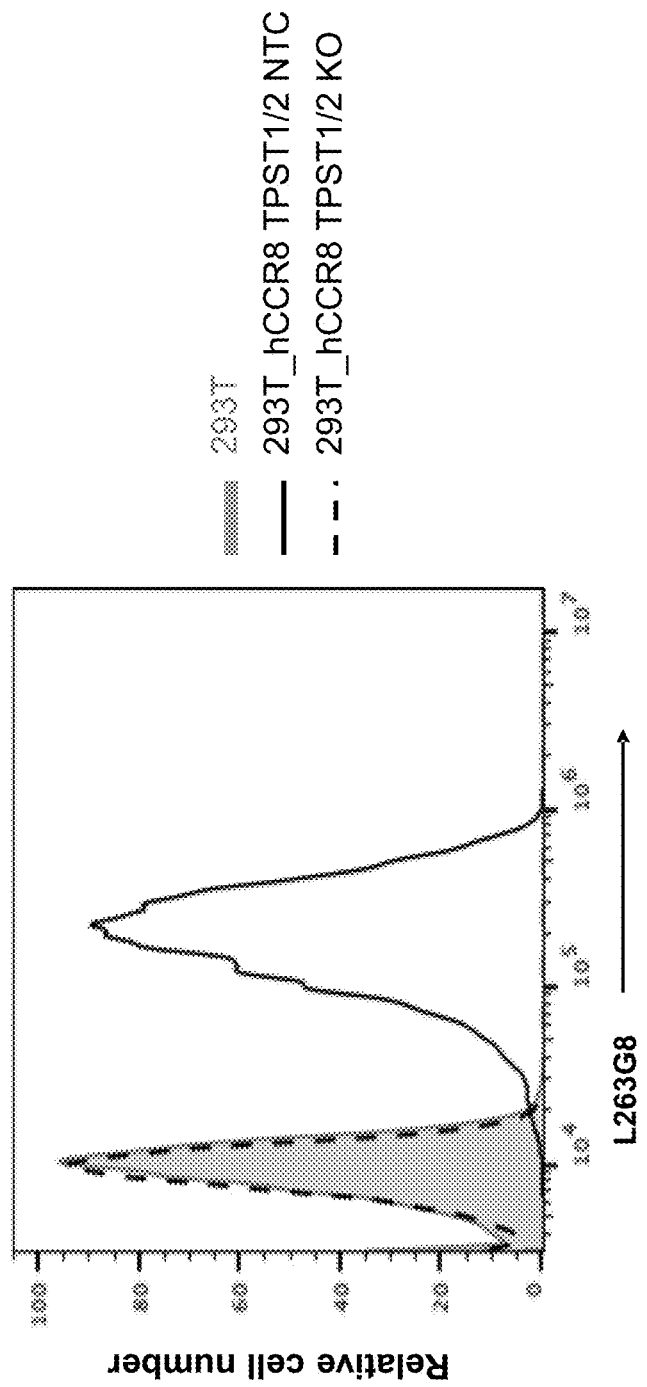

FIGS. 9A-9B depicts the effects of anti-CCR8 mAbs hu.Ab4.H12L3 and hu.Ab5.H13L1 on CCR8 activation as determined by $Ca^{2+}$ influx assay (FIG. 9A) and CCR8 CCL1 ligand binding (FIG. 9B). Similar to FIG. 3A data, FIG. 9A reconfirms neither the Ab4 nor the Ab5 anti-CCR8 mAbs variants show agonistic effects in the absence of CCR8 ligand CCL1. Similar to FIG. 3B data, FIG. 9B reconfirms the Ab4 variants demonstrates antagonistic effects against the CCR8 ligand CCL1 (20 nM of ligand), whereas the Ab5 variant demonstrates no ligand blocking activity at the concentration studied. The $IC_{50}$ values for the ligand blocking activity are provided in the Examples.

FIGS. 10A-10E depicts differences in staining of hu.Ab4.H12L3 and hu.Ab5.H13L1 compared to the humanized anti-human Yoshida CCR8 mAb and commercial antibodies murine anti-human CCR8 mAb 433H (BD Biosciences) and murine anti-human CCR8 mAb L263G8 (Biolegend) to CCR8+ HEK293 cells with (hCCR8.TPST1/2 NTC) and without tyrosyl protein sulfotransferase (TPST) 1 and tyrosyl protein sulfotransferase (TPST) 2 (hCCR8.TPST1/2 KO). hu.Ab4.H12L3 (FIG. 10A) and hu.Ab5.H13L1 (FIG. 10B) show similar binding/staining to both cell lines (hCCR8.TPST1/2 NTC and hCCR8.TPST1/2 KO), indicating they bind CCR8 independent of tyrosine sulfation ("sulfation independent"). In contrast, the humanized anti-human Yoshida CCR8 antibody (FIG. 10C) and commercial antibodies murine anti-human CCR8 mAb 433H (BD Biosciences) (FIG. 10D) and murine anti-human CCR8 mAb L263G8 (Biolegend) (FIG. 10E) failed to bind the TPST1/2 KO cells, indicating they require tyrosine sulfation of CCR8 for binding, and are thus considered "sulfation dependent."

Figure 11A:
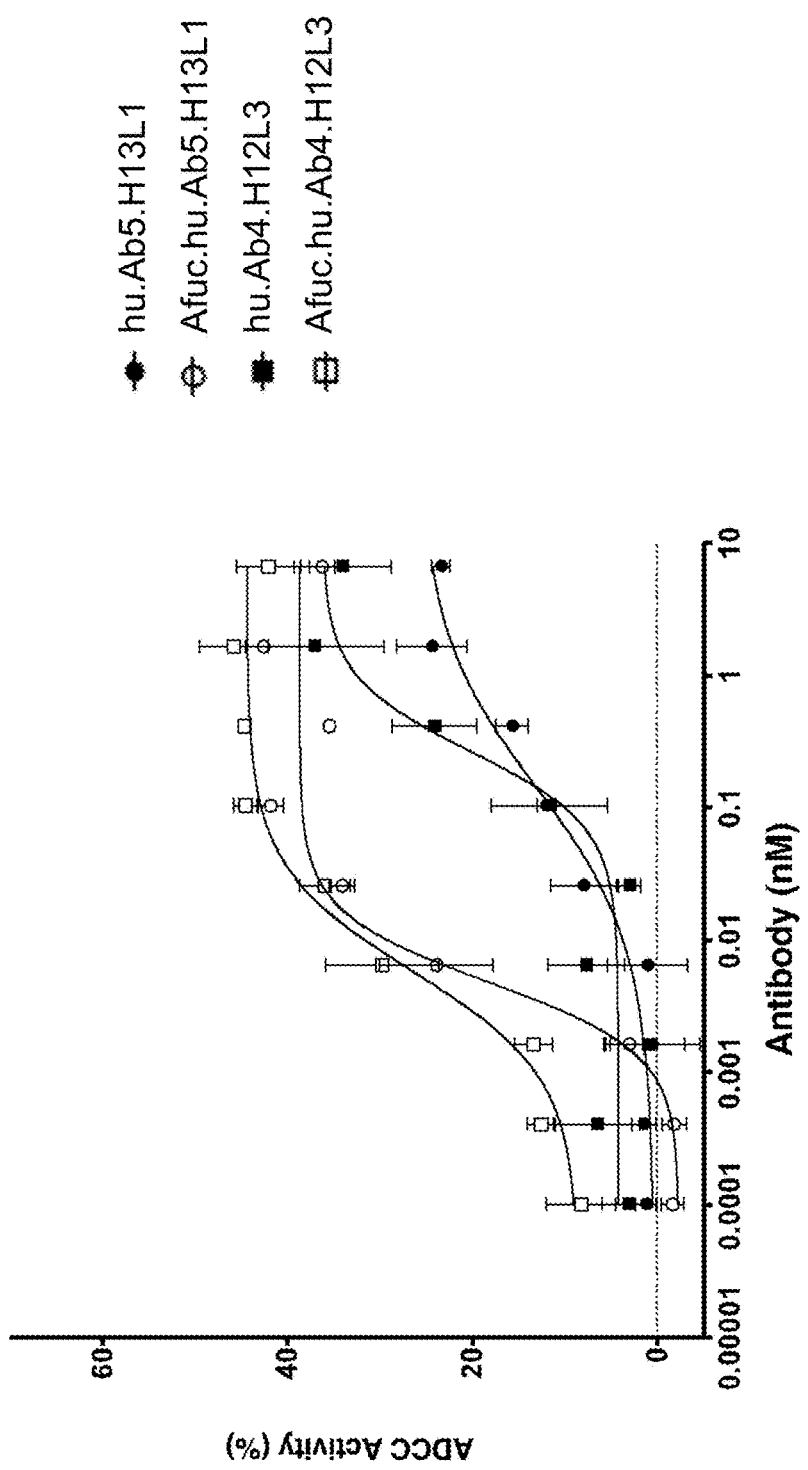
Figure 11B:
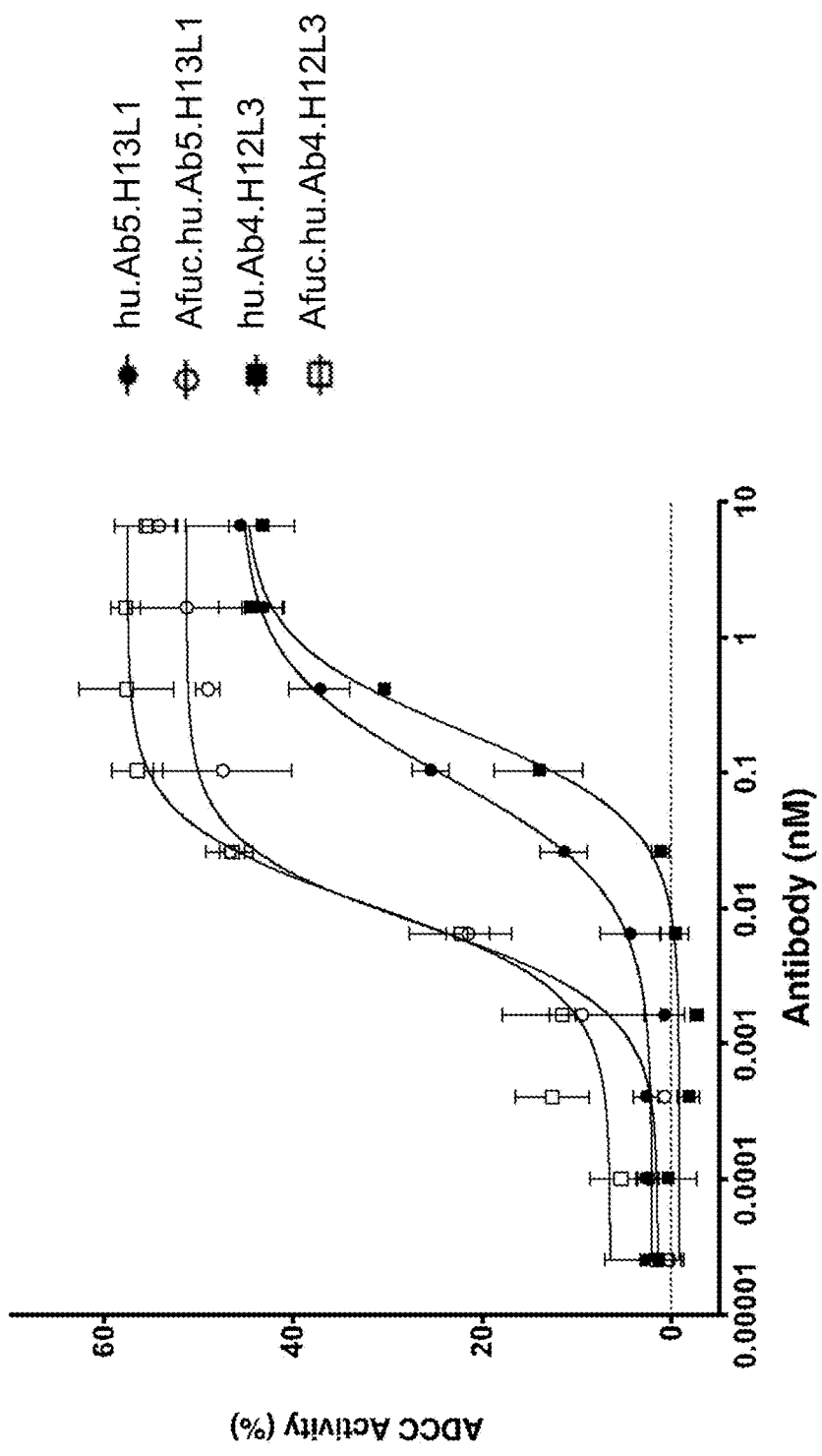
Figure 11C:
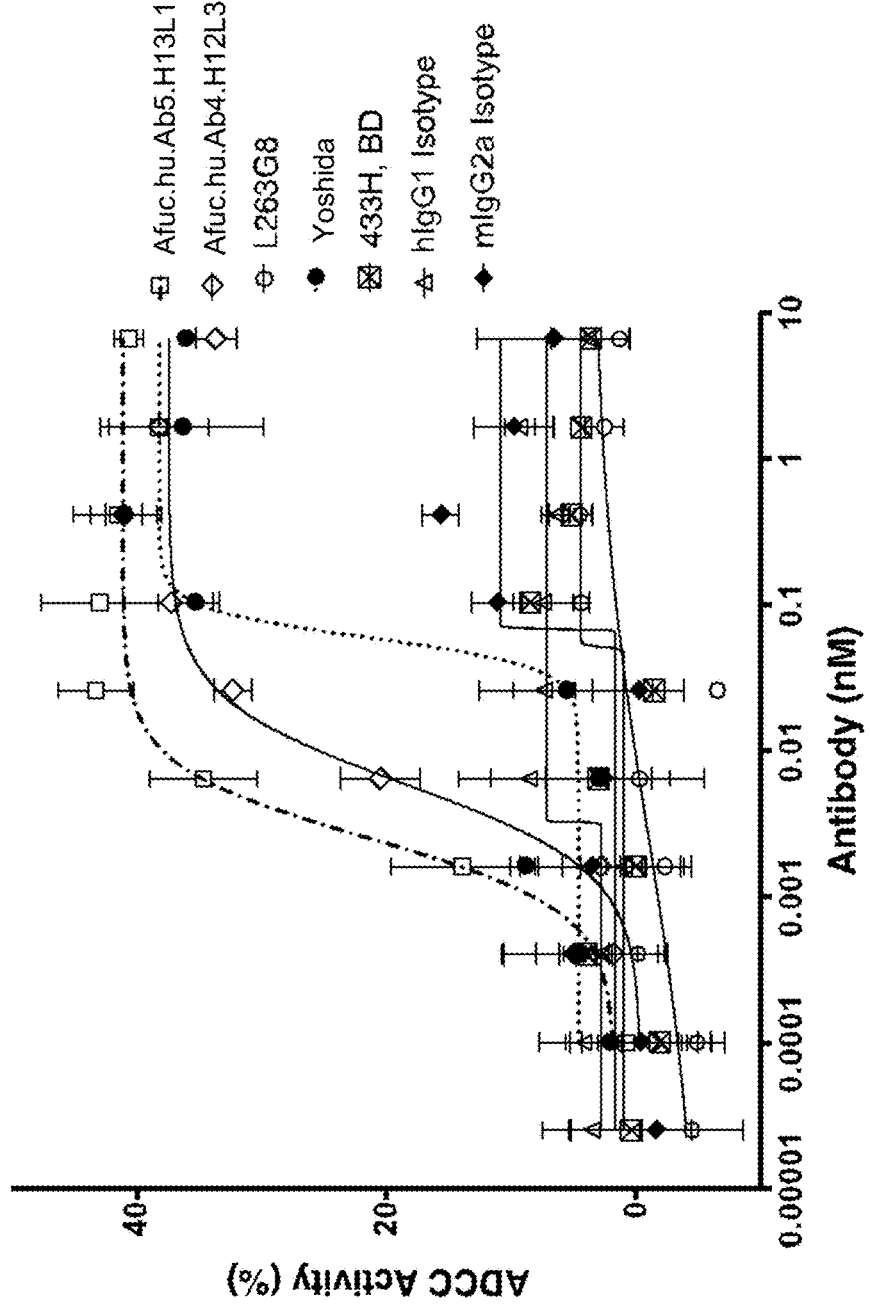
Figure 11D:
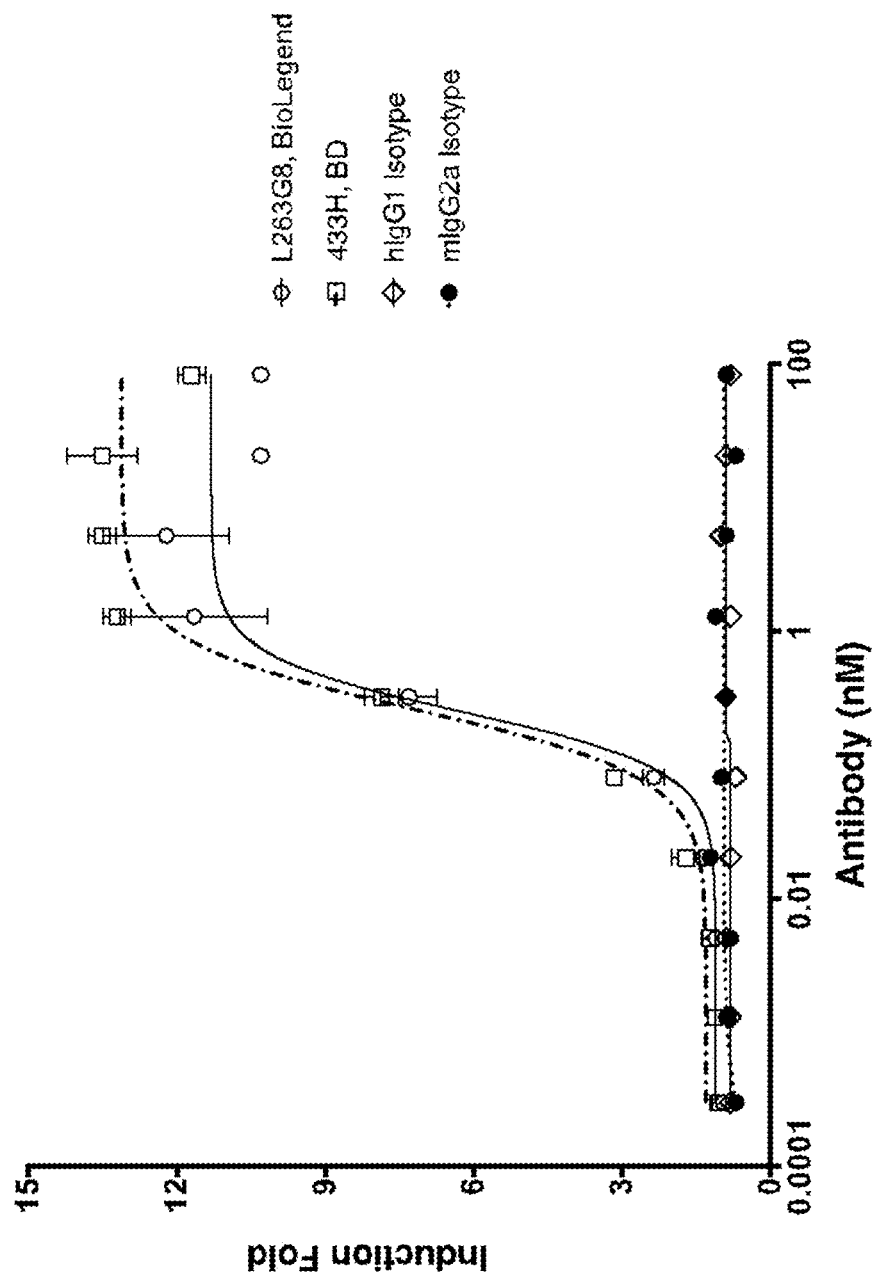
Figures 13A, 13B:
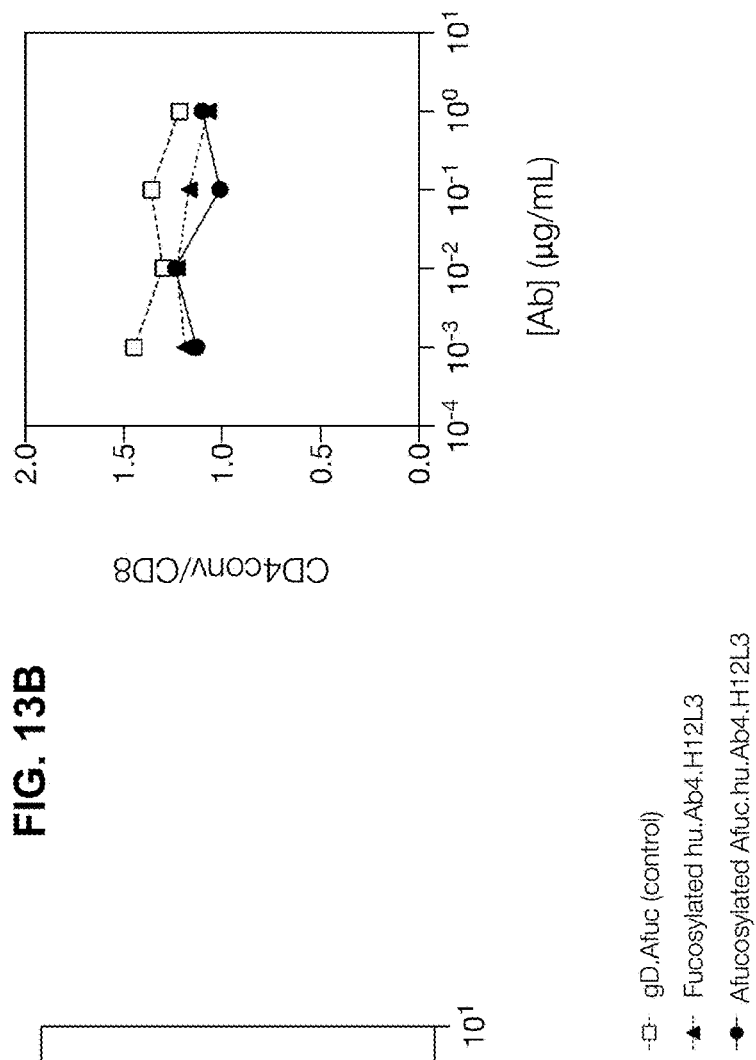

FIGS. 11A-11D depicts that afucosylated CCR8 mAbs Afuc.hu.Ab5.H13L1 and Afuc.hu.Ab4.H12L3 show enhanced (>10-fold improved) ADCC activity compared to their fucosylated CCR8 counterparts hu.Ab5.H13L1 and hu.Ab4.H12L3 against CHO cells stably expressing hCCR8 using NK-92 F158 (FIG. 11A) and NK-92 V158 (FIG. 11B) as effector cells, and also show a 10-20 fold improvement in ADCC activity compared the humanized anti-human Yoshida anti-CCR8 antibody (FIG. 11C). Commercial anti-CCR8 mAbs murine anti-human CCR8 mAb 433H (BD Biosciences) and murine anti-human CCR8 mAb L263G8 (Biolegend) demonstrated (as expected) no ADCC activity as the assay used is primarily relevant for antibodies comprising human Fc regions (FIG. 1C). FIG. 11D shows murine anti-human CCR8 mAb 433H (BD Biosciences) and murine anti-human CCR8 mAb L263G8 (Biolegend) have ADCC activity using an assay specific for antibodies comprising murine Fc regions and human anti-CCR8 activity. Activity data is also provided in the Examples.

FIGS. 12A-12D depicts the selective ADCC activity against human Treg cells compared to conventional human CD4 T cells from peripheral blood mononuclear cells (PBMC) that had been recovered after transfer into NOD.Cg-Prkd$^{scid}$ Il2rg$^{tm1Wjl}$/SzJ (NSG) mice to induce CCR8 expression when incubated with afucosylated, fucosylated (hIgG1), and the afucosylated isotype control mAb ("gD.afuc") and primary NK cells as effector cells. ADCC activity against Treg cells was measured by calculating the ratio of recovered Treg cells to recovered CD8 cells (Treg/CD8) or conventional CD4 T cells to recovered CD8 T cells (CD4conv/CD8). CCR8 mAbs Afuc.hu.Ab4.H12L3 and hu.Ab4.H12L3 selectively mediated ADCC activity against Treg cells (FIG. 12A) in comparison to conventional CD4 T cells (FIG. 12B), with the afucosylated variant demonstrating increased ADCC activity. Similarly, CCR8 mAbs Afuc.hu.Ab5.H13L1 and hu.Ab5.H13L1 selectively mediated ADCC activity against Treg cells (FIG. 12C) in comparison to conventional CD4 T cells (FIG. 12D), with the afucosylated variant demonstrating increased ADCC activity.

FIGS. 13A-13D depicts the selective ADCC activity against Treg cells compared to conventional CD4 T cells when human dissociated renal cell carcinoma (RCC) cells were incubated with afucosylated, fucosylated (hIgG1), and the afucosylated isotype control mAb ("gD.afuc") and primary NK cells as effector cells. ADCC activity against Treg cells was measured by calculating the ratio of recovered Treg cells to recovered CD8 cells (Treg/CD8) or conventional CD4 T cells to recovered CD8 T cells (CD4conv/CD8). CCR8 mAbs Afuc.hu.Ab4.H12L3 and hu.Ab4.H12L3 selectively mediated ADCC activity against Treg cells (FIG. 13A) in comparison to conventional CD4 T cells (FIG. 13B), with the afucosylated variant demonstrating increased ADCC activity. Similarly, CCR8 mAbs Afuc.hu.Ab5.H13L1 and hu.Ab5.H13L1 selectively mediated ADCC activity against Treg cells (FIG. 13C) in comparison to conventional CD4 T cells (FIG. 13D), with the afucosylated variant demonstrating increased ADCC activity.

Figure 14E:
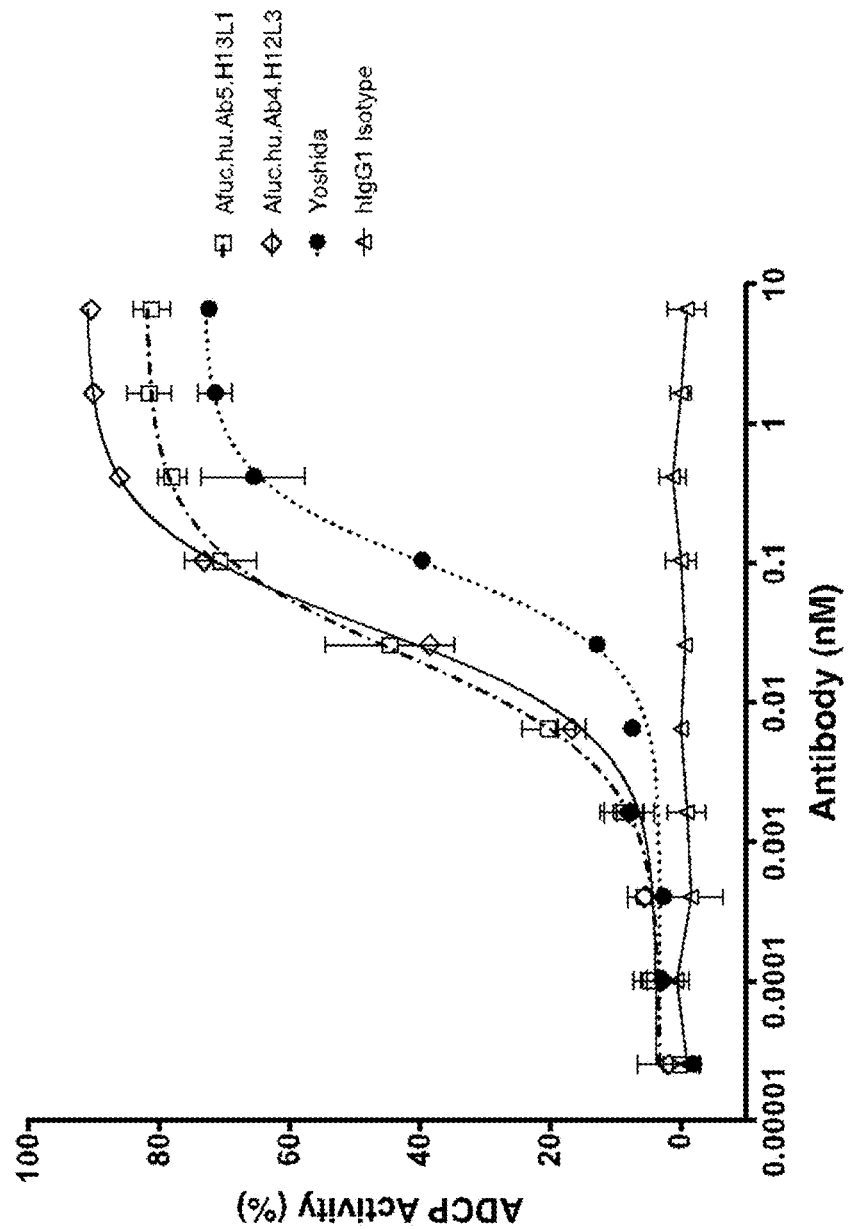

FIGS. 14A-14E show that the afucosylated anti-CCR8 mAbs Afuc.hu.Ab5.H13L1 and Afuc.hu.Ab4.H12L3 exhibit enhanced ADCP activities compared to fucosylated mAbs hu.Ab5.H13L1 and hu.Ab4.H12L3 in CD14+ monocytes-derived macrophages from four different donors with FcgRIIa (H131R)/FcgRIIIa (V158F) genotypes of HR/FF (FIG. 14A), RR/FF (FIG. 14B), HR/VF (FIG. 14C), and RR/VF (FIG. 14D), and also show a 3-4 fold improvement in ADCP activity compared the humanized anti-human Yoshida anti-CCR8 antibody (FIG. 14E). Activity data is also provided in the Examples.

FIGS. 15A-15D show that the afucosylated anti-CCR8 mAb Afuc.hu.Ab5.H13L1 exhibits similar improved ADCP activities compared to the FcgRIIa-enhanced G236A.I332E variant Afuc.hu.Ab5.H13L1.G236A.I332E in CD14+ monocytes-derived macrophages from four different donors with FcgRIIa (H131R)/FcgRIIIa (V158F) genotypes of genotypes of HR/FF (FIG. 15A), RR/FF (FIG. 15B), HR/VF (FIG. 15C), and RR/VF (FIG. 15D).

Figure 16A:
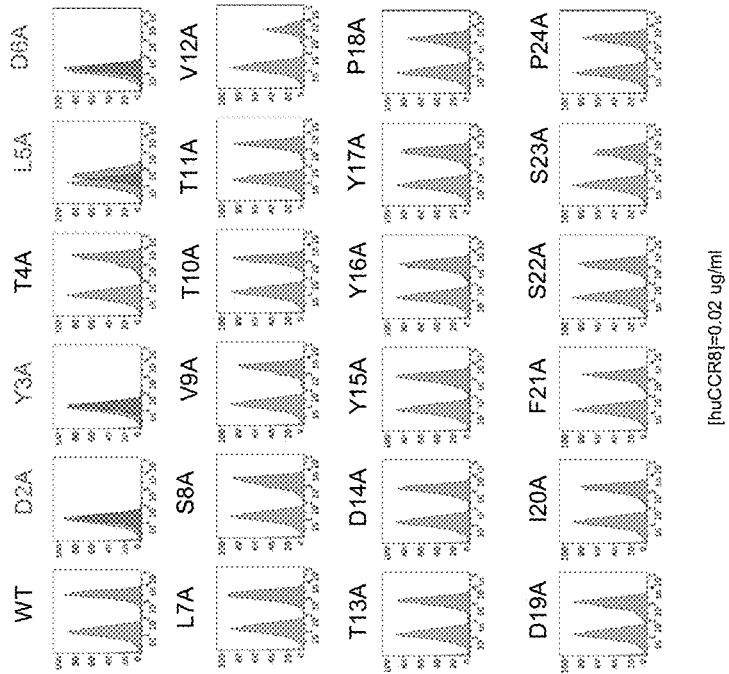
Figure 16B:
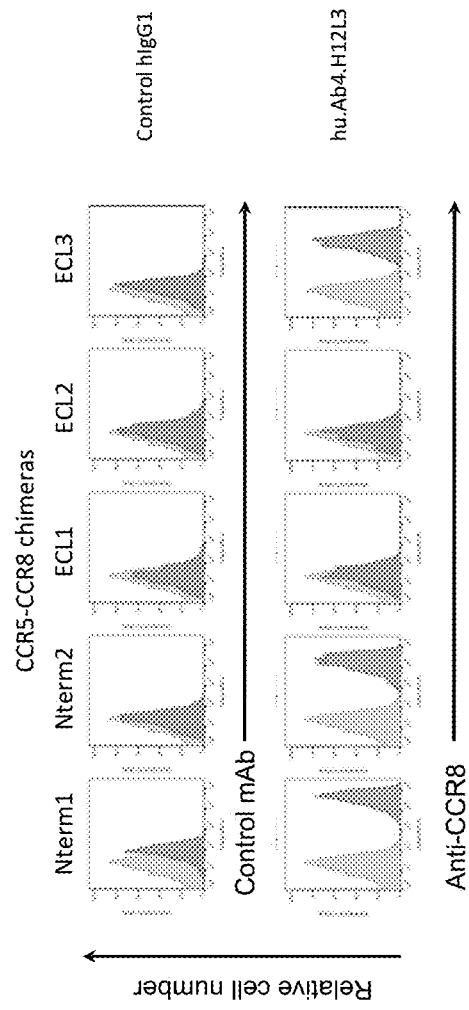

FIGS. 16A-16B depict the epitope maps for hu.Ab5.H13L1 (FIG. 16A) and hu.Ab4.H12L3 (FIG. 16B) mAbs. As shown in FIG. 16A, in which constructs encoding for individual alanine point mutations at positions 2-24 in hCCR8 with a C-terminal FLAG tag were generated, hu.Ab5.H13L1 does not bind D2A, Y3A, L5A, and D6A, indicating that the epitope includes at least the DYTLD region of the human CCR8 N-terminus. As shown in FIG. 16B, in which constructs encoding for human CCR8.CCR5 chimeras (N-term1, N-term2, ECL1, ECL2, and ECL3) in which different extracellular regions of hCCR8 were replaced with the corresponding region from CCR5 with a C-terminal FLAG tag were generated, hu.Ab4.H12L3 does not bind the ECL1 and ECL2 chimeras indicating that the epitope for this antibody includes at least the ECL1 and ECL2 regions of CCR8. huCCR8 N-terminus: MDYTLD-LSVTTVTDYYYPDIFSSP (SEQ ID NO: 110).

Figures 17A, 17B, 17C:
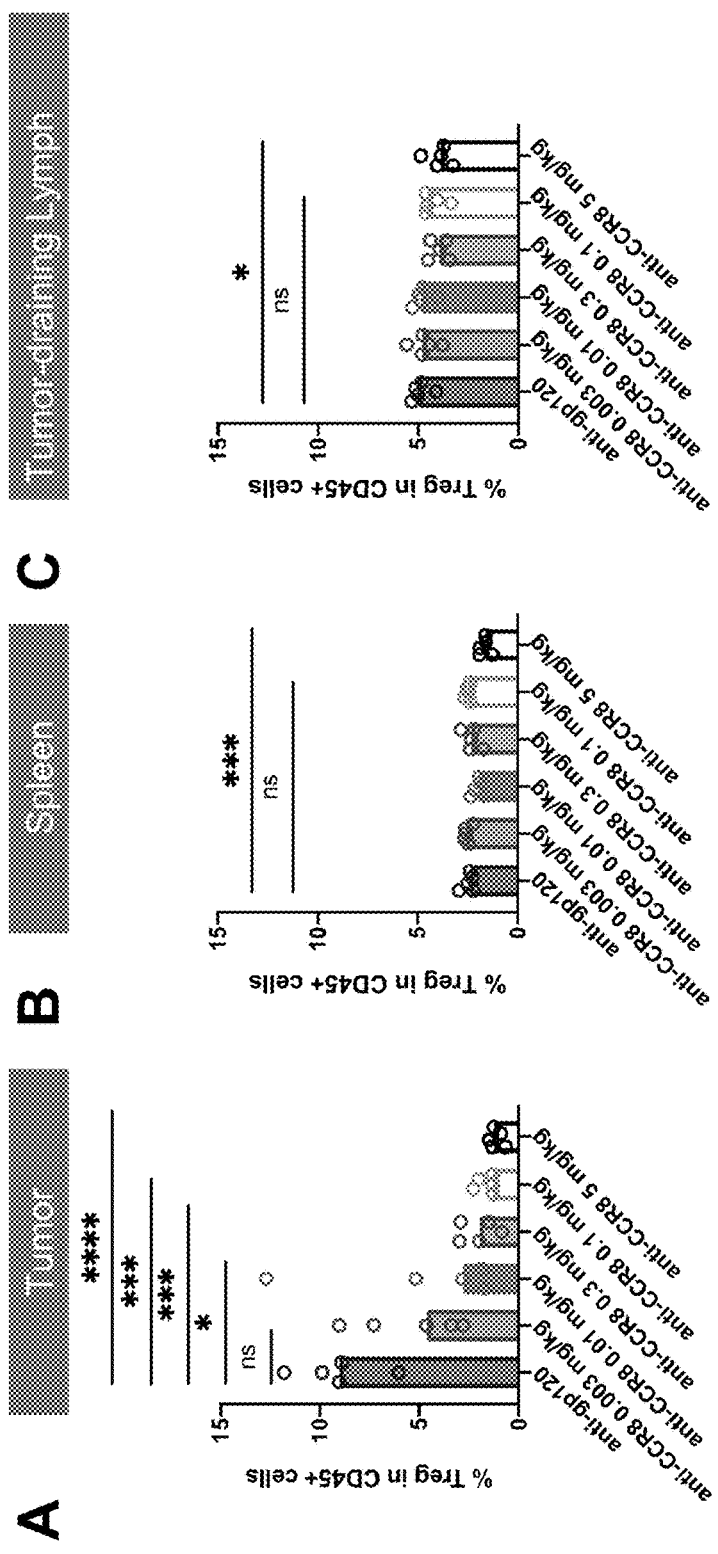
Figures 17D, 17E, 17F:
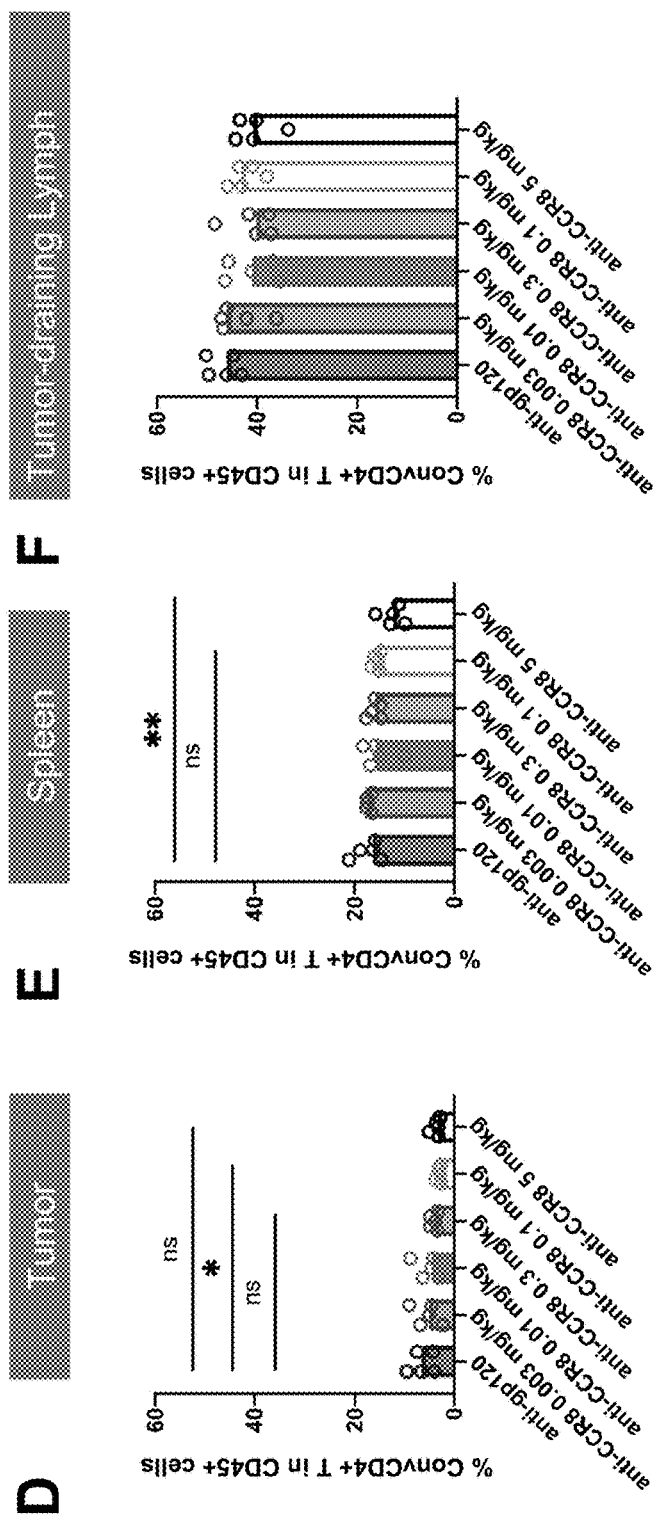
Figure 17G:
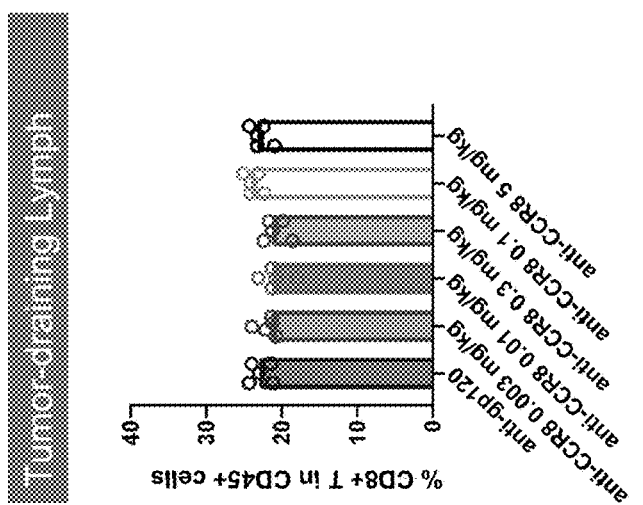
Figure 17H:
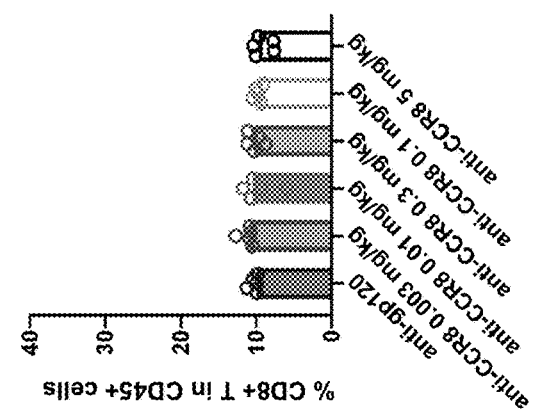
Figure 17I:
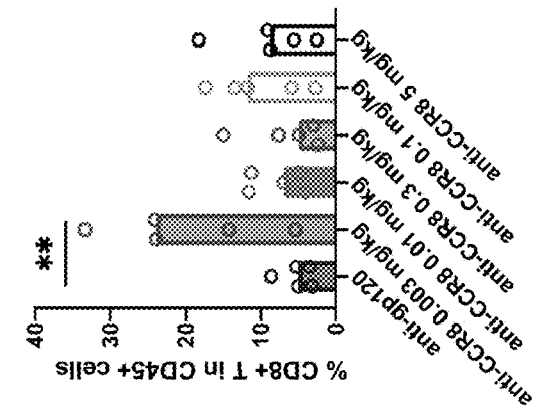

FIGS. 17A-17I depict the progressive depletion of Treg cells (measured as fraction of Treg cells with CD45+ leukocytes) in tumors (FIG. 17A) but not in spleen (FIG. 17B) or tumor-draining lymph nodes (FIG. 17C) in CT26 tumor-bearing mice three days after injection of a single dose of a mouse surrogate anti-CCR8 mAb of increasing concentration between 0.003-5 mg/kg. Anti-CCD8 mAb treatment did not result in CD4 conventional T cell (FIGS. 17D-17F) or CD8 T cell depletion (FIGS. 17G-I). An isotype control antibody (anti-gp120) was used.

Figures 18A, 18B, 18C, 18D:
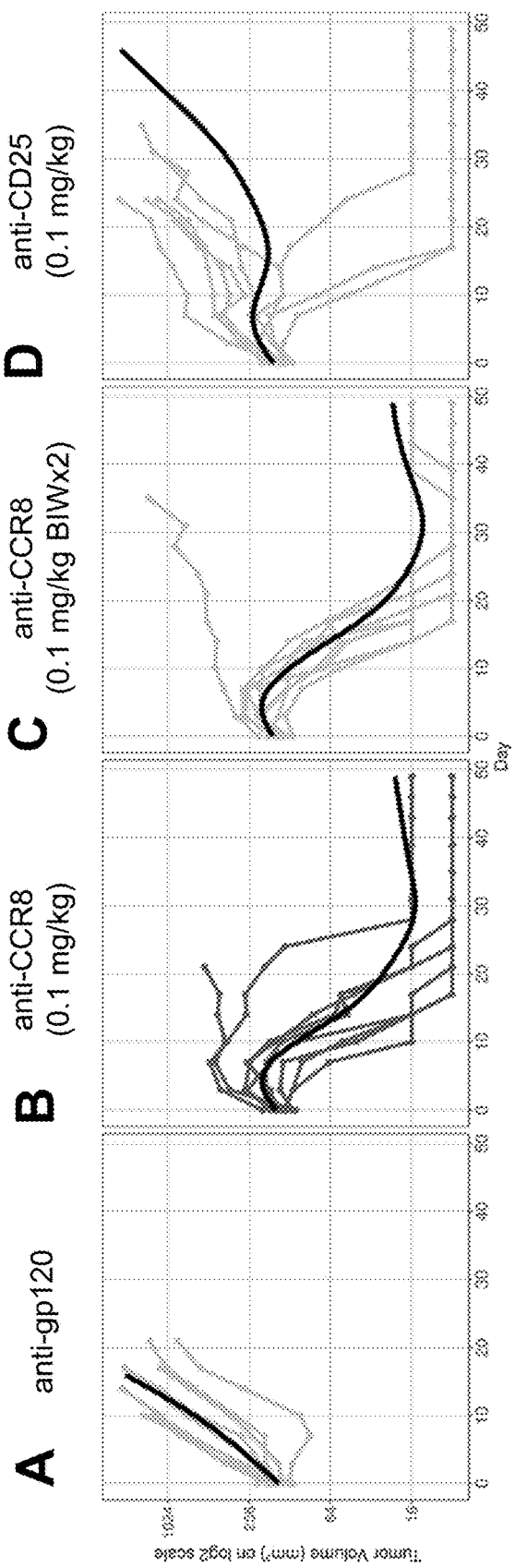

FIGS. 18A-18D depict tumor growth inhibition following treatment with a single dose (FIG. 18B) or twice weekly dosing (FIG. 18C) of a mouse surrogate anti-CCR8 mAb in mice with established CT26 syngeneic tumors compared to treatment with an anti-CD25 mAb (FIG. 18D) or an isotype control mAb (anti-gp120) (FIG. 18A). Treatment started when tumor reached a volume between 150-250 mm$^3$. Tumor volume is measured over time. Grey lines represent individual mice, black lines represent the group fit.

Figures 19A, 19B, 19C, 19D, 19E:
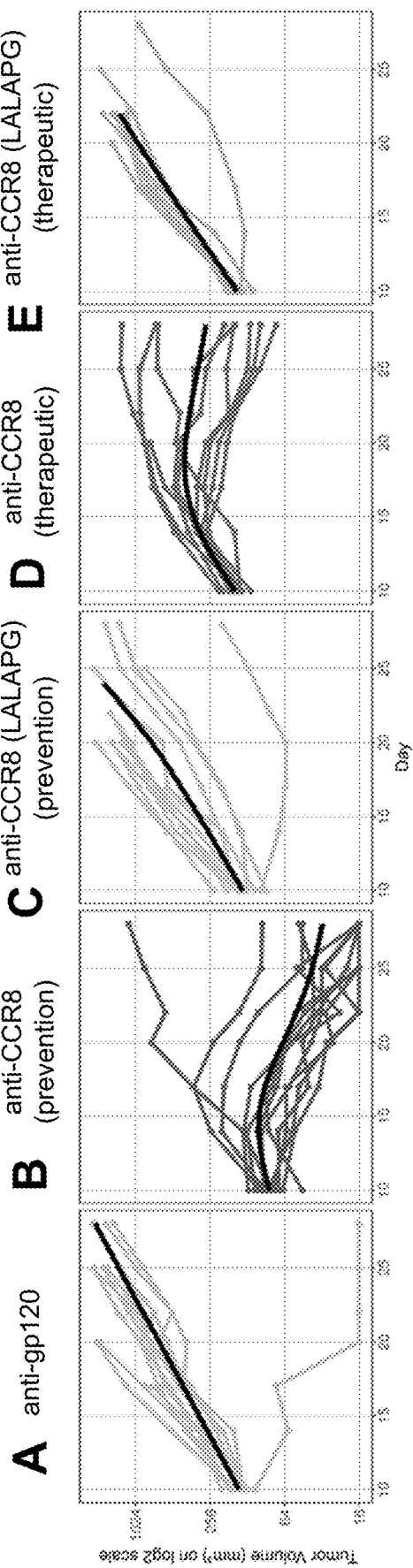

FIGS. 19A-19E depict growth inhibition of CT26 tumors observed with an effector-competent mouse surrogate anti-CCR8 mAb administered at the time of tumor inoculation (FIG. 19B) or with tumors reached 150-250 mm$^3$ (FIG. 19D). No tumor growth inhibition is observed with an effector-incompetent LALAPG variant of the same ligand-blocking anti-CCR8 mAb (FIGS. 19C and 19E). Tumor volume is measured over time. Grey lines represent individual mice, black lines represent the group fit. An isotype control mAb (anti-gp120) was used (FIG. 19A).

Figures 20A, 20B, 20C, 20D:
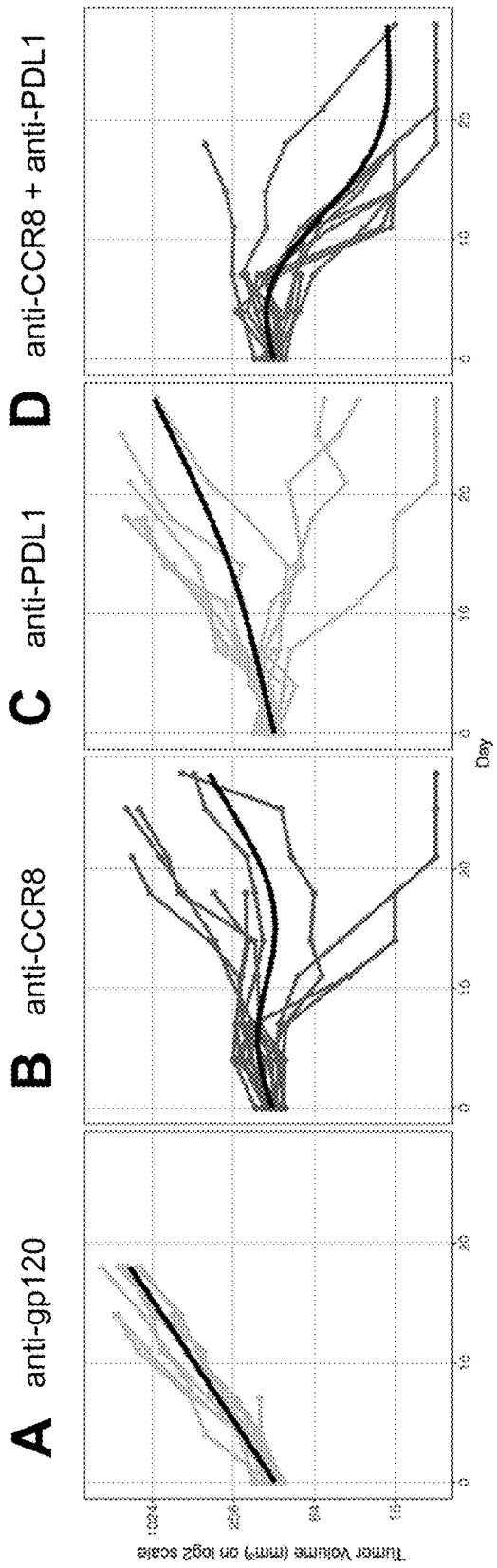

FIGS. 20A-20D show that the combination of a mouse surrogate anti-CCR8 mAb and an anti-PDL 1 mAb (FIG. 20D) is unexpectedly more efficacious in growth inhibition of EMT6 tumors than anti-CCR8 mAb alone (FIG. 20B) or anti-PDL1 mAb alone (FIG. 20C). Treatment started when tumors reached 150-250 mm$^3$. Tumor volume is measured over time. Grey lines represent individual mice, black lines represent the group fit. An isotype control mAb (anti-gp120) was used (FIG. 20A).

Figure 21:
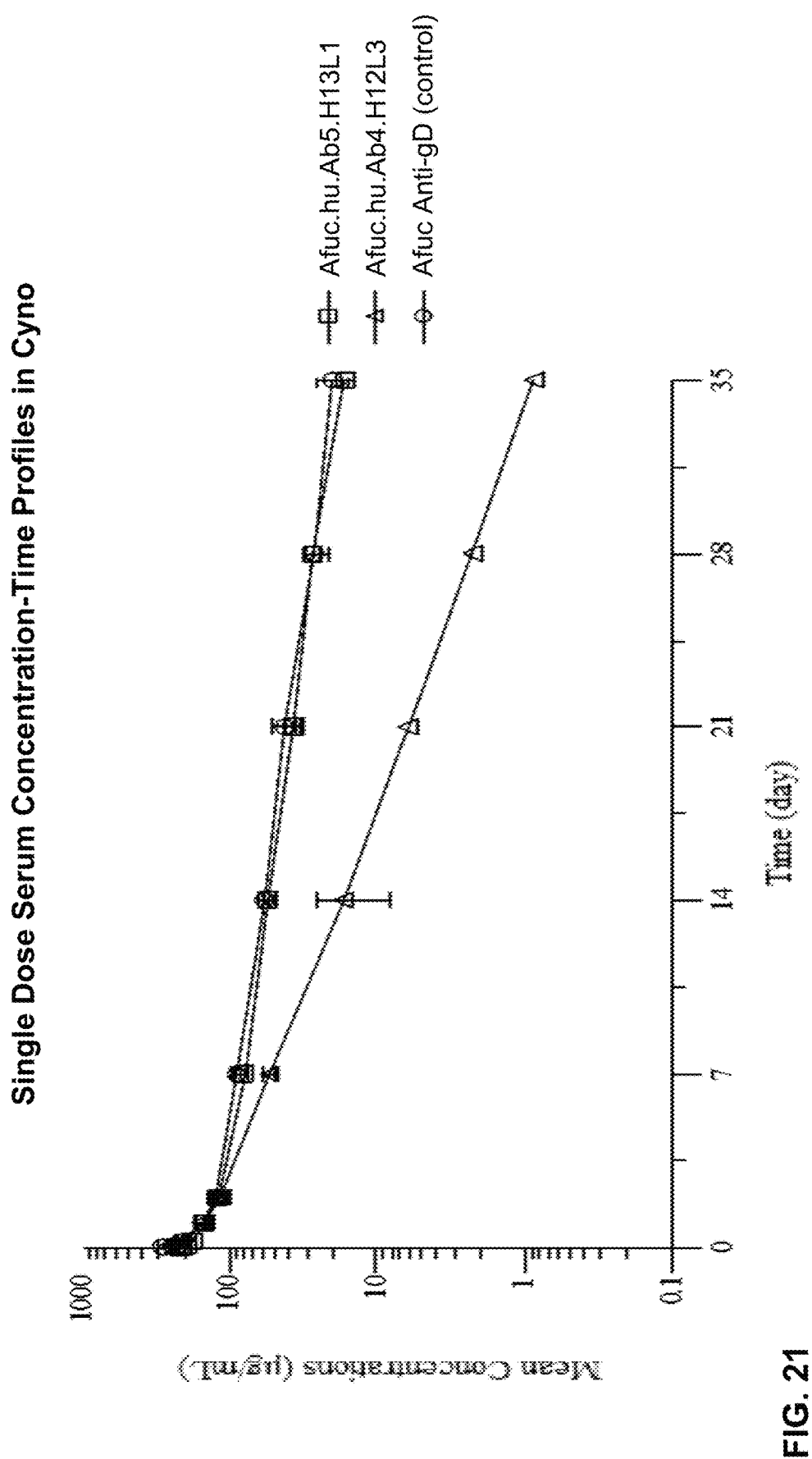

FIG. 21 depicts the serum pharmacokinetic profiles (mean±SD) of anti-gD (control)_and test anti-CCR8 mAbs Afuc.hu.Ab5.H13L1 and Afuc.hu.Ab4.H12L3 in cynomolgus monkey following a single dose 10 mg/kg IV bolus injection. Afuc.hu.Ab5.H13L1 exhibited desired sustained serum concentration levels over the 35-day post-dose period, which is expected to elicit a more sustained target engagement that may translate to better anti-cancer activity and less frequent dosing.

Figures 22A, 22B, 22C:
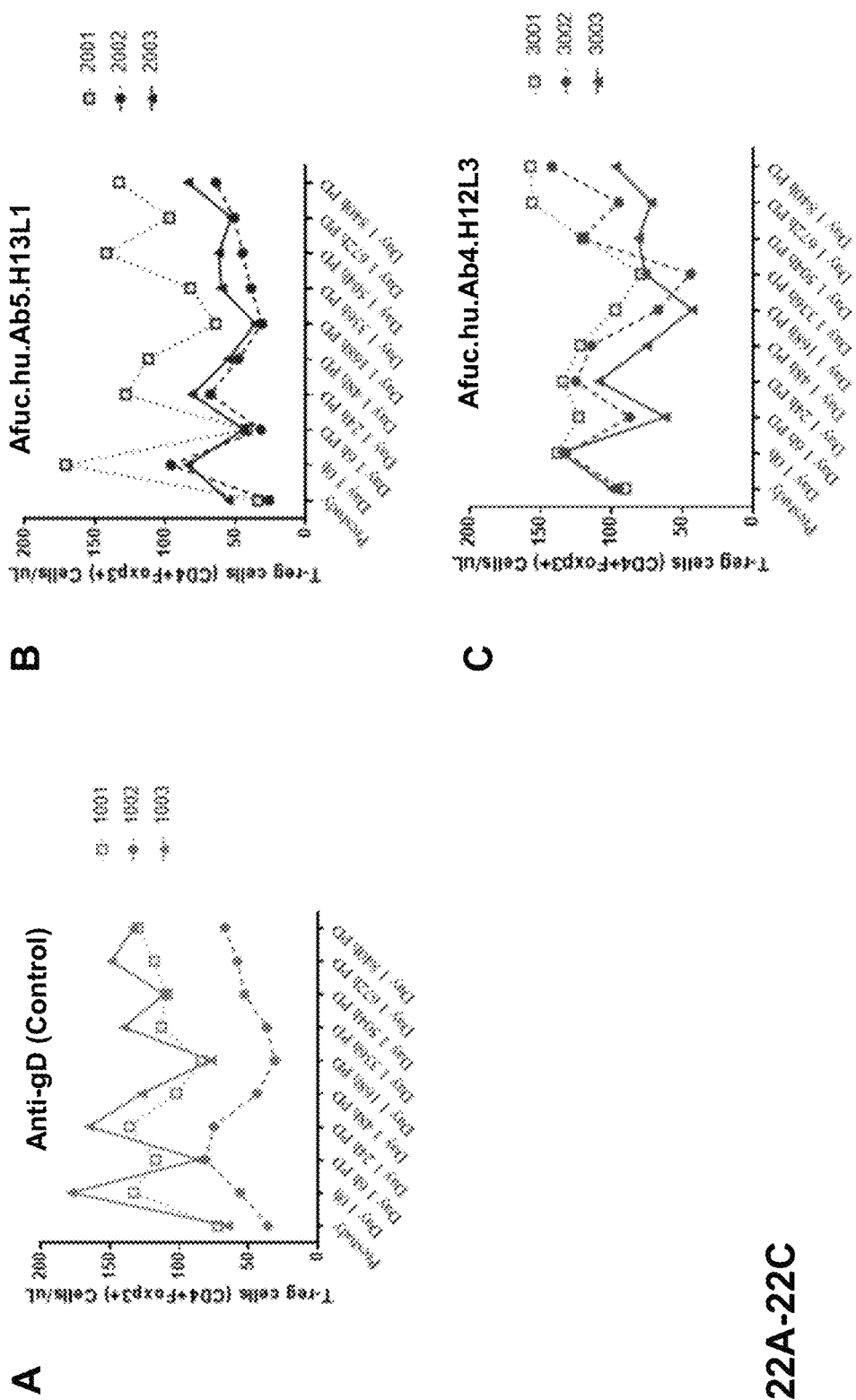

FIGS. 22A-22C depict the results of whole blood flow cytometry analysis for total Treg cell count of 9 male cynos dosed with 10 mg/kg afucosylated anti-gD (Control; Group 1, designated 1001, 1002, 1003; FIG. 22A), Afuc.hu.Ab5.H13L1 (Group 2, designated 2001, 2002, 2003; FIG. 22B), or Afuc.hu.Ab4.H12L3 (Group 3, designated 3001, 3002, 3003; FIG. 22C) via intravenous injection. Both test anti-CCR8 mAbs did not substantially reduce the total T-reg cell absolute counts in whole blood for up to 840 hours post dose.

Figures 23A, 23B, 23C:
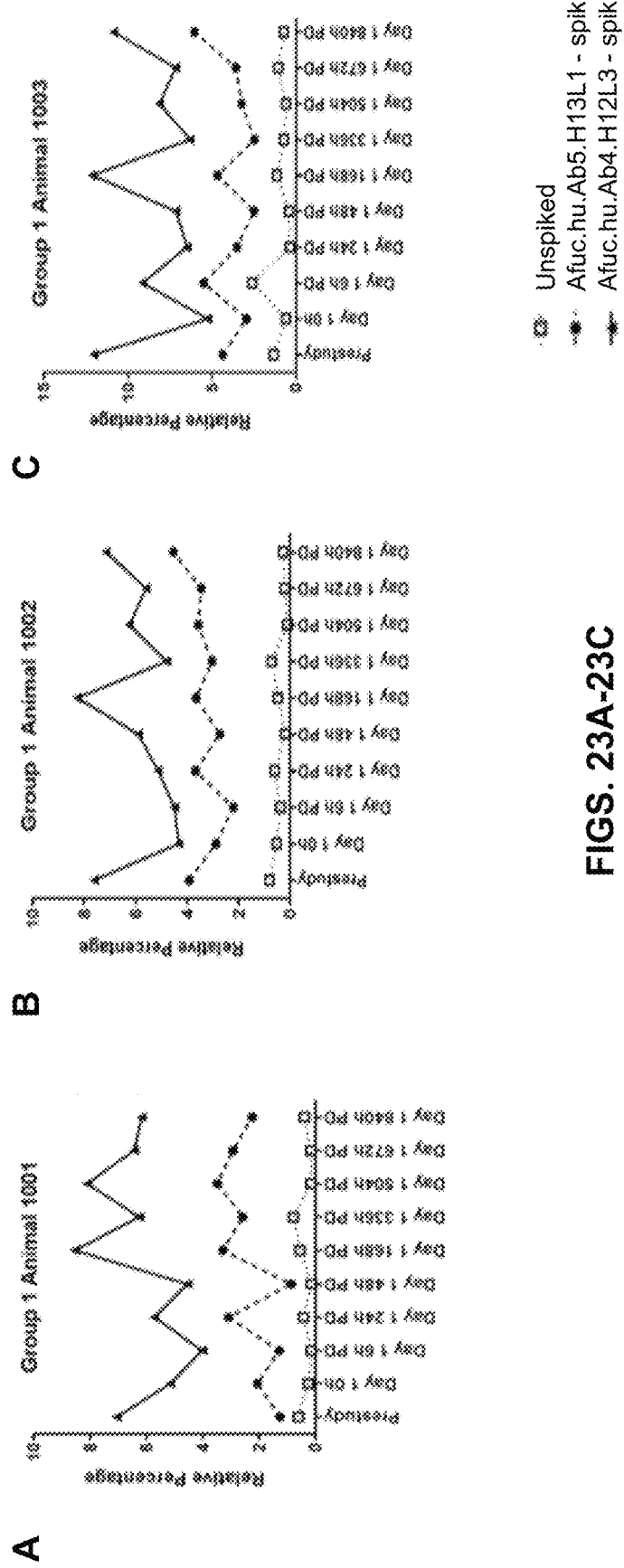
Figures 23D, 23E, 23F:
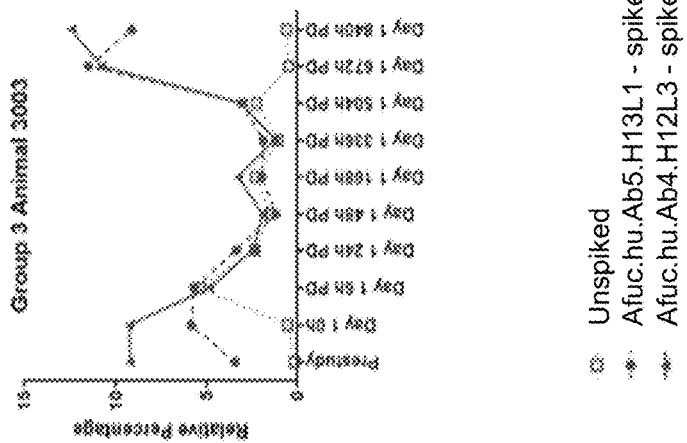
Figures 23G, 23H, 23I:
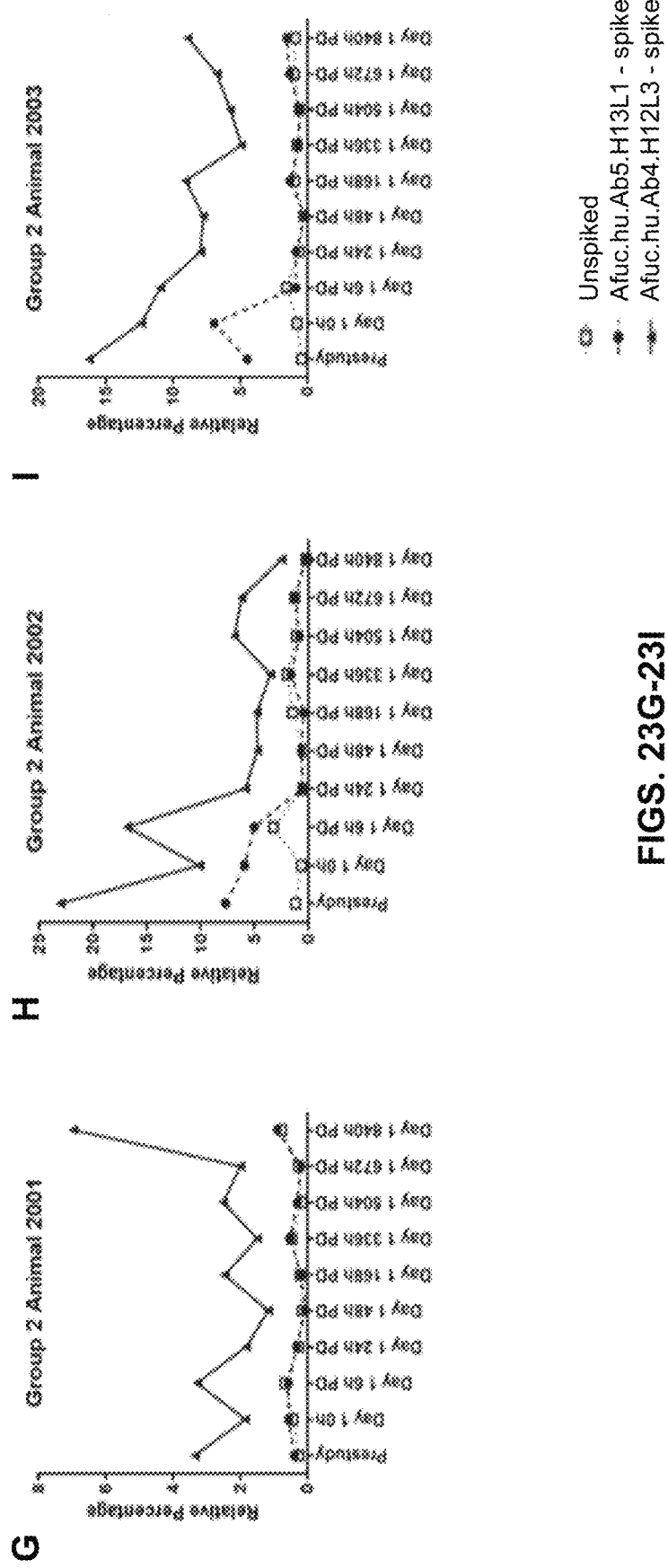

FIGS. 23A-23I depict the results of whole blood flow cytometry analysis for reduction of CCR8+FoxP3+ Treg cells of 9 male cynos dosed with afucosylated anti-gD (Control; Group 1, designated 1001 (FIG. 23A), 1002 (FIG. 23B), 1003 (FIG. 23C)) Afuc.hu.Ab4.H12L3 (Group 3, designated 3001 (FIG. 23D), 3002 (FIG. 23E), 3003 (FIG. 23F)), or, Afuc.hu.Ab5.H13L1 (Group 2, designated 2001 (FIG. 23G), 2002 (FIG. 23H), 2003 (FIG. 23I)). Blood was collected from each of the animals before dosing ("Pre-study"), as well as on Day 1 at 0 hours ("Pre-dose"). Each of the animals were then administered a single dose of 10 mg/kg afucosylated anti-gD (Control Group), Afuc.hu.Ab5.H13L1 (Group 2) or Afuc.hu.Ab4.H12L3 (Group 3) via intravenous injection. Blood was then collected from the animals and subjected to the following treatment prior to flow cytometry analysis: (i) blood sample not spiked with either test CCR8 mAb ("unspiked"), (ii) blood sample further spiked with a saturating concentration of Afuc.hu.Ab5.H13L1, and (iii) blood sample further spiked with a saturating concentration of Afuc.hu.Ab4.H12L3. Each of the unspiked and spiked samples were subsequently treated with a labeled goat anti-human IgG antibody and analyzed by flow cytometry. As can be seen in FIGS. 23A-23C, flow cytometry of blood initially treated with control (Group 1) but unspiked demonstrated no modulation of total CCR8+T-reg cells. Furthermore, flow cytometry of spiked blood also had very little effect on the total CCR8+T-reg cell count. With regard to Group 3, as can be seen in FIGS. 23D-23F, flow cytometry of blood analyzed in each of the three animals demonstrated a decrease in CCR8+T-reg cells up to 168 hours post dose. With regard to Group 2, as can be seen in FIGS. 23G-23I, flow cytometry of blood analyzed demonstrated a decrease in CCR8+T-reg cells in Animals 2002 and 2003. Both Group 2 and 3 animals demonstrated little to no effect on the overall Treg cell count (FIGS. 22A-22C), but demonstrated reduced numbers of peripheral blood CCR8+T-reg cells following administration (FIGS. 23D-23I), either spiked or unspiked, which is consistent with the proposed mechanism of action (see FIG. 2A).

DETAILED DESCRIPTION OF CERTAIN ASPECTS

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes are 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary methods for measuring binding affinity are also described herein.

An "affinity matured" antibody refers to an antibody with one or more alterations in one or more complementary determining regions (CDRs), compared to a parent antibody which does not possess such alterations, such alterations resulting in an improvement in the affinity of the antibody for antigen.

The terms "anti-CCR8 antibody" and "an antibody that binds to CCR8" refer to an antibody that is capable of binding CCR8 with sufficient affinity such that the antibody is useful as a diagnostic and/or therapeutic agent in targeting CCR8. In one aspect, the extent of binding of an anti-CCR8 antibody to an unrelated, non-CCR8 protein is less than about 10% of the binding of the antibody to CCR8 as measured, e.g., by surface plasmon resonance (SPR). In certain aspects, an antibody that binds to CCR8 has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-13}$ M to $10^{-8}$ M, e.g., from $10^{-13}$ M to $10^{-9}$ M). In certain aspects, an antibody that binds to CCR8 has a $K_D$ of from about $1\times10^{-12}$ M to about $1\times10^{-10}$ M, from about $1\times10^{-12}$ M to about $1\times10^{-11}$ M, or from about $1\times10^{-11}$ M to about $5\times10^{-11}$ M. In certain aspects, an antibody that binds to CCR8 has a $K_D$ of about $2\times10^{-11}$ M. In certain aspects, an antibody that binds to CCR8 has a $K_D$ of about $5\times10^{-12}$ M. An antibody is said to "specifically bind" to CCR8 when the antibody has a $K_D$ of 1 μM or less. In certain embodiments, an anti-CCR8 antibody binds to an epitope of CCR8 in at least two different species (e.g., human and cyno).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, *Nature Biotechnology* (2005) 23:1126-1136.

The term "epitope" denotes the site on an antigen, either proteinaceous or non-proteinaceous, to which an anti-CCR8 antibody binds. Epitopes can be formed both from contiguous amino acid stretches (linear epitope) or comprise non-contiguous amino acids (conformational epitope), e.g., coming in spatial proximity due to the folding of the antigen, i.e. by the tertiary folding of a proteinaceous antigen. Linear epitopes are typically still bound by an anti-CCR8 antibody after exposure of the proteinaceous antigen to denaturing agents, whereas conformational epitopes are typically destroyed upon treatment with denaturing agents. An epitope comprises at least 3, at least 4, at least 5, at least 6, at least 7, at least 8, at least 10, at least 15, at least 20, at least 30, or at least 35, or 3-25, 3-20, 3-15, 3-10, 3-5, 30-40, 35-40, or 5-10 amino acids in a unique spatial conformation.

Screening for antibodies binding to a particular epitope (i.e., those binding to the same epitope) can be done using methods routine in the art such as, e.g., without limitation, alanine scanning, peptide blots (see, e.g., Kobeissy et al., *Meth. Mol. Biol.* (2004) 248: 443-463), peptide cleavage analysis, epitope excision, epitope extraction, chemical modification of antigens (see Hochleitner et al., Prot. Sci. 9 (2000) 487-496), and cross-blocking (see "Antibodies", Harlow and Lane (Cold Spring Harbor Press, Cold Spring Harb., NY).

Antigen Structure-based Antibody Profiling (ASAP), also known as Modification-Assisted Profiling (MAP), allows to bin a multitude of monoclonal antibodies specifically binding to CCR8 based on the binding profile of each of the antibodies from the multitude to chemically or enzymatically modified antigen surfaces (see, e.g., US 2004/0101920). The antibodies in each bin bind to the same epitope which may be a unique epitope either distinctly different from or partially overlapping with epitope represented by another bin.

Also competitive binding can be used to easily determine whether an antibody binds to the same epitope of CCR8 as, or competes for binding with, a reference anti-CCR8 antibody. For example, an "antibody that binds to the same epitope" as a reference anti-CCR8 antibody refers to an antibody that blocks binding of the reference anti-CCR8 antibody to its antigen in a competition assay by 50% or more, and conversely, the reference antibody blocks binding of the antibody to its antigen in a competition assay by 50% or more. Also for example, to determine if an antibody binds to the same epitope as a reference anti-CCR8 antibody, the reference antibody is allowed to bind to CCR8 under saturating conditions. After removal of the excess of the reference anti-CCR8 antibody, the ability of an anti-CCR8 antibody in question to bind to CCR8 is assessed. If the anti-CCR8 antibody is able to bind to CCR8 after saturation binding of the reference anti-CCR8 antibody, it can be concluded that the anti-CCR8 antibody in question binds to a different epitope than the reference anti-CCR8 antibody. But, if the anti-CCR8 antibody in question is not able to bind to CCR8 after saturation binding of the reference anti-CCR8 antibody, then the anti-CCR8 antibody in question may bind to the same epitope as the epitope bound by the reference anti-CCR8 antibody. To confirm whether the antibody in question binds to the same epitope or is just hampered from binding by steric reasons routine experimentation can be used (e.g., peptide mutation and binding analyses using ELISA, RIA, surface plasmon resonance, flow cytometry or any other quantitative or qualitative antibody-binding assay available in the art). This assay should be carried out in two set-ups, i.e. with both of the antibodies being the saturating antibody. If, in both set-ups, only the first (saturating) antibody is capable of binding to CCR8, then it can be concluded that the anti-CCR8 antibody in question and the reference anti-CCR8 antibody compete for binding to CCR8.

In some aspects, two antibodies are deemed to bind to the same or an overlapping epitope if a 1-, 5-, 10-, 20- or 100-fold excess of one antibody inhibits binding of the other by at least 50%, at least 75%, at least 90% or even 99% or more as measured in a competitive binding assay (see, e.g., Junghans et al., *Cancer Res.* 50 (1990) 1495-1502).

In some aspects, two antibodies are deemed to bind to the same epitope if essentially all amino acid mutations in the antigen that reduce or eliminate binding of one antibody also reduce or eliminate binding of the other. Two antibodies are deemed to have "overlapping epitopes" if only a subset of the amino acid mutations that reduce or eliminate binding of one antibody reduce or eliminate binding of the other.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. In certain aspects, the antibody is of the IgG$_1$ isotype. In certain aspects, the antibody is of the IgG$_1$ isotype with the P329G, L234A and L235A mutation to reduce Fc-region effector function. In other aspects, the antibody is of the IgG2 isotype. In certain aspects, the antibody is of the IgG$_4$ isotype with the S228P mutation in the hinge region to improve stability of IgG$_4$ antibody. The heavy chain constant domains that correspond to the different classes of immunoglobulins are called α, δ, ε, γ, and μ, respectively. The light chain of an antibody may be assigned to one of two types, called kappa (κ) and lambda (Q), based on the amino acid sequence of its constant domain.

The terms "constant region derived from human origin" or "human constant region" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., et al., Sequences of Proteins of Immunological Interest, 5th ed., Public Health Service, National Institutes of Health, Bethesda, MD (1991) (see also e.g. Johnson, G., and Wu, T. T., Nucleic Acids Res. 28 (2000) 214-218; Kabat, E. A., et al., Proc. Natl. Acad. Sci. USA 72 (1975) 2785-2788). Unless otherwise specified herein, numbering of amino acid residues in the constant region is according to the EU numbering system, also called the EU index of Kabat, as described in Kabat, E. A. et al., Sequences of Proteins of Immunological Interest, 5th ed., Public Health Service, National Institutes of Health, Bethesda, MD (1991), NIH Publication 91-3242.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., in a pharmaceutical composition, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, EU numbering system). Therefore, the C-terminal lysine (Lys447), or the C-terminal glycine (Gly446) and lysine (Lys447), of the Fc region may or may not be present. In one aspect, a heavy chain including an Fc region as specified herein, comprised in an antibody according to the invention, comprises an additional C-terminal glycine-lysine dipeptide (G446 and K447, EU numbering system). In one aspect, a heavy chain including an Fc region as specified herein, comprised in an antibody according to the invention, comprises an additional C-terminal glycine residue (G446, numbering according to EU index). Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The terms "full-length antibody", "intact antibody", and "whole antibody" are used herein interchangeably to refer to an antibody having a structure substantially similar to a native antibody structure or having heavy chains that contain an Fc region as defined herein. It should be understood that the full-length antibody comprises a heavy chain variable domain and light chain variable domain, as defined herein, and an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one aspect, for the VL, the subgroup is subgroup kappa I as in Kabat et al., supra. In one aspect, for the VH, the subgroup is subgroup III as in Kabat et al., supra.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and which determine antigen binding specificity, for example "complementarity determining regions" ("CDRs").

In certain aspects, antibodies comprise six CDRs: three in the VH (CDR-H1, CDR-H2, CDR-H3), and three in the VL (CDR-L1, CDR-L2, CDR-L3). In certain aspects, the antibodies comprising six CDRs are full-length antibodies. In certain aspects, the antibodies comprising six CDRs are antibody fragments.

Exemplary CDRs Herein Include:
(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991)); and
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra and Chothia, supra. One of skill in the art will understand that the CDR designations can also be determined according to McCallum, supra, or any other scientifically accepted nomenclature system.

In one aspect, CDR residues comprise those identified in FIGS. 5A-5D and 6A-6D and Tables C1, C2, D1 and D2. In other aspects, CDR residues comprise those identified in Tables N1, N2, O1, and O2.

A "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the subject is a human.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., *J. Chromatogr. B* 848:79-87 (2007).

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody as described herein in vitro and/or in vivo, e.g., in a host or subject. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CCR8 antibody" refers to one or more nucleic acid molecules encoding anti-CCR8 antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical composition.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full-length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, percent amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", *PNAS* 85:2444-2448; W. R. Pearson (1996) "Effective protein sequence comparison" *Meth. Enzymol.* 266:227-258; and Pearson et. al. (1997) *Genomics* 46:24-36 and is publicly available from fasta.bioch.virginia.edu/fasta_www2/fasta_down.shtml or ebi.ac.uk/Tools/sss/fasta. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The terms "pharmaceutical composition" and "pharmaceutical formulation" are used interchangeably herein, and refer to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The term "CCR8", as used herein, refers to any native CCR8 from any vertebrate source, including mammals such as primates (e.g., humans, monkeys (cyno)), and rodents (e.g., mice and rats), unless otherwise indicated. The term encompasses "full-length", unprocessed CCR8 as well as any form of CCR8 that results from processing in the cell. The term also encompasses naturally occurring variants of CCR8, e.g., splice variants or allelic variants. In certain aspects, the CCR8 is a human CCR8 ("hCCR8" or "huCCR8"). The amino acid sequence of an exemplary human CCR8 is set forth in SEQ ID NO: 106, as shown in the below Table. In certain aspects, the CCR8 is a cynomolgus monkey ("cyno") CCR8. The amino acid sequence of an exemplary cyno CCR8 is set forth in SEQ ID NO: 107, as shown in the below Table. In certain aspects, the CCR8 is a mouse CCR8 ("mCCR8"). The amino acid sequence of an exemplary mouse CCR8 is set forth in SEQ ID NO: 108, as shown in the below Table.

TABLE 1

Exemplary CCR8 sequences

| Description | Sequence |
|---|---|
| human CCR8 SEQ ID NO: 106 | MDYTLDLSVTTVTDYYYPDIFSSPCDAELIQTNGKLLLAVFYCLLFVFS LLGNSLVILVLVVCKKLRSITDVYLLNLALSDLLFVFSFPFQTYYLLDQ WVFGTVMCKVVSGFYYIGFYSSMFFITLMSVDRYLAVVHAVYALKVRTI RMGTTLCLAVWLTAIMATIPLLVFYQVASEDGVLQCYSFYNQQTLKWKI FTNFKMNILGLLIPFTIFMFCYIKILHQLKRCQNHNKTKAIRLVLIVVI ASLLFWVPFNVVLFLTSLHSMHILDGCSISQQLTYATHVTEIISFTHCC VNPVIYAFVGEKFKKHLSEIFQKSCSQIFNYLGRQMPRESCEKSSSCQQ HSSRSSSVDYIL |
| cyno CCR8 SEQ ID NO: 107 | MDYTLDPSMTTMTDYYYPDSLSSPCDGELIQRNDKLLLAVFYCLLFVFS LLGNSLVILVLVVCKKLRNITDIYLLNLALSDLLFVFSFPFQTYYQLDQ WVFGTVMCKVVSGFYYIGFYSSMFFITLMSVDRYLAVVHAVYAIKVRTI RMGTTLSLVVWLTAIMATIPLLVFYQVASEDGVLQCYSFYNQQTLKWKI FTNFEMNILGLLIPFTIFMFCYIKILHQLKRCQNHNKTKAIRLVLIVVI ASLLFWVPFNVVLFLTSLHSMHILDGCSISQQLNYATHVTEIISFTHCC VNPVIYAFVGEKFKKHLSEIFQKSCSHIFIYLGRQMPRESCEKSSSCQQ HSFRSSSIDYIL |
| mouse CCR8 SEQ ID NO: 108 | MDYTMEPNVTMTDYYPDFFTAPCDAEFLLRGSMLYLAILYCVLFVLGLL GNSLVILVLVGCKKLRSITDIYLLNLAASDLLFVLSIPFQTHNLLDQWV FGTAMCKVVSGLYYIGFFSSMFFITLMSVDRYLAIVHAVYAIKVRTASV GTALSLTVWLAAVTATIPLMVFYQVASEDGMLQCFQFYEEQSLRWKLFT HFEINALGLLLPFAILLFCYVRILQQLRGCLNHNRTRAIKLVLTVVIVS LLFWVPFNVALFLTSLHDLHILDGCATRQRLALAIHVTEVISFTHCCVN PVIYAFIGEKFKKHLMDVFQKSCSHIFLYLGRQMPVGALERQLSSNQRS SHSSTLDDIL |

As used herein, "treatment" (and grammatical variations thereof such as "treat" or "treating") refers to clinical intervention in an attempt to alter the natural course of a disease (e.g., cancer) in the subject being treated, and can be performed either for prophylaxis ("preventative treatment" or "prophylactically treating") or during the course of clinical pathology ("therapeutic treatment" or "therapeutically treating"). Desirable effects of therapeutic treatment include, but are not limited to, alleviation of symptoms, diminishment of any direct or indirect pathological consequences of the disease, preventing metastasis of the cancer, decreasing the rate of disease progression, amelioration or palliation of the disease state, and remission or improved prognosis. Desirable effects of preventative treatment include, but are not limited to, preventing occurrence or recurrence of disease. In some aspects, antibodies as described herein are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). (See, e.g., Kindt et al. *Kuby Immunology, 6th* ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the present disclosure is based, in part, on the discovery of novel anti-CCR8 antibodies which have unique and improved binding and selectivity to CCR8. The presently disclosed anti-CCR8 antibodies also have improved antibody stability (e.g., low aggregation, good solubility, and low viscosity). The present disclosure is further based, in part, on the discovery that afucosylated forms of the presently disclosed antibodies had increased antibody-dependent cellular cytotoxicity (ADCC) and antibody-dependent cellular phagocytosis (ADCP) activities. In certain aspects, antibodies that bind to CCR8 are provided. Antibodies as described herein are useful, e.g., for the treatment of cancer.

A. Exemplary Anti-CCR8 Antibodies

In one aspect, the present disclosure provides antibodies that bind to CCR8. In one aspect, the antibodies provided are isolated antibodies that bind to CCR8. In one aspect, the present disclosure provides antibodies that specifically bind to CCR8. In certain aspects, an anti-CCR8 antibody binds to an epitope comprised of one or more of amino acid residues 2-6 of SEQ ID NO: 106. In certain aspects, an anti-CCR8 antibody binds to an epitope comprised of one or more of the amino acid residues 91-104 and 172-193 of SEQ ID NO: 106. In certain aspects, the CCR8 is a human CCR8, a mouse CCR8 or a cyno CCR8. In certain aspects, the CCR8 is a human CCR8. In one aspect, the present disclosure provides antibodies that bind to CCR8 independent of tyrosine sulfation of CCR8 ("sulfation independent"). Exemplary antibodies which the inventors have discovered are sulfation independent include Ab4 and Ab5, further described in more detail below.

In certain aspects, an antibody provided herein has a dissociation constant ($K_D$) of $\leq 1$ μM, $\leq 100$ nM, $\leq 10$ nM, $\leq 1$ nM, 0.1 nM, $\leq 0.01$ nM, or $\leq 0.001$ nM (e.g., $10^{-8}$ M or less, e.g., from $10^{-8}$ M to $10^{-11}$ M, e.g., from $10^{-9}$ M to $10^{-13}$ M). In certain aspects, the antibody that binds to CCR8 has a $K_D$ of from about $1 \times 10^{-12}$ M to about $1 \times 10^{-10}$ M, from about $1 \times 10^{-12}$ M to about $1 \times 10^{-10}$ M, or from about $1 \times 10^{-11}$ M to about $5 \times 10^{-11}$ M. In certain aspects, the antibody that binds to CCR8 has a $K_D$ of about $2 \times 10^{-11}$ M. In certain aspects, the antibody that binds to CCR8 has a $K_D$ of about $5 \times 10^{-12}$ M. In one aspect, $K_D$ is measured using radiolabeled IgGs and CHO cell lines stably expressing antigen. Stable CHO cells expressing the antigen are seeded in cold binding buffer (Opti-MEM+2% FBS+50 mM HEPES, pH 7.2+0.1% Sodium Azide) at 50,000 cells per well. A fixed concentration of $^{125}$I radiolabeled antigen of interest using the NEX244 Iodogen method (Perkin Elmer) is mixed with serially diluted antibodies of interest starting at 20 nM or 50 nM. The antibody mixture is added to the cells and incubated at room temperature for 12 hours under gentle agitation. The cells and antibodies are then transferred to Millipore multiscreen filter plates. The filter plates are washed 4 times with 250 μL of cold binding buffer and dried for at least 30 minutes and the filters are punched into 5 mL polystyrene tubes. The radioactivity is measured using a Perkin Elmer Wallac Wizard 2470 Gamma Counter set at 1 count per minute with 0.8 counting efficiency. The data are fitted using the heterologous one site-fit Ki competitive binding model in GraphPad Prism.

In certain aspects, an antibody provided herein exhibits mean clearance after a single 10 mg/kg dose administered intravenously on day 1 of between about 3 to about 5 mL/day/kg over a 35 day period. For example, but not by way of limitation, such administration can comprise a single 10 mg/kg IV bolus of mAb. Blood samples for analysis can be collected, e.g., at 0.25, 2, 6 hours; 1, 2, 7, 14, 21, 28 and 35 days post-dose, and serum can be assayed for concentrations of mAb using a variety of means, e.g. a qualified ELISA analytical method. In certain aspects, the administration is to a mammal. In certain aspects the administration is to a primate. In certain aspects, the administration is to a non-human primate, e.g., a cyno. In certain aspects, the administration is to a human.

(i) Embodiments of Ab5 and Fragments Thereof

In one aspect, the present disclosure provides an anti-CCR8 antibody comprising at least one, at least two, at least three, at least four, at least five, or all six CDRs selected from the group consisting of (a) CDR-H1 comprising the amino acid sequence of SEQ ID NO: 29 or SEQ ID NO: 30, (b) CDR-H2 comprising the amino acid sequence of SEQ ID NO: 31, (c) CDR-H3 comprising the amino acid sequence of SEQ ID NO: 32, (d) CDR-L1 comprising the amino acid sequence of SEQ ID NO: 26, (e) CDR-L2 comprising the amino acid sequence of SEQ ID NO: 27, and (f) CDR-L3 comprising the amino acid sequence of SEQ ID NO: 28. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to both human CCR8 and cyno CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In one aspect, the present disclosure provides an antibody comprising at least one, at least two, or all three VH CDR sequences selected from the group consisting of (a) CDR-H1 comprising the amino acid sequence of SEQ ID NO: 29 or SEQ ID NO: 30, (b) CDR-H2 comprising the amino acid sequence of SEQ ID NO: 31, and (c) CDR-H3 comprising the amino acid sequence of SEQ ID NO: 32. In one aspect, the antibody comprises CDR-H3 comprising the amino acid sequence of SEQ ID NO: 32. In another aspect, the antibody comprises CDR-H3 comprising the amino acid sequence of SEQ ID NO: 32 and CDR-L3 comprising the amino acid sequence of SEQ ID NO: 28. In a further aspect, the antibody comprises CDR-H3 comprising the amino acid sequence of SEQ ID NO: 32, CDR-L3 comprising the amino acid sequence of SEQ ID NO: 28, and CDR-H2 comprising the amino acid sequence of SEQ ID NO: 31. In a further aspect, the antibody comprises (a) CDR-H1 comprising the amino acid sequence of SEQ ID NO: 29 or SEQ ID NO: 30, (b) CDR-H2 comprising the amino acid sequence of SEQ ID NO: 31, and (c) CDR-H3 comprising the amino acid sequence of SEQ ID NO: 32.

In another aspect, the present disclosure provides an antibody comprising at least one, at least two, or all three VL CDR sequences selected from the group consisting of (a) CDR-L1 comprising the amino acid sequence of SEQ ID NO: 26; (b) CDR-L2 comprising the amino acid sequence of SEQ ID NO: 27; and (c) CDR-L3 comprising the amino acid sequence of SEQ ID NO: 28. In one aspect, the antibody comprises (a) CDR-L1 comprising the amino acid sequence of SEQ ID NO: 26; (b) CDR-L2 comprising the amino acid sequence of SEQ ID NO: 27; and (c) CDR-L3 comprising the amino acid sequence of SEQ ID NO: 28.

In another aspect, an antibody as described herein comprises (a) a VH domain comprising at least one, at least two, or all three VH CDR sequences selected from the group consisting of (i) CDR-H1 comprising the amino acid sequence of SEQ ID NO: 29 or SEQ ID NO: 30, (ii) CDR-H2 comprising the amino acid sequence of SEQ ID NO: 31, and (iii) CDR-H3 comprising the amino acid sequence of SEQ ID NO: 32; and (b) a VL domain comprising at least one, at least two, or all three VL CDR sequences selected from the group consisting of (i) CDR-L1 comprising the amino acid sequence of SEQ ID NO: 26; (ii) CDR-L2 comprising the amino acid sequence of SEQ ID NO: 27; and (iii) CDR-L3 comprising the amino acid sequence of SEQ ID NO: 28. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to both human CCR8 and cyno CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In another aspect, the present disclosure provides an antibody comprising (a) CDR-H1 comprising the amino acid sequence of SEQ ID NO: 29 or SEQ ID NO: 30, (b) CDR-H2 comprising the amino acid sequence of SEQ ID NO: 31, and (c) CDR-H3 comprising the amino acid sequence of SEQ ID NO: 32, and a light chain variable domain (VL) comprising (d) CDR-L1 comprising the amino acid sequence of SEQ ID NO: 26, (e) CDR-L2 comprising the amino acid sequence of SEQ ID NO: 27, and (f) CDR-L3 comprising the amino acid sequence of SEQ ID NO: 28.

In another aspect, an anti-CCR8 antibody comprises one or more of the CDR sequences of the VH sequence selected from the group consisting of SEQ ID NOs: 35-47. In another embodiment, an anti-CCR8 antibody comprises one or more of the CDR sequences of the VL sequence selected from the group consisting of SEQ ID NOs: 48-52. In another embodiment, an anti-CCR8 antibody comprises the CDR sequences of the VH sequence selected from the group consisting of SEQ ID NOs: 35-47 and the CDR sequences of the VL sequence selected from the group consisting of SEQ ID NOs: 48-52.

In another aspect, an anti-CCR8 antibody comprises one or more of the CDR sequences of the VH sequence of SEQ ID NO: 47. In another embodiment, an anti-CCR8 antibody comprises one or more of the CDR sequences of the VL sequence of SEQ ID NO: 48. In another embodiment, an anti-CCR8 antibody comprises the CDR sequences of the VH sequence of SEQ ID NO: 47. In another embodiment, an anti-CCR8 antibody comprises one or more of the CDR sequences of the VL sequence of SEQ ID NO: 48.

In a further aspect, an anti-CCR8 antibody comprises the CDR-H1, CDR-H2 and CDR-H3 amino acid sequences of the VH domain selected from the group consisting of SEQ ID NOs: 35-47 and the CDR-L1, CDR-L2 and CDR-L3 amino acid sequences of the VL domain selected from the group consisting of SEQ ID NOs: 48-52.

In a further aspect, an anti-CCR8 antibody comprises the CDR-H1, CDR-H2 and CDR-H3 amino acid sequences of the VH domain of SEQ ID NO: 47 and the CDR-L1, CDR-L2 and CDR-L3 amino acid sequences of the VL domain of SEQ ID NO: 48.

In one aspect, an anti-CCR8 antibody comprises one or more of the heavy chain CDR amino acid sequences of the VH domain selected from the group consisting of SEQ ID NOs: 35-47 and a framework of at least 85%, 86%, 87%, 88%, 89%, 90%, 91%, 92%, 93%, 94%, 95%, 96%, 97%, 98%, 99% sequence identity to the framework amino acid sequence of the VH domain selected from the group consisting of SEQ ID NOs: 35-47. In one aspect, the anti-CCR8 antibody comprises the three heavy chain CDR amino acid sequences of the VH domain selected from the group consisting of SEQ ID NOs: 35-47 and a framework of at least 85%, 86%, 87%, 88%, 89%, 90%, 91%, 92%, 93%, 94%, 95%, 96%, 97%, 98%, 99% sequence identity to the framework amino acid sequence of the VH domain selected from the group consisting of SEQ ID NOs: 35-47. In one aspect, the anti-CCR8 antibody comprises the three heavy chain CDR amino acid sequences of the VH domain of selected from the group consisting of SEQ ID NOs: 35-47 and a framework of at least 95% sequence identity to the framework amino acid sequence of the VH domain selected from the group consisting of SEQ ID NOs: 35-47. In another aspect, the anti-CCR8 antibody comprises the three heavy chain CDR amino acid sequences of the VH domain of selected from the group consisting of SEQ ID NOs: 35-47 and a framework of at least of at least 98% sequence identity to the framework amino acid sequence of the VH domain of selected from the group consisting of SEQ ID NOs: 35-47.

In one aspect, an anti-CCR8 antibody comprises one or more of the heavy chain CDR amino acid sequences of the VH domain of SEQ ID NO: 47 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 47. In one aspect, the anti-CCR8 antibody comprises the three heavy chain CDR amino acid sequences of the VH domain of SEQ ID NO: 47 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 47. In one aspect, the anti-CCR8 antibody comprises the three heavy chain CDR amino acid sequences of the VH domain of SEQ ID NO: 47 and a framework of at least 95% sequence identity to the framework amino acid sequence of the VH domain of SEQ ID NO: 47. In another aspect, the anti-CCR8 antibody comprises the three heavy chain CDR amino acid sequences of the VH domain of SEQ ID NO: 47 and a framework of at least of at least 98% sequence identity to the framework amino acid sequence of the VH domain of SEQ ID NO: 47.

In one aspect, an anti-CCR8 antibody comprises one or more of the light chain CDR amino acid sequences of the VL domain selected from the group consisting of SEQ ID NOs: 48-52 and a framework of at least 85%, 86%, 87%, 88%, 89%, 90%, 91%, 92%, 93%, 94%, 95%, 96%, 97%, 98%, 99% sequence identity to the framework amino acid sequence of the VL domain selected from the group consisting of SEQ ID NOs: 48-52. In one aspect, the anti-CCR8 antibody comprises the three light chain CDR amino acid sequences of the VL domain selected from the group consisting of SEQ ID NOs: 48-52 and a framework of at least 85%, 86%, 87%, 88%, 89%, 90%, 91%, 92%, 93%, 94%, 95%, 96%, 97%, 98%, 99% sequence identity to the framework amino acid sequence of the VL domain selected from the group consisting of SEQ ID NOs: 48-52. In one aspect, the anti-CCR8 antibody comprises the three light chain CDR amino acid sequences of the VL domain selected from the group consisting of SEQ ID NOs: 48-52 and a framework of at least 95% sequence identity to the framework amino acid sequence of the VL domain selected from the group consisting of SEQ ID NOs: 48-52. In another aspect, the anti-CCR8 antibody comprises the three light chain CDR amino acid sequences of the VL domain selected from the group consisting of SEQ ID NOs: 48-52 and a framework of at least particularly of at least 98% sequence identity to the framework amino acid sequence of the VL domain selected from the group consisting of SEQ ID NOs: 48-52.

In one aspect, an anti-CCR8 antibody comprises one or more of the light chain CDR amino acid sequences of the VL domain of SEQ ID NO: 48 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 48. In one aspect, the anti-CCR8 antibody comprises the three light chain CDR amino acid sequences of the VL domain of SEQ ID NO: 48 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 48. In one aspect, the anti-CCR8 antibody comprises the three light chain CDR amino acid sequences of the VL domain of SEQ ID NO: 48 and a framework of at least 95% sequence identity to the framework amino acid sequence of the VL domain of SEQ ID NO: 48. In another aspect, the anti-CCR8 antibody comprises the three light chain CDR amino acid sequences of the VL domain of SEQ ID NO: 48 and a framework of at least particularly of at least 98% sequence identity to the framework amino acid sequence of the VL domain of SEQ ID NO: 48.

In one aspect, the anti-CCR8 antibody comprises (a) CDR-H1 comprising the amino acid sequence of SEQ ID NO: 29 or SEQ ID NO: 30, (b) CDR-H2 comprising the amino acid sequence of SEQ ID NO: 31, (c) CDR-H3 comprising the amino acid sequence of SEQ ID NO: 32, (d) CDR-L1 comprising the amino acid sequence of SEQ ID NO: 26, (e) CDR-L2 comprising the amino acid sequence of SEQ ID NO: 27, and (f) CDR-L3 comprising the amino acid sequence of SEQ ID NO: 28, and a VH domain having at least 90%, 91%, 92%, 93%, 94%, 95%, 96%, 97%, 98%, 99%, or 100% sequence identity to an amino acid sequence selected from the group consisting of SEQ ID NOs: 35-47, and a VL domain having at least 90%, 91%, 92%, 93%, 94%, 95%, 96%, 97%, 98%, 99%, or 100% sequence identity to an amino acid sequence selected from the group consisting of SEQ ID NOs: 48-52. In one aspect, the VH domain has at least 95% sequence identity to an amino acid sequence selected from the group consisting of SEQ ID NOs: 35-47. In one aspect, the VL domain has at least 95% sequence identity to an amino acid sequence selected from the group consisting of SEQ ID NOs: 48-52. In one aspect, the antibody binds to CCR8 having a dissociation constant ($K_D$) that is up to 10 fold reduced or up to 10 fold increased when compared to the dissociation constant ($K_D$) of an antibody comprising a VH sequence selected from the group consisting of SEQ ID NOs: 35-47 and a VL sequence selected from the group consisting of SEQ ID NOs: 48-52.

In one aspect, the anti-CCR8 antibody comprises (a) CDR-H1 comprising the amino acid sequence of SEQ ID NO: 29 or SEQ ID NO: 30, (b) CDR-H2 comprising the amino acid sequence of SEQ ID NO: 31, (c) CDR-H3 comprising the amino acid sequence of SEQ ID NO: 32, (d) CDR-L1 comprising the amino acid sequence of SEQ ID NO: 26, (e) CDR-L2 comprising the amino acid sequence of SEQ ID NO: 27, and (f) CDR-L3 comprising the amino acid sequence of SEQ ID NO: 28, and a VH domain having at least 90%, 91%, 92%, 93%, 94%, 95%, 96%, 97%, 98%, 99%, or 100% sequence identity to the amino acid sequence of SEQ ID NO: 47, and a VL domain having at least 90%, 91%, 92%, 93%, 94%, 95%, 96%, 97%, 98%, 99%, or 100% sequence identity to the amino acid sequence of SEQ ID NO: 48. In one aspect, the VH domain has at least 95% sequence identity to the amino acid sequence of SEQ ID NO: 47. In one aspect, the VL domain has at least 95% sequence identity to the amino acid sequence of SEQ ID NO: 48. In one aspect, the antibody binds to CCR8 having a dissociation constant ($K_D$) that is up to 10 fold reduced or up to 10 fold increased when compared to the dissociation constant ($K_D$) of an antibody comprising a VH sequence of SEQ ID NO: 47 and a VL sequence of SEQ ID NO: 48.

In another aspect, an anti-CCR8 antibody comprises a heavy chain variable domain (VH) sequence having at least 90%, 91%, 92%, 93%, 94%, 95%, 96%, 97%, 98%, 99%, or 100% sequence identity to an amino acid sequence selected from the group consisting of SEQ ID NOs: 35-47. In one aspect, an anti-CCR8 antibody comprises a heavy chain variable domain (VH) sequence having at least 95%, sequence identity to an amino acid sequence selected from the group consisting of SEQ ID NOs: 35-47. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in an amino acid sequence selected from the group consisting of SEQ ID NOs: 35-47. In certain aspects, substitutions, insertions, or deletions occur in regions outside the CDRs (i.e., in the FRs). Optionally, the anti-CCR8 antibody comprises the VH sequence selected from the group consisting of SEQ ID NOs: 35-47, including post-translational modifications of that sequence. In a particular aspect, the VH comprises one, two or three CDRs selected from: (a) CDR-H1 comprising the amino acid sequence of SEQ ID NO: 29 or SEQ ID NO: 30, (b) CDR-H2 comprising the amino acid sequence of SEQ ID NO: 31, (c) CDR-H3 comprising the amino acid sequence of SEQ ID NO: 32. In another aspect, an anti-CCR8 antibody is provided, wherein the antibody comprises a light chain variable domain (VL) sequence having at least 90%, 91%, 92%, 93%, 94%, 95%, 96%, 97%, 98%, 99%, or 100% sequence identity to an amino acid sequence selected from the group consisting of SEQ ID NOs: 48-52. In one aspect, an anti-CCR8 antibody comprises a light chain variable domain (VL) sequence having at least 95% sequence identity to an amino acid sequence selected from the group consisting of SEQ ID NOs: 48-52. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence selected from the group consisting of SEQ ID NOs: 48-52. In certain aspects, the substitutions, insertions, or deletions occur in regions outside the CDRs (i.e., in the FRs). Optionally, the anti-CCR8 antibody comprises the VL sequence selected from the group consisting of SEQ ID NOs: 48-52, including post-translational modifications of that sequence. In a particular aspect, the VL comprises one, two or three CDRs selected from: (a) CDR-L1 comprising the amino acid sequence of SEQ ID NO: 26, (b) CDR-L2 comprising the amino acid sequence of SEQ ID NO: 27, and (c) CDR-L3 comprising the amino acid sequence of SEQ ID NO: 28.

In another aspect, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 47. In one aspect, an anti-CCR8 antibody comprises a heavy chain variable domain (VH) sequence having at least 95%, sequence identity to the amino acid sequence of SEQ ID NO: 47. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 47. In certain aspects, substitutions, insertions, or deletions occur in regions outside the CDRs (i.e., in the FRs). Optionally, the anti-CCR8 antibody comprises the VH sequence of SEQ ID NO: 47, including post-translational modifications of that sequence. In a particular aspect, the VH comprises one, two or three CDRs selected from: (a) CDR-H1 comprising the amino acid sequence of SEQ ID NO: 29 or SEQ ID NO: 30, (b) CDR-H2 comprising the amino acid sequence of SEQ ID NO: 31, (c) CDR-H3 comprising the amino acid sequence of SEQ ID NO: 32. In another aspect, an anti-CCR8 antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 48. In one aspect, an anti-CCR8 antibody comprises a light chain variable domain (VL) sequence having at least 95% sequence identity to the amino acid sequence of SEQ ID NO: 48. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 48. In certain aspects, the substitutions, insertions, or deletions occur in regions outside the CDRs (i.e., in the FRs). Optionally, the anti-CCR8 antibody comprises the VL sequence of SEQ ID NO: 48, including post-translational modifications of that sequence. In a particular aspect, the VL comprises one, two or three CDRs selected from: (a) CDR-L1 comprising the amino acid sequence of SEQ ID NO: 26, (b) CDR-L2 comprising the amino acid sequence of SEQ ID NO: 27, and (c) CDR-L3 comprising the amino acid sequence of SEQ ID NO: 28.

In another aspect, an anti-CCR8 antibody is provided, wherein the antibody comprises a VH sequence as in any of the aspects provided above, and a VL sequence as in any of the aspects provided above. In one aspect, the antibody comprises the VH sequence selected from the group consisting of SEQ ID NOs: 35-47 and the VL sequence selected from the group consisting of SEQ ID NOs: 48-52, including post-translational modifications of those sequences. In one aspect, the antibody comprises the VH sequence of SEQ ID NO: 47 and the VL sequence of SEQ ID NO: 48, including post-translational modifications of those sequences.

In one aspect, the VL sequence comprises a V4M mutation, a P43A mutation, a F46L mutation, a C90Q mutation, or a combination thereof. In one aspect, the VH comprises a G49S mutation, a K71R mutation, a S73N mutation, or a combination thereof.

In another aspect, an anti-CCR8 antibody is provided, wherein the antibody comprises a IgG1 constant domain comprising the amino acid sequence of SEQ ID NO: 53 or SEQ ID NO: 59. In one aspect, the antibody comprises a kappa constant domain comprising the amino acid sequence of SEQ ID NO: 54. In another aspect, an anti-CCR8 antibody is provided, wherein the antibody comprises (a) a IgG1 constant domain comprising the amino acid sequence of SEQ ID NO: 53 or SEQ ID NO: 59, and (b) a kappa constant domain comprising the amino acid sequence of SEQ ID NO: 54.

In another aspect, an anti-CCR8 antibody is provided, wherein the antibody comprises a heavy chain variable domain (VH) comprising (a) CDR-H1 comprising the amino acid sequence of SEQ ID NO: 29 or SEQ ID NO: 30, (b) CDR-H2 comprising the amino acid sequence of SEQ ID NO: 31, and (c) CDR-H3 comprising the amino acid sequence of SEQ ID NO: 32, and a light chain variable domain (VL) comprising (d) CDR-L1 comprising the amino acid sequence of SEQ ID NO: 26, (e) CDR-L2 comprising the amino acid sequence of SEQ ID NO: 27, and (f) CDR-L3 comprising the amino acid sequence of SEQ ID NO: 28. In one aspect, the anti-CCR8 antibody comprises a VH sequence of SEQ ID NO: 47 and a VL sequence of SEQ ID NO: 48.

In one aspect, the anti-CCR8 antibody comprises a heavy chain of SEQ ID NO: 55 and a light chain of SEQ ID NO: 56.

In one aspect, the anti-CCR8 antibody comprises a heavy chain of SEQ ID NO: 60 and a light chain of SEQ ID NO: 56.

In another aspect of any of the above described embodiments, an anti-CCR8 antibody is provided, wherein the heavy chain of the antibody comprises a shortened C-terminus in which one or two of the C terminal amino acid residues have been removed. In one aspect, the C-terminus of the heavy chain is a shortened C-terminus ending PG. In one aspect, the anti-CCR8 antibody comprises a heavy chain of SEQ ID NO: 111 and a light chain of SEQ ID NO: 56. In one aspect, the anti-CCR8 antibody comprises a heavy chain of SEQ ID NO: 113 and a light chain of SEQ ID NO: 56.

In another aspect of any of the above described embodiments, an anti-CCR8 antibody is provided, wherein the antibody does not bind to CCR8 ligands. In one aspect, the anti-CCR8 antibody has no CCR8 ligand blocking activity. In one aspect, the anti-CCR8 antibody is a non-neutralizing antibody. In one aspect, the CCR8 ligand is CCL1.

In another aspect of any of the above described embodiments, an anti-CCR8 antibody is provided, wherein the antibody binds to CCR8 independent of tyrosine sulfation of CCR8 for binding (i.e., sulfation independent).

In another aspect of any of the above described embodiments, an anti-CCR8 antibody is provided, wherein the antibody is an afucosylated antibody variant. In one aspect, the afucosylated antibody variant has enhanced FcγRIIIa receptor binding. In one aspect, the afucosylated anti-CCR8 antibody variant has enhanced antibody-dependent cellular cytotoxicity (ADCC). In one aspect, the anti-CCR8 afucosylated antibody variant has antibody-dependent cellular phagocytosis (ADCP) activities.

In another aspect of any of the above described embodiments, an anti-CCR8 antibody is provided, wherein the antibody has improved antibody stability. In one aspect, the anti-CCR8 antibody has low aggregation, good solubility, and/or low viscosity. In certain aspects of any of the above described embodiments, an anti-CCR8 antibody is provided, wherein the antibody has a $K_D$ of from about from about $1\times10^{-12}$ M to about $1\times10^{-11}$ M. In certain aspects, the antibody that binds to CCR8 has a $K_D$ of about $5\times10^{-12}$ M. In certain aspects, the antibody that binds to CCR8 has a $K_D$ of about $4\times10^{-12}$ M. In certain aspects, the antibody that binds to CCR8 has a $K_D$ of about $3\times10^{-12}$ M.

In one aspect, the anti-CCR8 antibody is named as "hu.Ab5.H13L1" in the present disclosure, which can be fucosylated or afucosylated, which optionally contains one or more heavy chain mutations at G236A and I331E, and which optionally comprises a shortened C-terminus of the heavy chain in which one or two of the C terminal amino acid residues have been removed.

In a further aspect, an anti-CCR8 antibody according to any of the above aspects is a monoclonal antibody, including a chimeric, humanized or human antibody. In one aspect, an anti-CCR8 antibody is an antibody fragment, e.g., a Fv, Fab, Fab', scFv, diabody, or F(ab')₂ fragment.

(ii) Embodiments of Ab4 and Fragments Thereof

In one aspect, the present disclosure provides an anti-CCR8 antibody comprising at least one, at least two, at least three, at least four, at least five, or all six CDRs selected from the group consisting of (a) CDR-H1 comprising the amino acid sequence of SEQ ID NO: 4 or SEQ ID NO: 5, (b) CDR-H2 comprising the amino acid sequence of SEQ ID NO: 6, (c) CDR-H3 comprising the amino acid sequence of SEQ ID NO: 7, (d) CDR-L1 comprising the amino acid sequence of SEQ ID NO: 1, (e) CDR-L2 comprising the amino acid sequence of SEQ ID NO: 2, and (f) CDR-L3 comprising the amino acid sequence of SEQ ID NO: 3. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to both human CCR8 and cyno CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In one aspect, the present disclosure provides an antibody comprising at least one, at least two, or all three VH CDR sequences selected from the group consisting of (a) CDR-H1 comprising the amino acid sequence of SEQ ID NO: 4 or SEQ ID NO: 5, (b) CDR-H2 comprising the amino acid sequence of SEQ ID NO: 6, and (c) CDR-H3 comprising the amino acid sequence of SEQ ID NO: 7. In one aspect, the antibody comprises CDR-H3 comprising the amino acid sequence of SEQ ID NO: 7. In another aspect, the antibody comprises CDR-H3 comprising the amino acid sequence of SEQ ID NO: 7 and CDR-L3 comprising the amino acid sequence of SEQ ID NO: 3. In a further aspect, the antibody comprises CDR-H3 comprising the amino acid sequence of SEQ ID NO: 7, CDR-L3 comprising the amino acid sequence of SEQ ID NO: 3, and CDR-H2 comprising the amino acid sequence of SEQ ID NO: 6. In a further aspect, the antibody comprises (a) CDR-H1 comprising the amino acid sequence of SEQ ID NO: 4 or SEQ ID NO: 5, (b) CDR-H2 comprising the amino acid sequence of SEQ ID NO: 6, and (c) CDR-H3 comprising the amino acid sequence of SEQ ID NO: 7.

In another aspect, the present disclosure provides an antibody comprising at least one, at least two, or all three VL CDR sequences selected from the group consisting of (a) CDR-L1 comprising the amino acid sequence of SEQ ID NO: 1; (b) CDR-L2 comprising the amino acid sequence of SEQ ID NO: 2; and (c) CDR-L3 comprising the amino acid sequence of SEQ ID NO: 3. In one aspect, the antibody comprises (a) CDR-L1 comprising the amino acid sequence of SEQ ID NO: 1; (b) CDR-L2 comprising the amino acid sequence of SEQ ID NO: 2; and (c) CDR-L3 comprising the amino acid sequence of SEQ ID NO: 3.

In another aspect, an antibody as described herein comprises (a) a VH domain comprising at least one, at least two, or all three VH CDR sequences selected from the group consisting of (i) CDR-H1 comprising the amino acid sequence of SEQ ID NO: 4 or SEQ ID NO: 5, (ii) CDR-H2 comprising the amino acid sequence of SEQ ID NO: 6, and (iii) CDR-H3 comprising the amino acid sequence of SEQ ID NO: 7; and (b) a VL domain comprising at least one, at least two, or all three VL CDR sequences selected from the group consisting of (i) CDR-L1 comprising the amino acid sequence of SEQ ID NO: 1; (ii) CDR-L2 comprising the amino acid sequence of SEQ ID NO: 2; and (iii) CDR-L3 comprising the amino acid sequence of SEQ ID NO: 3. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to both human CCR8 and cyno CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In another aspect, the present disclosure provides an antibody comprising (a) CDR-H1 comprising the amino acid sequence of SEQ ID NO: 4 or SEQ ID NO: 5, (b) CDR-H2 comprising the amino acid sequence of SEQ ID NO: 6, and (c) CDR-H3 comprising the amino acid sequence of SEQ ID NO: 7, and a light chain variable domain (VL) comprising (d) CDR-L1 comprising the amino acid sequence of SEQ ID NO: 1, (e) CDR-L2 comprising the amino acid sequence of SEQ ID NO: 2, and (f) CDR-L3 comprising the amino acid sequence of SEQ ID NO: 3.

In another aspect, an anti-CCR8 antibody comprises one or more of the CDR sequences of the VH sequence selected from the group consisting of SEQ ID NOs: 10-21. In another aspect, an anti-CCR8 antibody comprises one or more of the CDR sequences of the VL sequence selected from the group consisting of SEQ ID NOs: 22-25. In another aspect, an anti-CCR8 antibody comprises the CDR sequences of the VH sequence selected from the group consisting of SEQ ID NOs: 10-21 and the CDR sequences of the VL sequence selected from the group consisting of SEQ ID NOs: 22-25.

In another aspect, an anti-CCR8 antibody comprises one or more of the CDR sequences of the VH sequence of SEQ ID NO: 21. In another aspect, an anti-CCR8 antibody comprises one or more of the CDR sequences of the VL sequence of SEQ ID NO: 24. In another aspect, an anti-CCR8 antibody comprises the CDR sequences of the VH sequence of SEQ ID NO: 21. In another aspect, an anti-CCR8 antibody comprises one or more of the CDR sequences of the VL sequence of SEQ ID NO: 24.

In a further aspect, an anti-CCR8 antibody comprises the CDR-H1, CDR-H2 and CDR-H3 amino acid sequences of the VH domain selected from the group consisting of SEQ ID NOs: 10-21 and the CDR-L1, CDR-L2 and CDR-L3 amino acid sequences of the VL domain selected from the group consisting of SEQ ID NOs: 22-25.

In a further aspect, an anti-CCR8 antibody comprises the CDR-H1, CDR-H2 and CDR-H3 amino acid sequences of the VH domain of SEQ ID NO: 21 and the CDR-L1, CDR-L2 and CDR-L3 amino acid sequences of the VL domain of SEQ ID NO: 24.

In one aspect, an anti-CCR8 antibody comprises one or more of the heavy chain CDR amino acid sequences of the VH domain selected from the group consisting of SEQ ID NOs: 10-21 and a framework of at least 85%, 86%, 87%, 88%, 89%, 90%, 91%, 92%, 93%, 94%, 95%, 96%, 97%, 98%, 99% sequence identity to the framework amino acid sequence of the VH domain selected from the group consisting of SEQ ID NOs: 10-21. In one aspect, the anti-CCR8 antibody comprises the three heavy chain CDR amino acid sequences of the VH domain selected from the group consisting of SEQ ID NOs: 10-21 and a framework of at least 85%, 86%, 87%, 88%, 89%, 90%, 91%, 92%, 93%, 94%, 95%, 96%, 97%, 98%, 99% sequence identity to the framework amino acid sequence of the VH domain selected from the group consisting of SEQ ID NOs: 10-21. In one aspect, the anti-CCR8 antibody comprises the three heavy chain CDR amino acid sequences of the VH domain of selected from the group consisting of SEQ ID NOs: 10-21 and a framework of at least 95% sequence identity to the framework amino acid sequence of the VH domain selected from the group consisting of SEQ ID NOs: 10-21. In another aspect, the anti-CCR8 antibody comprises the three heavy chain CDR amino acid sequences of the VH domain of selected from the group consisting of SEQ ID NOs: 10-21 and a framework of at least of at least 98% sequence identity to the framework amino acid sequence of the VH domain of selected from the group consisting of SEQ ID NOs: 10-21.

In one aspect, an anti-CCR8 antibody comprises one or more of the heavy chain CDR amino acid sequences of the VH domain of SEQ ID NO: 21 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 21. In one aspect, the anti-CCR8 antibody comprises the three heavy chain CDR amino acid sequences of the VH domain of SEQ ID NO: 21 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 21. In one aspect, the anti-CCR8 antibody comprises the three heavy chain CDR amino acid sequences of the VH domain of SEQ ID NO: 21 and a framework of at least 95% sequence identity to the framework amino acid sequence of the VH domain of SEQ ID NO: 21. In another aspect, the anti-CCR8 antibody comprises the three heavy chain CDR amino acid sequences of the VH domain of SEQ ID NO: 21 and a framework of at least of at least 98% sequence identity to the framework amino acid sequence of the VH domain of SEQ ID NO: 21.

In one aspect, an anti-CCR8 antibody comprises one or more of the light chain CDR amino acid sequences of the VL domain selected from the group consisting of SEQ ID NOs: 22-25 and a framework of at least 85%, 86%, 87%, 88%, 89%, 90%, 91%, 92%, 93%, 94%, 95%, 96%, 97%, 98%, 99% sequence identity to the framework amino acid sequence of the VL domain selected from the group consisting of SEQ ID NOs: 22-25. In one aspect, the anti-CCR8 antibody comprises the three light chain CDR amino acid sequences of the VL domain selected from the group consisting of SEQ ID NOs: 22-25 and a framework of at least 85%, 86%, 87%, 88%, 89%, 90%, 91%, 92%, 93%, 94%, 95%, 96%, 97%, 98%, 99% sequence identity to the framework amino acid sequence of the VL domain selected from the group consisting of SEQ ID NOs: 22-25. In one aspect, the anti-CCR8 antibody comprises the three light chain CDR amino acid sequences of the VL domain selected from the group consisting of SEQ ID NOs: 22-25 and a framework of at least 95% sequence identity to the framework amino acid sequence of the VL domain selected from the group consisting of SEQ ID NOs: 22-25. In another aspect, the anti-CCR8 antibody comprises the three light chain CDR amino acid sequences of the VL domain selected from the group consisting of SEQ ID NOs: 22-25 and a framework of at least particularly of at least 98% sequence identity to the framework amino acid sequence of the VL domain selected from the group consisting of SEQ ID NOs: 22-25.

In one aspect, an anti-CCR8 antibody comprises one or more of the light chain CDR amino acid sequences of the VL domain of SEQ ID NO: 24 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 24. In one aspect, the anti-CCR8 antibody comprises the three light chain CDR amino acid sequences of the VL domain of SEQ ID NO: 24 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 24. In one aspect, the anti-CCR8 antibody comprises the three light chain CDR amino acid sequences of the VL domain of SEQ ID NO: 24 and a framework of at least 95% sequence identity to the framework amino acid sequence of the VL domain of SEQ ID NO: 24. In another aspect, the anti-CCR8 antibody comprises the three light chain CDR amino acid sequences of the VL domain of SEQ ID NO: 24 and a framework of at least particularly of at least 98% sequence identity to the framework amino acid sequence of the VL domain of SEQ ID NO: 24.

In one aspect, the anti-CCR8 antibody comprises (a) CDR-H1 comprising the amino acid sequence of SEQ ID NO: 4 or SEQ ID NO: 5, (b) CDR-H2 comprising the amino acid sequence of SEQ ID NO: 6, (c) CDR-H3 comprising the amino acid sequence of SEQ ID NO: 7, (d) CDR-L1 comprising the amino acid sequence of SEQ ID NO: 1, (e) CDR-L2 comprising the amino acid sequence of SEQ ID NO: 2, and (f) CDR-L3 comprising the amino acid sequence of SEQ ID NO: 3, and a VH domain having at least 90%, 91%, 92%, 93%, 94%, 95%, 96%, 97%, 98%, 99%, or 100% sequence identity to an amino acid sequence selected from the group consisting of SEQ ID NOs: 10-21, and a VL domain having at least 90%, 91%, 92%, 93%, 94%, 95%, 96%, 97%, 98%, 99%, or 100% sequence identity to an amino acid sequence selected from the group consisting of SEQ ID NOs: 22-25. In one aspect, the VH domain has at least 95% sequence identity to an amino acid sequence selected from the group consisting of SEQ ID NOs: 10-21. In one aspect, the VL domain has at least 95% sequence identity to an amino acid sequence selected from the group consisting of SEQ ID NOs: 22-25. In one aspect, the antibody binds to CCR8 having a dissociation constant ($K_D$) that is up to 10 fold reduced or up to 10 fold increased when compared to the dissociation constant ($K_D$) of an antibody comprising a VH sequence selected from the group consisting of SEQ ID NOs: 10-21 and a VL sequence selected from the group consisting of SEQ ID NOs: 22-25.

In one aspect, the anti-CCR8 antibody comprises (a) CDR-H1 comprising the amino acid sequence of SEQ ID NO: 4 or SEQ ID NO: 5, (b) CDR-H2 comprising the amino acid sequence of SEQ ID NO: 6, (c) CDR-H3 comprising the amino acid sequence of SEQ ID NO: 7, (d) CDR-L1 comprising the amino acid sequence of SEQ ID NO: 1, (e) CDR-L2 comprising the amino acid sequence of SEQ ID NO: 2, and (f) CDR-L3 comprising the amino acid sequence of SEQ ID NO: 3, and a VH domain having at least 90%, 91%, 92%, 93%, 94%, 95%, 96%, 97%, 98%, 99%, or 100% sequence identity to the amino acid sequence of SEQ ID NO: 21, and a VL domain having at least 90%, 91%, 92%, 93%, 94%, 95%, 96%, 97%, 98%, 99%, or 100% sequence identity to the amino acid sequence of SEQ ID NO: 24. In one aspect, the VH domain has at least 950% sequence identity to the amino acid sequence of SEQ ID NO: 21. In one aspect, the VL domain has at least 95% sequence identity to the amino acid sequence of SEQ ID NO: 24. In one aspect, the antibody binds to CCR8 having a dissociation constant ($K_D$) that is up to 10 fold reduced or up to 10 fold increased when compared to the dissociation constant ($K_D$) of an antibody comprising a VH sequence of SEQ ID NO: 21 and a VL sequence of SEQ ID NO: 24.

In another aspect, an anti-CCR8 antibody comprises a heavy chain variable domain (VH) sequence having at least 90%, 91%, 92%, 93%, 94%, 95%, 96%, 97%, 98%, 99%, or 100% sequence identity to an amino acid sequence selected from the group consisting of SEQ ID NOs: 10-21. In one aspect, an anti-CCR8 antibody comprises a heavy chain variable domain (VH) sequence having at least 95%, sequence identity to an amino acid sequence selected from the group consisting of SEQ ID NOs: 10-21. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in an amino acid sequence selected from the group consisting of SEQ ID NOs: 10-21. In certain aspects, substitutions, insertions, or deletions occur in regions outside the CDRs (i.e., in the FRs). Optionally, the anti-CCR8 antibody comprises the VH sequence selected from the group consisting of SEQ ID NOs: 10-21, including post-translational modifications of that sequence. In a particular aspect, the VH comprises one, two or three CDRs selected from: (a) CDR-H1 comprising the amino acid sequence of SEQ ID NO: 4 or SEQ ID NO: 5, (b) CDR-H2 comprising the amino acid sequence of SEQ ID NO: 6, and (c) CDR-H3 comprising the amino acid sequence of SEQ ID NO: 7. In another aspect, an anti-CCR8 antibody is provided, wherein the antibody comprises a light chain variable domain (VL) sequence having at least 90%, 91%, 92%, 93%, 94%, 95%, 96%, 97%, 98%, 99%, or 100% sequence identity to an amino acid sequence selected from the group consisting of SEQ ID NOs: 22-25. In one aspect, an anti-CCR8 antibody comprises a light chain variable domain (VL) sequence having at least 95% sequence identity to an amino acid sequence selected from the group consisting of SEQ ID NOs: 22-25. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence selected from the group consisting of SEQ ID NOs: 22-25. In certain aspects, the substitutions, insertions, or deletions occur in regions outside the CDRs (i.e., in the FRs). Optionally, the anti-CCR8 antibody comprises the VL sequence selected from the group consisting of SEQ ID NOs: 22-25, including post-translational modifications of that sequence. In a particular aspect, the VL comprises one, two or three CDRs selected from: (a) CDR-L1 comprising the amino acid sequence of SEQ ID NO: 1, (b) CDR-L2 comprising the amino acid sequence of SEQ ID NO: 2, and (c) CDR-L3 comprising the amino acid sequence of SEQ ID NO: 3.

In another aspect, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 21. In one aspect, an anti-CCR8 antibody comprises a heavy chain variable domain (VH) sequence having at least 95%, sequence identity to the amino acid sequence of SEQ ID NO: 21. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 21. In certain aspects, substitutions, insertions, or deletions occur in regions outside the CDRs (i.e., in the FRs). Optionally, the anti-CCR8 antibody comprises the VH sequence of SEQ ID NO: 21, including post-translational modifications of that sequence. In a particular aspect, the VH comprises one, two or three CDRs selected from: (a) CDR-H1 comprising the amino acid sequence of SEQ ID NO: 4 or SEQ ID NO: 5, (b) CDR-H2 comprising the amino acid sequence of SEQ ID NO: 6, (c) CDR-H3 comprising the amino acid sequence of SEQ ID NO: 7. In another aspect, an anti-CCR8 antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 24. In one aspect, an anti-CCR8 antibody comprises a light chain variable domain (VL) sequence having at least 95% sequence identity to the amino acid sequence of SEQ ID NO: 24. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 24. In certain aspects, the substitutions, insertions, or deletions occur in regions outside the CDRs (i.e., in the FRs). Optionally, the anti-CCR8 antibody comprises the VL sequence of SEQ ID NO: 24, including post-translational modifications of that sequence. In a particular aspect, the VL comprises one, two or three CDRs selected from: (a) CDR-L1 comprising the amino acid sequence of SEQ ID NO: 1, (b) CDR-L2 comprising the amino acid sequence of SEQ ID NO: 2, and (c) CDR-L3 comprising the amino acid sequence of SEQ ID NO: 3.

In another aspect, an anti-CCR8 antibody is provided, wherein the antibody comprises a VH sequence as in any of the aspects provided above, and a VL sequence as in any of the aspects provided above. In one aspect, the antibody comprises the VH sequence selected from the group consisting of SEQ ID NOs: 10-21 and the VL sequence selected from the group consisting of SEQ ID NOs: 22-25, including post-translational modifications of those sequences. In one aspect, the antibody comprises the VH sequence of SEQ ID NO: 21 and the VL sequence of SEQ ID NO: 24, including post-translational modifications of those sequences.

In one aspect, the VL sequence comprises a Y2I mutation. In one aspect, the VH sequence comprises a S73N mutation, a V78L mutation, a T76N mutation, a F91Y mutation, and a P105Q mutation, or a combination thereof.

In another aspect, an anti-CCR8 antibody is provided, wherein the antibody comprises a IgG1 constant domain comprising the amino acid sequence of SEQ ID NO: 53 or SEQ ID NO: 59. In one aspect, the antibody comprises a kappa constant domain comprising the amino acid sequence of SEQ ID NO: 54. In another aspect, an anti-CCR8 antibody is provided, wherein the antibody comprises (a) a IgG1 constant domain comprising the amino acid sequence of SEQ ID NO: 53 or SEQ ID NO: 59, and (b) a kappa constant domain comprising the amino acid sequence of SEQ ID NO: 54.

In another aspect, an anti-CCR8 antibody is provided, wherein the antibody comprises a heavy chain variable domain (VH) comprising (a) CDR-H1 comprising the amino acid sequence of SEQ ID NO: 4 or SEQ ID NO: 5, (b) CDR-H2 comprising the amino acid sequence of SEQ ID NO: 6, and (c) CDR-H3 comprising the amino acid sequence of SEQ ID NO: 7, and a light chain variable domain (VL) comprising (d) CDR-L1 comprising the amino acid sequence of SEQ ID NO: 1, (e) CDR-L2 comprising the amino acid sequence of SEQ ID NO: 2, and (f) CDR-L3 comprising the amino acid sequence of SEQ ID NO: 3. In one aspect, the anti-CCR8 antibody comprises a VH sequence of SEQ ID NO: 21 and a VL sequence of SEQ ID NO: 24.

In one aspect, the anti-CCR8 antibody comprises a heavy chain of SEQ ID NO: 57, and a light chain of SEQ ID NO: 58.

In one aspect, the anti-CCR8 antibody comprises a heavy chain of SEQ ID NO: 61, and a light chain of SEQ ID NO: 58.

In another aspect of any of the above described embodiments, an anti-CCR8 antibody is provided, wherein the heavy chain of the antibody comprises a shortened C-terminus in which one or two of the C terminal amino acid residues have been removed. In one aspect, the C-terminus of the heavy chain is a shortened C-terminus ending PG. In one aspect, the anti-CCR8 antibody comprises a heavy chain of SEQ ID NO: 112, and a light chain of SEQ ID NO: 58. In one aspect, the anti-CCR8 antibody comprises a heavy chain of SEQ ID NO: 114, and a light chain of SEQ ID NO: 58.

In another aspect of any of the above described embodiments, an anti-CCR8 antibody is provided, wherein the antibody binds to CCR8 ligands. In one aspect, the anti-CCR8 antibody has antagonistic effects against the CCR8 ligand. In one aspect, the anti-CCR8 antibody has CCR8 ligand blocking activity. In one aspect, the anti-CCR8 antibody is a neutralizing antibody. In one aspect, the CCR8 ligand is CCL1.

In another aspect of any of the above described embodiments, an anti-CCR8 antibody is provided, wherein the antibody binds to CCR8 independent of tyrosine sulfation of CCR8 for binding (i.e., sulfation independent).

In another aspect of any of the above described embodiments, an anti-CCR8 antibody is provided, wherein the antibody is an afucosylated antibody variant. In one aspect, the afucosylated antibody variant has enhanced FcγRIIIa receptor binding. In one aspect, the afucosylated anti-CCR8 antibody variant has enhanced antibody-dependent cellular cytotoxicity (ADCC). In one aspect, the anti-CCR8 afucosylated antibody variant has antibody-dependent cellular phagocytosis (ADCP) activities.

In another aspect of any of the above described embodiments, an anti-CCR8 antibody is provided, wherein the antibody has improved antibody stability. In one aspect, the anti-CCR8 antibody has low aggregation, good solubility, and/or low viscosity. In certain aspects of any of the above described embodiments, an anti-CCR8 antibody is provided, wherein the antibody has a $K_D$ of from about from about $1 \times 10^{-11}$ M to about $5 \times 10^{-11}$ M. In certain aspects, the antibody that binds to CCR8 has a $K_D$ of about $2 \times 10^{-11}$ M.

In one aspect, the anti-CCR8 antibody is named as "hu.Ab4.H12L3" in the present disclosure, which can be fucosylated or afucosylated, which optionally contains one or more heavy chain mutations at G236A and I331E, and which optionally comprises a shortened C-terminus of the heavy chain in which one or two of the C terminal amino acid residues have been removed.

In a further aspect, an anti-CCR8 antibody according to any of the above aspects is a monoclonal antibody, including a chimeric, humanized or human antibody. In one aspect, an anti-CCR8 antibody is an antibody fragment, e.g., a Fv, Fab, Fab', scFv, diabody, or F(ab')$_2$ fragment.

(iii) Embodiments of Ab1 and Fragments Thereof

In one aspect, the present disclosure provides an anti-CCR8 antibody comprising at least one, at least two, at least three, at least four, at least five, or all six CDRs selected from the group consisting of (a) CDR-H1 comprising the amino acid sequence of SEQ ID NO: 82 or SEQ ID NO: 83, (b) CDR-H2 comprising the amino acid sequence of SEQ ID NO: 84, (c) CDR-H3 comprising the amino acid sequence of SEQ ID NO: 85, (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 75. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In one aspect, the present disclosure provides an antibody comprising at least one, at least two, or all three VH CDR sequences selected from the group consisting of (a) CDR-H1 comprising the amino acid sequence of SEQ ID NO: 82 or SEQ ID NO: 83, (b) CDR-H2 comprising the amino acid sequence of SEQ ID NO: 84, and (c) CDR-H3 comprising the amino acid sequence of SEQ ID NO: 85. In one aspect, the antibody comprises CDR-H3 comprising the amino acid sequence of SEQ ID NO: 85. In another aspect, the antibody comprises CDR-H3 comprising the amino acid sequence of SEQ ID NO: 85 and CDR-L3 comprising the amino acid sequence of SEQ ID NO: 75. In a further aspect, the antibody comprises CDR-H3 comprising the amino acid sequence of SEQ ID NO: 85, CDR-L3 comprising the amino acid sequence of SEQ ID NO: 75, and CDR-H2 comprising the amino acid sequence of SEQ ID NO: 84. In a further aspect, the antibody comprises (a) CDR-H1 comprising the amino acid sequence of SEQ ID NO: 82 or SEQ ID NO: 83, (b) CDR-H2 comprising the amino acid sequence of SEQ ID NO: 84, and (c) CDR-H3 comprising the amino acid sequence of SEQ ID NO: 85.

In another aspect, the present disclosure provides an antibody comprising at least one, at least two, or all three VL CDR sequences selected from the group consisting of (a) CDR-L1 comprising the amino acid sequence of SEQ ID NO: 73; (b) CDR-L2 comprising the amino acid sequence of SEQ ID NO: 74; and (c) CDR-L3 comprising the amino acid sequence of SEQ ID NO: 75. In one aspect, the antibody comprises (a) CDR-L1 comprising the amino acid sequence of SEQ ID NO: 73; (b) CDR-L2 comprising the amino acid sequence of SEQ ID NO: 74; and (c) CDR-L3 comprising the amino acid sequence of SEQ ID NO: 75.

In another aspect, an antibody as described herein comprises (a) a VH domain comprising at least one, at least two, or all three VH CDR sequences selected from the group consisting of (i) CDR-H1 comprising the amino acid sequence of SEQ ID NO: 82 or SEQ ID NO: 83, (ii) CDR-H2 comprising the amino acid sequence of SEQ ID NO: 84, and (iii) CDR-H3 comprising the amino acid sequence of SEQ ID NO: 85; and (b) a VL domain comprising at least one, at least two, or all three VL CDR sequences selected from the group consisting of (i) CDR-L1 comprising the amino acid sequence of SEQ ID NO: 73; (ii) CDR-L2 comprising the amino acid sequence of SEQ ID NO: 74; and (iii) CDR-L3 comprising the amino acid sequence of SEQ ID NO: 75. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In another aspect, the present disclosure provides an antibody comprising (a) CDR-H1 comprising the amino acid sequence of SEQ ID NO: 82 or SEQ ID NO: 83, (b) CDR-H2 comprising the amino acid sequence of SEQ ID NO: 84, and (c) CDR-H3 comprising the amino acid sequence of SEQ ID NO: 85, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 75.

In another aspect, an anti-CCR8 antibody comprises one or more of the CDR sequences of the VH sequence of SEQ ID NO: 95. In another aspect, an anti-CCR8 antibody comprises one or more of the CDR sequences of the VL sequence of SEQ ID NO: 94. In another aspect, an anti-CCR8 antibody comprises the CDR sequences of the VH sequence of SEQ ID NO: 95. In another aspect, an anti-CCR8 antibody comprises one or more of the CDR sequences of the VL sequence of SEQ ID NO: 94.

In a further aspect, an anti-CCR8 antibody comprises the CDR-H1, CDR-H2 and CDR-H3 amino acid sequences of the VH domain of SEQ ID NO: 95 and the CDR-L1, CDR-L2 and CDR-L3 amino acid sequences of the VL domain of SEQ ID NO: 94.

In one aspect, an anti-CCR8 antibody comprises one or more of the heavy chain CDR amino acid sequences of the VH domain of SEQ ID NO: 95 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 95. In one aspect, the anti-CCR8 antibody comprises the three heavy chain CDR amino acid sequences of the VH domain of SEQ ID NO: 95 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 95. In one aspect, the anti-CCR8 antibody comprises the three heavy chain CDR amino acid sequences of the VH domain of SEQ ID NO: 95 and a framework of at least 95% sequence identity to the framework amino acid sequence of the VH domain of SEQ ID NO: 95. In another aspect, the anti-CCR8 antibody comprises the three heavy chain CDR amino acid sequences of the VH domain of SEQ ID NO: 95 and a framework of at least of at least 98% sequence identity to the framework amino acid sequence of the VH domain of SEQ ID NO: 95.

In one aspect, an anti-CCR8 antibody comprises one or more of the light chain CDR amino acid sequences of the VL domain of SEQ ID NO: 94 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 94. In one aspect, the anti-CCR8 antibody comprises the three light chain CDR amino acid sequences of the VL domain of SEQ ID NO: 94 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 94. In one aspect, the anti-CCR8 antibody comprises the three light chain CDR amino acid sequences of the VL domain of SEQ ID NO: 94 and a framework of at least 95% sequence identity to the framework amino acid sequence of the VL domain of SEQ ID NO: 94. In another aspect, the anti-CCR8 antibody comprises the three light chain CDR amino acid sequences of the VL domain of SEQ ID NO: 94 and a framework of at least particularly of at least 98% sequence identity to the framework amino acid sequence of the VL domain of SEQ ID NO: 94.

In one aspect, the anti-CCR8 antibody comprises (a) CDR-H1 comprising the amino acid sequence of SEQ ID NO: 82 or SEQ ID NO: 83, (b) CDR-H2 comprising the amino acid sequence of SEQ ID NO: 84, (c) CDR-H3 comprising the amino acid sequence of SEQ ID NO: 85, (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 75, and a VH domain having at least 90%, 91%, 92%, 93%, 94%, 95%, 96%, 97%, 98%, 99%, or 100% sequence identity to the amino acid sequence of SEQ ID NO: 95, and a VL domain having at least 90%, 91%, 92%, 93%, 94%, 95%, 96%, 97%, 98%, 99%, or 100% sequence identity to the amino acid sequence of SEQ ID NO: 94. In one aspect, the VH domain has at least 95% sequence identity to the amino acid sequence of SEQ ID NO: 95. In one aspect, the VL domain has at least 95% sequence identity to the amino acid sequence of SEQ ID NO: 94. In one aspect, the antibody binds to CCR8 having a dissociation constant ($K_D$) that is up to 10 fold reduced or up to 10 fold increased when compared to the dissociation constant ($K_D$) of an antibody comprising a VH sequence of SEQ ID NO: 95 and a VL sequence of SEQ ID NO: 94.

In another aspect, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 95. In one aspect, an anti-CCR8 antibody comprises a heavy chain variable domain (VH) sequence having at least 95%, sequence identity to the amino acid sequence of SEQ ID NO: 95. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 95. In certain aspects, substitutions, insertions, or deletions occur in regions outside the CDRs (i.e., in the FRs). Optionally, the anti-CCR8 antibody comprises the VH sequence of SEQ ID NO: 95, including post-translational modifications of that sequence. In a particular aspect, the VH comprises one, two or three CDRs selected from: (a) CDR-H1 comprising the amino acid sequence of SEQ ID NO: 82 or SEQ ID NO: 83, (b) CDR-H2 comprising the amino acid sequence of SEQ ID NO: 84, (c) CDR-H3 comprising the amino acid sequence of SEQ ID NO: 85. In another aspect, an anti-CCR8 antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 94. In one aspect, an anti-CCR8 antibody comprises a light chain variable domain (VL) sequence having at least 95% sequence identity to the amino acid sequence of SEQ ID NO: 94. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 94. In certain aspects, the substitutions, insertions, or deletions occur in regions outside the CDRs (i.e., in the FRs). Optionally, the anti-CCR8 antibody comprises the VL sequence of SEQ ID NO: 94, including post-translational modifications of that sequence. In a particular aspect, the VL comprises one, two or three CDRs selected from: (a) CDR-L1 comprising the amino acid sequence of SEQ ID NO: 73, (b) CDR-L2 comprising the amino acid sequence of SEQ ID NO: 74, and (c) CDR-L3 comprising the amino acid sequence of SEQ ID NO: 75.

In another aspect, an anti-CCR8 antibody is provided, wherein the antibody comprises a VH sequence as in any of the aspects provided above, and a VL sequence as in any of the aspects provided above. In one aspect, the antibody comprises the VH sequence of SEQ ID NO: 95 and the VL sequence of SEQ ID NO: 94, including post-translational modifications of those sequences.

In another aspect, an anti-CCR8 antibody is provided, wherein the antibody comprises a IgG1 constant domain comprising the amino acid sequence of SEQ ID NO: 53 or SEQ ID NO: 59. In one aspect, the antibody comprises a kappa constant domain comprising the amino acid sequence of SEQ ID NO: 54. In another aspect, an anti-CCR8 antibody is provided, wherein the antibody comprises (a) a IgG1 constant domain comprising the amino acid sequence of SEQ ID NO: 53 or SEQ ID NO: 59, and (b) a kappa constant domain comprising the amino acid sequence of SEQ ID NO: 54.

In another aspect, an anti-CCR8 antibody is provided, wherein the antibody comprises a heavy chain variable domain (VH) comprising (a) CDR-H1 comprising the amino acid sequence of SEQ ID NO: 82 or SEQ ID NO: 83, (b) CDR-H2 comprising the amino acid sequence of SEQ ID NO: 84, and (c) CDR-H3 comprising the amino acid sequence of SEQ ID NO: 85, and a light chain variable domain (VL) comprising (d) CDR-L1 comprising the amino acid sequence of SEQ ID NO: 73, (e) CDR-L2 comprising the amino acid sequence of SEQ ID NO: 74, and (f) CDR-L3 comprising the amino acid sequence of SEQ ID NO: 75. In one aspect, the anti-CCR8 antibody comprises a VH sequence of SEQ ID NO: 95 and a VL sequence of SEQ ID NO: 94.

In one aspect, the anti-CCR8 antibody comprises a heavy chain of SEQ ID NO: 101, and a light chain of SEQ ID NO: 100.

In another aspect of any of the above described embodiments, an anti-CCR8 antibody is provided, wherein the heavy chain of the antibody comprises a shortened C-terminus in which one or two of the C terminal amino acid residues have been removed. In one aspect, the C-terminus of the heavy chain is a shortened C-terminus ending PG. In one aspect, the anti-CCR8 antibody comprises a heavy chain of SEQ ID NO: 115, and a light chain of SEQ ID NO: 100.

In one aspect, the anti-CCR8 antibody is named as "hu.Ab1.HIL1" in the present disclosure, which can be fucosylated or afucosylated, which optionally contains one or more heavy chain mutations at G236A and I331E, and which optionally comprises a shortened C-terminus of the heavy chain in which one or two of the C terminal amino acid residues have been removed. In a further aspect, an anti-CCR8 antibody according to any of the above aspects is a monoclonal antibody, including a chimeric, humanized or human antibody. In one aspect, an anti-CCR8 antibody is an antibody fragment, e.g., a Fv, Fab, Fab', scFv, diabody, or F(ab')$_2$ fragment.

(iv) Embodiments of Ab2 and Fragments Thereof

In one aspect, the present disclosure provides an anti-CCR8 antibody comprising at least one, at least two, at least three, at least four, at least five, or all six CDRs selected from the group consisting of (a) CDR-H1 comprising the amino acid sequence of SEQ ID NO: 86 or SEQ ID NO: 87, (b) CDR-H2 comprising the amino acid sequence of SEQ ID NO: 88, (c) CDR-H3 comprising the amino acid sequence of SEQ ID NO: 89, (d) CDR-L1 comprising the amino acid sequence of SEQ ID NO: 76, (e) CDR-L2 comprising the amino acid sequence of SEQ ID NO: 77, and (f) CDR-L3 comprising the amino acid sequence of SEQ ID NO: 78. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In one aspect, the present disclosure provides an antibody comprising at least one, at least two, or all three VH CDR sequences selected from the group consisting of (a) CDR-H1 comprising the amino acid sequence of SEQ ID NO: 86 or SEQ ID NO: 87, (b) CDR-H2 comprising the amino acid sequence of SEQ ID NO: 88, and (c) CDR-H3 comprising the amino acid sequence of SEQ ID NO: 89. In one aspect, the antibody comprises CDR-H3 comprising the amino acid sequence of SEQ ID NO: 89. In another aspect, the antibody comprises CDR-H3 comprising the amino acid sequence of SEQ ID NO: 89 and CDR-L3 comprising the amino acid sequence of SEQ ID NO: 78. In a further aspect, the antibody comprises CDR-H3 comprising the amino acid sequence of SEQ ID NO: 89, CDR-L3 comprising the amino acid sequence of SEQ ID NO: 78, and CDR-H2 comprising the amino acid sequence of SEQ ID NO: 88. In a further aspect, the antibody comprises (a) CDR-H1 comprising the amino acid sequence of SEQ ID NO: 86 or SEQ ID NO: 87, (b) CDR-H2 comprising the amino acid sequence of SEQ ID NO: 88, and (c) CDR-H3 comprising the amino acid sequence of SEQ ID NO: 89.

In another aspect, the present disclosure provides an antibody comprising at least one, at least two, or all three VL CDR sequences selected from the group consisting of (a) CDR-L1 comprising the amino acid sequence of SEQ ID NO: 76; (b) CDR-L2 comprising the amino acid sequence of SEQ ID NO: 77; and (c) CDR-L3 comprising the amino acid sequence of SEQ ID NO: 78. In one aspect, the antibody comprises (a) CDR-L1 comprising the amino acid sequence of SEQ ID NO: 76; (b) CDR-L2 comprising the amino acid sequence of SEQ ID NO: 77; and (c) CDR-L3 comprising the amino acid sequence of SEQ ID NO: 78.

In another aspect, an antibody as described herein comprises (a) a VH domain comprising at least one, at least two, or all three VH CDR sequences selected from the group consisting of (i) CDR-H1 comprising the amino acid sequence of SEQ ID NO: 86 or SEQ ID NO: 87, (ii) CDR-H2 comprising the amino acid sequence of SEQ ID NO: 88, and (iii) CDR-H3 comprising the amino acid sequence of SEQ ID NO: 89; and (b) a VL domain comprising at least one, at least two, or all three VL CDR sequences selected from the group consisting of (i) CDR-L1 comprising the amino acid sequence of SEQ ID NO: 76; (ii) CDR-L2 comprising the amino acid sequence of SEQ ID NO: 77; and (iii) CDR-L3 comprising the amino acid sequence of SEQ ID NO: 78. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In another aspect, the present disclosure provides an antibody comprising (a) CDR-H1 comprising the amino acid sequence of SEQ ID NO: 86 or SEQ ID NO: 87, (b) CDR-H2 comprising the amino acid sequence of SEQ ID NO: 88, and (c) CDR-H3 comprising the amino acid sequence of SEQ ID NO: 89, and a light chain variable domain (VL) comprising (d) CDR-L1 comprising the amino acid sequence of SEQ ID NO: 76, (e) CDR-L2 comprising the amino acid sequence of SEQ ID NO: 77, and (f) CDR-L3 comprising the amino acid sequence of SEQ ID NO: 78.

In another aspect, an anti-CCR8 antibody comprises one or more of the CDR sequences of the VH sequence of SEQ ID NO: 97. In another aspect, an anti-CCR8 antibody comprises one or more of the CDR sequences of the VL sequence of SEQ ID NO: 96. In another aspect, an anti-CCR8 antibody comprises the CDR sequences of the VH sequence of SEQ ID NO: 97. In another aspect, an anti-CCR8 antibody comprises one or more of the CDR sequences of the VL sequence of SEQ ID NO: 96.

In a further aspect, an anti-CCR8 antibody comprises the CDR-H1, CDR-H2 and CDR-H3 amino acid sequences of the VH domain of SEQ ID NO: 97 and the CDR-L1, CDR-L2 and CDR-L3 amino acid sequences of the VL domain of SEQ ID NO: 96.

In one aspect, an anti-CCR8 antibody comprises one or more of the heavy chain CDR amino acid sequences of the VH domain of SEQ ID NO: 97 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 97. In one aspect, the anti-CCR8 antibody comprises the three heavy chain CDR amino acid sequences of the VH domain of SEQ ID NO: 97 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 97.

In one aspect, the anti-CCR8 antibody comprises the three heavy chain CDR amino acid sequences of the VH domain of SEQ ID NO: 97 and a framework of at least 95% sequence identity to the framework amino acid sequence of the VH domain of SEQ ID NO: 97. In another aspect, the anti-CCR8 antibody comprises the three heavy chain CDR amino acid sequences of the VH domain of SEQ ID NO: 97 and a framework of at least of at least 98% sequence identity to the framework amino acid sequence of the VH domain of SEQ ID NO: 97.

In one aspect, an anti-CCR8 antibody comprises one or more of the light chain CDR amino acid sequences of the VL domain of SEQ ID NO: 96 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 96. In one aspect, the anti-CCR8 antibody comprises the three light chain CDR amino acid sequences of the VL domain of SEQ ID NO: 96 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 96. In one aspect, the anti-CCR8 antibody comprises the three light chain CDR amino acid sequences of the VL domain of SEQ ID NO: 96 and a framework of at least 95% sequence identity to the framework amino acid sequence of the VL domain of SEQ ID NO: 96. In another aspect, the anti-CCR8 antibody comprises the three light chain CDR amino acid sequences of the VL domain of SEQ ID NO: 96 and a framework of at least particularly of at least 98% sequence identity to the framework amino acid sequence of the VL domain of SEQ ID NO: 96.

In one aspect, the anti-CCR8 antibody comprises (a) CDR-H1 comprising the amino acid sequence of SEQ ID NO: 86 or SEQ ID NO: 87, (b) CDR-H2 comprising the amino acid sequence of SEQ ID NO: 88, (c) CDR-H3 comprising the amino acid sequence of SEQ ID NO: 89, (d) CDR-L1 comprising the amino acid sequence of SEQ ID NO: 76, (e) CDR-L2 comprising the amino acid sequence of SEQ ID NO: 77, and (f) CDR-L3 comprising the amino acid sequence of SEQ ID NO: 78, and a VH domain having at least 90%, 91%, 92%, 93%, 94%, 95%, 96%, 97%, 98%, 99%, or 100% sequence identity to the amino acid sequence of SEQ ID NO: 97, and a VL domain having at least 90%, 91%, 92%, 93%, 94%, 95%, 96%, 97%, 98%, 99%, or 100% sequence identity to the amino acid sequence of SEQ ID NO: 96. In one aspect, the VH domain has at least 95% sequence identity to the amino acid sequence of SEQ ID NO: 97. In one aspect, the VL domain has at least 95% sequence identity to the amino acid sequence of SEQ ID NO: 96. In one aspect, the antibody binds to CCR8 having a dissociation constant ($K_D$) that is up to 10 fold reduced or up to 10 fold increased when compared to the dissociation constant ($K_D$) of an antibody comprising a VH sequence of SEQ ID NO: 97 and a VL sequence of SEQ ID NO: 96.

In another aspect, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 97. In one aspect, an anti-CCR8 antibody comprises a heavy chain variable domain (VH) sequence having at least 95%, sequence identity to the amino acid sequence of SEQ ID NO: 97. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 97. In certain aspects, substitutions, insertions, or deletions occur in regions outside the CDRs (i.e., in the FRs). Optionally, the anti-CCR8 antibody comprises the VH sequence of SEQ ID NO: 97, including post-translational modifications of that sequence. In a particular aspect, the VH comprises one, two or three CDRs selected from: (a) CDR-H1 comprising the amino acid sequence of SEQ ID NO: 86 or SEQ ID NO: 87, (b) CDR-H2 comprising the amino acid sequence of SEQ ID NO: 88, (c) CDR-H3 comprising the amino acid sequence of SEQ ID NO: 89. In another aspect, an anti-CCR8 antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 96. In one aspect, an anti-CCR8 antibody comprises a light chain variable domain (VL) sequence having at least 95% sequence identity to the amino acid sequence of SEQ ID NO: 96. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 96. In certain aspects, the substitutions, insertions, or deletions occur in regions outside the CDRs (i.e., in the FRs). Optionally, the anti-CCR8 antibody comprises the VL sequence of SEQ ID NO: 96, including post-translational modifications of that sequence. In a particular aspect, the VL comprises one, two or three CDRs selected from: (a) CDR-L1 comprising the amino acid sequence of SEQ ID NO: 76, (b) CDR-L2 comprising the amino acid sequence of SEQ ID NO: 75, and (c) CDR-L3 comprising the amino acid sequence of SEQ ID NO: 78.

In another aspect, an anti-CCR8 antibody is provided, wherein the antibody comprises a VH sequence as in any of the aspects provided above, and a VL sequence as in any of the aspects provided above. In one aspect, the antibody comprises the VH sequence of SEQ ID NO: 97 and the VL sequence of SEQ ID NO: 96, including post-translational modifications of those sequences.

In another aspect, an anti-CCR8 antibody is provided, wherein the antibody comprises a IgG1 constant domain comprising the amino acid sequence of SEQ ID NO: 53 or SEQ ID NO: 59. In one aspect, the antibody comprises a kappa constant domain comprising the amino acid sequence of SEQ ID NO: 54. In another aspect, an anti-CCR8 antibody is provided, wherein the antibody comprises (a) a IgG1 constant domain comprising the amino acid sequence of SEQ ID NO: 53 or SEQ ID NO: 59, and (b) a kappa constant domain comprising the amino acid sequence of SEQ ID NO: 54.

In another aspect, an anti-CCR8 antibody is provided, wherein the antibody comprises a heavy chain variable domain (VH) comprising (a) CDR-H1 comprising the amino acid sequence of SEQ ID NO: 86 or SEQ ID NO: 87, (b) CDR-H2 comprising the amino acid sequence of SEQ ID NO: 88, and (c) CDR-H3 comprising the amino acid sequence of SEQ ID NO: 89, and a light chain variable domain (VL) comprising (d) CDR-L1 comprising the amino acid sequence of SEQ ID NO: 76, (e) CDR-L2 comprising the amino acid sequence of SEQ ID NO: 77, and (f) CDR-L3 comprising the amino acid sequence of SEQ ID NO: 78.

In one aspect, the anti-CCR8 antibody comprises a VH sequence of SEQ ID NO: 97 and a VL sequence of SEQ ID NO: 96.

In one aspect, the anti-CCR8 antibody comprises a heavy chain of SEQ ID NO: 103, and a light chain of SEQ ID NO: 102.

In another aspect of any of the above described embodiments, an anti-CCR8 antibody is provided, wherein the heavy chain of the antibody comprises a shortened C-terminus in which one or two of the C terminal amino acid residues have been removed. In one aspect, the C-terminus of the heavy chain is a shortened C-terminus ending PG. In one aspect, the anti-CCR8 antibody comprises a heavy chain of SEQ ID NO: 116, and a light chain of SEQ ID NO: 102.

In one aspect, the anti-CCR8 antibody is named as "hu.Ab2.H1L1" in the present disclosure, which can be fucosylated or afucosylated, which optionally contains one or more heavy chain mutations at G236A and I331E, and which optionally comprises a shortened C-terminus of the heavy chain in which one or two of the C terminal amino acid residues have been removed In a further aspect, an anti-CCR8 antibody according to any of the above aspects is a monoclonal antibody, including a chimeric, humanized or human antibody. In one aspect, an anti-CCR8 antibody is an antibody fragment, e.g., a Fv, Fab, Fab', scFv, diabody, or F(ab')$_2$ fragment.

(v) Embodiments of Ab3 and Fragments Thereof

In one aspect, the present disclosure provides an anti-CCR8 antibody comprising at least one, at least two, at least three, at least four, at least five, or all six CDRs selected from the group consisting of (a) CDR-H1 comprising the amino acid sequence of SEQ ID NO: 90 or SEQ ID NO: 91, (b) CDR-H2 comprising the amino acid sequence of SEQ ID NO: 92, (c) CDR-H3 comprising the amino acid sequence of SEQ ID NO: 93, (d) CDR-L1 comprising the amino acid sequence of SEQ ID NO: 79, (e) CDR-L2 comprising the amino acid sequence of SEQ ID NO: 80, and (f) CDR-L3 comprising the amino acid sequence of SEQ ID NO: 81. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In one aspect, the present disclosure provides an antibody comprising at least one, at least two, or all three VH CDR sequences selected from the group consisting of (a) CDR-H1 comprising the amino acid sequence of SEQ ID NO: 90 or SEQ ID NO: 91, (b) CDR-H2 comprising the amino acid sequence of SEQ ID NO: 92, and (c) CDR-H3 comprising the amino acid sequence of SEQ ID NO: 93. In one aspect, the antibody comprises CDR-H3 comprising the amino acid sequence of SEQ ID NO: 93. In another aspect, the antibody comprises CDR-H3 comprising the amino acid sequence of SEQ ID NO: 93 and CDR-L3 comprising the amino acid sequence of SEQ ID NO: 81. In a further aspect, the antibody comprises CDR-H3 comprising the amino acid sequence of SEQ ID NO: 93, CDR-L3 comprising the amino acid sequence of SEQ ID NO: 81, and CDR-H2 comprising the amino acid sequence of SEQ ID NO: 92. In a further aspect, the antibody comprises (a) CDR-H1 comprising the amino acid sequence of SEQ ID NO: 90 or SEQ ID NO: 91, (b) CDR-H2 comprising the amino acid sequence of SEQ ID NO: 92, and (c) CDR-H3 comprising the amino acid sequence of SEQ ID NO: 93.

In another aspect, the present disclosure provides an antibody comprising at least one, at least two, or all three VL CDR sequences selected from the group consisting of (a) CDR-L1 comprising the amino acid sequence of SEQ ID NO: 79; (b) CDR-L2 comprising the amino acid sequence of SEQ ID NO: 80; and (c) CDR-L3 comprising the amino acid sequence of SEQ ID NO: 81. In one aspect, the antibody comprises (a) CDR-L1 comprising the amino acid sequence of SEQ ID NO: 79; (b) CDR-L2 comprising the amino acid sequence of SEQ ID NO: 80; and (c) CDR-L3 comprising the amino acid sequence of SEQ ID NO: 81.

In another aspect, an antibody as described herein comprises (a) a VH domain comprising at least one, at least two, or all three VH CDR sequences selected from the group consisting of (i) CDR-H1 comprising the amino acid sequence of SEQ ID NO: 90 or SEQ ID NO: 91, (ii) CDR-H2 comprising the amino acid sequence of SEQ ID NO: 92, and (iii) CDR-H3 comprising the amino acid sequence of SEQ ID NO: 93; and (b) a VL domain comprising at least one, at least two, or all three VL CDR sequences selected from the group consisting of (i) CDR-L1 comprising the amino acid sequence of SEQ ID NO: 79; (ii) CDR-L2 comprising the amino acid sequence of SEQ ID NO: 80; and (iii) CDR-L3 comprising the amino acid sequence of SEQ ID NO: 81. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to human CCR8. In certain aspects, the anti-CCR8 antibody is a full-length antibody which binds to human CCR8 and is a human antibody. In certain aspects, the anti-CCR8 antibody is a full-length antibody which binds to human CCR8 and is a humanized antibody. In certain aspects, the anti-CCR8 antibody is a full-length antibody which binds to human CCR8 and is a chimeric antibody.

In another aspect, the present disclosure provides an antibody comprising (a) CDR-H1 comprising the amino acid sequence of SEQ ID NO: 90 or SEQ ID NO: 91, (b) CDR-H2 comprising the amino acid sequence of SEQ ID NO: 92, and (c) CDR-H3 comprising the amino acid sequence of SEQ ID NO: 93, and a light chain variable domain (VL) comprising (d) CDR-L1 comprising the amino acid sequence of SEQ ID NO: 79, (e) CDR-L2 comprising the amino acid sequence of SEQ ID NO: 80, and (f) CDR-L3 comprising the amino acid sequence of SEQ ID NO: 81.

In another aspect, an anti-CCR8 antibody comprises one or more of the CDR sequences of the VH sequence of SEQ ID NO: 99. In another aspect, an anti-CCR8 antibody comprises one or more of the CDR sequences of the VL sequence of SEQ ID NO: 98. In another aspect, an anti-CCR8 antibody comprises the CDR sequences of the VH sequence of SEQ ID NO: 99. In another aspect, an anti-CCR8 antibody comprises one or more of the CDR sequences of the VL sequence of SEQ ID NO: 98.

In a further aspect, an anti-CCR8 antibody comprises the CDR-H1, CDR-H2 and CDR-H3 amino acid sequences of the VH domain of SEQ ID NO: 99 and the CDR-L1, CDR-L2 and CDR-L3 amino acid sequences of the VL domain of SEQ ID NO: 98.

In one aspect, an anti-CCR8 antibody comprises one or more of the heavy chain CDR amino acid sequences of the VH domain of SEQ ID NO: 99 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 99. In one aspect, the anti-CCR8 antibody comprises the three heavy chain CDR amino acid sequences of the VH domain of SEQ ID NO: 99 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 99. In one aspect, the anti-CCR8 antibody comprises the three heavy chain CDR amino acid sequences of the VH domain of SEQ ID NO: 99 and a framework of at least 95% sequence identity to the framework amino acid sequence of the VH domain of SEQ ID NO: 99. In another aspect, the anti-CCR8 antibody comprises the three heavy chain CDR amino acid sequences of the VH domain of SEQ ID NO: 99 and a framework of at least of at least 98% sequence identity to the framework amino acid sequence of the VH domain of SEQ ID NO: 99.

In one aspect, an anti-CCR8 antibody comprises one or more of the light chain CDR amino acid sequences of the VL domain of SEQ ID NO: 98 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 98. In one aspect, the anti-CCR8 antibody comprises the three light chain CDR amino acid sequences of the VL domain of SEQ ID NO: 98 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 98. In one aspect, the anti-CCR8 antibody comprises the three light chain CDR amino acid sequences of the VL domain of SEQ ID NO: 98 and a framework of at least 95% sequence identity to the framework amino acid sequence of the VL domain of SEQ ID NO: 98. In another aspect, the anti-CCR8 antibody comprises the three light chain CDR amino acid sequences of the VL domain of SEQ ID NO: 98 and a framework of at least particularly of at least 98% sequence identity to the framework amino acid sequence of the VL domain of SEQ ID NO: 98.

In one aspect, the anti-CCR8 antibody comprises (a) CDR-H1 comprising the amino acid sequence of SEQ ID NO: 90 or SEQ ID NO: 91, (b) CDR-H2 comprising the amino acid sequence of SEQ ID NO: 92, (c) CDR-H3 comprising the amino acid sequence of SEQ ID NO: 93, (d) CDR-L1 comprising the amino acid sequence of SEQ ID NO: 79, (e) CDR-L2 comprising the amino acid sequence of SEQ ID NO: 80, and (f) CDR-L3 comprising the amino acid sequence of SEQ ID NO: 81, and a VH domain having at least 90%, 91%, 92%, 93%, 94%, 95%, 96%, 97%, 98%, 99%, or 100% sequence identity to the amino acid sequence of SEQ ID NO: 99, and a VL domain having at least 90%, 91%, 92%, 93%, 94%, 95%, 96%, 97%, 98%, 99%, or 100% sequence identity to the amino acid sequence of SEQ ID NO: 98. In one aspect, the VH domain has at least 95% sequence identity to the amino acid sequence of SEQ ID NO: 99. In one aspect, the VL domain has at least 95% sequence identity to the amino acid sequence of SEQ ID NO: 98. In one aspect, the antibody binds to CCR8 having a dissociation constant ($K_D$) that is up to 10 fold reduced or up to 10 fold increased when compared to the dissociation constant ($K_D$) of an antibody comprising a VH sequence of SEQ ID NO: 99 and a VL sequence of SEQ ID NO: 98.

In another aspect, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 99. In one aspect, an anti-CCR8 antibody comprises a heavy chain variable domain (VH) sequence having at least 95%, sequence identity to the amino acid sequence of SEQ ID NO: 99. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 99. In certain aspects, substitutions, insertions, or deletions occur in regions outside the CDRs (i.e., in the FRs). Optionally, the anti-CCR8 antibody comprises the VH sequence of SEQ ID NO: 99, including post-translational modifications of that sequence. In a particular aspect, the VH comprises one, two or three CDRs selected from: SEQ ID NO: 90 or SEQ ID NO: 91, (b) CDR-H2 comprising the amino acid sequence of SEQ ID NO: 92, (c) CDR-H3 comprising the amino acid sequence of SEQ ID NO: 93. In another aspect, an anti-CCR8 antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 98. In one aspect, an anti-CCR8 antibody comprises a light chain variable domain (VL) sequence having at least 95% sequence identity to the amino acid sequence of SEQ ID NO: 98. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 98. In certain aspects, the substitutions, insertions, or deletions occur in regions outside the CDRs (i.e., in the FRs). Optionally, the anti-CCR8 antibody comprises the VL sequence of SEQ ID NO: 98, including post-translational modifications of that sequence. In a particular aspect, the VL comprises one, two or three CDRs selected from: (a) CDR-L1 comprising the amino acid sequence of SEQ ID NO: 79, (b) CDR-L2 comprising the amino acid sequence of SEQ ID NO: 80, and (c) CDR-L3 comprising the amino acid sequence of SEQ ID NO: 81.

In another aspect, an anti-CCR8 antibody is provided, wherein the antibody comprises a VH sequence as in any of the aspects provided above, and a VL sequence as in any of the aspects provided above. In one aspect, the antibody comprises the VH sequence of SEQ ID NO: 99 and the VL sequence of SEQ ID NO: 98, including post-translational modifications of those sequences.

In another aspect, an anti-CCR8 antibody is provided, wherein the antibody comprises a IgG1 constant domain comprising the amino acid sequence of SEQ ID NO: 53 or SEQ ID NO: 59. In one aspect, the antibody comprises a kappa constant domain comprising the amino acid sequence of SEQ ID NO: 54. In another aspect, an anti-CCR8 antibody is provided, wherein the antibody comprises (a) a IgG1 constant domain comprising the amino acid sequence of SEQ ID NO: 53 or SEQ ID NO: 59, and (b) a kappa constant domain comprising the amino acid sequence of SEQ ID NO: 54.

In another aspect, an anti-CCR8 antibody is provided, wherein the antibody comprises a heavy chain variable domain (VH) comprising (a) CDR-H1 comprising the amino acid sequence of SEQ ID NO: 90 or SEQ ID NO: 91, (b) CDR-H2 comprising the amino acid sequence of SEQ ID NO: 92, and (c) CDR-H3 comprising the amino acid sequence of SEQ ID NO: 93, and a light chain variable domain (VL) comprising (d) CDR-L1 comprising the amino acid sequence of SEQ ID NO: 79, (e) CDR-L2 comprising the amino acid sequence of SEQ ID NO: 80, and (f) CDR-L3 comprising the amino acid sequence of SEQ ID NO: 81. In one aspect, the anti-CCR8 antibody comprises a VH sequence of SEQ ID NO: 99 and a VL sequence of SEQ ID NO: 98.

In one aspect, the anti-CCR8 antibody comprises a heavy chain of SEQ ID NO: 105, and a light chain of SEQ ID NO: 104.

In another aspect of any of the above described embodiments, an anti-CCR8 antibody is provided, wherein the heavy chain of the antibody comprises a shortened C-terminus in which one or two of the C terminal amino acid residues have been removed. In one aspect, the C-terminus of the heavy chain is a shortened C-terminus ending PG. In one aspect, the anti-CCR8 antibody comprises a heavy chain of SEQ ID NO: 117, and a light chain of SEQ ID NO: 104.

In one aspect, the anti-CCR8 antibody is named as "hu.Ab3.H1L1" in the present disclosure, which can be fucosylated or afucosylated, which optionally contains one or more heavy chain mutations at G236A and I331E, and which optionally comprises a shortened C-terminus of the heavy chain in which one or two of the C terminal amino acid residues have been removed.

In a further aspect, an anti-CCR8 antibody according to any of the above aspects is a monoclonal antibody, including a chimeric, humanized or human antibody. In one aspect, an anti-CCR8 antibody is an antibody fragment, e.g., a Fv, Fab, Fab', scFv, diabody, or F(ab')$_2$ fragment.

(vi) Embodiments of a Mouse Surrogate

In one aspect, the present disclosure provides an anti-CCR8 antibody which binds to mouse CCR8, and comprises at least one, at least two, at least three, at least four, at least five, or all six CDRs selected from the group consisting of (a) CDR-H1 comprising the amino acid sequence of SEQ ID NO: 65 or SEQ ID NO: 66, (b) CDR-H2 comprising the amino acid sequence of SEQ ID NO: 67, (c) CDR-H3 comprising the amino acid sequence of SEQ ID NO: 68, (d) CDR-L1 comprising the amino acid sequence of SEQ ID NO: 62, (e) CDR-L2 comprising the amino acid sequence of SEQ ID NO: 63, and (f) CDR-L3 comprising the amino acid sequence of SEQ ID NO: 64. In certain aspects, the anti-CCR8 antibody comprises all six of the aforementioned CDRs. In certain aspects, the anti-CCR8 antibody is a full-length antibody. In certain aspects, the anti-CCR8 antibody is a full-length antibody which binds to mouse CCR8. In certain aspects, the anti-CCR8 antibody is a full-length antibody which binds to mouse CCR8 and is a chimeric antibody (e.g., a rabbit and mouse chimera).

In one aspect, the present disclosure provides an antibody comprising at least one, at least two, or all three VH CDR sequences selected from the group consisting of (a) CDR-H1 comprising the amino acid sequence of SEQ ID NO: 65 or SEQ ID NO: 66, (b) CDR-H2 comprising the amino acid sequence of SEQ ID NO: 67, and (c) CDR-H3 comprising the amino acid sequence of SEQ ID NO: 68. In one aspect, the antibody comprises CDR-H3 comprising the amino acid sequence of SEQ ID NO: 68. In another aspect, the antibody comprises CDR-H3 comprising the amino acid sequence of SEQ ID NO: 68 and CDR-L3 comprising the amino acid sequence of SEQ ID NO: 64. In a further aspect, the antibody comprises CDR-H3 comprising the amino acid sequence of SEQ ID NO: 68, CDR-L3 comprising the amino acid sequence of SEQ ID NO: 64, and CDR-H2 comprising the amino acid sequence of SEQ ID NO: 6. In a further aspect, the antibody comprises (a) CDR-H1 comprising the amino acid sequence of SEQ ID NO: 65 or SEQ ID NO: 66, (b) CDR-H2 comprising the amino acid sequence of SEQ ID NO: 67, and (c) CDR-H3 comprising the amino acid sequence of SEQ ID NO: 68.

In another aspect, the present disclosure provides an antibody comprising at least one, at least two, or all three VL CDR sequences selected from the group consisting of (a) CDR-L1 comprising the amino acid sequence of SEQ ID NO: 62; (b) CDR-L2 comprising the amino acid sequence of SEQ ID NO: 63; and (c) CDR-L3 comprising the amino acid sequence of SEQ ID NO: 64. In one aspect, the antibody comprises (a) CDR-L1 comprising the amino acid sequence of SEQ ID NO: 62; (b) CDR-L2 comprising the amino acid sequence of SEQ ID NO: 63; and (c) CDR-L3 comprising the amino acid sequence of SEQ ID NO: 64.

In another aspect, an antibody as described herein comprises (a) a VH domain comprising at least one, at least two, or all three VH CDR sequences selected from the group consisting of (i) CDR-H1 comprising the amino acid sequence of SEQ ID NO: 65 or SEQ ID NO: 66, (ii) CDR-H2 comprising the amino acid sequence of SEQ ID NO: 67, and (iii) CDR-H3 comprising the amino acid sequence of SEQ ID NO: 68; and (b) a VL domain comprising at least one, at least two, or all three VL CDR sequences selected from the group consisting of (i) CDR-L1 comprising the amino acid sequence of SEQ ID NO: 62; (ii) CDR-L2 comprising the amino acid sequence of SEQ ID NO: 63; and (iii) CDR-L3 comprising the amino acid sequence of SEQ ID NO: 64.

In another aspect, the present disclosure provides an antibody comprising (a) CDR-H1 comprising the amino acid sequence of SEQ ID NO: 65 or SEQ ID NO: 66, (b) CDR-H2 comprising the amino acid sequence of SEQ ID NO: 67, and (c) CDR-H3 comprising the amino acid sequence of SEQ ID NO: 68, and a light chain variable domain (VL) comprising (d) CDR-L1 comprising the amino acid sequence of SEQ ID NO: 62, (e) CDR-L2 comprising the amino acid sequence of SEQ ID NO: 63, and (f) CDR-L3 comprising the amino acid sequence of SEQ ID NO: 64.

In another aspect, an anti-CCR8 antibody comprises one or more of the CDR sequences of the VH sequence of SEQ ID NO: 70. In another aspect, an anti-CCR8 antibody comprises one or more of the CDR sequences of the VL sequence of SEQ ID NO: 69. In another aspect, an anti-CCR8 antibody comprises the CDR sequences of the VH sequence of SEQ ID NO: 70. In another aspect, an anti-CCR8 antibody comprises one or more of the CDR sequences of the VL sequence of SEQ ID NO: 69.

In a further aspect, an anti-CCR8 antibody comprises the CDR-H1, CDR-H2 and CDR-H3 amino acid sequences of the VH domain of SEQ ID NO: 70 and the CDR-L1, CDR-L2 and CDR-L3 amino acid sequences of the VL domain of SEQ ID NO: 69.

In one aspect, an anti-CCR8 antibody comprises one or more of the heavy chain CDR amino acid sequences of the VH domain of SEQ ID NO: 70 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 70. In one aspect, the anti-CCR8 antibody comprises the three heavy chain CDR amino acid sequences of the VH domain of SEQ ID NO: 70 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 70. In one aspect, the anti-CCR8 antibody comprises the three heavy chain CDR amino acid sequences of the VH domain of SEQ ID NO: 70 and a framework of at least 95% sequence identity to the framework amino acid sequence of the VH domain of SEQ ID NO: 70. In another aspect, the anti-CCR8 antibody comprises the three heavy chain CDR amino acid sequences of the VH domain of SEQ ID NO: 70 and a framework of at least of at least 98% sequence identity to the framework amino acid sequence of the VH domain of SEQ ID NO: 70.

In one aspect, an anti-CCR8 antibody comprises one or more of the light chain CDR amino acid sequences of the VL domain of SEQ ID NO: 69 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 69. In one aspect, the anti-CCR8 antibody comprises the three light chain CDR amino acid sequences of the VL domain of SEQ ID NO: 69 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO: 69. In one aspect, the anti-CCR8 antibody comprises the three light chain CDR amino acid sequences of the VL domain of SEQ ID NO: 69 and a framework of at least 95% sequence identity to the framework amino acid sequence of the VL domain of SEQ ID NO: 69. In another aspect, the anti-CCR8 antibody comprises the three light chain CDR amino acid sequences of the VL domain of SEQ ID NO: 69 and a framework of at least particularly of at least 98% sequence identity to the framework amino acid sequence of the VL domain of SEQ ID NO: 69.

In one aspect, the anti-CCR8 antibody comprises (a) CDR-H1 comprising the amino acid sequence of SEQ ID NO: 65 or SEQ ID NO: 66, (b) CDR-H2 comprising the amino acid sequence of SEQ ID NO: 67, (c) CDR-H3 comprising the amino acid sequence of SEQ ID NO: 68, (d) CDR-L1 comprising the amino acid sequence of SEQ ID NO: 62, (e) CDR-L2 comprising the amino acid sequence of SEQ ID NO: 63, and (f) CDR-L3 comprising the amino acid sequence of SEQ ID NO: 64, and a VH domain having at least 90%, 91%, 92%, 93%, 94%, 95%, 96%, 97%, 98%, 99%, or 100% sequence identity to the amino acid sequence of SEQ ID NO: 70, and a VL domain having at least 90%, 91%, 92%, 93%, 94%, 95%, 96%, 97%, 98%, 99%, or 100% sequence identity to the amino acid sequence of SEQ ID NO: 69. In one aspect, the VH domain has at least 95% sequence identity to the amino acid sequence of SEQ ID NO: 70. In one aspect, the VL domain has at least 95% sequence identity to the amino acid sequence of SEQ ID NO: 69. In one aspect, the antibody binds to mouse CCR8 having a dissociation constant ($K_D$) that is up to 10 fold reduced or up to 10 fold increased when compared to the dissociation constant ($K_D$) of an antibody comprising a VH sequence of SEQ ID NO: 70 and a VL sequence of SEQ ID NO: 69.

In another aspect, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 70. In one aspect, an anti-CCR8 antibody comprises a heavy chain variable domain (VH) sequence having at least 95%, sequence identity to the amino acid sequence of SEQ ID NO: 70. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to mouse CCR8. In certain aspects, a total of 1 to 10 amino acids have been substituted, inserted and/or deleted in the amino acid sequence of SEQ ID NO: 70. In certain aspects, substitutions, insertions, or deletions occur in regions outside the CDRs (i.e., in the FRs). Optionally, the anti-CCR8 antibody comprises the VH sequence of SEQ ID NO: 70, including post-translational modifications of that sequence. In a particular aspect, the VH comprises one, two or three CDRs selected from: SEQ ID NO: 65 or SEQ ID NO: 66, (b) CDR-H2 comprising the amino acid sequence of SEQ ID NO: 67, (c) CDR-H3 comprising the amino acid sequence of SEQ ID NO: 68. In another aspect, an anti-CCR8 antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 69. In one aspect, an anti-CCR8 antibody comprises a light chain variable domain (VL) sequence having at least 95% sequence identity to the amino acid sequence of SEQ ID NO: 69. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CCR8 antibody comprising that sequence retains the ability to bind to CCR8. In certain aspects, a total of 1 to 10 amino acids have been substituted, inserted and/or deleted in the amino acid sequence of SEQ ID NO: 69. In certain aspects, the substitutions, insertions, or deletions occur in regions outside the CDRs (i.e., in the FRs). Optionally, the anti-CCR8 antibody comprises the VL sequence of SEQ ID NO: 69, including post-translational modifications of that sequence. In a particular aspect, the VL comprises one, two or three CDRs selected from: (a) CDR-L1 comprising the amino acid sequence of SEQ ID NO: 62, (b) CDR-L2 comprising the amino acid sequence of SEQ ID NO: 63, and (c) CDR-L3 comprising the amino acid sequence of SEQ ID NO: 64.

In another aspect, an anti-CCR8 antibody is provided, wherein the antibody comprises a VH sequence as in any of the aspects provided above, and a VL sequence as in any of the aspects provided above. In one aspect, the antibody comprises the VH sequence of SEQ ID NO: 70 and the VL sequence of SEQ ID NO: 69, including post-translational modifications of those sequences.

In another aspect, an anti-CCR8 antibody is provided which binds to mouse CCR8, wherein the antibody comprises a heavy chain variable domain (VH) comprising (a) CDR-H1 comprising the amino acid sequence of SEQ ID NO: 65 or SEQ ID NO: 66, (b) CDR-H2 comprising the amino acid sequence of SEQ ID NO: 67 and (c) CDR-H3 comprising the amino acid sequence of SEQ ID NO: 68, and a light chain variable domain (VL) comprising (d) CDR-L1 comprising the amino acid sequence of SEQ ID NO: 62, (e) CDR-L2 comprising the amino acid sequence of SEQ ID NO: 63, and (f) CDR-L3 comprising the amino acid sequence of SEQ ID NO: 64. In one aspect, the anti-CCR8 antibody comprises a VH sequence of SEQ ID NO: 70 and a VL sequence of SEQ ID NO: 69.

In one aspect, the anti-CCR8 antibody comprises a heavy chain of SEQ ID NO: 72, and a light chain of SEQ ID NO: 71.

In a further aspect, an anti-CCR8 antibody according to any of the above aspects is a monoclonal antibody, including a chimeric antibody. In one aspect, an anti-CCR8 antibody is an antibody fragment, e.g., a Fv, Fab, Fab', scFv, diabody, or F(ab')₂ fragment.

(vii) Other Embodiments

In a further aspect, an anti-CCR8 antibody according to any of the above aspects may incorporate any of the features, singly or in combination, as described in Sections 1-5 below:
1. Antibody Fragments In certain aspects, an antibody provided herein is an antibody fragment.

In one aspect, the antibody fragment is a Fab, Fab', Fab'-SH, or F(ab')₂ fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. "Fab' fragments" differ from Fab fragments by the addition of residues at the carboxy terminus of the CH1 domain including one or more cysteines from the antibody hinge region. Fab'-SH are Fab' fragments in which the cysteine residue(s) of the constant domains bear a free thiol group. Pepsin treatment yields an F(ab')₂ fragment that has two antigen-binding sites (two Fab fragments) and a part of the Fc region. For discussion of Fab and F(ab')₂ fragments comprising salvage receptor binding epitope residues and having increased in vivo half-life, see U.S. Pat. No. 5,869,046.

In another aspect, the antibody fragment is a diabody, a triabody or a tetrabody. "Diabodies" are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab fragment. A "single chain Fab fragment" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab fragments are stabilized via the natural disulfide bond between the CL domain and the CH1 domain. In addition, these single chain Fab fragments might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as recombinant production by recombinant host cells (e.g., E. coli), as described herein.

2. Chimeric and Humanized Antibodies

In certain aspects, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain aspects, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

3. Human Antibodies

In certain aspects, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating variable domain sequences selected from human-derived phage display libraries. Such variable domain sequences may then be combined with a desired human constant domain. Techniques for selecting human antibodies from antibody libraries are described below.

4. Multispecific Antibodies

In certain aspects, an antibody provided herein is a multispecific antibody, e.g., a bispecific antibody. "Multispecific antibodies" are monoclonal antibodies that have binding specificities for at least two different sites, i.e., different epitopes on different antigens or different epitopes on the same antigen. In certain aspects, the multispecific antibody has three or more binding specificities. In certain aspects, one of the binding specificities is for CCR8 and the other specificity is for any other antigen. In certain aspects, bispecific antibodies may bind to two (or more) different epitopes of CCR8. Multispecific (e.g., bispecific) antibodies may also be used to localize cytotoxic agents or cells to cells which express CCR8. Multispecific antibodies may be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991).

5. Antibody Variants

In certain aspects, amino acid sequence variants of the antibodies provided herein are contemplated. For example, it may be desirable to alter the binding affinity and/or other biological properties of the antibody. Amino acid sequence variants of an antibody may be prepared by introducing appropriate modifications into the nucleotide sequence encoding the antibody, or by peptide synthesis.

Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain aspects, antibody variants having one or more amino acid substitutions are provided. Sites of interest for substitutional mutagenesis include the CDRs and FRs.

In one aspect, the VL sequence of the antibody disclosed herein comprises a V4M mutation, a P43A mutation, a F46L mutation, a C90Q mutation, or a combination thereof. In one aspect, the VH sequence of the antibodies disclosed herein comprises a G49S mutation, a K71R mutation, a S73N mutation, or a combination thereof. In one aspect, the VL sequence of the antibodies disclosed herein comprises a Y2I mutation. In one aspect, the VH sequence of the antibodies disclosed herein comprises a S73N mutation, a V78L mutation, a T76N mutation, a F91Y mutation, and a P105Q mutation, or a combination thereof.

Conservative substitutions are shown in Table 2 under the heading of "conservative substitutions". More substantial changes are provided in Table 2 under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

Contemplated amino acid substitutions

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for a member of another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more. CDR residues are mutated and the variant antibodies displayed on phage and screened for a particular biological activity (e.g., binding affinity).

Alterations (e.g., substitutions) may be made in CDRs, e.g., to improve antibody affinity. Such alterations may be made in CDR "hotspots", i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some aspects of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain aspects, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in the CDRs. Such alterations may, for example, be outside of antigen contacting residues in the CDRs. In certain variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT (antibody directed enzyme prodrug therapy)) or a polypeptide which increases the serum half-life of the antibody.

b) Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody as described herein may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure, and such antibodies are further-referred to herein as an "afucosylated antibodies." In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). In certain embodiments, the proportion of afucosylation is between about 65% to about 100%, between about 80% to about 100%, or between about 80% to about 95%. The percentage of non-fucosylated oligosaccharides is the (average) amount of oligosaccharides lacking fucose residues, relative to the sum of all oligosaccharides attached to Asn 297 (e.g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies, e.g., Asn299. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

In one aspect, the present disclosure provides afucosylated antibody variants that have enhanced FcγRIIIa receptor binding. In one aspect, the present disclosure provides afucosylated antibody variants that have enhanced antibody-dependent cellular cytotoxicity (ADCC). In one aspect, the present disclosure provides afucosylated antibody variants that have antibody-dependent cellular phagocytosis (ADCP) activities.

Examples of cell lines capable of producing antibodies with reduced fucosylation include Lec13 CHO cells deficient in protein fucosylation (Ripka et al. Arch. Biochem. Biophys. 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. Biotech. Bioeng. 87:614-622 (2004); Kanda, Y. et al., Biotechnol. Bioeng., 94(4):680-688 (2006); and WO 2003/085107), or cells with reduced or abolished activity of a GDP-fucose synthesis or transporter protein (see, e.g., US2004259150, US2005031613, US2004132140, US2004110282). See also Pereira et al., MABS (2018) 693-711.

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain aspects, one or more amino acid modifications may be introduced into the Fc region of an antibody provided herein, thereby generating an Fc region variant. The Fc region variant may comprise a human Fc region sequence (e.g., a human $IgG_1$, $IgG_2$, $IgG_3$ or $IgG_4$ Fc region) comprising an amino acid modification (e.g., a substitution) at one or more amino acid positions.

In certain aspects, the invention contemplates an antibody variant that possesses some but not all effector functions, which make it a desirable candidate for applications in which the half-life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g., Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96© non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056).

Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain aspects, an antibody variant comprises an Fc region with one or more amino acid substitutions which improve ADCC, e.g., substitutions at positions 298, 333, and/or 334 of the Fc region (EU numbering of residues).

In certain aspects, an antibody variant comprises an Fc region with one or more amino acid substitutions which diminish FcγR binding, e.g., substitutions at positions 234 and 235 of the Fc region (EU numbering of residues). In one aspect, the substitutions are L234A and L235A (LALA). In certain aspects, the antibody variant further comprises D265A and/or P329G in an Fc region derived from a human IgG$_1$ Fc region. In one aspect, the substitutions are L234A, L235A and P329G (LALA-PG) in an Fc region derived from a human IgG$_1$ Fc region. (See, e.g., WO 2012/130831). In another aspect, the substitutions are L234A, L235A and D265A (LALA-DA) in an Fc region derived from a human IgG$_1$ Fc region.

In certain aspects, an antibody variant comprises an Fc region with one or more amino acid substitutions which improve FcγR binding (and thereby improve effector function), e.g., substitutions at positions. In certain aspects, the antibody variant comprises an Fc region with at least one amino acid substitutions of G236A, I332E, S298A, E333A, K334A, S239D, A330L, F243L, R292P, Y300L, V305I, P396L, L235V, L234Y, L235Q, G236W, S239M, H268D, D270E, K326D, A330M, K334E (See, e.g., Liu et al., *Antibodies (Basel)* (2020); 9(4):64).

In some aspects, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (See, e.g., U.S. Pat. No. 7,371,826; Dall'Acqua, W. F., et al. *J. Biol. Chem.* 281 (2006) 23514-23524).

Fc region residues critical to the mouse Fc-mouse FcRn interaction have been identified by site-directed mutagenesis (see e.g. Dall'Acqua, W. F., et al. *J. Immunol* 169 (2002) 5171-5180). Residues I253, H310, H433, N434, and H435 (EU numbering of residues) are involved in the interaction (Medesan, C., et al., *Eur. J. Immunol.* 26 (1996) 2533; Firan, M., et al., *Int. Immunol.* 13 (2001) 993; Kim, J. K., et al., *Eur. J. Immunol.* 24 (1994) 542). Residues I253, H310, and H435 were found to be critical for the interaction of human Fc with murine FcRn (Kim, J. K., et al., *Eur. J. Immunol.* 29 (1999) 2819). Studies of the human Fc-human FcRn complex have shown that residues I253, S254, H435, and Y436 are crucial for the interaction (Firan, M., et al., *Int. Immunol.* 13 (2001) 993; Shields, R. L., et al., *J. Biol. Chem.* 276 (2001) 6591-6604). In Yeung, Y. A., et al. (*J. Immunol.* 182 (2009) 7667-7671) various mutants of residues 248 to 259 and 301 to 317 and 376 to 382 and 424 to 437 have been reported and examined.

In certain aspects, an antibody variant comprises an Fc region with one or more amino acid substitutions, which reduce FcRn binding, e.g., substitutions at positions 253, and/or 310, and/or 435 of the Fc-region (EU numbering of residues). In certain aspects, the antibody variant comprises an Fc region with the amino acid substitutions at positions 253, 310 and 435. In one aspect, the substitutions are I253A, H310A and H435A in an Fc region derived from a human IgG1 Fc-region. See, e.g., Grevys, A., et al., J. Immunol. 194 (2015) 5497-5508.

In certain aspects, an antibody variant comprises an Fc region with one or more amino acid substitutions, which reduce FcRn binding, e.g., substitutions at positions 310, and/or 433, and/or 436 of the Fc region (EU numbering of residues). In certain aspects, the antibody variant comprises an Fc region with the amino acid substitutions at positions 310, 433 and 436. In one aspect, the substitutions are H310A, H433A and Y436A in an Fc region derived from a human IgG1 Fc-region. (See, e.g., WO 2014/177460 A1).

In certain aspects, an antibody variant comprises an Fc region with one or more amino acid substitutions which increase FcRn binding, e.g., substitutions at positions 252, and/or 254, and/or 256 of the Fc region (EU numbering of residues). In certain aspects, the antibody variant comprises an Fc region with amino acid substitutions at positions 252, 254, and 256. In one aspect, the substitutions are M252Y, S254T and T256E in an Fc region derived from a human IgG$_1$ Fc-region. See also Duncan & Winter, *Nature* 322:738-40 (1988); U.S. Pat. Nos. 5,648,260; 5,624,821; and WO 94/29351 concerning other examples of Fc region variants.

The C-terminus of the heavy chain of the antibody as reported herein can be a complete C-terminus ending with the amino acid residues PGK. The C-terminus of the heavy chain can be a shortened C-terminus in which one or two of the C terminal amino acid residues have been removed. In one aspect, the C-terminus of the heavy chain is a shortened C-terminus ending PG. In one aspect of all aspects as reported herein, an antibody comprising a heavy chain including a C-terminal CH3 domain as specified herein, comprises the C-terminal glycine-lysine dipeptide (G446 and K447, EU index numbering of amino acid positions). In one aspect of all aspects as reported herein, an antibody comprising a heavy chain including a C-terminal CH3 domain, as specified herein, comprises a C-terminal glycine residue (G446, EU index numbering of amino acid positions). In one aspect of all aspects as reported herein, an antibody comprising a heavy chain including a C-terminal CH3 domain, as specified herein, comprises a C-terminal proline residue (P445, EU index numbering of amino acid positions).

d) Cysteine Engineered Antibody Variants

In certain aspects, it may be desirable to create cysteine engineered antibodies, e.g., THIOMAB™ antibodies, in which one or more residues of an antibody are substituted with cysteine residues. In particular aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

e) Antibody Derivatives

In certain aspects, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

B. Recombinant Methods and Compositions

Antibodies may be produced using recombinant methods and compositions, e.g., as described in U.S. Pat. No. 4,816,567. For these methods one or more isolated nucleic acid(s) encoding an antibody are provided.

In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors.

In case of a bispecific antibody with heterodimeric heavy chains four nucleic acids are required, one for the first light chain, one for the first heavy chain comprising the first heteromonomeric Fc-region polypeptide, one for the second light chain, and one for the second heavy chain comprising the second heteromonomeric Fc-region polypeptide. The four nucleic acids can be comprised in one or more nucleic acid molecules or expression vectors. Such nucleic acid(s) encode an amino acid sequence comprising the first VL and/or an amino acid sequence comprising the first VH including the first heteromonomeric Fc-region and/or an amino acid sequence comprising the second VL and/or an amino acid sequence comprising the second VH including the second heteromonomeric Fc-region of the antibody (e.g., the first and/or second light and/or the first and/or second heavy chains of the antibody). These nucleic acids can be on the same expression vector or on different expression vectors, normally these nucleic acids are located on two or three expression vectors, i.e. one vector can comprise more than one of these nucleic acids. Examples of these bispecific antibodies are CrossMabs (see, e.g., Schaefer, W. et al, PNAS, 108 (2011) 11187-1191). For example, one of the heteromonomeric heavy chain comprises the so-called "knob mutations" (T366W and optionally one of S354C or Y349C) and the other comprises the so-called "hole mutations" (T366S, L368A and Y407V and optionally Y349C or S354C) (see, e.g., Carter, P. et al., Immunotechnol. 2 (1996) 73) according to EU index numbering.

In one aspect, isolated nucleic acids encoding an antibody as used in the methods as reported herein are provided.

In one aspect, a method of making an anti-CCR8 antibody is provided, wherein the method comprises culturing a host cell comprising nucleic acid(s) encoding the antibody, as provided above, under conditions suitable for expression of the antibody, and optionally recovering the antibody from the host cell (or host cell culture medium).

For recombinant production of an anti-CCR8 antibody, nucleic acids encoding the antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gemgross, T. U., Nat. Biotech. 22 (2004) 1409-1414; and Li, H. et al., Nat. Biotech. 24 (2006) 210-215.

Suitable host cells for the expression of (glycosylated) antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (WI38); human liver cells (Hep G2); mouse mammary tumor (MMT 060562); TRI cells (as described, e.g., in Mather, J. P. et al., Annals NY Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

In one aspect, the host cell is eukaryotic, e.g., a Chinese Hamster Ovary (CHO) cell or lymphoid cell (e.g., Y0, NS0, Sp20 cell).

C. Assays

Anti-CCR8 antibodies provided herein may be identified, screened for, or characterized for their physical/chemical properties and/or biological activities by various assays known in the art.

1. Binding Assays and Other Assays

In one aspect, an antibody as described herein is tested for its antigen binding activity, e.g., by known methods such as ELISA, Western blot, etc.

In another aspect, competition assays may be used to identify an antibody that competes with an anti-CCR8 antibody of the presently disclosed subject matter, e.g., Ab1, Ab2, Ab3, Ab4, and Ab5, for binding to CCR8. In certain aspects, such a competing antibody binds to the same epitope (e.g., a linear or a conformational epitope) that is bound by an anti-CCR8 antibody of the presently disclosed subject matter, e.g., Ab1, Ab2, Ab3, Ab4, and Ab5. Detailed exemplary methods for mapping an epitope to which an antibody binds are provided in Moms (1996) "Epitope Mapping Protocols", in *Methods in Molecular Biology* vol. 66 (Humana Press, Totowa, NJ).

In an exemplary competition assay, immobilized CCR8 is incubated in a solution comprising a first labeled antibody that binds to CCR8 (e.g., an anti-CCR8 antibody of the presently disclosed subject matter, e.g., Ab1, Ab2, Ab3, Ab4, and Ab5) and a second unlabeled antibody that is being tested for its ability to compete with the first antibody for binding to CCR8. The second antibody may be present in a hybridoma supernatant. As a control, immobilized CCR8 is incubated in a solution comprising the first labeled antibody but not the second unlabeled antibody. After incubation under conditions permissive for binding of the first antibody to CCR8, excess unbound antibody is removed, and the amount of label associated with immobilized CCR8 is measured. If the amount of label associated with immobilized CCR8 is substantially reduced in the test sample relative to the control sample, then that indicates that the second antibody is competing with the first antibody for binding to CCR8. See Harlow and Lane (1988) *Antibodies: A Laboratory Manual* ch. 14 (Cold Spring Harbor Laboratory, Cold Spring Harbor, NY).

2. Activity Assays

In one aspect, assays are provided for identifying anti-CCR8 antibodies thereof having biological activity. Biological activity may include, e.g., antibody-dependent cellular cytotoxicity (ADCC), ADCC against Tregs, antibody-dependent cellular phagocytosis (ADCP), depletion of Tregs. Antibodies having such biological activity in vivo and/or in vitro are also provided.

In certain aspects, an anti-CCR8 antibody as described herein is tested for measuring ADCC of the antibody. ADCC assays are performed as previously reported in Kamen, L., et al., *Development of a kinetic antibody-dependent cellular cytotoxicity assay*. J. Immunol Methods, 2019. 468: p. 49-54, and Schnueriger, A., et al., *Development of a quantitative, cell-line based assay to measure ADCC activity mediated by therapeutic antibodies*. Mol Immunol, 2011. 48(12-13): p. 1512-17, with some modifications, using CD16 engineered NK-92_F158 as effector cells and CHO cells that stably express human CCR8 and Ga 15 subunit (CHO/hCCR8.Gna15) as target cells. Briefly, lysis of target cells by ADCC is measured by the calcein release method. The target cells are labeled with Calcein-AM, then washed and plated onto 384-well plates at a density of 3000 cells/well. Anti-CCR8 antibody is added at various concentrations from 0.004 to 1 µg/mL, followed by the addition of NK-92_F158 cells at an effector:target (E:T) ratio of 10:1. The plates are then incubated for 2.5 hours at 37° C. After incubation, the plates are centrifuged at 200×g for 3 minutes, the supernatants are transferred to a white opaque 384-well microplate, and fluorescent signals are measured in relative fluorescence units (RFU). Signals from the wells containing only the target cells represent spontaneous release of the calcein from labeled cells (spontaneous release), whereas wells containing target cells lysed with Triton X-100 provide the maximal signal available (maximal release). Antibody-independent cell-mediated cytotoxicity (AICC) are measured in wells containing target and effector cells without the addition of the antibody. Samples and controls are tested at least in duplicate in the same plates. The extent of specific ADCC activity is calculated as follows:

% ADCC=100×(mean experimental release-mean AICC)/(mean maximum release-mean spontaneous release)

The ADCC activity is plotted as a function of antibody concentrations and the data are fitted to an asymmetric sigmoidal four-parameter logistic (4PL) model.

In certain aspects, an anti-CCR8 antibody as described herein is tested for measuring ADCC against Treg cells. To induce CCR8 expression on T cells from human peripheral blood mononuclear cells (PBMC), 107 human PBMC are intraperitoneally transferred to NOD.Cg-Prkd$^{scid}$ Il2rg$^{tm1Wjl}$/SzJ (NSG) mice (JAX) and spleens are collected 2-3 weeks post-transfer. Human T cells are enriched from single cell suspensions of NSG splenocytes and primary NK cells are enriched from human PBMC. Human T cells are incubated with 0.001-1 µg/mL anti-CCR8 antibody for 30 minutes at room temperature prior to the addition of primary NK cells at an effector:target ratio of 2:1. After overnight incubation at 37° C., cells are collected, surface stained, and intracellularly stained. Antibodies used to define T cell populations are CD45 (H130), CD3 (SK7), CD8 (RPA-T8), and CD14 (63D3), CD4 (RPA-T4), and FOXP3 (236A/E7). CountBright Absolute Counting Beads is added to each sample prior to acquisition. Flow cytometry is performed. Absolute cell counts are calculated. ADCC activity against Treg cells is measured by calculating the ratio of recovered Treg cells to recovered CD8 cells (Treg/CD8) or conventional CD4 T cells to recovered CD8 T cells (CD4conv/CD8).

In certain aspects, an anti-CCR8 antibody as described herein is tested for measuring its binding to regulatory T cells (Treg cells or Tregs) by Fluorescence-Activated Cell Sorting (FACS) flow cytometry. Human colorectal dissociated tumor cells (DTC) are thawed. Cells are surface stained with eFluor 780-conjugated Fixable Viability Dye and 2 ug/mL mAb specific for CCR8, OX40 (positive control), Herceptin (negative control), or anti-hIgG (negative control) for 20 min at 4° C. followed by secondary detection with AF647-conjugated AffiniPure F(ab')2 Fragment Goat anti-Human IgG, Fcg fragment-specific for 10 min at 4° C. Cells are then intracellularly stained. Antibodies used to define T cell populations are CD45 (H130), CD3 (SK7), CD8 (RPA-T8), and CD14 (63D3) from BD Biosciences, CD4 (RPA-T4), and FOXP3 (236A/E7). Flow cytometry is performed and analyzed.

In certain aspects, an anti-CCR8 antibody as described herein is tested for measuring ADCP of the antibody. Human $CD14_+$ monocytes are first isolated from blood of donors with known FcgRIIa and FcgRIIIa genotype information. The purified CD14+ monocytes are differentiated into macrophages. Then 50 ng/mL of hIL-10 are added to polarize the macrophages for 24 hours prior to ADCP assay. NucLight Red transfected CHO/hCCR8.Gna15 target cells are pre-incubated with anti-CCR8 antibodies for 20 minutes in the presence of 20 mg/mL of non-specific human IgG. Then the above cell mixtures are added to the macrophage (effector cell) plate at an E:T ratio of 1:1. Cell images are obtained with bright field and red laser settings every one hour for a period of 6 hours. The red cell count in each well (remaining target cells) is normalized by the macrophage numbers. The ADCP activity is calculated as the percentage of decrease of the normalized red cell count in each sample compared to the negative control where isotype control antibody is present. Then the ADCP activity is plotted as a function of antibody concentrations and the data are fitted to an asymmetric sigmoidal four-parameter logistic (4PL) model. The $EC_{50}$ value for each antibody is determined as the concentration reaching 50% target cell killing.

In certain aspects, an anti-CCR8 antibody (e.g., a mouse surrogate antibody) as described herein is tested for measuring depletion of Treg cells in vivo, mice with established tumors are treated with an anti-CCR8 antibody (e.g., a mouse surrogate antibody disclosed herein) and the proportion of Treg cells, conventional CD4 T cells and CD8 T cells among leukocytes in tumors, spleen and tumor-draining lymph nodes are analyzed. To this end, tumor cells are harvested in log-phase growth and resuspended in HBSS containing matrigel at a 1:1 ratio. Mice are inoculated subcutaneously in the flank with 0.1 million tumor cells in 100 microliters of HBSS+ matrigel. Tumors are monitored until they became established and reached a mean tumor volume 130-230 mm$^3$. Mice are then randomized into treatment groups. Treatment with an anti-CCR8 or an anti-gp120 isotype control Ab is administered intravenously. Three days later mice are sacrificed and tumors, spleens and tumor-draining lymph nodes obtained for analysis. To generate single cell suspensions, tumors are minced and digested. Single cell suspensions are surface stained with fluorescently labelled anti-CD45, anti-CD4 and anti-CD8 antibodies and intracellularly stained with fluorescently labelled anti-Foxp3 antibody. Flow cytometry may be performed on a Fortessa X-20 or FACSymphony and analyzed with FlowJo software.

In certain aspects, an anti-CCR8 antibody (e.g., a mouse surrogate antibody) as described herein is tested for tumor growth inhibition following anti-CCR8-mediated depletion of tumor-infiltrating Treg cells in vivo. Mice with established tumors are treated with a mouse surrogate anti-CCR8 antibody and are monitored for tumor growth over time.

D. Methods and Compositions for Diagnostics and Detection

In certain aspects, any of the anti-CCR8 antibodies provided herein is useful for detecting the presence of CCR8 in a biological sample. The term "detecting" as used herein encompasses quantitative or qualitative detection. In certain aspects, a biological sample comprises a cell or tissue, such as tumor.

In one aspect, an anti-CCR8 antibody for use in a method of diagnosis or detection is provided. In a further aspect, a method of detecting the presence of CCR8 in a biological sample is provided. In certain aspects, the method comprises contacting the biological sample with an anti-CCR8 antibody as described herein under conditions permissive for binding of the anti-CCR8 antibody to CCR8, and detecting whether a complex is formed between the anti-CCR8 antibody and CCR8. Such method may be an in vitro or in vivo method. In one aspect, an anti-CCR8 antibody is used to select subjects eligible for therapy with an anti-CCR8 antibody, e.g., where CCR8 is a biomarker for selection of subjects.

In certain aspects, labeled anti-CCR8 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}O$, $^{14}C$, $^{125}I$, $^3H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, 0-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Compositions

In a further aspect, provided are pharmaceutical compositions comprising any of the antibodies provided herein, e.g., for use in any of the below therapeutic methods. In one aspect, a pharmaceutical composition comprises any of the antibodies provided herein and a pharmaceutically acceptable carrier. In another aspect, a pharmaceutical composition comprises any of the antibodies provided herein and at least one additional therapeutic agent, e.g., as described below.

Pharmaceutical compositions (formulations) of an anti-CCR8 antibody as described herein can be prepared by combining the antibody with pharmaceutically acceptable carriers or excipients known to the skilled person. See, for example *Remington's Pharmaceutical Sciences* 16th edition, Osol, A. Ed. (1980), Shire S., *Monoclonal Antibodies: Meeting the Challenges in Manufacturing, Formulation, Delivery and Stability of Final Drug Product*, 1$^{st}$ Ed., Woodhead Publishing (2015), § 4 and Falconer R. J., Biotechnology Advances (2019), 37, 107412. Exemplary pharmaceutical compositions of an anti-CCR8 antibody as described herein are lyophilized, aqueous, frozen, etc.

Pharmaceutically acceptable carriers are generally non-toxic to recipients at the dosages and concentrations employed, and include, but are not limited to: buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol;

alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

The pharmaceutical composition herein may also contain more than one active ingredients as necessary for the particular indication being treated, preferably those with complementary activities that do not adversely affect each other. For example, it may be desirable to further provide an additional therapeutic agent useful for treatment of the same disease. Such active ingredients are suitably present in combination in amounts that are effective for the purpose intended.

The pharmaceutical compositions to be used for in vivo administration are generally sterile. Sterility may be readily accomplished, e.g., by filtration through sterile filtration membranes.

F. Therapeutic Methods and Routes of Administration

Any of the anti-CCR8 antibodies provided herein may be used in therapeutic methods.

In one aspect, an anti-CCR8 antibody for use as a medicament is provided. In further aspects, an anti-CCR8 antibody for use in treating cancer is provided. In certain aspects, an anti-CCR8 antibody for use in a method of treatment is provided. In certain aspects, the present disclosure provides an anti-CCR8 antibody for use in a method of treating a subject (e.g., a human subject) in need thereof comprising administering to the subject an effective amount of the anti-CCR8 antibody. In one such aspect, the method further comprises administering to the subject an effective amount of at least one additional therapeutic agent (e.g., one, two, three, four, five, or six additional therapeutic agents), e.g., as described below. In further aspects, the present disclosure provides an anti-CCR8 antibody for use in depleting Regulatory T cells ("Tregs") in a tumor microenvironment. In certain aspects, the present disclosure provides an anti-CCR8 antibody for use in a method of depleting Tregs in a tumor microenvironment in a subject comprising administering to the subject an effective amount of the anti-CCR8 antibody in depletion of Tregs in the tumor microenvironment.

In a further aspect, the present disclosure provides for the use of an anti-CCR8 antibody in the manufacture or preparation of a medicament. In one aspect, the medicament is for treatment of cancer. In a further aspect, the medicament is for use in a method of treating cancer comprising administering to the subject (e.g., a human subject) in need thereof an effective amount of the medicament. In one such aspect, the method further comprises administering to the subject an effective amount of at least one additional therapeutic agent, e.g., as described below. In a further aspect, the medicament is for depleting Tregs in a tumor microenvironment. In a further aspect, the medicament is for use in a method of depleting Tregs in a tumor microenvironment in a subject comprising administering to the subject an effective amount of the medicament to deplete the Tregs in the tumor microenvironment.

In a further aspect, the present disclosure provides a method for treating cancer. In one aspect, the method comprises administering to a subject (e.g., a human subject) in need thereof an effective amount of an anti-CCR8 antibody in order to treat the cancer. In one such aspect, the method further comprises administering to the subject an effective amount of at least one additional therapeutic agent, as described below.

In a further aspect, the present disclosure provides an anti-CCR8 antibody for use in depleting Treg cells, e.g., outside or in a tumor microenvironment. For example, in certain embodiments, the present disclosure provides a method for depleting Treg cells in a tumor microenvironment in a subject (e.g., a human subject) in need thereof having cancer comprising administering to the subject an effective amount of an anti-CCR8 antibody sufficient to deplete the Treg cells in the tumor microenvironment, thereby treating the cancer. In certain aspects, the present disclosure provides a method for depleting Treg cells outside of a tumor microenvionment (e.g., in circulation) in a subject (e.g., a human subject) in need thereof having cancer comprising administering to the subject an effective amount of an anti-CCR8 antibody sufficient to deplete the Treg cells outside the tumor microenvironment, thereby treating the cancer. Without wishing to be bound by any particular theory, by reducing the number of Treg cells outside the tumor microenvironment, the cancer is treated as the number of Treg cells infiltrating into the tumor microenvironment is reduced, thereby reducing the number of Treg cells in the tumor microenvironment.

Exemplary cancers includes, but is not limited to, bladder cancer (e.g., urothelial cancer), blastoma, blood cancer (e.g., lymphomas such as Non-Hodgkin's, leukemias), bone cancer, brain cancer, breast cancer (e.g., triple negative breast cancer), cervical cancer, colorectal cancer (e.g., colon cancer, rectal cancer), endometrial cancer, esophageal cancer, gastric cancer, head and neck cancer (e.g., squamous cell carcinoma of the head and neck), kidney cancer (e.g., renal cell carcinoma), liver cancer (e.g., hepatocellular carcinoma), lung cancer (e.g., non-small cell lung cancer, small cell lung carcinoma), ovarian cancer, pancreatic cancer, prostate cancer, sarcoma, skin cancer (e.g., melanoma, squamous cell carcinoma), testicular cancer, and uterine cancer.

In certain aspects, the cancer is bladder cancer, blood cancer, breast cancer, cervical cancer, colorectal cancer, esophageal cancer, gastric cancer, head and neck cancer, kidney cancer, liver cancer, lung cancer, and skin cancer.

In certain aspects, the cancer is bladder cancer, breast cancer, cervical cancer, colorectal cancer, esophageal cancer, head and neck cancer, liver cancer, lung cancer, or skin cancer.

In certain aspects, the cancer is a solid tumor.

In certain aspects, the cancer expresses CCR8.

In certain aspects, the cancer is a T cell-inflamed tumor or comprises a T-cell-inflamed tumor microenvironment.

In certain aspects, the cancer comprises regulatory T cells in the tumor microenvironment, and for which exposure of the cancer to the CCR8 antibody, as described herein, results in depletion of the regulatory T cell in the tumor microenvironment. In a further aspect, the present disclosure provides pharmaceutical compositions comprising any of the anti-CCR8 antibodies described herein, e.g., for use in any of the above therapeutic methods. In one aspect, a pharmaceutical composition comprises any of the anti-CCR8 antibodies provided herein and a pharmaceutically acceptable carrier. In another aspect, a pharmaceutical composition comprises any of the anti-CCR8 antibodies provided herein and at least one additional therapeutic agent, e.g., as described below.

Antibodies as described herein can be administered alone or used in a combination therapy, e.g., useful in treating cancer. For instance, the combination therapy includes administering an antibody as described herein and administering at least one additional therapeutic agent (e.g. one, two, three, four, five, or six additional therapeutic agents).

The at least one additional therapeutic agent encompasses any agent that can be administered for treatment. In certain aspects, the additional therapeutic agent is an additional anti-cancer agent. Exemplary anti-cancer agents include, but are not limited to, a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, antiangiogenic agent, an immunomodulatory agent, an inhibitor of cell adhesion, a cytotoxic or cytostatic agent, an activator of cell apoptosis, an agent that increases the sensitivity of cells to apoptotic inducers, a cytokine, an anti-cancer vaccine or oncolytic virus, a toll-like receptor (TLR) agent, a bispecific antibody, a cellular therapy, and immune cell engager. In certain aspects, the additional therapeutic agent is an immunomodulatory anti-cancer agent, e.g., a checkpoint inhibitor (CPI) such as an anti-CTLA4 antibody (e.g. ipilimumab), a PD-L1 binding antagonist, or a PD-1 binding antagonist The term "PD-L1 binding antagonist" refers to a molecule that decreases, blocks, inhibits, abrogates, or interferes with signal transduction resulting from the interaction of PD-L1 with either one or more of its binding partners, such as PD-1 and/or B7-1. In some instances, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some instances, the PD-L1 binding antagonists include anti-PD-L1 antibodies, antigen-binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1 and/or B7-1. In one instance, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some instances, the PD-L1 binding antagonist binds to PD-L1. In some instances, a PD-L1 binding antagonist is an anti-PD-L1 antibody (e.g., an anti-PD-L1 antagonist antibody). Exemplary anti-PD-L1 antagonist antibodies include atezolizumab, MDX-1105, MEDI4736 (durvalumab), MSB0010718C (avelumab), SHR-1316, CS1001, envafolimab, TQB2450, ZKAB001, LP-002, CX-072, IMC-001, KL-A167, APL-502, cosibelimab, lodapolimab, FAZ053, TG-1501, BGB-A333, BCD-135, AK-106, LDP, GR1405, HLX20, MSB2311, RC98, PDL-GEX, KD036, KY1003, YBL-007, and HS-636. In some aspects, the anti-PD-L1 antibody is atezolizumab, MDX-1105, MEDI4736 (durvalumab), or MSB0010718C (avelumab). In one specific aspect, the PD-L1 binding antagonist is MDX-1105. In another specific aspect, the PD-L1 binding antagonist is MEDI4736 (durvalumab). In another specific aspect, the PD-L1 binding antagonist is MSB0010718C (avelumab). In other aspects, the PD-L1 binding antagonist may be a small molecule, e.g., GS-4224, INCB086550, MAX-10181, INCB090244, CA-170, or ABSK041, which in some instances may be administered orally. Other exemplary PD-L1 binding antagonists include AVA-004, MT-6035, VXM10, LYN192, GB7003, and JS-003. In one aspect, the PD-L1 binding antagonist is atezolizumab.

The term "PD-1 binding antagonist" refers to a molecule that decreases, blocks, inhibits, abrogates or interferes with signal transduction resulting from the interaction of PD-1 with one or more of its binding partners, such as PD-L1 and/or PD-L2. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. In some instances, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen-binding fragments thereof, immunoadhesins, fusion proteins, oligopeptides, and other molecules that decrease, block, inhibit, abrogate or interfere with signal transduction resulting from the interaction of PD-1 with PD-L1 and/or PD-L2. In one instance, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some instances, the PD-1 binding antagonist binds to PD-1. In some instances, the PD-1 binding antagonist is an anti-PD-1 antibody (e.g., an anti-PD-1 antagonist antibody). Exemplary anti-PD-1 antagonist antibodies include nivolumab, pembrolizumab, MEDI-0680, PDR001 (spartalizumab), REGN2810 (cemiplimab), BGB-108, prolgolimab, camrelizumab, sintilimab, tislelizumab, toripalimab, dostarlimab, retifanlimab, sasanlimab, penpulimab, CS1003, HLX10, SCT-I10A, zimberelimab, balstilimab, genolimzumab, BI 754091, cetrelimab, YBL-006, BAT1306, HX008, budigalimab, AMG 404, CX-188, JTX-4014, 609A, Sym021, LZM009, F520, SG001, AM0001, ENUM 244C8, ENUM 388D4, STI-1110, AK-103, and hAb21. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is a PD-L2 Fc fusion protein, e.g., AMP-224. In another specific aspect, a PD-1 binding antagonist is MEDI-0680. In another specific aspect, a PD-1 binding antagonist is PDR001 (spartalizumab). In another specific aspect, a PD-1 binding antagonist is REGN2810 (cemiplimab). In another specific aspect, a PD-1 binding antagonist is BGB-108. In another specific aspect, a PD-1 binding antagonist is prolgolimab. In another specific aspect, a PD-1 binding antagonist is camrelizumab. In another specific aspect, a PD-1 binding antagonist is sintilimab. In another specific aspect, a PD-1 binding antagonist is tislelizumab. In another specific aspect, a PD-1 binding antagonist is toripalimab. Other exemplary PD-1 binding antagonists include BION-004, CB201, AUNP-012, ADG104, and LBL-006. Such combination therapies noted above encompass combined administration (where two or more therapeutic agents are included in the same or separate pharmaceutical compositions), and separate administration, in which case, administration of the antibody as described herein can occur prior to, simultaneously, and/or following, administration of the additional therapeutic agent or agents. In one aspect, administration of the anti-CCR8 antibody and administration of an additional therapeutic agent occur within about one month, or within about one, two or three weeks, or within about one, two, three, four, five, or six days, of each other. In one aspect, the antibody and additional therapeutic agent are administered to the subject on Day 1 of the treatment. Antibodies as described herein can also be used in combination with radiation therapy.

An antibody as described herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies as described herein would be formulated, dosed, and administered in a fashion consistent with good medical practice. Factors for consideration in this context include the particular disorder being treated, the particular subject species being treated, the clinical condition of the subject, the cause of the disorder, the site of delivery of the agent, the method of administration, the scheduling of administration, and other factors known to medical practitioners. The antibody need not be, but is optionally formulated with, one or more agents currently used to r treat the disorder in question. The effective amount of such other agents depends on the amount of antibody present in the pharmaceutical composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

The antibody is suitably administered to the subject at one time or over a series of treatments. For repeated administrations over several days or longer, depending on the condition, the treatment would generally be sustained until a desired suppression of disease symptoms occurs. However, other dosage regimens may be useful. The progress of this therapy is easily monitored by conventional techniques and assays.

In an additional embodiment, use of the mouse surrogate is contemplated, e.g., for use as an in vitro or in vivo tool molecule. For example, in one aspect, provided is a method of treating a disease in a mouse comprising administering an effective amount of the mouse surrogate antibody, as described herein, to the mouse to treat the disease. In certain embodiments, the mouse comprises a xenograft. In certain embodiments, the mouse model is a cancer model, e.g., a skin cancer model.

G. Articles of Manufacture

In another aspect, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody as disclosed herein. The label or package insert indicates that the composition is used for treating the condition of choice. Moreover, the article of manufacture may comprise (a) a first container with a composition contained therein, wherein the composition comprises an antibody as disclosed herein; and (b) a second container with a composition contained therein, wherein the composition comprises a further cytotoxic or otherwise therapeutic agent. The article of manufacture in this aspect as described herein may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXEMPLIFICATION

The following are further non-limiting examples of antibodies, methods and compositions as described herein. It is understood that various other embodiments may be practiced, given the general description provided above.

Example 1. Discovery and Engineering of Anti-CCR8 Monoclonal Antibodies

New Zealand White rabbits were immunized with recombinant huCCR8, a huCCR8+ rabbit cell line, extracellular vesicles containing huCCR8, and sulfated and unsulfated peptides derived from N-terminal regions of huCCR8. Single B cells were isolated following the protocol set forth in Lin et al., *PLoS ONE* 15(12), 2020. The B cell culture supernatants were then assayed by direct Flow Activated Cell Sorting (FACS; flow cytometry) of IgG+ B cells into single wells for binding to human and cyno CCR8+ CHO cells and control CHO cells. CCR8 specific B cells were lysed and immediately frozen in −80° C. for storage until molecular cloning. Variable regions (VH and VL) of each monoclonal antibody from rabbit B cells were cloned into expression vectors from extracted mRNA as described in Lin et al., *PLoS ONE* 15(12), 2020. Individual recombinant rabbit antibodies were expressed in Expi293 cells and subsequently purified with protein A.

Over 480 anti-CCR8 antibodies were obtained that bound to either human or cyno CCR8 CHO cells. Antibodies were further selected based on their relative mean fluorescent intensities (MFIs) on the human and cyno CCR8 CHO cell lines and sequence diversity. From the antibodies that showed MFI differences less than 5-fold on human and cyno CCR8 CHO cells, five unique groups of antibodies were identified (designated Ab1-Ab5). One representative sequence from each group was selected for humanization.

Variants constructed during the humanization of the rabbit monoclonal antibodies were assessed in the form of human IgG1. Hypervariable regions from each of the rabbit antibodies (namely positions 24-34 (L1), 50-56 (L2) and 89-97 (L3) in VL domain, and 26-35 (H1), 50-65 (H2) and 95-102 (H3) in VH domain) were grafted into various acceptor frameworks. Residue numbers are according to Kabat et al., *Sequences of proteins of immunological interest,* 5th Ed., Public Health Service, National Institutes of Health, Bethesda, MD (1991). All VL and VH Vernier positions from rabbit antibodies were also grafted into their respective human germline frameworks. The grafts with all rabbit amino acids in Vernier positions are referred to as H1L1. The binding ability of humanized CCR8 antibodies to CHO-huCCR8.Gna15 stable cell line was compared to their chimeric parental clones. Rabbit Vernier positions of version H1L1 antibodies were converted back to human residues to evaluate the contribution of each rabbit Vernier positions to binding to huCCR8.

Figure 1:
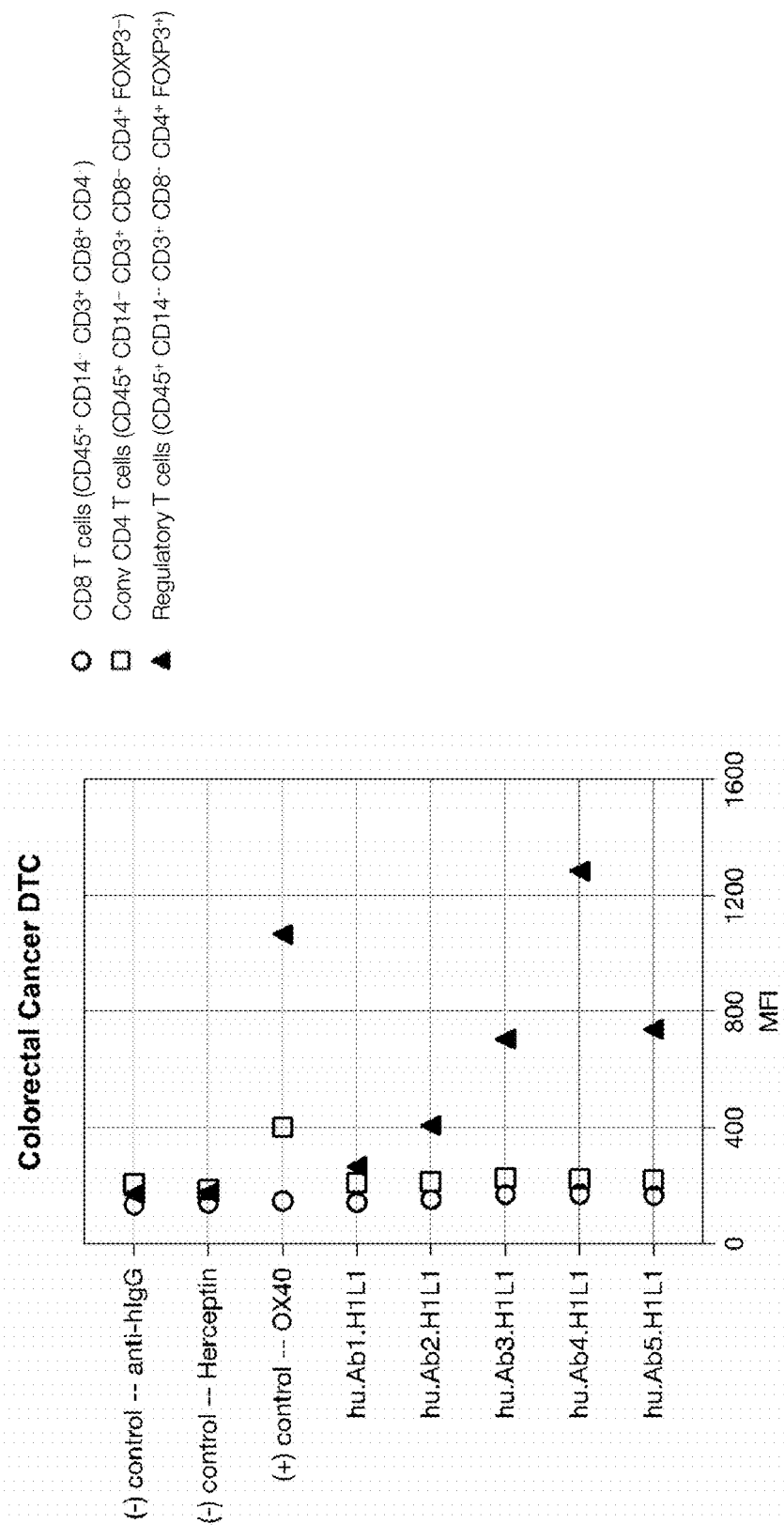
FIG. 1 depicts the results of a screening of anti-CCR8 monoclonal antibodies (mAbs) selectively binding to Treg cells (Tregs) from human colorectal cancer dissociated tumor cells (DTC) (obtained from Discovery Life Sciences). Shown are mean fluorescent intensity (MFI) values for CD8 T cells (defined as CD45+CD14−CD3+CD8+CD4−) (circles, ○), conventional CD4 T cells (defined as CD45+CD14−CD3+CD8−CD4+FOXP3−) (squares, □), and Treg cells (defined as CD45+CD14−CD3+CD8−CD4+FOXP3+) (triangles, ▲). Three of the five anti-CCR8 mAb clones Ab1-Ab5 specifically stained intratumoral Treg cells and not conventional CD4 or CD8 T cells, and were ranked based on CCR8 MFI: hu.Ab4.H1L1>hu.Ab5.H1L1>hu.Ab3.H1L1.

The mAbs were evaluated for binding to regulatory T cells (Treg cells or Tregs) by Fluorescence-Activated Cell Sorting (FACS) flow cytometry. Human colorectal dissociated tumor cells (DTC) (Discovery Life Sciences) were thawed according to vendor's protocol. Cells were surface stained with eFluor 780-conjugated Fixable Viability Dye (ThermoFisher Scientific) and 2 ug/mL mAb specific for CCR8, OX40 (positive control), Herceptin (negative control), or anti-hIgG (negative control) for 20 min at 4° C. followed by secondary detection with AF647-conjugated AffiniPure F(ab')2 Fragment Goat anti-Human IgG, Fcg fragment-specific (Jackson ImmunoResearch) for 10 min at 4° C. Cells were then intracellularly stained using the eBioscience Foxp3/Transcription Factor Staining Buffer Set (ThermoFisher Scientific) according to the manufacturer's protocol. Antibodies used to define T cell populations were CD45 (HI30), CD3 (SK7), CD8 (RPA-T8), and CD14 (63D3) from BD Biosciences, CD4 (RPA-T4) from BioLegend, and FOXP3 (236A/E7) from ThermoFisher Scientific. Flow cytometry was performed on a Fortessa X-20 (BD Biosciences) and analyzed with FlowJo software (BD Biosciences, Version 10.5.3). Shown in FIG. 1 are mean fluorescent intensity (MFI) values for CD8 T cells (defined as CD45+CD14−CD3+CD8+CD4−) (circles, ○), conventional CD4 T cells (defined as CD45+CD14−CD3+CD8−CD4+FOXP3−) (squares, □), and Treg cells (defined as CD45+CD14−CD3+CD8−CD4+FOXP3+) (triangles, ▲). Three of the five CCR8 mAb clones specifically stained Treg cells and not conventional CD4 or CD8 T cells and were ranked according to CCR8 MFI, greater than 500 MFI: hu.Ab4.H1L1>hu.Ab5.H1L1>hu.Ab3.H1L1. Upon confirmation that these three CCR8 mAb clones, namely, hu.Ab3.H1L1, hu.Ab4.H1L1, and hu.Ab5.H1L1, also retained human-cyno cross-reactivity (differences less than 5-fold on human and cyno CCR8 CHO cells), these antibodies carried forward for further exploration.

For example, hu.Ab3.H1L1, hu.Ab4.H1L1, and hu.Ab5.H1L1 were further studied for antibody-dependent cellular cytotoxicity (ADCC). hIgG1 isotype was used as a negative control. See FIG. 2. ADCC assays were performed as previously reported in Kamen, L., et al., *Development of a kinetic antibody-dependent cellular cytotoxicity assay*. J. Immunol Methods, 2019. 468: p. 49-54, and Schnueriger, A., et al., *Development of a quantitative, cell-line based assay to measure ADCC activity mediated by therapeutic antibodies*. Mol Immunol, 2011. 48(12-13): p. 1512-17, with some modifications, using CD16 engineered NK-92_F158 as effector cells and CHO cells that stably express human CCR8 and G-alpha 15 subunit (CHO/hCCR8.Gna15) as target cells. Briefly, lysis of target cells by ADCC was measured by the calcein release method. The target cells were labeled with Calcein-AM (C3100MP, ThermoFisher Scientific) according to the manufacturer's protocol, then washed and plated onto 384-well plates at a density of 3000 cells/well. Anti-CCR8 antibody was added at various concentrations from 0.004 to 1 µg/mL, followed by the addition of NK-92_F158 cells at an effector:target (E:T) ratio of 10:1. The plates were then incubated for 2.5 hours at 37° C. After incubation, the plates were centrifuged at 200×g for 3 minutes, the supernatants were transferred to a white opaque 384-well microplate (OptiPlate-384, PerkinElmer, Waltham, MA), and fluorescent signals were measured in relative fluorescence units (RFU) using an EnSight Multimode Plate Reader (PerkinElmer) with excitation/emission at 485/520 nm. Signals from the wells containing only the target cells represented spontaneous release of the calcein from labeled cells (spontaneous release), whereas wells containing target cells lysed with Triton X-100 (Sigma-Aldrich, St. Louis, MO) provided the maximal signal available (maximal release). Antibody-independent cell-mediated cytotoxicity (AICC) was measured in wells containing target and effector cells without the addition of the antibody. Samples and controls were tested at least in duplicate in the same plates. The extent of specific ADCC activity was calculated as follows:

% ADCC=100×(mean experimental release−mean AICC)/(mean maximum release−mean spontaneous release)

The ADCC activity was plotted as a function of antibody concentrations and the data were fitted to an asymmetric sigmoidal four-parameter logistic (4PL) model using Prism (Graphpad; La Jolla, CA). See FIG. 2. The $EC_{50}$ value was determined as the concentration reaching 50% maximum ADCC activity of each individual antibody. $EC_{50}$ values are also tabulated below.

TABLE A

| ADCC Activity | |
|---|---|
| Antibody | $EC_{50}$ (nM) |
| hu.Ab3.H1L1 | 0.02 |
| hu.Ab5.H1L1 | 0.02 |
| hu.Ab4.H1L1 | 0.08 | hu.Ab3.H1L1, hu.Ab4.H1L1, and hu.Ab5.H1L1 were further analyzed for their agonist (CCR8 activation) and antagonist (inhibition of CCL1; neutralizing) activity. hIgG1 isotype was used as a negative control. CCR8 activation was monitored by $Ca^{2+}$ influx using Fluorescent Imaging Plate Reader (FLIPR) FDSS/µCell (Hamamatsu, Japan). Briefly, the CHO/hCCR8.Gna 15 cells were loaded with fluorescence $Ca^{2+}$ dye Fluo-8 NW (Cat #36307, AAT Bioquest) and incubated 30 minutes at 37° C., and then at room temperature for another 30 minutes. Serial diluted test anti-CCR8 antibodies were prepared in HHBS buffer in a clear 384-well plate and hCCL1 in HHBS buffer was also aliquoted in a clear 384-well plate. Set-up FLIPR assay on FDSS/µCell with antibody addition at 10 second and hCCL1 addition at 300 second and monitoring total 500 seconds. Set excitation and emission wavelength at 485 nm and 525 nm respectively. After the run, negative control correction is applied and data were normalized against hCCL1 signal (100%) and plotted as a function of antibody concentrations using Prism.

Figure 3A:
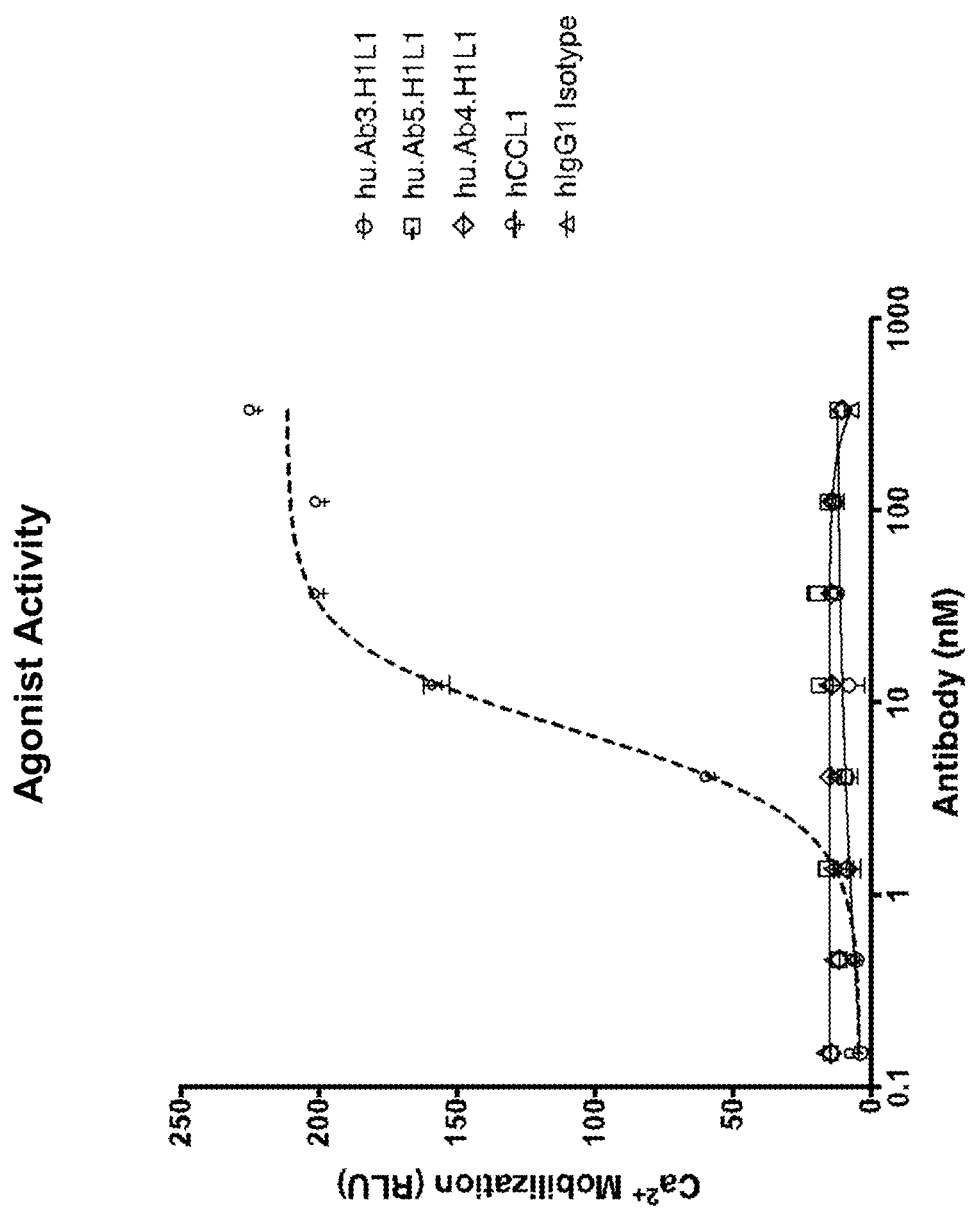
FIGS. 3A-3D depict the agonist and antagonist activities of the human/cyno cross-reactive anti-CCR8 mAbs hu.Ab4.H1L1, hu.Ab5.H1L1, and hu.Ab3.H1L1, as well as comparator anti-CCR8 mAbs (the humanized anti-human Yoshida anti-CCR8 antibody, murine anti-human CCR8 mAb 433H (BD Biosciences), and murine anti-human CCR8 mAb L263G8 (Biolegend)).

As shown in FIG. 3A, CCL1, a known ligand for CCR8, shows agonist activity, but none of the anti-CCR8 test antibodies show agonistic effects. The data in FIG. 3B indicates anti-CCR8 antibody hu.Ab4.H1L1 has antagonistic (neutralizing) activity against the CCR8 ligand CCL1 (20 nM of ligand), whereas anti-CCR8 antibody hu.Ab5.H1L1 and hu.Ab3.H1L1 demonstrates no ligand blocking (non-neutralizing) activity at the concentration studied. The data in FIG. 3C further demonstrates comparator anti-CCR8 antibodies (the Yoshida humanized anti-human CCR8 antibody, murine anti-human CCR8 mAb 433H (BD Biosciences), and murine anti-human CCR8 mAb L263G8 (Biolegend)) also show antagonistic (neutralizing) activity by blocking the activation of CCR8 by the CCR8 ligand CCL1. The $IC_{50}$ values for the ligand blocking activity are provided in Table B. As noted in Van Damme et al., *J. Immunother. Cancer* (2021), 9: e001749, ligand blocking alone is not sufficient for Treg cell depletion in mouse tumors. Thus, even though hu.Ab5.H1L1 and hu.Ab3.H1L1 demonstrated no ligand blocking, these two antibodies were considered still promising candidates, as the goal was to find a selective anti-CCR8 antibody which binds to CCR8 and depletes Treg cells.

TABLE B

CCL1 blocking potencies of anti-CCR8 antibodies

| Antibody | $IC_{50}$ (nM) |
|---|---|
| hu.Ab5.H1L1 | No inhibition |
| hu.Ab4.H1L1 | 57.9 |
| hu.Ab3.H1L1 | No inhibition |
| murine anti-human CCR8 Ab L263G8 (Biolegend, Commercial Ab) | 23.6 |
| murine anti-human CCR8 Ab 433H (BD Biosciences, Commercial Ab) | 17.6 |
| Yoshida humanized anti-human CCR8 antibody (Comparator) | 13.3 |

To confirm the selectivity to CCR8, the binding of hu.Ab3.H1L1, hu.Ab4.H1L1, and hu.Ab5.H1L1, as well as the Yoshida humanized anti-human CCR8, murine anti-human CCR8 mAb L263G8 (Biolegend, Commercial Ab) and murine anti-human CCR8 mAb 433H (BD Biosciences, Commercial Ab), were characterized by flow cytometry on HEK293 cells that were transiently transfected with plasmids encoding for FLAG-tagged other related human GPCRs (CCR2-5, CXCR4, ACKR2, and ACKR4). Cell surface expression of each GPCR was confirmed by staining with an anti-FLAG antibody control. See FIG. 4A-4F. In particular, HEK293 cells were transfected with N-term FLAG-tagged human CCR2, CCR3, CCR4, CCR5, CXCR4, ACKR2, ACKR4, hCCR8 constructs, or with a Mock construct using transIT X2 (reagent:DNA=3:1) for 24 hours, and surface stained with various anti-hCCR8 monoclonal antibodies at 5 ug/ml, or rabbit anti-Flag pAb (Sigma) followed by AF647-anti-hIgG or AF647-anti-RbIgG respectively. Antibodies hu.Ab4.H1L1, and hu.Ab5.H1L1, only stained the hCCR8-containing cells, confirming their specificity to hCCR8. Antibody hu.Ab3.H1L1 showed staining of multiple other GPCRs, indicating lack of specificity. Thus, the CCR8 selective hu.Ab4.H1L1 and hu.Ab5.H1L1 antibodies with the best ADCC activities were carried forward.

Example 2. Mutational Analysis of Ab4 and Ab5 Anti-CCR8 Antibodies

Variants of hu.Ab4.H1L1 and hu.Ab5.H1L1 anti-CCR8 antibodies were further explored and characterized. FIGS. 5A-5D depict the alignment of light chain variable region (FIG. 5A) and heavy chain variable region (FIGS. 5B-5D)) of the sequences for rabbit (rb.Ab4) and humanized Ab4 (L1-L4 and H1-H12) CCR8 antibodies studied. FIGS. 6A-6D depict the alignment of light chain variable region (FIG. 6A) and heavy chain variable region (FIGS. 61B-61D) of the sequences for rabbit (rb.Ab5) and humanized Ab5 (L1-L5 and H1-H13) CCR8 antibodies studied. See also Tables C1-C3 and D1-D3, below. Table E provides the heavy and light constant domains.

TABLE C1

Light Chain CDR Regions for Ab4 Variants

| Description | CDR L1 (Kabat and Chothia) | CDR L2 (Kabat and Chothia) | CDR L3 (Kabat and (Chothia) |
|---|---|---|---|
| rb.Ab4 | QASQSISSYLS (SEQ ID NO: 1) | KASTLAS (SEQ ID NO: 2) | QQGYTSSNIDNI (SEQ ID NO: 3) |
| hu.Ab4.L1 | QASQSISSYLS (SEQ ID NO: 1) | KASTLAS (SEQ ID NO: 2) | QQGYTSSNIDNI (SEQ ID NO: 3) |
| hu.Ab4.L2 | QASQSISSYLS (SEQ ID NO: 1) | KASTLAS (SEQ ID NO: 2) | QQGYTSSNIDNI (SEQ ID NO: 3) |
| hu.Ab4.L3 | QASQSISSYLS (SEQ ID NO: 1) | KASTLAS (SEQ ID NO: 2) | QQGYTSSNIDNI (SEQ ID NO: 3) |
| hu.Ab4.L4 | QASQSISSYLS (SEQ ID NO: 1) | KASTLAS (SEQ ID NO: 2) | QQGYTSSNIDNI (SEQ ID NO: 3) |

TABLE C2

Heavy Chain CDR Regions for Ab4 Variants

| Description | CDR H1 (Kabat) | CDRH1 (Chothia) | CDR H2 (Kabat and Chothia) | CDR H3 (Kabat and Chothia) |
|---|---|---|---|---|
| rb.Ab4 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H1 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H2 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H3 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H4 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H5 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H6 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H7 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H8 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H9 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H10 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H11 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |
| hu.Ab4.H12 | NYAMI (SEQ ID NO: 4) | GFSLSNY (SEQ ID NO: 5) | TISLGGYTYYA NWAKG (SEQ ID NO: 6) | ARWSTDSAIYT YAFDP (SEQ ID NO: 7) |

TABLE C3

Heavy Chain and Light Chain Variable Regions for Ab4 Variants

| Description | Sequence |
|---|---|
| rb.Ab4 Heavy Chain Variable Region (SEQ ID NO: 8) | QSVEESGGRLVTPGTPLTLTCTVSGFSLSNYAMIWVRQAPGEGL EWVGTISLGGYTYYANWAKGRFTISKTSTTVDLKISSPTTEDTA TYFCARARWSTDSAIYTYAFDPWGPGTLVTVSS |
| rb.Ab4 Light Chain Variable Region (SEQ ID NO: 9) | AYDMTQTPASVEVAVGGTVTIKCQASQSISSYLSWYQQKPGQRP ELLIYKASTLASGVSSRFKGSGSGTQFTLTISDLECADAATYYC QQGYTSSNIDNIFGGGTEVVVK |

TABLE C3-continued

Heavy Chain and Light Chain Variable Regions for Ab4 Variants

| Description | Sequence |
| --- | --- |
| hu.Ab4.H1 Heavy Chain Variable Region (SEQ ID NO: 10) | EQQLLESGGGLVQPGGSLRLSCAVSGFSLSNYAMIWVRQAPGKGLEWVGTISLGGYTYYANWAKGRFTISKDSSKTTVYLQMNSLRAEDTAVYFCARARWSTDSAIYTYAFDPWGPGTLVTVSS |
| hu.Ab4.H2 Heavy Chain Variable Region (SEQ ID NO: 11) | EVQLLESGGGLVQPGGSLRLSCAVSGFSLSNYAMIWVRQAPGKGLEWVGTISLGGYTYYANWAKGRFTISKDSSKTTVYLQMNSLRAEDTAVYFCARARWSTDSAIYTYAFDPWGPGTLVTVSS |
| hu.Ab4.H3 Heavy Chain Variable Region (SEQ ID NO: 12) | EQQLLESGGGLVQPGGSLRLSCAASGFSLSNYAMIWVRQAPGKGLEWVGTISLGGYTYYANWAKGRFTISKDSSKTTVYLQMNSLRAEDTAVYFCARARWSTDSAIYTYAFDPWGPGTLVTVSS |
| hu.Ab4.H4 Heavy Chain Variable Region (SEQ ID NO: 13) | EQQLLESGGGLVQPGGSLRLSCAVSGFSLSNYAMIWVRQAPGKGLEWVSTISLGGYTYYANWAKGRFTISKDSSKTTVYLQMNSLRAEDTAVYFCARARWSTDSAIYTYAFDPWGPGTLVTVSS |
| hu.Ab4.H5 Heavy Chain Variable Region (SEQ ID NO: 14) | EQQLLESGGGLVQPGGSLRLSCAVSGFSLSNYAMIWVRQAPGKGLEWVGTISLGGYTYYANWAKGRFTISRDSSKTTVYLQMNSLRAEDTAVYFCARARWSTDSAIYTYAFDPWGPGTLVTVSS |
| hu.Ab4.H6 Heavy Chain Variable Region (SEQ ID NO: 15) | EQQLLESGGGLVQPGGSLRLSCAVSGFSLSNYAMIWVRQAPGKGLEWVGTISLGGYTYYANWAKGRFTISKDNSKTTVYLQMNSLRAEDTAVYFCARARWSTDSAIYTYAFDPWGPGTLVTVSS |
| hu.Ab4.H7 Heavy Chain Variable Region (SEQ ID NO: 16) | EQQLLESGGGLVQPGGSLRLSCAVSGFSLSNYAMIWVRQAPGKGLEWVGTISLGGYTYYANWAKGRFTISKDSSKNTVYLQMNSLRAEDTAVYFCARARWSTDSAIYTYAFDPWGPGTLVTVSS |
| hu.Ab4.H8 Heavy Chain Variable Region (SEQ ID NO: 17) | EQQLLESGGGLVQPGGSLRLSCAVSGFSLSNYAMIWVRQAPGKGLEWVGTISLGGYTYYANWAKGRFTISKDSSKTTLYLQMNSLRAEDTAVYFCARARWSTDSAIYTYAFDPWGPGTLVTVSS |
| hu.Ab4.H9 Heavy Chain Variable Region (SEQ ID NO: 18) | EQQLLESGGGLVQPGGSLRLSCAVSGFSLSNYAMIWVRQAPGKGLEWVGTISLGGYTYYANWAKGRFTISKDSSKTTVYLQMNSLRAEDTAVYYCARARWSTDSAIYTYAFDPWGPGTLVTVSS |
| hu.Ab4.H10 Heavy Chain Variable Region (SEQ ID NO: 19) | EQQLLESGGGLVQPGGSLRLSCAVSGFSLSNYAMIWVRQAPGKGLEWVGTISLGGYTYYANWAKGRFTISKDSSKTTVYLQMNSLRAEDTAVYFCARARWSTDSAIYTYAFDPWGQGTLVTVSS |
| hu.Ab4.H11 Heavy Chain Variable Region (SEQ ID NO: 20) | EVQLLESGGGLVQPGGSLRLSCAASGFSLSNYAMIWVRQAPGKGLEWVSTISLGGYTYYANWAKGRFTISRDNSKNTLYLQMNSLRAEDTAVYYCARARWSTDSAIYTYAFDPWGQGTLVTVSS |
| hu.Ab4.H12 Heavy Chain Variable Region (SEQ ID NO: 21) | EVQLLESGGGLVQPGGSLRLSCAASGFSLSNYAMIWVRQAPGKGLEWVSTISLGGYTYYANWAKGRFTISRDSSKTTVYLQMNSLRAEDTAVYFCARARWSTDSAIYTYAFDPWGPGTLVTVSS |
| hu.Ab4.L1 Light Chain Variable Region (SEQ ID NO: 22) | DYQMTQSPSSLSASVGDRVTITCQASQSISSYLSWYQQKPGKRPKLLIYKASTLASGVPSRFSGSGSGTDFTLTISSLQPEDFATYYCQQGYTSSNIDNIFGGGTKVEIK |
| hu.Ab4.L2 Light Chain Variable Region (SEQ ID NO: 23) | DIQMTQSPSSLSASVGDRVTITCQASQSISSYLSWYQQKPGKRPKLLIYKASTLASGVPSRFSGSGSGTDFTLTISSLQPEDFATYYCQQGYTSSNIDNIFGGGTKVEIK |

TABLE C3-continued

Heavy Chain and Light Chain Variable Regions for Ab4 Variants

| Description | Sequence |
| --- | --- |
| hu.Ab4.L3 Light Chain Variable Region (SEQ ID NO: 24) | DYQMTQSPSSLSASVGDRVTITCQASQSISSYLSWYQQKPGKAPKLLIYKASTLASGVPSRFSGSGSGTDFTLTISSLQPEDFATYYCQQGYTSSNIDNIFGGGTKVEIK |
| hu.Ab4.L4 Light Chain Variable Region (SEQ ID NO: 25) | DIQMTQSPSSLSASVGDRVTITCQASQSISSYLSWYQQKPGKAPKLLIYKASTLASGVPSRFSGSGSGTDFTLTISSLQPEDFATYYCQQGYTSSNIDNIFGGGTKVEIK |

TABLE D1

Light Chain CDR Regions for Ab5 Variants

| Description | CDR L1 (Kabat and Chothia) | CDR L2 (Kabat and Chothia) | CDR L3 (Kabat and Chothia) |
| --- | --- | --- | --- |
| rb.Ab5 | QASENIANALA (SEQ ID NO: 26) | GASNLAS (SEQ ID NO: 27) | QCAYYGNSFVEGT (SEQ ID NO: 109) |
| hu.Ab5.L1 | QASENIANALA (SEQ ID NO: 26) | GASNLAS (SEQ ID NO: 27) | QQAYYGNSFVEGT (SEQ ID NO: 28) |
| hu.Ab5.L2 | QASENIANALA (SEQ ID NO: 26) | GASNLAS (SEQ ID NO: 27) | QQAYYGNSFVEGT (SEQ ID NO: 28) |
| hu.Ab5.L3 | QASENIANALA (SEQ ID NO: 26) | GASNLAS (SEQ ID NO: 27) | QQAYYGNSFVEGT (SEQ ID NO: 28) |
| hu.Ab5.L4 | QASENIANALA (SEQ ID NO: 26) | GASNLAS (SEQ ID NO: 27) | QQAYYGNSFVEGT (SEQ ID NO: 28) |
| hu.Ab5.L5 | QASENIANALA (SEQ ID NO: 26) | GASNLAS (SEQ ID NO: 27) | QQAYYGNSFVEGT (SEQ ID NO: 28) |

TABLE D2

Heavy Chain CDR Regions for Ab5 Variants

| Description | CDR H1 (Kabat) | CDR H1 (Chothia) | CDR H2 (Kabat and Chothia) | CDR H3 (Kabat and Chothia) |
| --- | --- | --- | --- | --- |
| rb.Ab5 | TYAMG (SEQ ID NO: 29) | GIDLSTY (SEQ ID NO: 30) | LIHRSGRTYYATWAKG (SEQ ID NO: 31) | SYPDYSATASI (SEQ ID NO: 32) |
| hu.Ab5.H1 | TYAMG (SEQ ID NO: 29) | GIDLSTY (SEQ ID NO: 30) | LIHRSGRTYYATWAKG (SEQ ID NO: 31) | SYPDYSATASI (SEQ ID NO: 32) |
| hu.Ab5.H2 | TYAMG (SEQ ID NO: 29) | GIDLSTY (SEQ ID NO: 30) | LIHRSGRTYYATWAKG (SEQ ID NO: 31) | SYPDYSATASI (SEQ ID NO: 32) |
| hu.Ab5.H3 | TYAMG (SEQ ID NO: 29) | GIDLSTY (SEQ ID NO: 30) | LIHRSGRTYYATWAKG (SEQ ID NO: 31) | SYPDYSATASI (SEQ ID NO: 32) |
| hu.Ab5.H4 | TYAMG (SEQ ID NO: 29) | GIDLSTY (SEQ ID NO: 30) | LIHRSGRTYYATWAKG (SEQ ID NO: 31) | SYPDYSATASI (SEQ ID NO: 32) |
| hu.Ab5.H5 | TYAMG (SEQ ID NO: 29) | GIDLSTY (SEQ ID NO: 30) | LIHRSGRTYYATWAKG (SEQ ID NO: 31) | SYPDYSATASI (SEQ ID NO: 32) |
| hu.Ab5.H6 | TYAMG (SEQ ID NO: 29) | GIDLSTY (SEQ ID NO: 30) | LIHRSGRTYYATWAKG (SEQ ID NO: 31) | SYPDYSATASI (SEQ ID NO: 32) |

TABLE D2-continued

Heavy Chain CDR Regions for Ab5 Variants

| Description | CDR H1 (Kabat) | CDR H1 (Chothia) | CDR H2 (Kabat and Chothia) | CDR H3 (Kabat and Chothia) |
|---|---|---|---|---|
| hu.Ab5.H7 | TYAMG (SEQ ID NO: 29) | GIDLSTY (SEQ ID NO: 30) | LIHRSGRTYYA TWAKG (SEQ ID NO: 31) | SYPDYSATASI (SEQ ID NO: 32) |
| hu.Ab5.H8 | TYAMG (SEQ ID NO: 29) | GIDLSTY (SEQ ID NO: 30) | LIHRSGRTYYA TWAKG (SEQ ID NO: 31) | SYPDYSATASI (SEQ ID NO: 32) |
| hu.Ab5.H9 | TYAMG (SEQ ID NO: 29) | GIDLSTY (SEQ ID NO: 30) | LIHRSGRTYYA TWAKG (SEQ ID NO: 31) | SYPDYSATASI (SEQ ID NO: 32) |
| hu.Ab5.H10 | TYAMG (SEQ ID NO: 29) | GIDLSTY (SEQ ID NO: 30) | LIHRSGRTYYA TWAKG (SEQ ID NO: 31) | SYPDYSATASI (SEQ ID NO: 32) |
| hu.Ab5.H11 | TYAMG (SEQ ID NO: 29) | GIDLSTY (SEQ ID NO: 30) | LIHRSGRTYYA TWAKG (SEQ ID NO: 31) | SYPDYSATASI (SEQ ID NO: 32) |
| hu.Ab5.H12 | TYAMG (SEQ ID NO: 29) | GIDLSTY (SEQ ID NO: 30) | LIHRSGRTYYA TWAKG (SEQ ID NO: 31) | SYPDYSATASI (SEQ ID NO: 32) |
| hu.Ab5.H13 | TYAMG (SEQ ID NO: 29) | GIDLSTY (SEQ ID NO: 30) | LIHRSGRTYYA TWAKG (SEQ ID NO: 31) | SYPDYSATASI (SEQ ID NO: 32) |

TABLE D3

Heavy Chain and Light Chain Variable Regions for Ab5 Variants

| Description | Sequence |
|---|---|
| rb.Ab5 Heavy Chain Variable Region (SEQ ID NO: 33) | QSVEESGGRLVSPGTPLTLTCTVSGIDLSTYAMGWVRQAPGKGLEWIGLIHRSGRTYYATWAKGRFTISKTSSTTVDLKITSPTTEDTATYFCTRSYPDYSATASIWGPGTLVTVSS |
| rb.Ab5 Light Chain Variable Region (SEQ ID NO: 34) | DIVVTQTPASVEAAVGGTVTIKCQASENIANALAWYQQKSGQPPMFLIYGASNLASGVSSRFKGSGSGTEFTLTISDLECADAAVYYCQCAYYGNSFVEGTFGGGTEVVVK |
| hu.Ab5.H1 Heavy Chain Variable Region (SEQ ID NO: 35) | EQQLLESGGGLVQPGGSLRLSCAVSGIDLSTYAMGWVRQAPGKGLEWIGLIHRSGRTYYATWAKGRFTISKDSSKTTVYLQMNSLRAEDTAVYFCTRSYPDYSATASIWGPGTTVTVSS |
| hu.Ab5.H2 Heavy Chain Variable Region (SEQ ID NO: 36) | EVQLLESGGGLVQPGGSLRLSCAVSGIDLSTYAMGWVRQAPGKGLEWIGLIHRSGRTYYATWAKGRFTISKDSSKTTVYLQMNSLRAEDTAVYFCTRSYPDYSATASIWGPGTTVTVSS |
| hu.Ab5.H3 Heavy Chain Variable Region (SEQ ID NO: 37) | EQQLLESGGGLVQPGGSLRLSCAASGIDLSTYAMGWVRQAPGKGLEWIGLIHRSGRTYYATWAKGRFTISKDSSKTTVYLQMNSLRAEDTAVYFCTRSYPDYSATASIWGPGTTVTVSS |
| hu.Ab5.H4 Heavy Chain Variable Region (SEQ ID NO: 38) | EQQLLESGGGLVQPGGSLRLSCAVSGIDLSTYAMGWVRQAPGKGLEWVGLIHRSGRTYYATWAKGRFTISKDSSKTTVYLQMNSLRAEDTAVYFCTRSYPDYSATASIWGPGTTVTVSS |
| hu.Ab5.H5 Heavy Chain Variable Region (SEQ ID NO: 39) | EQQLLESGGGLVQPGGSLRLSCAVSGIDLSTYAMGWVRQAPGKGLEWISLIHRSGRTYYATWAKGRFTISKDSSKTTVYLQMNSLRAEDTAVYFCTRSYPDYSATASIWGPGTTVTVSS |

TABLE D3-continued

Heavy Chain and Light Chain Variable Regions for Ab5 Variants

| Description | Sequence |
|---|---|
| hu.Ab5.H6 Heavy Chain Variable Region (SEQ ID NO: 40) | EQQLLESGGGLVQPGGSLRLSCAVSGIDLSTYAMGWVRQAPGKGLEWIGLIHRSGRTYYATWAKGRFTISRDSSKTTVYLQMNSLRAEDTAVYFCTRSYPDYSATASIWGPGTTVTVSS |
| hu.Ab5.H7 Heavy Chain Variable Region (SEQ ID NO: 41) | EQQLLESGGGLVQPGGSLRLSCAVSGIDLSTYAMGWVRQAPGKGLEWIGLIHRSGRTYYATWAKGRFTISKDNSKTTVYLQMNSLRAEDTAVYFCTRSYPDYSATASIWGPGTTVTVSS |
| hu.Ab5.H8 Heavy Chain Variable Region (SEQ ID NO: 42) | EQQLLESGGGLVQPGGSLRLSCAVSGIDLSTYAMGWVRQAPGKGLEWIGLIHRSGRTYYATWAKGRFTISKDSSKNTVYLQMNSLRAEDTAVYFCTRSYPDYSATASIWGPGTTVTVSS |
| hu.Ab5.H9 Heavy Chain Variable Region (SEQ ID NO: 43) | EQQLLESGGGLVQPGGSLRLSCAVSGIDLSTYAMGWVRQAPGKGLEWIGLIHRSGRTYYATWAKGRFTISKDSSKTTLYLQMNSLRAEDTAVYFCTRSYPDYSATASIWGPGTTVTVSS |
| hu.Ab5.H10 Heavy Chain Variable Region (SEQ ID NO: 44) | EQQLLESGGGLVQPGGSLRLSCAVSGIDLSTYAMGWVRQAPGKGLEWIGLIHRSGRTYYATWAKGRFTISKDSSKTTVYLQMNSLRAEDTAVYYCTRSYPDYSATASIWGPGTTVTVSS |
| hu.Ab5.H11 Heavy Chain Variable Region (SEQ ID NO: 45) | EQQLLESGGGLVQPGGSLRLSCAVSGIDLSTYAMGWVRQAPGKGLEWIGLIHRSGRTYYATWAKGRFTISKDSSKTTVYLQMNSLRAEDTAVYFCTRSYPDYSATASIWGQGTTVTVSS |
| hu.Ab5.H12 Heavy Chain Variable Region (SEQ ID NO: 46) | EVQLLESGGGLVQPGGSLRLSCAASGIDLSTYAMGWVRQAPGKGLEWVSLIHRSGRTYYATWAKGRFTISRDNSKNTLYLQMNSLRAEDTAVYYCTRSYPDYSATASIWGQGTTVTVSS |
| hu.Ab5.H13 Heavy Chain Variable Region (SEQ ID NO: 47) | EVQLLESGGGLVQPGGSLRLSCAASGIDLSTYAMGWVRQAPGKGLEWVGLIHRSGRTYYATWAKGRFTISKDSSKNTLYLQMNSLRAEDTAVYYCTRSYPDYSATASIWGQGTTVTVSS |
| hu.Ab5.L1 Light Chain Variable Region (SEQ ID NO: 48) | DIQVTQSPSSLSASVGDRVTITCQASENIANALAWYQQKPGKPPKFLIYGASNLASGVPSRFSGSGSGTDFTFTISSLQPEDIATYYCQQAYYGNSFVEGTFGGGTKVEIK |
| hu.Ab5.L2 Light Chain Variable Region (SEQ ID NO: 49) | DIQMTQSPSSLSASVGDRVTITCQASENIANALAWYQQKPGKPPKFLIYGASNLASGVPSRFSGSGSGTDFTFTISSLQPEDIATYYCQQAYYGNSFVEGTFGGGTKVEIK |
| hu.Ab5.L3 Light Chain Variable Region (SEQ ID NO: 50) | DIQVTQSPSSLSASVGDRVTITCQASENIANALAWYQQKPGKAPKFLIYGASNLASGVPSRFSGSGSGTDFTFTISSLQPEDIATYYCQQAYYGNSFVEGTFGGGTKVEIK |
| hu.Ab5.L4 Light Chain Variable Region (SEQ ID NO: 51) | DIQVTQSPSSLSASVGDRVTITCQASENIANALAWYQQKPGKPPKLLIYGASNLASGVPSRFSGSGSGTDFTFTISSLQPEDIATYYCQQAYYGNSFVEGTFGGGTKVEIK |
| hu.Ab5.L5 Light Chain Variable Region (SEQ ID NO: 52) | DIQMTQSPSSLSASVGDRVTITCQASENIANALAWYQQKPGKAPKLLIYGASNLASGVPSRFSGSGSGTDFTFTISSLQPEDIATYYCQQAYYGNSFVEGTFGGGTKVEIK |

TABLE E

Constant Domains

| Description | Sequence |
|---|---|
| hIgG1 constant domain (Heavy Chain) (SEQ ID NO: 53) | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPELLGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSREEMTKNQVSLTC LVKGFYPSDIAVEWESNGQPENNYK TTPPVLDSDGSFFLYSKLTVDKSRW QQGNVFSCSVMHEALHNHYTQKSLS LSPGK |
| Kappa constant domain (Light Chain) (SEQ ID NO: 54) | RTVAAPSVFIFPPSDEQLKSGTASV VCLLNNFYPREAKVQWKVDNALQSG NSQESVTEQDSKDSTYSLSSTLTLS KADYEKHKVYACEVTHQGLSSPVTK SFNRGEC |

Evaluation of CCR8 binding of the humanized variants with a hIgG1 Fc involved screening by flow cytometry, and comparing the relative $EC_{50}$ and MFI on human CCR8 CHO cells to the parental rabbit antibodies. Specifically, stable CHO-huCCR8.Gna15 cells were stained with various concentrations (starting from 10 ug/ml or 66.66 nM, 1:4 serial dilution for total 8 concentration points) of Ab4 and Ab5 variants at 4° C. for 30 minutes, then washed twice with FACS buffer (PBS with 0.5% BSA and 0.2 mM EDTA) and followed by staining with AF647-anti-hIgG at 4° C. for 15 min. Cells were washed twice with FACS buffer, and resuspended in FACS buffer with propidium iodide (0.5 ug/ml) and analyzed with iQue3 (Sartorius).

For the Ab4 LC variants L1-L4, as provided in Table F1, variants L2 and L4, containing a Y21 mutation, showed significant changes in either $EC_{50}$ or MFI. It was thus determined that Y2 on light chain is a key rabbit Vernier residue. Variants L1 and L3 contained this Y2 residue, and variant L3 was selected for further analysis.

TABLE F1

Relative $EC_{50}$ and MFIs for Ab4 LC variants

| Antibody | Relative $EC_{50}$ | Relative MFI |
|---|---|---|
| rb.Ab4 | 1.0 | 1.0 |
| hu.Ab4.H1L1 | 0.88 | 0.95 |
| hu.Ab4.H1L2 | 1.06 | 0.73 |
| hu.Ab4.H1L3 | 1.23 | 1.00 |
| hu.Ab4.H1L4 | 1.04 | 0.80 |

For the Ab4 HC variants H2-H11, as provided in Table F2, variant H6 (with a S73N mutation), variant H7 (with a T76N mutation), variant H8 (with a V78L mutation), variant H9 (with a F91Y mutation), variant H10 (with a P105Q mutation), and variant H11 (with a S73N, V78L, F91Y, and P105Q mutations) showed significant changes in either $EC_{50}$ or MFI. It was thus determined that S73, T76, V78, F91 and P105 on the heavy chain were the key rabbit Vernier residues. These five residues were combined to construct variant H12 (hu.Ab4.H12).

TABLE F2

Relative $EC_{50}$ and MFIs for Ab4 HC variants

| Antibody | Relative $EC_{50}$ | Relative MFI |
|---|---|---|
| rb.Ab4 | 1.0 | 1.0 |
| hu.Ab4.H2L1 | 0.99 | 1.07 |
| hu.Ab4.H3L1 | 1.00 | 1.02 |
| hu.Ab4.H4L1 | 0.96 | 1.06 |
| hu.Ab4.H5L1 | 1.02 | 0.90 |
| hu.Ab4.H6L1 | 1.06 | 0.68 |
| hu.Ab4.H7L1 | 1.05 | 0.44 |
| hu.Ab4.H8L1 | 1.03 | 0.72 |
| hu.Ab4.H9L1 | 1.04 | 0.87 |
| hu.Ab4.H10L1 | 1.07 | 0.77 |
| hu.Ab4.H11L1 | 0.88 | 0.66 |

For the Ab5 LC variants L2-L5, as provided in Table F3, variant L2 (with a V4M mutation), variant L3 (with a P43A mutation), variant L4 (with a F46L mutation), and variant L5 (with a V4M, P43A, and F46L mutation) showed significant changes in either $EC_{50}$ or MFI. It was thus determined that V4, P43 and F46 on the light chain were the key rabbit Vernier residues. All variants contained a C90Q mutation in CDR L3, which was introduced to remove an unpaired cysteine that would be a liability during manufacturing. Variant L1, which contains all three V4, P43 and F46 residues, was selected for further study.

TABLE F3

Relative $EC_{50}$ and MFIs for Ab5 LC variants

| Antibody | Relative $EC_{50}$ | Relative MFI |
|---|---|---|
| rb.Ab5 | 1.0 | 1.0 |
| hu.Ab5.H1L2 | 1.4 | 0.79 |
| hu.Ab5.H1L3 | 1.5 | 0.81 |
| hu.Ab5.H1L4 | 1.7 | 0.51 |
| hu.Ab5.H1L5 | 0.3 | 0.31 |

For the Ab5 HC variants H2-H12, as provided in Table F4, variant H5 (with a G49S mutation), variant H6 (with a K71R mutation), variant H7 (with a S73N mutation), and H12 (with a G49S, K71R, and S73N mutation) showed significant changes in either $EC_{50}$ or MFI. Thus, it was determined that G49, K71 and S73 on the heavy chain were the key rabbit Vernier residues. These three residues were combined to construct variant H13.

TABLE F4

Relative $EC_{50}$ and MFIs for Ab5 HC variants

| Antibody | Relative $EC_{50}$ | Relative MFI |
|---|---|---|
| rb.Ab5 | 1 | 1 |
| hu.Ab5.H2L1 | 1.1 | 0.93 |
| hu.Ab5.H3L1 | 1.5 | 1.0 |
| hu.Ab5.H4L1 | 1.5 | 0.95 |
| hu.Ab5.H5L1 | 7.6 | 0.35 |
| hu.Ab5.H6L1 | 2.4 | 0.97 |
| hu.Ab5.H7L1 | 2.2 | 0.96 |
| hu.Ab5.H8L1 | 1.4 | 0.94 |
| hu.Ab5.H9L1 | 1.3 | 0.92 |
| hu.Ab5.H10L1 | 1.2 | 0.87 |
| hu.Ab5.H11L1 | 1.3 | 0.87 |
| hu.Ab5.H12L1 | 2.3 | 0.26 |

Example 3. Characterization of hu.Ab4.H12L3 and hu.Ab5.H13L1 Variants (a) Human-Cyno Cross-Reactivity Cell-based affinity measurements were performed using radiolabeled IgGs and CHO cell lines stably expressing human or cyno CCR8 for hu.Ab5.H13L1 and hu.Ab4.H12L3.

TABLE G1 hu.Ab4.H12L3 Full-length Sequence

| Description | Sequence |
|---|---|
| hu.Ab4.H12 Full-length Heavy Chain (SEQ ID NO: 57) | EVQLLESGGGLVQPGGSLRLSCAASGFSLSNYAMIWVRQAPGKGLEWVS TISLGGYTYYANWAKGRFTISRDSSKTTVYLQMNSLRAEDTAVYFCARA RWSTDSAIYTYAFDPWGPGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHN HYTQKSLSLSPGK |
| hu.Ab4.L3 Full-length Light Chain (SEQ ID NO: 58) | DYQMTQSPSSLSASVGDRVTITCQASQSISSYLSWYQQKPGKAPKLLIY KASTLASGVPSRFSGSGSGTDFTLTISSLQPEDFATYYCQQGYTSSNID NIFGGGTKVEIKRTVAAPSVFIFPPSDEQLKSGTASVVCLLNNFYPREA KVQWKVDNALQSGNSQESVTEQDSKDSTYSLSSTLTLSKADYEKHKVYA CEVTHQGLSSPVTKSFNRGEC |

TABLE G2 hu.Ab5.H13L1 Full-length Sequence

| Description | Sequence |
|---|---|
| hu.Ab5.H13 Full-length Heavy Chain (SEQ ID NO: 55) | EVQLLESGGGLVQPGGSLRLSCAASGIDLSTYAMGWVRQAPGKGLEWV GLIHRSGRTYYATWAKGRFTISKDSSKNTLYLQMNSLRAEDTAVYYCT RSYPDYSATASIWGQGTTVTVSSASTKGPSVFPLAPSSKSTSGGTAAL GCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEK TISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHE ALHNHYTQKSLSLSPGK |
| hu.Ab5.L1 Full-length Light Chain (SEQ ID NO: 56) | DIQVTQSPSSLSASVGDRVTITCQASENIANALAWYQQKPGKPPKFLI YGASNLASGVPSRFSGSGSGTDFTFTISSLQPEDIATYYCQQAYYGNS FVEGTFGGGTKVEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |

Briefly, stable CHO cells expressing human or cyno CCR8 were seeded in cold binding buffer (Opti-MEM+2% FBS+50 mM HEPES, pH 7.2+0.1% Sodium Azide) at 50,000 cells per well. A fixed concentration of $^{125}$I-anti-CCR8 radiolabeled using the NEX244 Iodogen method (Perkin Elmer) was mixed with serially diluted anti-CCR8 antibodies starting at 20 nM or 50 nM. The antibody mixture was added to the cells and incubated at room temperature for 12 hours under gentle agitation. The cells and antibodies were then transferred to Millipore multiscreen filter plates. The filter plates were washed 4 times with 250 μL of cold binding buffer and dried for at least 30 minutes and the filters were punched into 5 mL polystyrene tubes. The radioactivity was measured using a Perkin Elmer Wallac Wizard 2470 Gamma Counter set at 1 count per minute with 0.8 counting efficiency. The data were fitted using the heterologous one site-fit Ki competitive binding model in GraphPad Prism.

As shown in FIGS. 7A-7D, both hu.Ab4.H12L3 and hu.Ab5.H13L1 have similar affinity for both human and cyno CCR8, indicating desirable cross-reactivity. Tabulated affinity Kd (nM) data from these studies is provided below.

TABLE G3

| | CCR8 human and cyno affinity | |
|---|---|---|
| Antibody | $K_D$ (nM) CCR8 human | $K_D$ (nM) CCR8 cyno |
| hu.Ab4.H12L3 | 0.0284 | 0.0243 |
| hu.Ab5.H13L1 | 0.0040 | 0.0034 |

(b) CCR8 Selectivity

Figure 8A:
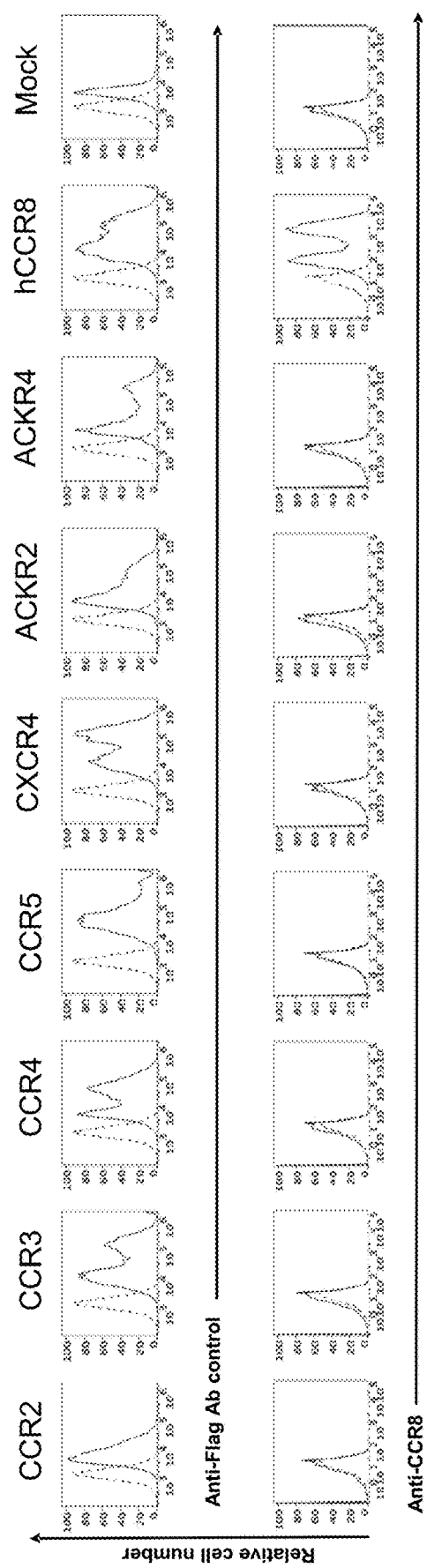
FIGS. 8A-8B depict the binding data of hu.Ab4.H12L3 (FIG. 8A) and hu.Ab5.H13L1 (FIG. 8B) mAbs to a panel of sulfated GPCRs, and reconfirm that these Ab4 and Ab5 variants, similar to the Ab4 and Ab5 data provided in FIG. 4B and FIG. 4C, show selectivity for CCR8. Due to the weaker binding to the N-terminal FLAG tag of hCCR8
Figure 8B:
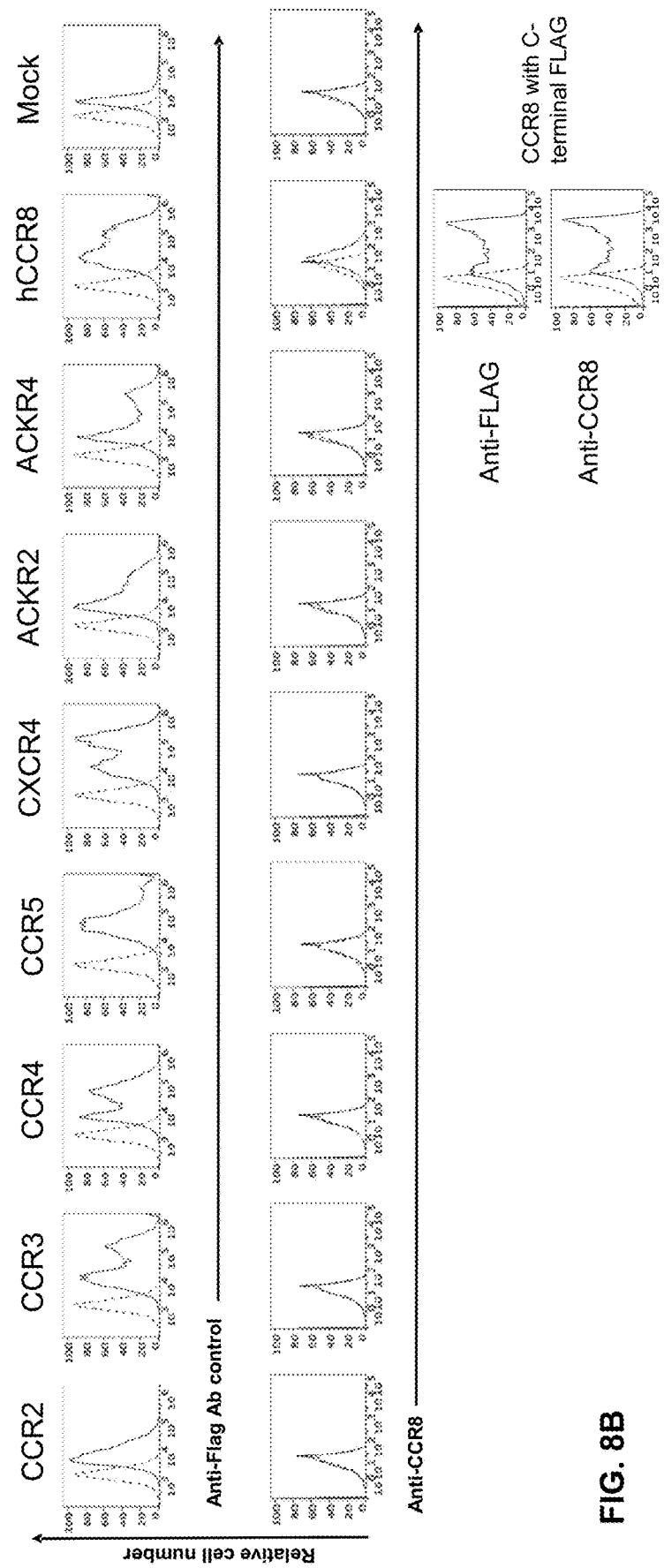

To reconfirm that the Ab4 and Ab5 variants remained selective to CCR8 compared to the corresponding HIL1 variants, binding was analyzed by flow cytometry following the procedure as described for FIG. 4A and FIG. 4B. As before, both hu.Ab4.H12L3 (FIG. 8A) and hu.Ab5.H13L1 (FIG. 8B) bound selectively to CCR8-expressing cells.

(c) CCR8 Activation and Ligand Blocking

Figure 3B:
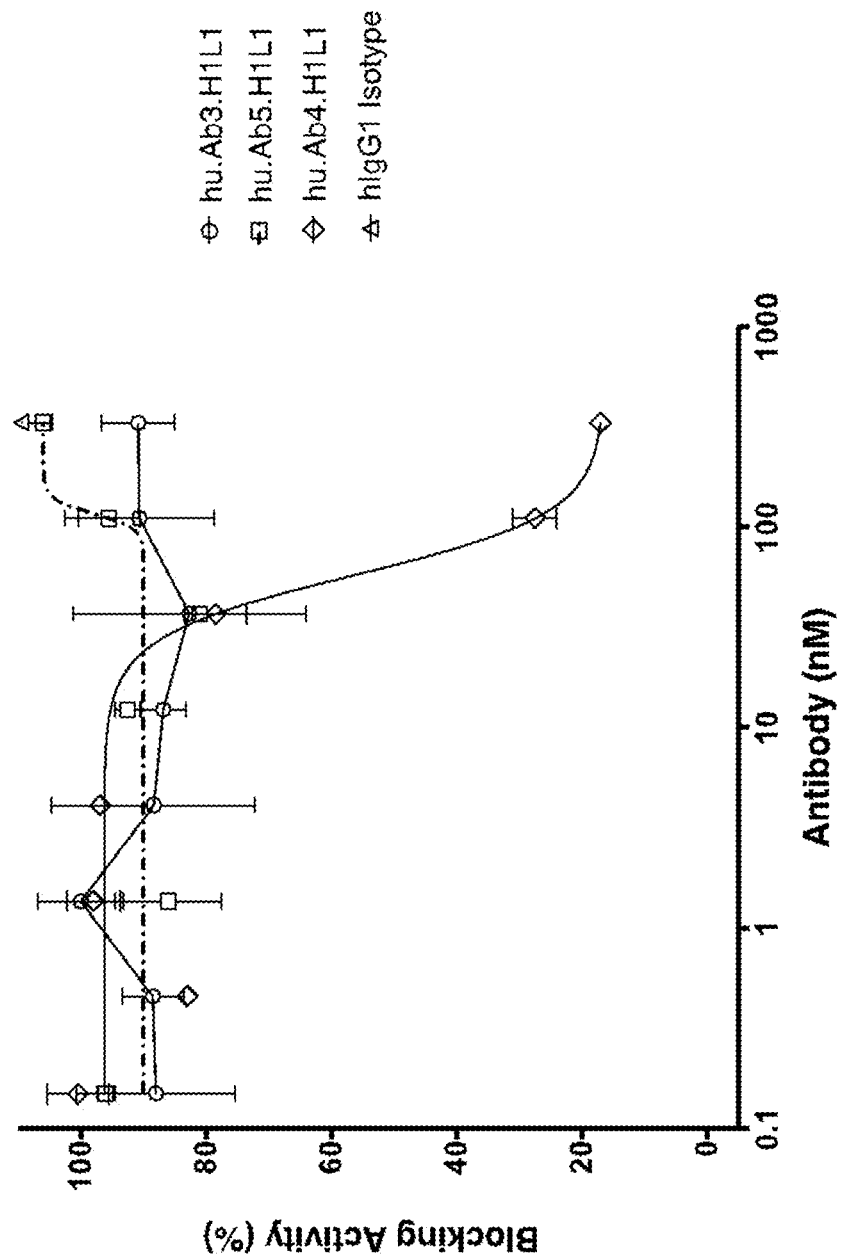
Figure 3C:
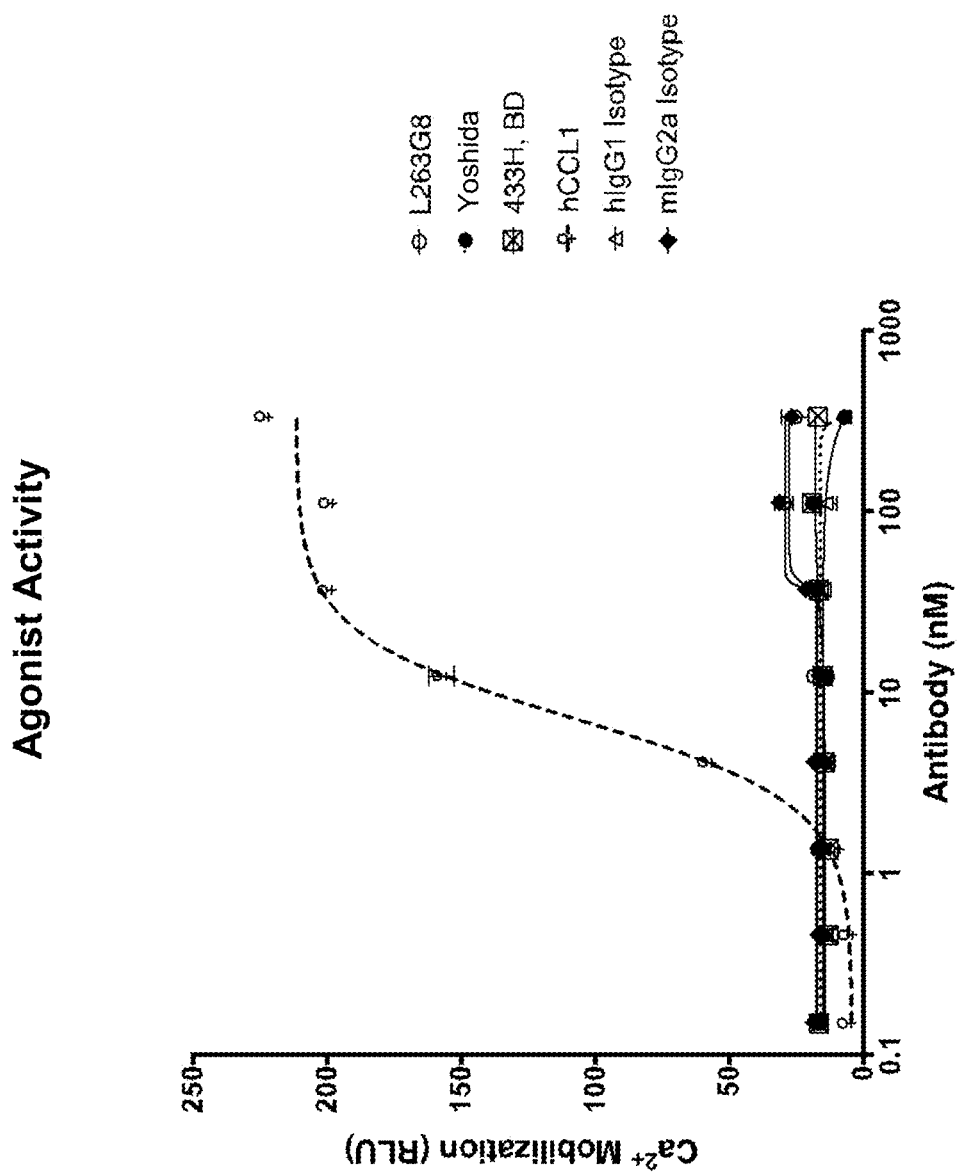
Figure 3D:
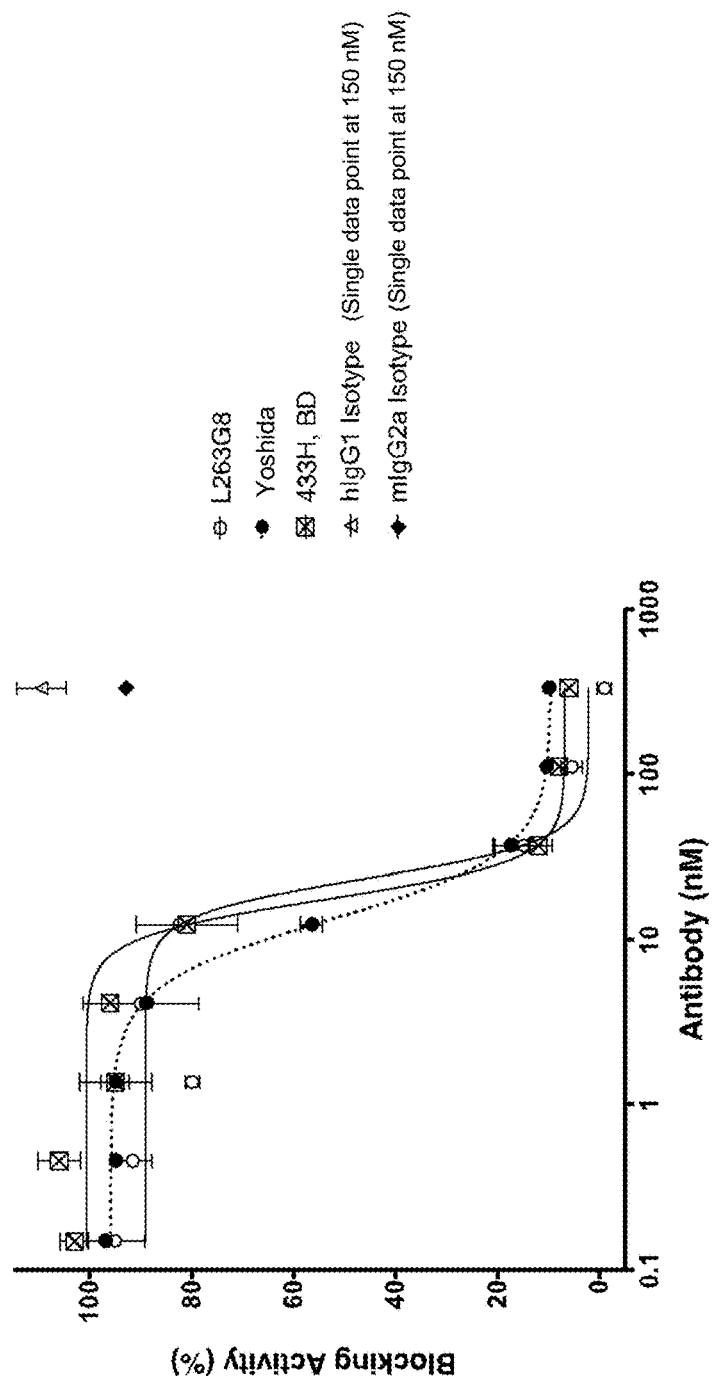

To reconfirm that the Ab4 and Ab5 variants retained their properties regarding CCR8 activation and ligand blocking ability, experiments were conducted with hu.Ab4.H12L3 and hu.Ab5.H13L1 antibodies as previously described in Example 1 and FIG. 3A-3C. See FIGS. 9A-9B. Similar to FIG. 3A, the data in FIG. 9A reconfirms neither the Ab4 nor the Ab5 anti-CCR8 antibody variants show agonistic effects in the absence of CCR8 ligand CCL1. Similar to FIG. 3B data, the data in FIG. 9B reconfirms the Ab4 variant demonstrates antagonistic effects by blocking the activation of CCR8 by the CCR8 ligand CCL1 (20 nM of ligand), whereas the Ab5 variant demonstrates no ligand blocking activity at the concentration studied. The $IC_{50}$ values for the ligand blocking activity are provided in the below Table.

TABLE H1

Ligand Blocking Activity

| Antibody | $IC_{50}$ (nM) |
|---|---|
| hu.Ab5.H13L1 | No inhibition |
| hu.Ab4.H12L3 | 57.9 |

(d) Sulfation Independence

Human CCR8 contains four potential sites of tyrosine sulfation within the N-terminus and existing evidences indicates that modification at these sites exhibits some heterogeneity (Gutierrez et al. JBC 2004; Jen, et al. Biochemistry 2010). As such, antibodies that recognize these sulfated tyrosines in CCR8 may exhibit variability in CCR8 binding, and thus mediate variable Treg cell depletion. Human CCR8+ HEK293 cells were generated that lack tyrosyl protein sulfotransferase (TPST) 1 and 2, which are the enzymes that catalyze tyrosine sulfation. Binding was then analyzed of various anti-CCR8 mAbs to wild type (293T) and TPST1/2 NTC and KO cells.

In particular, HEK293, HEK293-hCCR8.TPST1/2 NTC and HEK293-hCCR8.TPST1/2 KO stable cell lines were stained with test and comparator anti-CCR8 antibodies (1 ug/ml) at 4° C. for 30 minutes, then washed twice with FACS buffer (PBS with 0.5% BSA and 0.2 mM EDTA) and followed by staining with AF647-anti-hIgG at 4° C. for 15 minutes. Cells were washed twice with FACS buffer, and re-suspended in FACS buffer with propidium iodide (0.5 ug/ml) and analyzed with BD FACSCelesta Flow Cytometer or iQue3 (Sartorius).

FIGS. 10A-10E depicts differences in staining of hu.Ab4.H12L3 and hu.Ab5.H13L1 compared to the Yoshida humanized anti-human CCR8 antibody and commercial antibodies murine anti-human CCR8 mAb 433H (BD Biosciences) and murine anti-human CCR8 mAb L263G8 (Biolegend) to CCR8+HEK293 cells with (hCCR8.TPST1/2 NTC) and without tyrosyl protein sulfotransferase (TPST) 1 and tyrosyl protein sulfotransferase (TPST) 2 (hCCR8.TPST1/2 KO). hu.Ab4.H12L3 (FIG. 10A) and hu.Ab5.H13L1 (FIG. 10B) show similar binding/staining to both cell lines (hCCR8.TPST1/2 NTC and hCCR8.TPST1/2 KO), indicating they bind CCR8 independent of tyrosine sulfation ("sulfation independent"). In contrast, the Yoshida humanized anti-human CCR8 antibody (FIG. 10C) and commercial antibodies murine anti-human CCR8 mAb 433H (BD Biosciences) (FIG. 10D) and murine anti-human CCR8 mAb L263G8 (Biolegend) (FIG. 10E) failed to bind the TPST1/2 KO cells, indicating they require tyrosine sulfation of CCR8 for binding, and are thus considered "sulfation dependent."

Example 4. hu.Ab4.H12L3 and hu.Ab5.H13L1 Afucosylated Variants

Afucosylated hu.Ab5.H13L1 and hu.Ab4.H12L3 variants (at Fc N-glycan position Asn299), and the afucosylated anti-gD control, were prepared by expression and purification from FUT8 knock-out (KO) CHO cells as described in Wong et al, *Biotechnology and Bioengineering* (2010) 106: 751-763.

(a) Percent Afucosylation

Titration of fucose in media of CHO FUT8KO yielded a panel of hu.Ab5.H13L1 with varying levels of afucosylation, e.g., between about 14% to about 93% afucosylated hu.Ab5.H13L1.

As noted in the below table, increasing the afucosylation level from 14% to 49% produced a greater than 4-fold increase in ADCC activity, and a greater than 3-fold increase in ADCP activity.

Afucosylated hu.Ab5.H13L1 and hu.Ab4.H12L3 studied in the in vitro and in vivo experiments to follow contained levels of between about 80% to about 95% afucosylation.

TABLE H2

Percent Afucosylation Effect on ADCC and ADCP activity

| % afucosylation | ADCC $EC_{50}$ (pM) | ADCP $EC_{50}$ (pM) |
|---|---|---|
| 93 | 3.53 | 0.049 |
| 89 | 4.63 | 0.052 |
| 73 | 5.42 | 0.047 |
| 62 | 6.61 | 0.068 |
| 53 | 8.45 | 0.093 |
| 49 | 9.24 | 0.075 |
| 14 | 39.7 | 0.25 |

(b) Enhanced Fcgamma RIIIa Binding of Afucosylated Variants

The binding of fucosylated and afucosylated variants of hu.Ab5.H13L1 and hu.Ab4.H12L3 to both FcgR3a proteins by ELISA was studied. Briefly, an anti-GST antibody was coated on Nunc Maxisorp plates. GST-FcgR3a.V158 and GST-FcgR3a.F158 were captured at 500 ng/mL. Plates were then washed and then serially diluted anti-CCR8 antibodies starting at 100 ug/mL were incubated on the plate for 1 hour at room temperature. Plates were washed and bound antibody was detected by a HRP-conjugated anti-human IgG secondary antibody. Absorbance at 450 nm was measured by a plate reader. The data were fitted using a 4-parameter logistic curve in Softmax Pro. As shown in the Table below, afucosylated IgG1 anti-CCR8 antibodies Afuc.hu.Ab5.H13L1 and Afuc.hu.Ab4.H12L3 exhibited enhanced Fcgamma RIIIa binding activities (approximately a 10-fold increase in binding potency) compared to their fucosylated counterparts hu.Ab5.H13L1 and hu.Ab4.H12L3.

TABLE 1

Fcgamma RIIIa Binding Activity

| Antibody | FcgR3a.F158 protein $EC_{50}$ (ug/mL) | FcgR3a.V158 protein $EC_{50}$ (ug/mL) |
|---|---|---|
| hu.Ab5.H13L1 | 4.107 ± 1.036 | 0.39 ± 0.049 |
| Afuc.hu.Ab5.H13L1 | 0.101 ± 0.057 | 0.035 ± 0.006 |
| hu.Ab4.H12L3 | 3.74 ± 2.03 | 0.388 ± 0.178 |
| Afuc.hu.Ab4.H12L3 | 0.08 ± 0.025 | 0.033 ± 0.006 |

(c) Enhanced ADCC Activity of Afucosylated Variants

Afuc.hu.Ab4.H12L3, hu.Ab4.H12L3, Afuc.hu.Ab5.H13L1, and hu.Ab5.H13L1 were analyzed for antibody-dependent cellular cytotoxicity (ADCC). ADCC assays were performed as previously reported in Kamen et al., *Development of a kinetic antibody-dependent cellular cytotoxicity assay.* J Immunol Methods (2019)468:49-54, and Schnueriger et al., *Development of a quantitative, cell-line based assay to measure ADCC activity mediated by therapeutic antibodies.* Mol Immunol (2011) 48:1512-17, with some modifications, using CD16 engineered NK-92_F158 as effector cells and CHO cells that stably express human CCR8 and Ga 15 subunit (CHO/hCCR8.Gna15) as target cells. Briefly, lysis of target cells by ADCC was measured by the calcein release method. The target cells were labeled with Calcein-AM (C3100MP, ThermoFisher Scientific) according to the manufacturer's protocol, then washed and plated onto 384-well plates at a density of 3000 cells/well. Anti-CCR8 antibody was added at various concentrations from 0.004 to 1 μg/mL, followed by the addition of NK-92_F158 cells at an effector:target (E:T) ratio of 10:1. The plates were then incubated for 2.5 hours at 37° C. After incubation, the plates were centrifuged at 200×g for 3 minutes, the supernatants were transferred to a white opaque 384-well microplate (OptiPlate-384, PerkinElmer, Waltham, MA), and fluorescent signals were measured in relative fluorescence units (RFU) using an EnSight Multimode Plate Reader (PerkinElmer) with excitation/emission at 485/520 nm. Signals from the wells containing only the target cells represented spontaneous release of the calcein from labeled cells (spontaneous release), whereas wells containing target cells lysed with Triton X-100 (Sigma-Aldrich, St. Louis, MO) provided the maximal signal available (maximal release). Antibody-independent cell-mediated cytotoxicity (AICC) was measured in wells containing target and effector cells without the addition of the antibody. Samples and controls were tested at least in duplicate in the same plates. The extent of specific ADCC activity was calculated as follows:

% ADCC=100×(mean experimental release-mean AICC)/(mean maximum release-mean spontaneous release)

The ADCC activity was plotted as a function of antibody concentrations and the data were fitted to an asymmetric sigmoidal four-parameter logistic (4PL) model using Prism (Graphpad; La Jolla, CA). FIGS. 11A-11B show afucosylated CCR8 antibodies Afuc.hu.Ab5.H13L1 and Afuc.hu.Ab4.H12L3 have enhanced (>10-fold improved) ADCC activity compared to their fucosylated counterparts hu.Ab5.H13L1 and hu.Ab4.H12L3 against CHO cells stably expressing hCCR8 using NK-92 F158 (FIG. 11A) and NK-92 V158 (FIG. 11B) as effector cells.

The ADCC activity for Afuc.hu.Ab5.H13L1 and Afuc.hu.Ab4.H12L3 was also measured against the Yoshida humanized anti-human CCR8 antibody and commercial antibodies murine anti-human CCR8 mAb 433H (BD Biosciences) and murine anti-human CCR8 mAb L263G8 (Biolegend). See FIG. 11C. The data demonstrates the Yoshida humanized anti-human CCR8 antibody exhibits weaker ADCC activity (less than 10-20 fold less ADCC activity) than the anti-CCR8 antibodies Afuc.Ab5.H13L1, Afuc.Ab4.H12L3. Commercially available antibodies murine anti-human CCR8 mAb 433H (BD Biosciences) and murine anti-human CCR8 mAb L263G8 (Biolegend), which comprise murine Fc domains, as expected demonstrated no ADCC activity as the assay employed in this instance is primarily relevant for antibodies comprising human Fc domains.

Murine anti-human CCR8 mAb 433H (BD Biosciences) and murine anti-human CCR8 mAb L263G8 (Biolegend) were tested for ADCC activity in an assay relevant for antibodies comprising murine Fc regions but anti-human CCR8 activity, i.e., using Jurkat/mFcgR4 stable line as the effector cells and CHO/hCCR8 as the target cells. Human CCR8 (hCCR8) was used to mimic a human clinical setting. Specifically, the assay consists of a genetically engineered Jurkat T cell line that expresses mouse FcgRIV receptor and a luciferase reporter driven by an NFAT-response element (NFAT-RE). When co-cultured with a target cell and relevant antibody, the mFcgRIV Effector Cells bind the Fc domain of the antibody, resulting in mFcgRIV signaling and NFAT-RE-mediated luciferase activity. Materials and Reagents: Assay buffer: RPMI1640 without phenol red supplemented with 4% low IgG; 96-well White Flat Bottom Polystyrene TC-treated Microplates, Corning #3601; Bio-Glo reagent. Assay Procedures: Add 25 μL/well diluted antibody in assay buffer (Prepared 3×, staring at 30 ug/mL serial diluted at 1:4 for 10 points). Resuspend the target cell in assay buffer, adjust final density to $1\times10^6$/ml; dispense 25 μL cells to each well for target cell density of 25,000/well; Incubate the plate for 20 minutes at room temperature. Add 25 μL/well Jurkat/mFcgRIV cell (at $5\times10^6$ cells/mL) to each well for effector cell density of 125,000/well; re-mix the cells in the reservoir regularly during the process to prevent settling of cells to the bottom. Cover the assay plates with a lid and incubate the plate at 37° C. with 5% $CO_2$ incubator for 16 hours. Do not stack the plates inside the incubator. Remove the assay plates from the incubator and equilibrate to ambient temperature for 15 minutes. Using a multichannel pipette, add 75 μl of Bio-Glo™ Reagent to the assay plates, taking care not to create bubbles. Incubate the plate 15 minutes at room temperature. Measure luminescence using EnSight luminescence plate reader. mIgG2a isotype, hIgG1 and ratIgG2b were tested as controls. Human CCR8 (hCCR8) was used to mimic a human clinical setting. As can be seen from the data, each of the anti-hCCR8 mAb tested—L263G8 (BioLegend) and 433H (BD Biosciences)—displayed high induction fold results at antibody concentration levels of about 1 nM—showing induction fold results of more than about 10 and about 12, respectively. The high induction fold for each of these antibodies plateaus at an antibody concentration level of about 40 nM—with induction fold values of about 11 and 13, respectively. The results of these experiments are provided in FIG. 11D.

Activity data from these studies is also provided in the below Table. In summary, each of the antibodies studied, whether having humanized or murine Fc regions, demonstrated ADCC activity in the assay to which the antibody isotype was species-matched to relevant effector reporter cells.

TABLE J

ADCC Activity

| Ab tested | NK-92 F158 cells EC$_{50}$ (nM) FIG. 11A | NK-92 V158 cells EC$_{50}$ (nM) FIG. 11B | NK-92 F158 cells EC$_{50}$ (nM) FIG. 11C | mFcgRIV Jurkat cells with CHO/ hCCR8 EC$_{50}$ (nM) FIG. 11D |
|---|---|---|---|---|
| hu.Ab5.H13L1 | 0.14 | 0.094 | | |
| Afuc.hu.Ab5.H13L1 | 0.0047 | 0.0073 | 0.003 | |
| hu.Ab4.H12L3 | 0.27 | 0.21 | | |
| Afuc.hu.Ab4.H12L3 | 0.006 | 0.011 | 0.006 | |
| Yoshida Ab | | | 0.060 | |
| L263G8 (Biolegend) | | | No activity* | 0.28 |
| 433H (BD Biosciences) | | | No activity* | 0.26 |

*No activity = assay conditions not relevant for specific Ab isotype (d) ADCC Enhancement Against Treg Cells To induce CCR8 expression on Treg cells from human peripheral blood mononuclear cells (PBMC), 10$^7$ human PBMC were intraperitoneally transferred to NOD.Cg-Prkd-$^{scid}$ Il2rg$^{tm1Wjl}$/SzJ (NSG) mice (JAX) and spleens collected 2-3 weeks post-transfer. Human T cells were enriched from single cell suspensions of NSG splenocytes using the Mouse Lineage Cell Depletion Kit (Miltenyi Biotec), separately primary NK cells were enriched from human PBMC using the Human NK Cell Isolation Kit (Miltenyi Biotec) according to manufacturer's protocol. Human T cells were incubated with 0.001-1 ug/mL CCR8 mAb for 30 minutes at room temperature prior to the addition of primary NK cells at an effector:target ratio of 2:1. After overnight incubation at 37° C., cells were collected, surface stained, and intracellularly stained using the eBioscience Foxp3/Transcription Factor Staining Buffer Set (ThermoFisher Scientific) according to the manufacturer's protocol. Antibodies used to define T cell populations were CD45 (H130), CD3 (SK7), CD8 (RPA-T8), and CD14 (63D3) from BD Biosciences, CD4 (RPA-T4) from BioLegend, and FOXP3 (236A/E7) from ThermoFisher Scientific. CountBright Absolute Counting Beads (ThermoFisher Scientific) was added to each sample prior to acquisition. Flow cytometry was performed on a Fortessa X-20 (BD Biosciences) and analyzed with FlowJo software (BD Biosciences, Version 10.5.3). Absolute cell counts were calculated according to manufacturer's protocol.

ADCC activity against Treg cells was measured by calculating the ratio of recovered regulatory T cells to recovered CD8 cells (Treg/CD8) or conventional CD4 T cells to recovered CD8 T cells (CD4conv/CD8). The number of CD8 T cells recovered was similar across all concentrations of CCR8 mAbs and isotype control mAb tested ("gD.afuc"). As depicted in FIGS. 12A-12D, afucosylated CCR8 antibodies Afuc.hu.Ab5.H13L1 and Afuc.hu.Ab4.H12L3 and fucosylated CCR8 antibodies hu.Ab5.H13L1 and hu.Ab4.H12L3 selectively mediated ADCC activity with increased depletion of Tregs from in vivo mixed lymphocyte reaction (MLR)-activated human PBMCs (FIGS. 12A and 12C) in comparison to conventional CD4 T cells (FIGS. 12B and 12D), and with the afucosylated variants mediating increased ADCC activity. Low level afucosylated anti-CCR8-mediated ADCC was observed in conventional CD4 T cells, consistent with the moderate upregulation of CCR8 on conventional CD4 T cells upon transfer into NSG mice (data not shown).

Additional data demonstrates afucosylated CCR8 mAbs Afuc.hu.Ab5.H13L1 and Afuc.hu.Ab4.H12L3 exhibit selective ADCC against Tregs from RCC tumors. Briefly, human dissociated tumor cells (Renal cell carcinoma, Discovery Life Sciences) were thawed according to the vendor's protocol. Primary NK cells were enriched from human PBMC using the Human NK Cell Isolation Kit (Miltenyi Biotec) according to manufacturer's protocol. Human dissociated tumor cells were incubated with 0.001-1 ug/mL CCR8 mAb for 30 min at room temperature prior to the addition of primary NK cells at an effector:target ratio of 2:1. After overnight incubation at 37° C., cells were processed as above to determine absolute cell counts for CD8, conventional CD4, and regulatory T cells.

As depicted in FIGS. 13A-13D, afucosylated CCR8 antibodies Afuc.hu.Ab5.H13L1 and Afuc.hu.Ab4.H12L3 and fucosylated CCR8 antibodies hu.Ab5.H13L1 and hu.Ab4.H12L3 mediated selective ADCC activity with increased depletion of Treg cells from human dissociated tumor cells from RCC (FIGS. 13A and 3C) in comparison to conventional CD4 T cells (FIGS. 13B and 13D), and with the afucosylated variants mediating increased ADCC activity. Consistent with the absence of CCR8 staining on intratumoral conventional CD4 T cells, CCR8 mAb-mediated ADCC activity was not observed on conventional CD4 T cells, demonstrating the selectivity of CCR8 mAb-mediated ADCC against intratumoral regulatory T cells.

(e) ADCP Enhancement

Conflicting reports exist on the impact of afucosylation on ADCP. See, e.g., Herter, et al. *J Immunol* (2014) 192:2252-2260; Silence et al., mAbs (2013) 6:523-532; and Kwiatkowski et al., *mAbs* (2020) 12: e1803645 (9 pages). Furthermore, the G236A.I332E mutant has previously been shown to increase ADCP via enhanced FcgR2a binding. See Richards et al., *Molecular Cancer Therapeutics* (2008) 7:2517-2527. Therefore, fucosylated and afucosylated hIgGL.G236A.V332E Fc versions of both hu.Ab5.H13L1 and hu.Ab4.H12L3 were prepared to investigate whether ADCP activity would be observed. The G236A.I332E mutant hIgG1 constant domain is provided in the below Table, with mutational differences from the normal hIgG1 constant domain underlined, along with full-length heavy chain sequences of the Ab4 and Ab5 G236A.I332E variants.

TABLE K hIgG1.G236A.I332E variants

| Description | Sequence |
|---|---|
| hIgG1.G236A. I332E Constant domain (SEQ ID NO: 59) | ASTKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKKVEPKSCDKT HTCPPCPAPELLAGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APEEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNH YTQKSLSLSPGK |

TABLE K-continued hIgG1.G236A.I332E variants

| Description | Sequence |
|---|---|
| Afuc.hu.Ab5.H13.G236A.I332E Full-length Heavy Chain (SEQ ID NO: 60)[a] | EVQLLESGGGLVQPGGSLRLSCAASGIDLSTYAMGWVRQAPGKGLEWVGLIHR SGRTYYATWAKGRFTISKDSSKNTLYLQMNSLRAEDTAVYYCTRSYPDYSATA SIWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLAGPSVFLFPPKPKDTLMISRTPEVTCVV VDVSHEDPEVKFNWYVDGVEVHNAK̄TKPREEQYNSTYRVVSVLTVLHQDWLNG KEYKCKVSNKALPAPEEKTISKAKGQPREPQVYTLPPSREEMTKNQVSLTCLV KGFYPSDIAVEWESNḠQPENNYKTTPPVLDSDGSFFLYSKLTVDKSRWQQGNV FSCSVMHEALHNHYTQKSLSLSPGK |
| Afuc.hu.Ab4.H12.G236A.I332E Full-length Heavy Chain (SEQ ID NO: 61)[b] | EVQLLESGGGLVQPGGSLRLSCAASGFSLSNYAMIWVRQAPGKGLEWVSTISL GGYTYYANWAKGRFTISRDSSKTTVYLQMNSLRAEDTAVYFCARARWSTDSAI YTYAFDPWGPGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNHK PSNTKVDKKVEPKSCDKTHTCPPCPAPELLAGPSVFLFPPKPKDTLMISRTPE VTCVVVDVSHEDPEVKFNWYVDGVEVHNAK̄TKPREEQYNSTYRVVSVLTVLHQ DWLNGKEYKCKVSNKALPAPEEKTISKAKGQPREPQVYTLPPSREEMTKNQVS LTCLVKGFYPSDIAVEWESNḠQPENNYKTTPPVLDSDGSFFLYSKLTVDKSRW QQGNVFSCSVMHEALHNHYTQKSLSLSPGK |

[a] The light chain full-length sequence for the Ab5 G236A.I332E variant corresponds to hu.Ab5.L1 (SEQ ID NO: 56).
[b] The light chain full-length sequence for the Ab4 G236A.I332E variant corresponds to hu.Ab4.L3 (SEQ ID NO: 58).

Human CD14+ monocytes were first isolated from blood of Genentech donors with known FcgRIIa and FcgRIIIa genotype information, by using EasySep Human Monocyte Enrichment Kit (Stem Cell Technologies). The purified CD14+ monocytes were differentiated into macrophages in RPMI+10% FBS with 100 ng/mL hM-CSF(PeproTech, Inc) for 5 days. Then 50 ng/mL of hIL-10 ((PeproTech, Inc) were added to polarize the macrophages for 24 hours prior to ADCP assay. NucLight Red transfected CHO/hCCR8.Gna15 target cells were pre-incubated with anti-CCR8 antibodies for 20 minutes in the presence of 20 mg/mL of non-specific human IgG. Then the above cell mixtures were added to the macrophage (effector cell) plate at an E:T ratio of 1:1. After the plate was placed inside the IncuCyte Zoom instrument (Essen Biosciences; Ann Harbor, MI), cell images were obtained with bright field and red laser settings every one hour for a period of 6 hours. The red cell count in each well (remaining target cells) was normalized by the macrophage numbers in the same well using the instrument-embedded software. The ADCP activity was calculated as the percentage of decrease of the normalized red cell count in each sample compared to the negative control where isotype control antibody was present. Then the ADCP activity was plotted as a function of antibody concentrations and the data were fitted to an asymmetric sigmoidal four-parameter logistic (4PL) model using Prism. The $EC_{50}$ value for each antibody was determined as the concentration reaching 50% target cell killing.

As depicted in FIGS. 14A-14D, afucosylated anti-CCR8 antibodies Afuc.hu.Ab5.H13L1 and Afuc.hu.Ab4.H12L3 exhibited enhanced ADCP activities compared to fucosylated antibodies hu.Ab5.H13L1 and hu.Ab4.H12L3 in CD14+ monocytes-derived macrophages from four different donors with FcgRIIa (H131R)/FcgRIIIa (V158F) genotypes of HR/FF (FIG. 14A), RR/FF (FIG. 14B), HR/VF (FIG. 14C), and RR/VF (FIG. 14D). The results indicate that in the context of the antibodies targeting CCR8, afucosylation results in enhanced ADCP.

Afucosylated anti-CCR8 antibodies Afuc.hu.Ab5.H13L1 and Afuc.hu.Ab4.H12L3 also exhibited enhanced ADCP activities compared to the Yoshida humanized anti-human CCR8 antibody (3-4 fold improvement) (FIG. 14E).

Activity data from these studies is also provided in the below Table.

TABLE L

ADCP Activity

| Antibody | HR/FF $EC_{50}$ (nM) FIG. 14A | RR/FF $EC_{50}$ (nM) FIG. 14B | HR/VF $EC_{50}$ (nM) FIG. 14C | RR/VF $EC_{50}$ (nM) FIG. 14D | HR/FF $EC_{50}$ (nM) FIG. 14E |
|---|---|---|---|---|---|
| hu.Ab5.H13L1 | n.d. | n.d. | n.d. | n.d. | |
| Afuc.hu.Ab5.H13L1 | 0.017 | 0.2 | 0.01 | 0.50 | 0.022 |
| hu.Ab4.H12L3 | 0.35 | 0.81 | n.d. | 0.41 | |
| Afuc.hu.Ab4.H12L3 | 0.025 | 0.12 | 0.017 | 0.079 | 0.035 |
| Yoshida Ab | | | | | 0.096 | n.d. = not determined

Furthermore, as depicted in FIGS. 15A-15D, the afucosylated anti-CCR8 antibody Afuc.hu.Ab5.H13L1 exhibited similar improved ADCP activities compared to the FcgRIIa-enhanced G236A.I332E variant Afuc.hu.Ab5.H13L1G236A.I332E in CD14+ monocytes-derived macrophages from four different donors with FcgRIIa (H131R)/FcgRIIIa (V158F) genotypes of genotypes of HR/FF (FIG. 15A), RR/FF (FIG. 15B), HR/VF (FIG. 15C), and RR/VF (FIG. 15D). The similarity in ADCP activities between the afucosylated hIgG1 variant and the G236A.I332E mutant are surprising given a previous report that incorporating G236A.I332E mediates substantially higher levels of ADCP, albeit with an anti-EPCAM mAb. See Richards et al., *Molecular Cancer Therapeutics* (2008) 7:2517-2527.

(f) Physical Characterization of Ab4 and Ab5 Antibodies

The solubility, viscosity, and behavior under thermal stress (shelf life stability), of both Afuc.hu.Ab5.H13L1 and Afuc.hu.Ab4.H12L3 were evaluated at high concentrations. As shown in the below Table, both antibodies showed favorable chemical and physical properties useful in their manufacture and formulation, demonstrating low aggregation, good solubility, low viscosity, and good shelf life stability.

TABLE M

Antibody Physical Characterization

| Assay | Afuc.hu.Ab5.H13L1 | Afuc.hu.Ab4.H12L3 |
|---|---|---|
| Thermal stress (150 mg/mL in 200 mM Arginine Succinate, pH5.5) | 2.0% SEC Monomer loss | 1.9% SEC Monomer loss |
| Solubility in PBS, pH7.4 (OD) | 0.383 | 0.376 |
| Viscosity (in 200 mM Arginine Succinate, pH5.5) | 9.6 cP (180.3 mg/mL) | 12.4 cP (187.1 mg/mL) |

Thermal Stress Conditions: Antibody samples were incubated at 150 mg/mL in 200 mM Arginine Succinate, pH 5.5, for 2 weeks at 40° C. Control samples were stored at −70° C. Size variants were evaluated for the control and stress samples using size exclusion chromatography (SEC). SEC was performed with a Waters Acquity UPLC H-Class (Waters, Milford, MA) with a TSKgel® UP-SW3000 column, 4.6×300 mm (Tosoh Biosciences, King of Prussia, PA). The mobile phase was 0.2 M potassium phosphate buffer (pH 6.2) containing 0.25 M potassium chloride. The separation was conducted at ambient temperature with a flow rate of 0.3 mL/min and column effluent was monitored at 280 nm UV wavelength.

Solubility in Phosphate Buffered Saline (PBS): The antibodies were formulated at 150 mg/mL in 200 mM arginine succinate, pH 5.5 and dialyzed into PBS, pH 7.4 for 24 hours at 37° C. to determine their solubility. After dialysis, samples were visually inspected for visible particulates and the turbidity was determined by using a SpectraMax M2/M2e plate reader (Molecular Devices, San Jose, CA) to measure the absorbance at 340, 345, 350, 355, and 360 nanometers. The values at the 5 wavelengths were averaged resulting in the final solubility value.

Viscosity Determination: The viscosity of the sample at 100, 150, and 180 mg/mL in 200 mM Arginine Succinate, pH 5.5 was determined using an AR G2 Rheometer (TA Instruments, New Castle, DE). A 20 mm cone geometry was used and measurements where conducted over 2.5 minutes at a constant shear rate of 1,000 inverse seconds.

(g) Epitope mapping of hu.Ab5.H13L1

To epitope map fucosylated hu.Ab5.H13L1, the binding to alanine point mutations in human CCR8 was analyzed by flow cytometry.

Constructs encoding for individual alanine point mutations at positions 2-24 in hCCR8 with a C-terminal FLAG tag were generated. HEK 293 cells were transfected with constructs encoding for mutant hCCR8 or with a mock construct using transIT X2 (reagent:DNA=3:1) for 24 hrs, and surface stained with the huCCR8 antibody hu.Ab5.H13L1 (hIgG1), then fixed and permeabilized and followed by FITC-anti-Flag (Sigma F4049).

As shown in FIG. 16A, hu.Ab5.H13L1 does not bind D2A, Y3A, L5A, and D6A, indicating that the epitope includes at least one amino acid residue of the DYTLD region of the human CCR8 N-terminus.

(h) Epitope Mapping Of hu.Ab4.H12L3

To epitope map fucosylated hu.Ab4.H12L3, the binding to chimeric forms of human CCR8 was analyzed by flow cytometry.

Constructs encoding for human CCR8.CCR5 chimeras (N-term1 (amino acid residues 1-23 of human CCR8), N-term2 (amino acid residues 1-36 of human CCR8), ECL1 (amino acid residues 91-104 of human CCR8), ECL2 (amino acid residues 172-193 of human CCR8), and ECL3 (amino acid residues 264-271 of human CCR8) in which different extracellular regions of CCR8 were replaced with the corresponding region from CCR5 with a C-terminal FLAG tag were generated. ECL is defined as an extracellular loop. 293 cells were transfected with constructs encoding for mutant hCCR8 or with a mock construct using transIT X2 (reagent:DNA=3:1) for 24 hrs, and surface stained with huCCR8-Ab4.H12L3.hIgG1, then fixed and permeabilized and followed by FITC-anti-Flag (Sigma F4049).

As shown in FIG. 16B, hu.Ab4.H12L3 does not bind the ECL1 and ECL2 chimeras indicating that the epitope includes at least one amino acid residue of the ECL1 and ECL2 regions of CCR8.

Example 5. Mouse Surrogate Anti-CCR8 Monoclonal Antibody (mAb) in Murine Colon Cancer Model CT26

(a) Treg Cell Depletion

To demonstrate the ability of an anti-CCR8 Ab to deplete tumor-infiltrating Treg cells in vivo, BALB/c mice with established CT26 tumors were treated with a mouse surrogate anti-CCR8 mAb and the proportion of Treg cells, conventional CD4 T cells and CD8 T cells among leukocytes in tumors, spleen and tumor-draining lymph nodes was analyzed by flow cytometry.

The light chain and heavy chain CDR regions, light and heavy variable regions, and full-length heavy chain and light chain sequences, of the mouse surrogate anti-CCR8 mAb is provided in the below Tables.

TABLE N1

Light Chain CDR Regions for Mouse Surrogate

| Description | CDR L1 (Kabat and Chothia) | CDR L2 (Kabat and Chothia) | CDR L3 (Kabat and Chothia) |
|---|---|---|---|
| Anti-mCCR8 | RSSKSVYSNYLS (SEQ ID NO: 62) | RASTLTP (SEQ ID NO: 63) | AGGYSSGSDNT (SEQ ID NO: 64) |

TABLE N2

Heavy Chain CDR Regions for Mouse Surrogate

| Description | CDR H1 (Kabat) | CDR H1 (Chothia) | CDR H2 (Kabat and Chothia) | CDR H3 (Kabat and Chothia) |
|---|---|---|---|---|
| Anti-mCCR8 | EYSMA (SEQ ID NO: 65) | RIDLNEY (SEQ ID NO: 66) | YIDAGSGSAYY ASWAKG (SEQ ID NO: 67) | DVYPGYTTGTN LGL (SEQ ID NO: 68) |

TABLE N3

Light Chain and Heavy Chain Variable Regions for Mouse Surrogate

| Description | Sequence |
|---|---|
| Anti-mCCR8 Variable Light Chain (SEQ ID NO: 69) | AAVLTQTPASVSAAVGGTVSISCRSSKSVYSNYLSWYQQKPGQPP KLLIYRASTLTPGVPSRFKGSGSGTQFSLTIRDVQSADAGSYYCA GGYSSGSDNTFGGGTKLEIK |
| Anti-mCCR8 Variable Heavy Chain (SEQ ID NO: 70) | QSVKESGGRLVTPGGSLTLTCTVSRIDLNEYSMAWVRQAPGKGLE WIGYIDAGSGSAYYASWAKGRFTISKTSSTTVDLEMTTLTTEDTA TYFCARDVYPGYTTGTNLGLWGPGTLVTVSS |
| Anti-mCCR8 Full-length Light Chain (SEQ ID NO: 71) | AAVLTQTPASVSAAVGGTVSISCRSSKSVYSNYLSWYQQKPGQPP KLLIYRASTLTPGVPSRFKGSGSGTQFSLTIRDVQSADAGSYYCA GGYSSGSDNTFGGGTKLEIKRADAAPTVSIFPPSSEQLTSGGASV VCFLNNFYPKDINVKWKIDGSERQNGVLNSWTDQDSKDSTYSMSS TLTLTKDEYERHNSYTCEATHKTSTSPIVKSFNRNEC |
| Anti-mCCR8 Full-length Heavy Chain (SEQ ID NO: 72) | QSVKESGGRLVTPGGSLTLTCTVSRIDLNEYSMAWVRQAPGKGLE WIGYIDAGSGSAYYASWAKGRFTISKTSSTTVDLEMTTLTTEDTA TYFCARDVYPGYTTGTNLGLWGPGTLVTVSSAKTTAPSVYPLAPV CGDTTGSSVTLGCLVKGYFPEPVTLTWNSGSLSSGVHTFPAVLQS DLYTLSSSVTVTSSTWPSQSITCNVAHPASSTKVDKKIEPRGPTI KPCPPCKCPAPNLLGGPSVFIFPPKIKDVLMISLSPIVTCVVVDV SEDDPDVQISWFVNNVEVHTAQTQTHREDYNSTLRVVSALPIQHQ DWMSGKEFKCKVNNKDLPAPIERTISKPKGSVRAPQVYVLPPPEE EMTKKQVTLTCMVTDFMPEDIYVEWTNNGKTELNYKNTEPVLDSD GSYFMYSKLRVEKKNWVERNSYSCSVVHEGLHNHHTTKSFSRTPG K |

CT26 tumor cells were harvested in log-phase growth and resuspended in HBSS containing matrigel at a 1:1 ratio. BALB/c mice were inoculated subcutaneously in the flank with 0.1 million CT26 cells in 100 microliters of HBSS+ matrigel. Tumors were monitored until they became established and reached a mean tumor volume 130-230 mm$^3$. Mice were then randomized into treatment groups. Treatment with a mouse surrogate anti-CCR8 (mIgG2a) or an anti-gp120 isotype control Ab was administered intravenously at doses between 0.003 mg/kg and 5 mg/kg anti-CCR8 Ab in Histidine Buffer #08: 20 mM histidine acetate, 240 mM sucrose, 0.02% Polysorbate 20 (Tween-20), pH5.5.

Three days later mice were sacrificed and tumors, spleens and tumor-draining lymph nodes obtained for analysis. To generate single cell suspensions, tumors were minced and digested in RPMI-1640 media containing 1% fetal bovine serum (FBS), 0.2 U/mL Liberase DL (Sigma), and 0.2 mg/mL DNaseI (Sigma) for 30 min with agitation at 37° C. Tumor cells were passed through a 100 mm filter and washed with RPMI-1640 media containing 10% FBS. Single cell suspensions were surface stained for 15 min at 4° C. with fluorescently labelled anti-CD45, anti-CD4 and anti-CD8 antibodies and intracellularly stained with fluorescently labelled anti-Foxp3 using the eBioscience Foxp3/ Transcription Factor Staining Buffer Set (Thermo Fisher) according to the manufacturer's protocol. Flow cytometry was performed on a Fortessa X-20 (BD Biosciences) or FACSymphony (BD Biosciences) and analyzed with FlowJo software (BD Biosciences).

FIGS. 17A-17I depict the dose-dependent depletion of Treg cells (graphed as fraction of Treg cells among CD45+ leukocytes) in tumors, but not in spleens or tumor-draining lymph nodes (FIGS. 17A-17C) of CT26 tumor-bearing mice relative to the isotype-treated group. No reduction in the proportion of conventional CD4 T cells ((FIGS. 17D-17F)) or CD8 T cells (FIGS. 17G-17I) relative to the isotype control group was observed with anti-CCR8 treatment. These observations demonstrate the specificity of anti-CCR8-mediated depletion of intratumoral Treg cells.

(b) Tumor Growth Inhibition

To demonstrate tumor growth inhibition following anti-CCR8-mediated depletion of tumor-infiltrating Treg cells in vivo, BALB/c mice with established CT26 tumors were treated with a mouse surrogate anti-CCR8 mAb and monitored for tumor growth over time.

CT26 tumor cells were harvested in log-phase growth and resuspended in HBSS containing Matrigel at a 1:1 ratio. BALB/c mice were inoculated subcutaneously in the flank with 0.1 million CT26 cells in 100 microliters of HBSS+ matrigel. Tumors were monitored until they became established and reached a mean tumor volume 130-230 mm$^3$. Mice were then randomized into treatment groups. Mice were treated intravenously with a single or twice weekly dose (first dose intravenous, following doses intraperitoneally) of 0.1 mg/kg anti-CCR8 (mIgG2a), 0.1 mg/kg of an anti-CD25 antibody (clone PC61 mIgG2a) or an anti-gp120 isotype control Ab in Histidine Buffer #08: 20 mM histidine acetate, 240 mM sucrose, 0.02% Polysorbate 20 (Tween-20), pH5.5. Tumor volumes were measured in two dimensions (length and width) using Ultra Cal-IV calipers (Fred V. Fowler Co.) and volume was calculated using the formula: Tumor size $(mm^3)=(length \times width^2) \times 0.5$.

FIGS. 18A-18D depicts the change in tumor volume over time for individual mice (grey lines) and the treatment group (fitted curve, black line). Potent tumor growth inhibition was observed with a mouse surrogate anti-CCR8 mAb administered as single dose (FIG. 18B) or twice weekly (FIG. 18C) in the CT26 colon cancer model. Both treatment regimens resulted in complete tumor regression in 8/9 mice. Treatment with anti-CCR8 mAb was more effective than anti-CD25 Ab treatment (FIG. 18D) which resulted in tumor regression in 3/9 mice. An isotype control mAb (anti-gp120) was used (FIG. 18A).

Example 6. Comparison of Effector-Competent and Effector-Less Mouse Surrogate Anti-CCR8 Ab To assess whether anti-CCR8 Ab treatment worked primarily by facilitating ADCC- and ADCP-mediated Treg cell depletion or also by inhibiting ligand-dependent activation of CCR8, we compared a ligand blocking effector-competent mIgG2a mouse surrogate anti-CCR8 Ab to a ligand blocking effector-less mIgG2a.LALAPG mutant of the same anti-CCR8 clone in the CT26 tumor model.

CT26 tumor cells were harvested in log-phase growth and resuspended in HBSS containing Matrigel at a 1:1 ratio. BALB/c mice were inoculated subcutaneously in the flank with 0.1 million CT26 cells in 100 microliters of HBSS+ matrigel. In the first treatment groups, a mouse surrogate anti-CCR8 mAb (mIgG2a) or an effector-less mIgG2a.LALAPG mutant anti-CCR8 or an anti-gp120 isotype control mAb were administered at a dose of 5 mg/kg twice per week starting on the day of tumor inoculation (first dose was given intravenously, all following doses given intraperitoneally) in Histidine Buffer #08: 20 mM histidine acetate, 240 mM sucrose, 0.02% Polysorbate 20 (Tween-20), pH5.5. For the second treatment groups, tumors were monitored until they became established and reached a mean tumor volume 130-230 $mm^3$, mice were then randomized into treatment groups and treated with anti-CCR8 (mIgG2a) or an effector-less mIgG2a.LALAPG mutant anti-CCR8 Ab dosed at 5 mg/kg twice per week (firsts dose intravenously, all following doses intraperitoneally) in Histidine Buffer #08: 20 mM histidine acetate, 240 mM sucrose, 0.02% Polysorbate 20 (Tween-20), pH5.5. Tumor volumes were measured in two dimensions (length and width) using Ultra Cal-IV calipers (Fred V. Fowler Co.) and volume was calculated using the formula: Tumor size $(mm^3)=(length \times width^2) \times 0.5$. Mice body weights were measured using an Adventurer Pro AV812 scale (Ohaus Corporation).

FIGS. 19A-19E depicts the change in tumor volume over time for individual mice (grey lines) and the treatment group (fitted curve, black line). Tumor growth inhibition is observed with an effector-competent mIgG2a mouse surrogate anti-CCR8 mAb (FIGS. 19B and 19D), but not with a ligand-blocking effector-less mIgG2a.LALAPG mutant anti-CCR8 mAb (FIGS. 19C and 19E). The mIgG2a anti-CCR8 Ab is effective when it was given at tumor inoculation (FIG. 19B) or in established tumors (FIG. 19D). These findings demonstrate that blocking of ligand binding to the CCR8 receptor is not sufficient to mediate tumor growth inhibition following anti-CCR8 mAb treatment. An isotype control mAb (anti-gp120) was used (FIG. 19A).

Example 7. Combination Efficacy of Anti-CCR8 and Anti-PDL1 mAb Treatment

To assess the potential of increased tumor growth inhibition by a combination of anti-CCR8 mAb and checkpoint inhibition, mice with established EMT6 tumors were treated with anti-CCR8 and anti-PDL1 mAb individually or in combination.

EMT6 tumor cells were harvested in log-phase growth and resuspended in HBSS containing Matrigel at a 1:1 ratio. BALB/c mice were inoculated subcutaneously in the 5th mammary fat pad with 0.1 million EMT6 cells in 100 microliters of HBSS+ matrigel. Tumors were monitored until they became established and reached a mean tumor volume of 130-230 $mm^3$. Mice were then randomized into treatment groups. A mouse surrogate anti-CCR8 (mIgG2a) or isotype control Ab were administered as a single dose of 0.1 mg/kg intravenously. An effector-less anti-PDL1 (mIgG2a.LALAPG) Ab was dosed at 10 mg/kg intravenously for the first dose, and 5 mg/kg intraperitoneally for subsequent doses twice a week. Antibodies were diluted in Histidine Buffer #08: 20 mM histidine acetate, 240 mM sucrose, 0.02% Polysorbate 20 (Tween-20), pH5.5. Tumor volumes and body weights were measured twice per week. Tumor volumes were measured in two dimensions (length and width) using Ultra Cal-IV calipers (Fred V. Fowler Co.) and volume was calculated using the formula: Tumor size $(mm^3)=(length \times width^2) \times 0.5$. Mice body weights were measured using an Adventurer Pro AV812 scale (Ohaus Corporation).

FIGS. 20A-20D depicts the change in tumor volume over time for individual mice (grey lines) and the treatment group (fitted curve, black line). Whereas a mouse surrogate anti-CCR8 and anti-PDL1 mAbs result in partial tumor growth inhibition as single treatments (FIGS. 20B-20C), the combination of both mAbs (FIG. 20D) unexpectedly leads to complete tumor rejection. An isotype control mAb (anti-gp120) was used (FIG. 20A).

Example 8. Ab1-Ab3 HIL1 Variants and Anti-CCR8 Antibodies Comparators (i) Ab1-Ab3 HIL1 Variants The light chain and heavy chain CDR regions, light and heavy variable regions, and full-length heavy chain and light chain sequences, of the Ab1-Ab3 H1L1 variants is provided in the below Tables.

TABLE O1

Light Chain CDR Regions for Ab1, Ab2, and Ab3 Variants

| Description | CDR L1 (Kabat and Chothia) | CDR L2 (Kabat and Chothia) | CDR L3 (Kabat and Chothia) |
| --- | --- | --- | --- |
| hu.Ab1.H1L1 | QASQRIGNALA (SEQ ID NO: 73) | RASTLES (SEQ ID NO: 74) | LGGYISIGNVYT (SEQ ID NO: 75) |
| hu.Ab2.H1L1 | QSSKSVNNNNLA (SEQ ID NO: 76) | FASALAS (SEQ ID NO: 77) | QGAYSGGSDSYA (SEQ ID NO: 78) |
| hu.Ab3.H1L1 | QASQSISNALA (SEQ ID NO: 79) | EVSKVAS (SEQ ID NO: 80) | QSAYYGNSYVWGA (SEQ ID NO: 81) |

TABLE O2

Heavy Chain CDR Regions for Ab1, Ab2, and Ab3 Variants

| Description | CDR H1 (Kabat) | CDR H1 (Chothia) | CDR H2 (Kabat and Chothia) | CDR H3 (Kabat and Chothia) |
| --- | --- | --- | --- | --- |
| hu.Ab1.H1L1 | SNYYMC (SEQ ID NO: 82) | GFDFSSN (SEQ ID NO: 83) | CIHISSVTNTWYASWATG (SEQ ID NO: 84) | VGNSDYRYFNL (SEQ ID NO: 85) |
| hu.Ab2.H1L1 | YGYDMC (SEQ ID NO: 86) | GFSFSYG (SEQ ID NO: 87) | CISAGSSDNTWYASWAKG (SEQ ID NO: 88) | YLGL (SEQ ID NO: 89) |
| hu.Ab3.H1L1 | SYAMS (SEQ ID NO: 90) | GFSLSSY (SEQ ID NO: 91) | VISASGRIIYATWAKG (SEQ ID NO: 92) | GVPSYSLVMSD (SEQ ID NO: 93) |

TABLE O3

Heavy Chain and Light Chain Variable Regions for Ab1, Ab2, and Ab3 Variants

| Description | Sequence |
| --- | --- |
| hu.Ab1.H1L1 Light Chain Variable Region (SEQ ID NO: 94) | DIQMTQSPSSLSASVGDRVTITCQASQRIGNALAWYQQKPGKPPKLLIYRASTLESGVPSRFSGSGSGTDFTLTISSLQPEDVATYYCLGGYISIGNVYTFGGGTKVEIK |
| hu.Ab1.H1L1 Heavy Chain Variable Region (SEQ ID NO: 95) | EQQLVESAGGLVQPGGSLRLSCAASGFDFSSNYYMCWVRQAPGKGLEWIGCIHISSVTNTWYASWATGRFTISKDTSSTTVYLQMISLKTEDTAVYFCTRVGNSDYRYFNLWGPGTLVTVSS |
| hu.Ab2.H1L1 Light Chain Variable Region (SEQ ID NO: 96) | EQVLTQSPGTLSLSPGERATLSCQSSKSVNNNNLAWYQQKPGQPPRLLIYFASALASGVPDRFSGSGSGTDFTLTISRLEPEDFAVYYCQGAYSGGSDSYAFGGGTKVEIK |
| hu.Ab2.H1L1 Heavy Chain Variable Region (SEQ ID NO: 97) | EQQLVESGGGVVQPGRSLRLSCAASGFSFSYGYDMCWVRQAPGKGLEWIACISAGSSDNTWYASWAKGRFTISKDTSKTTVYLQMNSLRAEDTAVYFCSRYLGLWGPGTLVTVSS |
| hu.Ab3.H1L1 Light Chain Variable Region (SEQ ID NO: 98) | EPVMTQSPATLSVSPGERATLSCQASQSISNALAWYQQKPGQPPRLLIYEVSKVASGVPARFSGSGSGTEFTLTISSLQSEDFAVYYCQSAYYGNSYVWGAFGQGTKVEIK |
| hu.Ab3.H1L1 Heavy Chain Variable Region (SEQ ID NO: 99) | EQQLVESGGGLVQPGGSLRLSCAVSGFSLSSYAMSWVRQAPGKGLEWIGVISASGRIIYATWAKGRFTISKDSAKTSVYLQMNSLRDEDTAVYFCARGVPSYSLVMSDWGPGTTVTVSS |

TABLE O4

Heavy Chain and Light Chain Full-length Sequences for Ab1, Ab2, and Ab3 Variants

| Description | Sequence |
|---|---|
| hu.Ab1.H1L1 Full-length Light Chain (SEQ ID NO: 100) | DIQMTQSPSSLSASVGDRVTITCQASQRIGNALAWYQQKPGKPPKLLIY RASTLESGVPSRFSGSGSGTDFTLTISSLQPEDVATYYCLGGYISIGNV YTFGGGTKVEIKRTVAAPSVFIFPPSDEQLKSGTASVVCLLNNFYPREA KVQWKVDNALQSGNSQESVTEQDSKDSTYSLSSTLTLSKADYEKHKVYA CEVTHQGLSSPVTKSFNRGEC |
| hu.Ab1.H1L1 Full-length Heavy Chain (SEQ ID NO: 101) | EQQLVESAGGLVQPGGSLRLSCAASGFDFSSNYYMCWVRQAPGKGLEWI GCIHISSVTNTWYASWATGRFTISKDTSSTTVYLQMISLKTEDTAVYFC TRVGNSDYRYFNLWGPGTLVTVSSASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHY TQKSLSLSPGK |
| hu.Ab2.H1L1 Full-length Light Chain (SEQ ID NO: 102) | EQVLTQSPGTLSLSPGERATLSCQSSKSVNNNNLAWYQQKPGQPPRLLI YFASALASGVPDRFSGSGSGTDFTLTISRLEPEDFAVYYCQGAYSGGSD SYAFGGGTKVEIKRTVAAPSVFIFPPSDEQLKSGTASVVCLLNNFYPRE AKVQWKVDNALQSGNSQESVTEQDSKDSTYSLSSTLTLSKADYEKHKVY ACEVTHQGLSSPVTKSFNRGEC |
| hu.Ab2.H1L1 Full-length Heavy Chain (SEQ ID NO: 103) | EQQLVESGGGVVQPGRSLRLSCAASGFSFSYGYDMCWVRQAPGKGLEWI ACISAGSSDNTWYASWAKGRFTISKDTSKTTVYLQMNSLRAEDTAVYFC SRYLGLWGPGTLVTVSSASTKGPSVFPLAPSSKSTSGGTAALGCLVKDY FPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSL SPGK |
| hu.Ab3.H1L1 Full-length Light Chain (SEQ ID NO: 104) | EPVMTQSPATLSVSPGERATLSCQASQSISNALAWYQQKPGQPPRLLIY EVSKVASGVPARFSGSGSGTEFTLTISSLQSEDFAVYYCQSAYYGNSYV WGAFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVY ACEVTHQGLSSPVTKSFNRGEC |
| hu.Ab3.H1L1 Full-length Heavy Chain (SEQ ID NO: 105) | EQQLVESGGGLVQPGGSLRLSCAVSGFSLSSYAMSWVRQAPGKGLEWIG VISASGRIIYATWAKGRFTISKDSAKTSVYLQMNSLRDEDTAVYFCARG VPSYSLVMSDWGPGTTVTVSSASTKGPSVFPLAPSSKSTSGGTAALGCL VKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLF PPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQK SLSLSPGK |

(ii) Anti-CCR8 Antibodies Comparators

The full-length heavy chain and full-length light chain sequence of the Yoshida humanized anti-human CCR8 antibody studied herein was disclosed in a U.S. Declaration filed on Oct. 30, 2019 during prosecution of U.S. Ser. No. 16/183,216 (published as US 2019/0071508, and later granted as U.S. Pat. No. 10,550,191). The light chain variable region, light chain constant region, heavy chain variable region, and heavy chain constant region of this same antibody were disclosed in PCT Application Publication No. WO2020138489 as sequences 59, 52, 41, and 53. The Yoshida antibody was expressed as a human hIgG1 antibody (i.e., having a human Fc region). The commercially available murine anti-human CCR8 antibody 433H (BD Biosciences), and murine anti-human CCR8 antibody L263G8 (Biolegend) were purchased for these studies. 433H (BD Biosciences) and L263G8 (Biolegend) are mouse monoclonal antibodies comprising mouse IgG2a isotype Fc regions. See also Mutalithas et al., *Clinical & Experimental Allergy* (2010) 40:1175 (433H, BD Biosciences), Mitson-Salazar et al., *J. Allergy Clin. Immunol.* (2016) 907-918 (L263G8, Biolegend) and www.labome.com/review/gene/human/CCR8-antibody.html (L263G8, Biolegend).

Example 9: Terminal Lysine Variants of Ab1-Ab5

Additional Fc variants of the presently disclosed anti-CCR8 antibodies are contemplated, where the C-terminus of the heavy chain of the parent antibody is a shortened C-terminus in which the C-terminal lysine has been removed, resulting in a shortened C-terminus ending PG. The terminal lysine variants of Ab1-Ab-5 are provided in the below Table P.

The light chain full-length sequence for the Ab5 terminal lysine variant corresponds to hu.Ab5.L1 (SEQ ID NO: 56).

The light chain full-length sequence for the Ab4 terminal lysine variant corresponds to hu.Ab4.L3 (SEQ ID NO: 58).

The light chain full-length sequence for the Ab5 G236A.I332E terminal lysine variant corresponds to hu.Ab5.L1 (SEQ ID NO: 56).

The light chain full-length sequence for the Ab4 G236A.I332E terminal lysine variant corresponds to hu.Ab4.L3 (SEQ ID NO: 58).

The light chain full-length sequence for the Ab1 terminal lysine variant corresponds to hu.Ab1.L1 (SEQ ID NO: 100).

The light chain full-length sequence for the Ab2 terminal lysine variant corresponds to hu.Ab2.L1 (SEQ ID NO: 102).

The light chain full-length sequence for the Ab3 terminal lysine variant corresponds to hu.Ab3.L1 (SEQ ID NO: 104).

TABLE P

Heavy Chain Terminal Lysine Variant Sequences for Ab1, Ab2, Ab3, Ab4, and Ab5 Variants

| Description | Sequence |
| --- | --- |
| hu.Ab5.H13 Terminal Lysine Variant Heavy Chain (SEQ ID NO: 111) | EVQLLESGGGLVQPGGSLRLSCAASGIDLSTYAMGWVRQAPGKGLEW VGLIHRSGRTYYATWAKGRFTISKDSSKNTLYLQMNSLRAEDTAVYY CTRSYPDYSATASIWGQGTTVTVSSASTKGPSVFPLAPSSKSTSGGT AALGCLVKDYFPEPVTVSWNSGALTSGVHTFPAVLQSSGLYSLSSVV TVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPG |
| hu.Ab4.H12 Terminal Lysine Variant Heavy Chain (SEQ ID NO: 112) | EVQLLESGGGLVQPGGSLRLSCAASGFSLSNYAMIWVRQAPGKGLEW VSTISLGGYTYYANWAKGRFTISRDSSKTTVYLQMNSLRAEDTAVYF CARARWSTDSAIYTYAFDPWGPGTLVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKEYKCK VSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| Afuc.hu.Ab5.H13. G236A.I332E Terminal Lysine Variant Heavy Chain (SEQ ID NO: 113) | EVQLLESGGGLVQPGGSLRLSCAASGIDLSTYAMGWVRQAPGKGLEW VGLIHRSGRTYYATWAKGRFTISKDSSKNTLYLQMNSLRAEDTAVYY CTRSYPDYSATASIWGQGTTVTVSSASTKGPSVFPLAPSSKSTSGGT AALGCLVKDYFPEPVTVSWNSGALTSGVHTFPAVLQSSGLYSLSSVV TVPSSSLGTQTYICNVNHKPSNTKVDKKVEPKSCDKTHTCPPCPAPE LLAGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPAPEEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPG |
| Afuc.hu.Ab4.H12. G236A.I332E Terminal Lysine Variant Heavy Chain (SEQ ID NO: 114) | EVQLLESGGGLVQPGGSLRLSCAASGFSLSNYAMIWVRQAPGKGLEW VSTISLGGYTYYANWAKGRFTISRDSSKTTVYLQMNSLRAEDTAVYF CARARWSTDSAIYTYAFDPWGPGTLVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLAGPSVFLFPPKPKDTLMISRTPEVTCVVVDVSHEDPEVKF NWYVDGVEVHNAKTKPREEQYNSTYRVVSVLTVLHQDWLNGKEYKCK VSNKALPAPEEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG |
| hu.Ab1.H1L1 Terminal Lysine Variant Heavy Chain (SEQ ID NO: 115) | EQQLVESAGGLVQPGGSLRLSCAASGFDFSSNYYMCWVRQAPGKGLE WIGCIHISSVTNTWYASWATGRFTISKDTSSTTVYLQMISLKTEDTA VYFCTRVGNSDYRYFNLWGPGTLVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKVEPKSCDKTHTCPPCP APELLGGPSVFLFPPKPKDTLMISRTPEVTCVVVDVSHEDPEVKFNW YVDGVEVHNAKTKPREEQYNSTYRVVSVLTVLHQDWLNGKEYKCKVS NKALPAPIEKTISKAKGQPREPQVYTLPPSREEMTKNQVSLTCLVKG FYPSDIAVEWESNGQPENNYKTTPPVLDSDGSFFLYSKLTVDKSRWQ QGNVFSCSVMHEALHNHYTQKSLSLSPG |
| hu.Ab2.H1L1 Terminal Lysine Variant Heavy Chain (SEQ ID NO: 116) | EQQLVESGGGVVQPGRSLRLSCAASGFSFSYGYDMCWVRQAPGKGLE WIACISAGSSDNTWYASWAKGRFTISKDTSKTTVYLQMNSLRAEDTA VYFCSRYLGLWGPGTLVTVSSASTKGPSVFPLAPSSKSTSGGTAALG CLVKDYFPEPVTVSWNSGALTSGVHTFPAVLQSSGLYSLSSVVTVPS SSLGTQTYICNVNHKPSNTKVDKKVEPKSCDKTHTCPPCPAPELLGG PSVFLFPPKPKDTLMISRTPEVTCVVVDVSHEDPEVKFNWYVDGVEV HNAKTKPREEQYNSTYRVVSVLTVLHQDWLNGKEYKCKVSNKALPAP IEKTISKAKGQPREPQVYTLPPSREEMTKNQVSLTCLVKGFYPSDIA VEWESNGQPENNYKTTPPVLDSDGSFFLYSKLTVDKSRWQQGNVFSC SVMHEALHNHYTQKSLSLSPG |

TABLE P-continued

Heavy Chain Terminal Lysine Variant Sequences
for Ab1, Ab2, Ab3, Ab4, and Ab5 Variants

| Description | Sequence |
|---|---|
| hu.Ab3.H1L1 Terminal Lysine Variant Heavy Chain (SEQ ID NO: 117) | EQQLVESGGGLVQPGGSLRLSCAVSGFSLSSYAMSWVRQAPGKGLEW IGVISASGRIIYATWAKGRFTISKDSAKTSVYLQMNSLRDEDTAVYF CARGVPSYSLVMSDWGPGTTVTVSSASTKGPSVFPLAPSSKSTSGGT AALGCLVKDYFPEPVTVSWNSGALTSGVHTFPAVLQSSGLYSLSSVV TVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPG |

Example 10. Serum Concentration and ADA of Test Anti-CCR8 mAbs in Cyno

Anti-CCR8 antibodies Afuc.hu.Ab5.H13L1, Afuc.hu.Ab4.H12L3, and the control anti-gD were used for this study. There were three male cynomolgus monkeys in each of the three dose groups—Control: designated 1001, 1002, 1003; Afuc.hu.Ab5.H13L1: designated 2001, 2002, 2003; and Afuc.hu.Ab4.H12L3: designated 3001, 3002, 3003. Each were given a single 10 mg/kg IV bolus of anti-gD or test anti-CCR8 mAb. Blood samples for analysis were collected at 0.25, 2, and 6 hours; 1, 2, 7, 14, 21, 28 and 35 days post-dose, and serum was assayed for concentrations of anti-gD (control group) and the anti-CCR8 antibodies using a qualified ELISA analytical method. The lower limit of quantitation (LLOQ) of the assay was 0.015625 µg/mL. PK parameters were estimated using Phoenix 1.4 (WinNonlin pharmacokinetic software version 6.4) (Certara, USA) using a non-compartmental analysis consistent with IV bolus administration. Blood samples for anti-drug antibody (ADA) analysis were collected at pre-dose and on Day 1, 8, 15, 22, 29 and 36, and serum was analyzed for antibodies against the test items using a qualified ELISA assay.

The serum concentration profiles of anti-gD, Afuc.hu.Ab5.H13L1 or Afuc.hu.Ab4.H12L3 in cynomolgus monkeys following administration of single 10 mg/kg IV dose are shown in FIG. 21. Systemic exposures were found to be comparable between the anti-gD and Afuc.hu.Ab5.H13L1 groups, exhibiting sustained serum concentration levels over the 35-day post-dose period, with a respective mean clearance of 3.96±0.412 mL/day/kg and 4.38±0.291 mL/day/kg. In contrast, Afuc.hu.Ab4.H12L3 exhibited lower exposure over that same 35 day post-dose period, with a mean clearance of 9.00±1.01 mL/day/kg. Maintaining serum concentration levels over a longer period of time, with slower clearance, as exhibited by Afuc.hu.Ab5.H13L1, is expected to elicit a more sustained target engagement that may translate to better anti-cancer activity and less frequent dosing.

The difference in systemic exposures observed for Afuc.hu.Ab4.H12L3 compared to anti-gD and Afuc.hu.Ab5.H13L1 groups could be partially explained by the presence of anti-drug antibodies (ADAs) in Afuc.hu.Ab4.H12L3 treated group at later time points. For example, Animals 1001, 1002, and 1003 dosed with anti-gD were negative for the presence of ADAs. Following administration of Afuc.hu.Ab5.H13L1, Animal 2001 was ADA-positive but the presence of ADAs appeared to have no impact on exposure when compared to the other two Afuc.hu.Ab5.H13L1 dosed animals (Nos. 2002 and 2003) that were ADA-negative. Following administration of Afuc.hu.Ab4.H12L3, Animals 3002 and 3003 were found to be ADA-positive and the presence of ADAs appeared to have an impact on the systemic exposures when compared to ADA-negative Animal 3001.

Example 11. Monitoring Levels of CCR8+T-Reg Cells in Cyno

Anti-CCR8 antibodies Afuc.hu.Ab5.H13L1, Afuc.hu.Ab4.H12L3, and the control anti-gD were used for this study. There were three male cynomolgus monkeys in each of the three dose groups—Control Group: designated 1001, 1002, 1003; Afuc.hu.Ab5.H13L1 Group 2: designated 2001, 2002, 2003; and Afuc.hu.Ab4.H12L3 Group 3: designated 3001, 3002, 3003. Blood was collected from each of the animals before dosing on Day 1 ("Pre-study"), as well as on Day 1 at 0 hours ("Pre-dose"). Each of the animals was then dosed with a single dose of 10 mg/kg afucosylated anti-gD (Control Group), Afuc.hu.Ab5.H13L1 (Group 2) or Afuc.hu.Ab4.H12L3 (Group 3) via intravenous injection. Blood containing the initial dose of the test CCR8 mAb was collected at the following time points post-dose starting on Day 1: 6, 24, 48, 168, 336, 504, 668 and 840 hours, and subjected to the following treatment prior to flow cytometry analysis: (i) blood sample not spiked with either test CCR8 mAb ("unspiked"), (ii) blood sample further spiked with a saturating concentration of Afuc.hu.Ab5.H13L1, and (iii) blood sample further spiked with a saturating concentration of Afuc.hu.Ab4.H12L3. Each of the unspiked and spiked samples were then treated with a labeled goat anti-human IgG antibody, which detects for binding of the test anti-CCR8 mAb to cynoCCR8, and analyzed by flow cytometry.

T cell subsets were identified using specific antibodies against phenotypic marker antigens. Specifically, T regulatory (T-reg) cells were identified as CD3+CD4+Foxp3+ cells. Drug bound CCR8+T-reg cells were identified using unspiked blood samples.

Both test anti-CCR8 mAbs, as observed in the unspiked samples, did not substantially reduce the total T-reg cell absolute counts in whole blood for up to 840 hours post dose. See FIGS. 22A-22C. Both test anti-CCR8 mAbs also did not substantially reduce the total lymphocyte counts in whole blood for up to 840 hours post dose total (data not shown).

As described earlier, both Afuc.hu.Ab5.H13L1 and Afuc.hu.Ab4.H12L3 bind to CCR8, with Afuc.hu.Ab4.H12L3 and Afuc.hu.Ab5.H13L1 both acting as non-competitive CCR8 binders to each other, and with Afuc.hu.Ab4.H12L3 having slightly higher affinity for human and cyno CCR8. See, e.g., FIGS. 16A-16B, and affinity Kd (nM) data provided in Table G3. Afuc.hu.Ab4.H12L3 also has an increased propensity for ADA formation at later time points. See Example 10.

As can be seen in FIGS. 23A-23C, flow cytometry analysis of unspiked blood from cynos initially treated with control (Group 1) demonstrated no modulation of total CCR8+T-reg cells. Furthermore, flow cytometry of spiked blood (i.e., blood initially treated with control (Group 1) then spiked with a saturating concentration of Afuc.hu.Ab5.H13L1 or blood initially treated with control (Group 1) then spiked with a saturating concentration of Afuc.hu.Ab4.H12L3) also had very little effect on the total CCR8+T-reg cell count. Relative percentage refers to the percent of CCR8+T-reg cells as detected by each of the test anti-CCR8 mAbs. Since Afuc.hu.Ab4.H12L3 has a slightly higher affinity compared to Afuc.hu.Ab5.H13L1, the relative percentage of the spiked Afuc.hu.Ab4.H12L3 sample has a higher percentage detected.

With regard to Group 3, as can be seen in FIGS. 23D-23F, flow cytometry of (i) blood initially treated with Afuc.hu.Ab4.H12L3 ("unspiked"), (ii) blood initially treated with Afuc.hu.Ab4.H12L3 then spiked with Afuc.hu.Ab5.H13L1, or (iii) blood initially treated with Afuc.hu.Ab4.H12L3 then spiked with Afuc.hu.Ab4.H12L3, in each of the three animals, demonstrated a decrease in CCR8+T-reg cells up to 168 hours post dose. A partial recovery in the frequency of CCR8+ Treg cells was noticed in two of the animals starting at 336 hours post dose, likely due to the increased presence of ADAs against Afuc.hu.Ab4.H12L3.

With regard to Group 2, as can be seen in FIGS. 23G-23I, flow cytometry of (i) blood initially treated with Afuc.hu.Ab5.H13L1 ("unspiked"), (ii) blood initially treated with Afuc.hu.Ab5.H13L1 then spiked with a saturating concentration of Afuc.hu.Ab5.H13L1, or (iii) blood initially treated with Afuc.hu.Ab5.H13L1 then spiked with a saturating concentration of Afuc.hu.Ab4.H12L3, demonstrated a decrease in CCR8+T-reg cells in Animals 2002 and 2003.

Figure 2A:
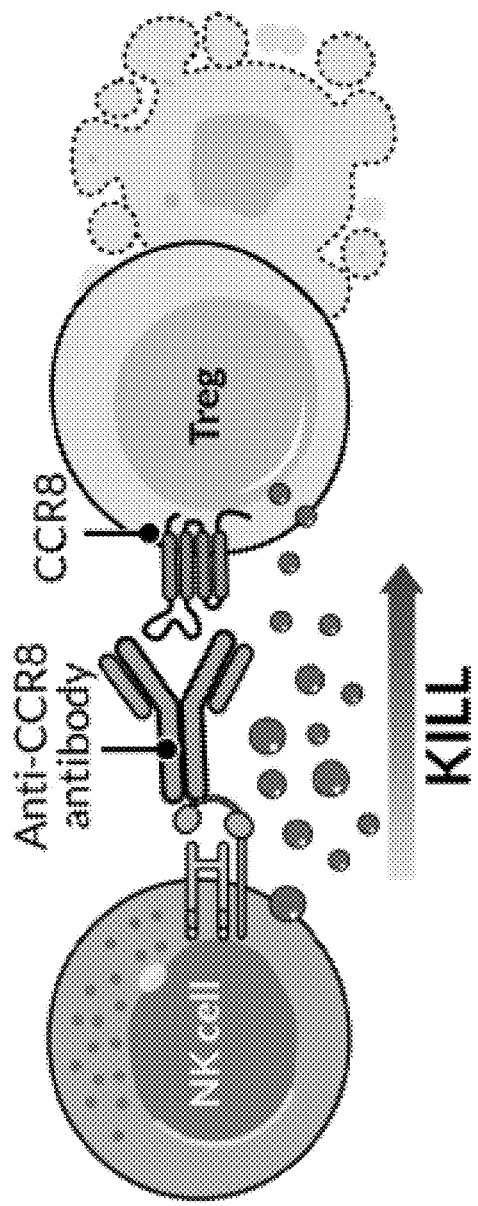
FIGS. 2A-2B depicts the proposed mechanism of action of natural killer (NK) cell-mediated antibody-dependent cellular cytotoxicity (ADCC), resulting in depletion of tumor-infiltrating CCR8-expressing Tregs (FIG. 2A) and the ADCC activities of human/cyno cross-reactive anti-CCR8 mAbs brought forward for further study (FIG. 2B). $EC_{50}$ values were determined as 0.02 nM, 0.02 nM, and 0.08 nM for anti-CCR8 mAbs hu.Ab3.H1L1, hu.Ab5.H1L1, and hu.Ab4.H1L1, respectively.
Figure 2B:
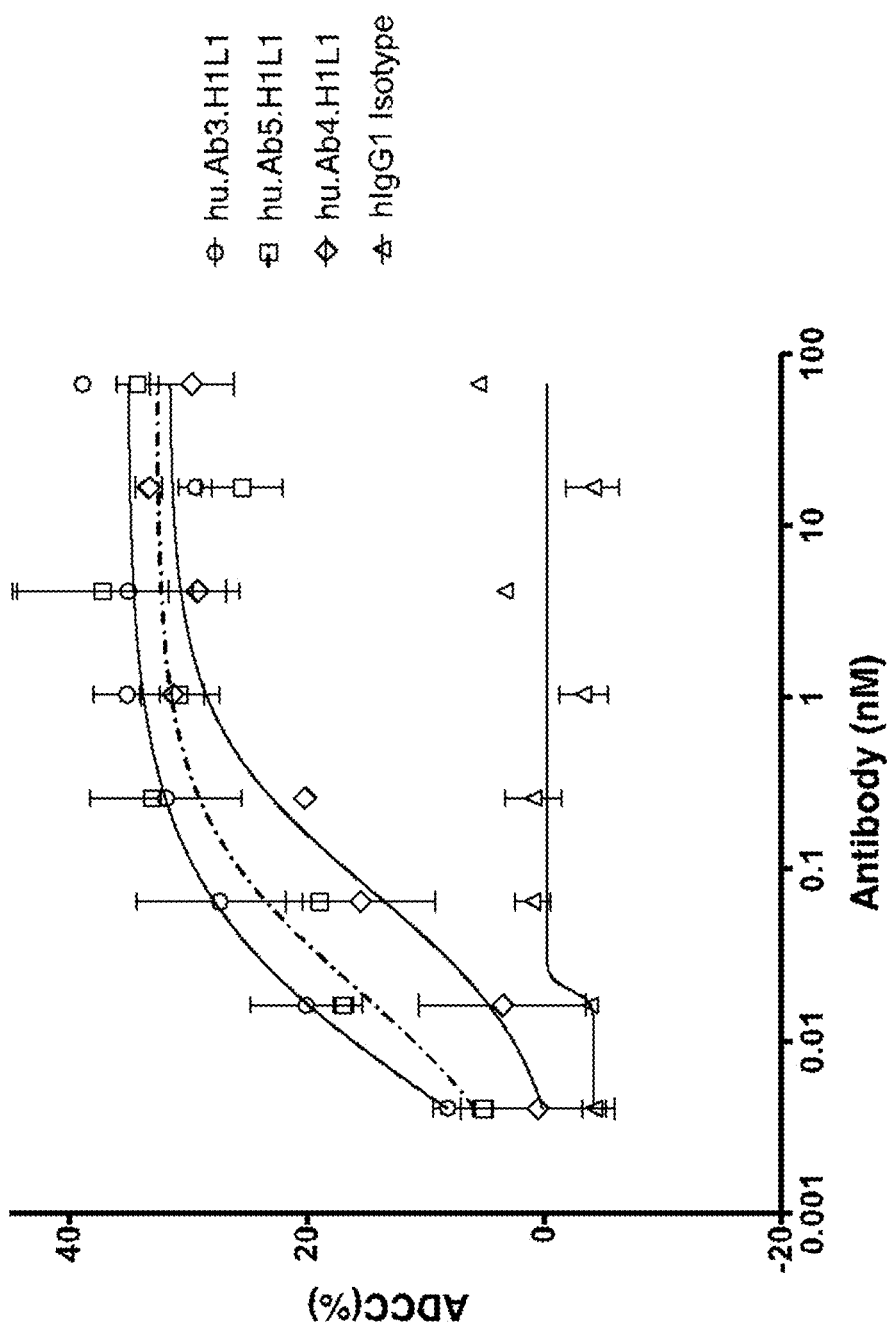

Both Group 2 and 3 animals demonstrated little to no effect on the overall Treg cell count (FIGS. 22A-22C), but demonstrated reduced numbers of peripheral blood CCR8+ T-reg cells following administration (FIGS. 23D-23I), either spiked or unspiked, which is consistent with the proposed mechanism of action (see FIG. 2A).

OTHER EMBODIMENTS

Although the foregoing has been described in some detail by way of illustration and example for purposes of clarity of understanding, the descriptions and examples should not be construed as limiting the scope of the present disclosure. All patent and scientific literature cited herein are expressly incorporated in their entirety by reference.

What is claimed is:

1. A monoclonal antibody that binds to C—C motif chemokine receptor 8 (CCR8), wherein the antibody comprises a heavy chain variable domain (VH) comprising (a) a CDR-H1 comprising the amino acid sequence of SEQ ID NO: 29 or SEQ ID NO: 30, (b) a CDR-H2 comprising the amino acid sequence of SEQ ID NO: 31, and (c) a CDR-H3 comprising the amino acid sequence of SEQ ID NO: 32, and a light chain variable domain (VL) comprising (d) a CDR-L1 comprising the amino acid sequence of SEQ ID NO: 26, (e) a CDR-L2 comprising the amino acid sequence of SEQ ID NO: 27, and (f) a CDR-L3 comprising the amino acid sequence of SEQ ID NO: 28.

2. The antibody of claim 1, which binds to CCR8 independent of sulfation of CCR8.

3. The antibody of claim 1, wherein the antibody binds to an epitope comprising one or more of amino acid residues 2-6 of SEQ ID NO: 106.

4. The antibody of claim 1, wherein:
(a) the VH comprises an amino acid sequence having at least about 95%, at least about 96%, at least about 97%, at least about 98%, or at least about 99% sequence identity to an amino acid sequence selected from the group consisting of SEQ ID NOs: 35-47;
(b) the VL comprises an amino acid sequence having at least about 95%, at least about 96%, at least about 97%, at least about 98%, or at least about 99% sequence identity to an amino acid sequence selected from the group consisting of SEQ ID NOs: 48-52; or
(c) the antibody comprises the VH as defined in (a) and the VL as defined in (b).

5. The antibody of claim 1, wherein the VH comprises an amino acid sequence selected from the group consisting of SEQ ID NOs: 35-47 and the VL comprises an amino acid sequence selected from the group consisting of SEQ ID NOs: 48-52.

6. The antibody of claim 1, wherein:
(a) the VH comprises an amino acid sequence having at least about 95%, at least about 96%, at least about 97%, at least about 98%, or at least about 99% sequence identity to an amino acid sequence of SEQ ID NO: 47;
(b) the VL comprises an amino acid sequence having at least about 95%, at least about 96%, at least about 97%, at least about 98%, or at least about 99% sequence identity to an amino acid sequence of SEQ ID NO: 48; or
(c) the antibody comprises the VH as defined in (a) and the VL sequence as defined in (b).

7. The antibody of claim 1, wherein the VH comprises an amino acid sequence having at least about 95%, at least about 96%, at least about 97%, at least about 98%, or at least about 99% sequence identity to the amino acid sequence of SEQ ID NO: 47 and the VL comprises an amino acid sequence having at least about 95%, at least about 96%, at least about 97%, at least about 98%, or at least about 99% sequence identity to the amino acid sequence of SEQ ID NO: 48.

8. The antibody of claim 1, wherein the VL comprises a V4M mutation, a P43A mutation, a F46L mutation, a C90Q mutation, or a combination thereof, and wherein the amino acid positions are numbered according to Kabat.

9. The antibody of claim 1, wherein the VH comprises a G49S mutation, a K71R mutation, a S73N mutation, or a combination thereof, and wherein the amino acid positions are numbered according to Kabat.

10. The antibody of claim 1, comprising a heavy chain comprising the amino acid sequence of SEQ ID NO: 55, and a light chain comprising the amino acid sequence of SEQ ID NO: 56.

11. The antibody of claim 1, comprising a heavy chain comprising the amino acid sequence of SEQ ID NO: 60, and a light chain comprising the amino acid sequence of SEQ ID NO: 56.

12. The antibody of claim 1, comprising a heavy chain comprising the amino acid sequence of SEQ ID NO: 111, and a light chain comprising the amino acid sequence of SEQ ID NO: 56.

13. The antibody of claim 1, comprising a heavy chain comprising the amino acid sequence of SEQ ID NO: 113, and a light chain comprising the amino acid sequence of SEQ ID NO: 56.

14. A monoclonal antibody that binds to CCR8, wherein the antibody comprises a VH comprising the amino acid sequence selected from the group consisting of SEQ ID NOs: 35-47 and a VL comprising the amino acid sequence selected from the group consisting of SEQ ID NOs: 48-52.

15. A monoclonal antibody that binds to CCR8, wherein the antibody comprises a VH comprising the amino acid sequence of SEQ ID NO: 47 and a VL comprising the amino acid sequence of SEQ ID NO: 48.

16. The antibody of claim 1, which is a humanized antibody.

17. The antibody of claim 1, which is a chimeric antibody.

18. The antibody of claim 1 or 15, which is an antibody fragment that binds to CCR8.

19. The antibody of claim 1 or 15, which is a full-length antibody.

20. The antibody of claim 19, which is a full-length IgG1 antibody.

21. The antibody of claim 1, comprising an IgG1 constant domain comprising the amino acid sequence of SEQ ID NO: 53 or SEQ ID NO: 59.

22. The antibody of claim 1, comprising a kappa constant domain comprising the amino acid sequence of SEQ ID NO: 54.

23. The antibody of claim 1, wherein the antibody binds to CCR8 with a binding affinity ($K_d$) of from about $1\times10^{-12}$ M to about $1\times10^{-11}$ M.

24. The antibody of claim 1, wherein the CCR8 is a human CCR8.

25. The antibody of claim 1, wherein the antibody is afucosylated.

26. A pharmaceutical composition comprising the antibody of claim 1 and a pharmaceutically acceptable carrier.

27. The pharmaceutical composition of claim 26, further comprising an additional therapeutic agent.

28. The antibody of claim 25, wherein the proportion of afucosylation is between about 80% to about 95%.

29. The antibody of claim 1, which is a humanized, full-length IgG1 antibody.

30. The antibody of claim 1, wherein the VH comprises a V78L mutation, a T76N mutation, a F91Y mutation, and a P105Q mutation, and wherein the amino acid positions are numbered according to Kabat.

31. The antibody of claim 1, wherein the VL comprises a C90Q mutation and a Y2I mutation, and wherein the amino acid positions are numbered according to Kabat.

32. The antibody of claim 1, wherein the VH comprises a V78L mutation, a T76N mutation, a F91Y mutation, and a P105Q mutation, and the VL comprises a C90Q mutation and a Y2I mutation, and wherein the amino acid positions are numbered according to Kabat.

33. The antibody of claim 1, comprising an IgG1 constant domain comprising the amino acid sequence of SEQ ID NO: 53 and a kappa constant domain comprising the amino acid sequence of SEQ ID NO: 54.

34. The antibody of claim 33, which is a humanized, full-length IgG1 antibody.

35. The antibody of claim 33, wherein the VH comprises a V78L mutation, a T76N mutation, a F91Y mutation, and a P105Q mutation, and the VL comprises a C90Q mutation and a Y2I mutation, and wherein the amino acid positions are numbered according to Kabat.

36. The antibody of claim 7, which is a humanized, full-length IgG1 antibody.

37. The antibody of claim 7, wherein the VH comprises a V78L mutation, a T76N mutation, a F91Y mutation, and a P105Q mutation, and the VL comprises a C90Q mutation and a Y2I mutation, and wherein the amino acid positions are numbered according to Kabat.

38. The antibody of claim 7, comprising an IgG1 constant domain comprising the amino acid sequence of SEQ ID NO: 53 and a kappa constant domain comprising the amino acid sequence of SEQ ID NO: 54.

39. The antibody of claim 38, which is a humanized, full-length IgG1 antibody.

40. The antibody of claim 38, wherein the VH comprises a V78L mutation, a T76N mutation, a F91Y mutation, and a P105Q mutation, and the VL comprises a C90Q mutation and a Y2I mutation, and wherein the amino acid positions are numbered according to Kabat.

41. The antibody of claim 1, wherein the VH comprises (a) a CDR-H1 comprising the amino acid sequence of SEQ ID NO: 29, (b) a CDR-H2 comprising the amino acid sequence of SEQ ID NO: 31, and (c) a CDR-H3 comprising the amino acid sequence of SEQ ID NO: 32, and the VL comprises (d) a CDR-L1 comprising the amino acid sequence of SEQ ID NO: 26, (e) a CDR-L2 comprising the amino acid sequence of SEQ ID NO: 27, and (f) a CDR-L3 comprising the amino acid sequence of SEQ ID NO: 28.

42. The antibody of claim 41, wherein the VH comprises an amino acid sequence having at least about 95%, at least about 96%, at least about 97%, at least about 98%, or at least about 99% sequence identity to the amino acid sequence of SEQ ID NO: 47 and the VL comprises an amino acid sequence having at least about 95%, at least about 96%, at least about 97%, at least about 98%, or at least about 99% sequence identity to the amino acid sequence of SEQ ID NO: 48.

43. The antibody of claim 41, which is a humanized, full-length IgG1 antibody.

44. The antibody of claim 41, wherein the VH comprises a V78L mutation, a T76N mutation, a F91Y mutation, and a P105Q mutation, and the VL comprises a C90Q mutation and a Y2I mutation, and wherein the amino acid positions are numbered according to Kabat.

45. The antibody of claim 41, comprising an IgG1 constant domain comprising the amino acid sequence of SEQ ID NO: 53 and a kappa constant domain comprising the amino acid sequence of SEQ ID NO: 54.

46. The antibody of claim 45, which is a humanized, full-length IgG1 antibody.

47. The antibody of claim 45, wherein the VH comprises a V78L mutation, a T76N mutation, a F91Y mutation, and a P105Q mutation, and the VL comprises a C90Q mutation and a Y2I mutation, and wherein the amino acid positions are numbered according to Kabat.

* * * * *

SEQUENCE LISTING

```
Sequence total quantity: 117
SEQ ID NO: 1            moltype = AA  length = 11
FEATURE                 Location/Qualifiers
REGION                  1..11
                        note = Synthetic
source                  1..11
                        mol_type = protein
                        organism = synthetic construct
SEQUENCE: 1
QASQSISSYL S                                                            11

SEQ ID NO: 2            moltype = AA  length = 7
FEATURE                 Location/Qualifiers
REGION                  1..7
                        note = Synthetic
source                  1..7
                        mol_type = protein
                        organism = synthetic construct
SEQUENCE: 2
KASTLAS                                                                 7

SEQ ID NO: 3            moltype = AA  length = 12
FEATURE                 Location/Qualifiers
REGION                  1..12
                        note = Synthetic
source                  1..12
                        mol_type = protein
                        organism = synthetic construct
SEQUENCE: 3
QQGYTSSNID NI                                                           12

SEQ ID NO: 4            moltype = AA  length = 5
FEATURE                 Location/Qualifiers
REGION                  1..5
                        note = Synthetic
source                  1..5
                        mol_type = protein
                        organism = synthetic construct
SEQUENCE: 4
NYAMI                                                                   5

SEQ ID NO: 5            moltype = AA  length = 7
```

```
FEATURE              Location/Qualifiers
REGION               1..7
                     note = Synthetic
source               1..7
                     mol_type = protein
                     organism = synthetic construct
SEQUENCE: 5
GFSLSNY                                                                      7

SEQ ID NO: 6         moltype = AA  length = 16
FEATURE              Location/Qualifiers
REGION               1..16
                     note = Synthetic
source               1..16
                     mol_type = protein
                     organism = synthetic construct
SEQUENCE: 6
TISLGGYTYY ANWAKG                                                           16

SEQ ID NO: 7         moltype = AA  length = 16
FEATURE              Location/Qualifiers
REGION               1..16
                     note = Synthetic
source               1..16
                     mol_type = protein
                     organism = synthetic construct
SEQUENCE: 7
ARWSTDSAIY TYAFDP                                                           16

SEQ ID NO: 8         moltype = AA  length = 121
FEATURE              Location/Qualifiers
REGION               1..121
                     note = Synthetic
source               1..121
                     mol_type = protein
                     organism = synthetic construct
SEQUENCE: 8
QSVEESGGRL VTPGTPLTLT CTVSGFSLSN YAMIWVRQAP GEGLEWVGTI SLGGYTYYAN            60
WAKGRFTISK TSTTVDLKIS SPTTEDTATY FCARARWSTD SAIYTYAFDP WGPGTLVTVS           120
S                                                                          121

SEQ ID NO: 9         moltype = AA  length = 110
FEATURE              Location/Qualifiers
REGION               1..110
                     note = Synthetic
source               1..110
                     mol_type = protein
                     organism = synthetic construct
SEQUENCE: 9
AYDMTQTPAS VEVAVGGTVT IKCQASQSIS SYLSWYQQKP GQRPELLIYK ASTLASGVSS            60
RFKGSGSGTQ FTLTISDLEC ADAATYYCQQ GYTSSNIDNI FGGGTEVVVK                     110

SEQ ID NO: 10        moltype = AA  length = 124
FEATURE              Location/Qualifiers
REGION               1..124
                     note = Synthetic
source               1..124
                     mol_type = protein
                     organism = synthetic construct
SEQUENCE: 10
EQQLLESGGG LVQPGGSLRL SCAVSGFSLS NYAMIWVRQA PGKGLEWVGT ISLGGYTYYA            60
NWAKGRFTIS KDSSKTTVYL QMNSLRAEDT AVYFCARARW STDSAIYTYA FDPWGPGTLV           120
TVSS                                                                       124

SEQ ID NO: 11        moltype = AA  length = 124
FEATURE              Location/Qualifiers
REGION               1..124
                     note = Synthetic
source               1..124
                     mol_type = protein
                     organism = synthetic construct
SEQUENCE: 11
EVQLLESGGG LVQPGGSLRL SCAVSGFSLS NYAMIWVRQA PGKGLEWVGT ISLGGYTYYA            60
NWAKGRFTIS KDSSKTTVYL QMNSLRAEDT AVYFCARARW STDSAIYTYA FDPWGPGTLV           120
TVSS                                                                       124

SEQ ID NO: 12        moltype = AA  length = 124
FEATURE              Location/Qualifiers
REGION               1..124
```

```
                              note = Synthetic
source                        1..124
                              mol_type = protein
                              organism = synthetic construct
SEQUENCE: 12
EQQLLESGGG LVQPGGSLRL SCAASGFSLS NYAMIWVRQA PGKGLEWVGT ISLGGYTYYA    60
NWAKGRFTIS KDSSKTTVYL QMNSLRAEDT AVYFCARARW STDSAIYTYA FDPWGPGTLV   120
TVSS                                                                124

SEQ ID NO: 13                 moltype = AA  length = 124
FEATURE                       Location/Qualifiers
REGION                        1..124
                              note = Synthetic
source                        1..124
                              mol_type = protein
                              organism = synthetic construct
SEQUENCE: 13
EQQLLESGGG LVQPGGSLRL SCAVSGFSLS NYAMIWVRQA PGKGLEWVST ISLGGYTYYA    60
NWAKGRFTIS KDSSKTTVYL QMNSLRAEDT AVYFCARARW STDSAIYTYA FDPWGPGTLV   120
TVSS                                                                124

SEQ ID NO: 14                 moltype = AA  length = 124
FEATURE                       Location/Qualifiers
REGION                        1..124
                              note = Synthetic
source                        1..124
                              mol_type = protein
                              organism = synthetic construct
SEQUENCE: 14
EQQLLESGGG LVQPGGSLRL SCAVSGFSLS NYAMIWVRQA PGKGLEWVGT ISLGGYTYYA    60
NWAKGRFTIS RDSSKTTVYL QMNSLRAEDT AVYFCARARW STDSAIYTYA FDPWGPGTLV   120
TVSS                                                                124

SEQ ID NO: 15                 moltype = AA  length = 124
FEATURE                       Location/Qualifiers
REGION                        1..124
                              note = Synthetic
source                        1..124
                              mol_type = protein
                              organism = synthetic construct
SEQUENCE: 15
EQQLLESGGG LVQPGGSLRL SCAVSGFSLS NYAMIWVRQA PGKGLEWVGT ISLGGYTYYA    60
NWAKGRFTIS KDNSKTTVYL QMNSLRAEDT AVYFCARARW STDSAIYTYA FDPWGPGTLV   120
TVSS                                                                124

SEQ ID NO: 16                 moltype = AA  length = 124
FEATURE                       Location/Qualifiers
REGION                        1..124
                              note = Synthetic
source                        1..124
                              mol_type = protein
                              organism = synthetic construct
SEQUENCE: 16
EQQLLESGGG LVQPGGSLRL SCAVSGFSLS NYAMIWVRQA PGKGLEWVGT ISLGGYTYYA    60
NWAKGRFTIS KDSSKNTVYL QMNSLRAEDT AVYFCARARW STDSAIYTYA FDPWGPGTLV   120
TVSS                                                                124

SEQ ID NO: 17                 moltype = AA  length = 124
FEATURE                       Location/Qualifiers
REGION                        1..124
                              note = Synthetic
source                        1..124
                              mol_type = protein
                              organism = synthetic construct
SEQUENCE: 17
EQQLLESGGG LVQPGGSLRL SCAVSGFSLS NYAMIWVRQA PGKGLEWVGT ISLGGYTYYA    60
NWAKGRFTIS KDSSKTTLYL QMNSLRAEDT AVYFCARARW STDSAIYTYA FDPWGPGTLV   120
TVSS                                                                124

SEQ ID NO: 18                 moltype = AA  length = 124
FEATURE                       Location/Qualifiers
REGION                        1..124
                              note = Synthetic
source                        1..124
                              mol_type = protein
                              organism = synthetic construct
SEQUENCE: 18
EQQLLESGGG LVQPGGSLRL SCAVSGFSLS NYAMIWVRQA PGKGLEWVGT ISLGGYTYYA    60
NWAKGRFTIS KDSSKTTVYL QMNSLRAEDT AVYYCARARW STDSAIYTYA FDPWGPGTLV   120
```

```
TVSS                                                                     124

SEQ ID NO: 19           moltype = AA  length = 124
FEATURE                 Location/Qualifiers
REGION                  1..124
                        note = Synthetic
source                  1..124
                        mol_type = protein
                        organism = synthetic construct
SEQUENCE: 19
EQQLLESGGG LVQPGGSLRL SCAVSGFSLS NYAMIWVRQA PGKGLEWVGT ISLGGYTYYA        60
NWAKGRFTIS KDSSKTTVYL QMNSLRAEDT AVYFCARARW STDSAIYTYA FDPWGQGTLV       120
TVSS                                                                     124

SEQ ID NO: 20           moltype = AA  length = 124
FEATURE                 Location/Qualifiers
REGION                  1..124
                        note = Synthetic
source                  1..124
                        mol_type = protein
                        organism = synthetic construct
SEQUENCE: 20
EVQLLESGGG LVQPGGSLRL SCAASGFSLS NYAMIWVRQA PGKGLEWVST ISLGGYTYYA        60
NWAKGRFTIS RDNSKNTLYL QMNSLRAEDT AVYYCARARW STDSAIYTYA FDPWGQGTLV       120
TVSS                                                                     124

SEQ ID NO: 21           moltype = AA  length = 124
FEATURE                 Location/Qualifiers
REGION                  1..124
                        note = Synthetic
source                  1..124
                        mol_type = protein
                        organism = synthetic construct
SEQUENCE: 21
EVQLLESGGG LVQPGGSLRL SCAASGFSLS NYAMIWVRQA PGKGLEWVST ISLGGYTYYA        60
NWAKGRFTIS RDSSKTTVYL QMNSLRAEDT AVYFCARARW STDSAIYTYA FDPWGPGTLV       120
TVSS                                                                     124

SEQ ID NO: 22           moltype = AA  length = 110
FEATURE                 Location/Qualifiers
REGION                  1..110
                        note = Synthetic
source                  1..110
                        mol_type = protein
                        organism = synthetic construct
SEQUENCE: 22
DYQMTQSPSS LSASVGDRVT ITCQASQSIS SYLSWYQQKP GKRPKLLIYK ASTLASGVPS        60
RFSGSGSGTD FTLTISSLQP EDFATYYCQQ GYTSSNIDNI FGGGTKVEIK                  110

SEQ ID NO: 23           moltype = AA  length = 110
FEATURE                 Location/Qualifiers
REGION                  1..110
                        note = Synthetic
source                  1..110
                        mol_type = protein
                        organism = synthetic construct
SEQUENCE: 23
DIQMTQSPSS LSASVGDRVT ITCQASQSIS SYLSWYQQKP GKRPKLLIYK ASTLASGVPS        60
RFSGSGSGTD FTLTISSLQP EDFATYYCQQ GYTSSNIDNI FGGGTKVEIK                  110

SEQ ID NO: 24           moltype = AA  length = 110
FEATURE                 Location/Qualifiers
REGION                  1..110
                        note = Synthetic
source                  1..110
                        mol_type = protein
                        organism = synthetic construct
SEQUENCE: 24
DYQMTQSPSS LSASVGDRVT ITCQASQSIS SYLSWYQQKP GKAPKLLIYK ASTLASGVPS        60
RFSGSGSGTD FTLTISSLQP EDFATYYCQQ GYTSSNIDNI FGGGTKVEIK                  110

SEQ ID NO: 25           moltype = AA  length = 110
FEATURE                 Location/Qualifiers
REGION                  1..110
                        note = Synthetic
source                  1..110
                        mol_type = protein
                        organism = synthetic construct
SEQUENCE: 25
```

```
DIQMTQSPSS LSASVGDRVT ITCQASQSIS SYLSWYQQKP GKAPKLLIYK ASTLASGVPS    60
RFSGSGSGTD FTLTISSLQP EDFATYYCQQ GYTSSNIDNI FGGGTKVEIK              110
```

SEQ ID NO: 26   moltype = AA  length = 11
FEATURE         Location/Qualifiers
REGION          1..11
                note = Synthetic
source          1..11
                mol_type = protein
                organism = synthetic construct
SEQUENCE: 26
QASENIANAL A                                                         11

SEQ ID NO: 27   moltype = AA  length = 7
FEATURE         Location/Qualifiers
REGION          1..7
                note = Synthetic
source          1..7
                mol_type = protein
                organism = synthetic construct
SEQUENCE: 27
GASNLAS                                                              7

SEQ ID NO: 28   moltype = AA  length = 13
FEATURE         Location/Qualifiers
REGION          1..13
                note = Synthetic
source          1..13
                mol_type = protein
                organism = synthetic construct
SEQUENCE: 28
QQAYYGNSFV EGT                                                       13

SEQ ID NO: 29   moltype = AA  length = 5
FEATURE         Location/Qualifiers
REGION          1..5
                note = Synthetic
source          1..5
                mol_type = protein
                organism = synthetic construct
SEQUENCE: 29
TYAMG                                                                5

SEQ ID NO: 30   moltype = AA  length = 7
FEATURE         Location/Qualifiers
REGION          1..7
                note = Synthetic
source          1..7
                mol_type = protein
                organism = synthetic construct
SEQUENCE: 30
GIDLSTY                                                              7

SEQ ID NO: 31   moltype = AA  length = 16
FEATURE         Location/Qualifiers
REGION          1..16
                note = Synthetic
source          1..16
                mol_type = protein
                organism = synthetic construct
SEQUENCE: 31
LIHRSGRTYY ATWAKG                                                    16

SEQ ID NO: 32   moltype = AA  length = 11
FEATURE         Location/Qualifiers
REGION          1..11
                note = Synthetic
source          1..11
                mol_type = protein
                organism = synthetic construct
SEQUENCE: 32
SYPDYSATAS I                                                         11

SEQ ID NO: 33   moltype = AA  length = 117
FEATURE         Location/Qualifiers
REGION          1..117
                note = Synthetic
source          1..117
                mol_type = protein

```
                    organism = synthetic construct
SEQUENCE: 33
QSVEESGGRL VSPGTPLTLT CTVSGIDLST YAMGWVRQAP GKGLEWIGLI HRSGRTYYAT    60
WAKGRFTISK TSSTTVDLKI TSPTTEDTAT YFCTRSYPDY SATASIWGPG TLVTVSS      117

SEQ ID NO: 34           moltype = AA   length = 111
FEATURE                 Location/Qualifiers
REGION                  1..111
                        note = Synthetic
source                  1..111
                        mol_type = protein
                        organism = synthetic construct
SEQUENCE: 34
DIVVTQTPAS VEAAVGGTVT IKCQASENIA NALAWYQQKS GQPPMFLIYG ASNLASGVSS    60
RFKGSGSGTE FTLTISDLEC ADAAVYYCQC AYYGNSFVEG TFGGGTEVVV K            111

SEQ ID NO: 35           moltype = AA   length = 119
FEATURE                 Location/Qualifiers
REGION                  1..119
                        note = Synthetic
source                  1..119
                        mol_type = protein
                        organism = synthetic construct
SEQUENCE: 35
EQQLLESGGG LVQPGGSLRL SCAVSGIDLS TYAMGWVRQA PGKGLEWIGL IHRSGRTYYA    60
TWAKGRFTIS KDSSKTTVYL QMNSLRAEDT AVYFCTRSYP DYSATASIWG PGTTVTVSS   119

SEQ ID NO: 36           moltype = AA   length = 119
FEATURE                 Location/Qualifiers
REGION                  1..119
                        note = Synthetic
source                  1..119
                        mol_type = protein
                        organism = synthetic construct
SEQUENCE: 36
EVQLLESGGG LVQPGGSLRL SCAVSGIDLS TYAMGWVRQA PGKGLEWIGL IHRSGRTYYA    60
TWAKGRFTIS KDSSKTTVYL QMNSLRAEDT AVYFCTRSYP DYSATASIWG PGTTVTVSS   119

SEQ ID NO: 37           moltype = AA   length = 119
FEATURE                 Location/Qualifiers
REGION                  1..119
                        note = Synthetic
source                  1..119
                        mol_type = protein
                        organism = synthetic construct
SEQUENCE: 37
EQQLLESGGG LVQPGGSLRL SCAASGIDLS TYAMGWVRQA PGKGLEWIGL IHRSGRTYYA    60
TWAKGRFTIS KDSSKTTVYL QMNSLRAEDT AVYFCTRSYP DYSATASIWG PGTTVTVSS   119

SEQ ID NO: 38           moltype = AA   length = 119
FEATURE                 Location/Qualifiers
REGION                  1..119
                        note = Synthetic
source                  1..119
                        mol_type = protein
                        organism = synthetic construct
SEQUENCE: 38
EQQLLESGGG LVQPGGSLRL SCAVSGIDLS TYAMGWVRQA PGKGLEWVGL IHRSGRTYYA    60
TWAKGRFTIS KDSSKTTVYL QMNSLRAEDT AVYFCTRSYP DYSATASIWG PGTTVTVSS   119

SEQ ID NO: 39           moltype = AA   length = 119
FEATURE                 Location/Qualifiers
REGION                  1..119
                        note = Synthetic
source                  1..119
                        mol_type = protein
                        organism = synthetic construct
SEQUENCE: 39
EQQLLESGGG LVQPGGSLRL SCAVSGIDLS TYAMGWVRQA PGKGLEWISL IHRSGRTYYA    60
TWAKGRFTIS KDSSKTTVYL QMNSLRAEDT AVYFCTRSYP DYSATASIWG PGTTVTVSS   119

SEQ ID NO: 40           moltype = AA   length = 119
FEATURE                 Location/Qualifiers
REGION                  1..119
                        note = Synthetic
source                  1..119
                        mol_type = protein
                        organism = synthetic construct
SEQUENCE: 40
```

```
EQQLLESGGG LVQPGGSLRL SCAVSGIDLS TYAMGWVRQA PGKGLEWIGL IHRSGRTYYA    60
TWAKGRFTIS RDSSKTTVYL QMNSLRAEDT AVYFCTRSYP DYSATASIWG PGTTVTVSS    119

SEQ ID NO: 41             moltype = AA  length = 119
FEATURE                   Location/Qualifiers
REGION                    1..119
                          note = Synthetic
source                    1..119
                          mol_type = protein
                          organism = synthetic construct
SEQUENCE: 41
EQQLLESGGG LVQPGGSLRL SCAVSGIDLS TYAMGWVRQA PGKGLEWIGL IHRSGRTYYA    60
TWAKGRFTIS KDNSKTTVYL QMNSLRAEDT AVYFCTRSYP DYSATASIWG PGTTVTVSS    119

SEQ ID NO: 42             moltype = AA  length = 119
FEATURE                   Location/Qualifiers
REGION                    1..119
                          note = Synthetic
source                    1..119
                          mol_type = protein
                          organism = synthetic construct
SEQUENCE: 42
EQQLLESGGG LVQPGGSLRL SCAVSGIDLS TYAMGWVRQA PGKGLEWIGL IHRSGRTYYA    60
TWAKGRFTIS KDSSKNTVYL QMNSLRAEDT AVYFCTRSYP DYSATASIWG PGTTVTVSS    119

SEQ ID NO: 43             moltype = AA  length = 119
FEATURE                   Location/Qualifiers
REGION                    1..119
                          note = Synthetic
source                    1..119
                          mol_type = protein
                          organism = synthetic construct
SEQUENCE: 43
EQQLLESGGG LVQPGGSLRL SCAVSGIDLS TYAMGWVRQA PGKGLEWIGL IHRSGRTYYA    60
TWAKGRFTIS KDSSKTTLYL QMNSLRAEDT AVYFCTRSYP DYSATASIWG PGTTVTVSS    119

SEQ ID NO: 44             moltype = AA  length = 119
FEATURE                   Location/Qualifiers
REGION                    1..119
                          note = Synthetic
source                    1..119
                          mol_type = protein
                          organism = synthetic construct
SEQUENCE: 44
EQQLLESGGG LVQPGGSLRL SCAVSGIDLS TYAMGWVRQA PGKGLEWIGL IHRSGRTYYA    60
TWAKGRFTIS KDSSKTTVYL QMNSLRAEDT AVYYCTRSYP DYSATASIWG PGTTVTVSS    119

SEQ ID NO: 45             moltype = AA  length = 119
FEATURE                   Location/Qualifiers
REGION                    1..119
                          note = Synthetic
source                    1..119
                          mol_type = protein
                          organism = synthetic construct
SEQUENCE: 45
EQQLLESGGG LVQPGGSLRL SCAVSGIDLS TYAMGWVRQA PGKGLEWIGL IHRSGRTYYA    60
TWAKGRFTIS KDSSKTTVYL QMNSLRAEDT AVYFCTRSYP DYSATASIWG QGTTVTVSS    119

SEQ ID NO: 46             moltype = AA  length = 119
FEATURE                   Location/Qualifiers
REGION                    1..119
                          note = Synthetic
source                    1..119
                          mol_type = protein
                          organism = synthetic construct
SEQUENCE: 46
EVQLLESGGG LVQPGGSLRL SCAASGIDLS TYAMGWVRQA PGKGLEWVSL IHRSGRTYYA    60
TWAKGRFTIS RDNSKNTLYL QMNSLRAEDT AVYYCTRSYP DYSATASIWG QGTTVTVSS    119

SEQ ID NO: 47             moltype = AA  length = 119
FEATURE                   Location/Qualifiers
REGION                    1..119
                          note = Synthetic
source                    1..119
                          mol_type = protein
                          organism = synthetic construct
SEQUENCE: 47
EVQLLESGGG LVQPGGSLRL SCAASGIDLS TYAMGWVRQA PGKGLEWVGL IHRSGRTYYA    60
TWAKGRFTIS KDSSKNTLYL QMNSLRAEDT AVYYCTRSYP DYSATASIWG QGTTVTVSS    119
```

```
SEQ ID NO: 48          moltype = AA  length = 111
FEATURE                Location/Qualifiers
REGION                 1..111
                       note = Synthetic
source                 1..111
                       mol_type = protein
                       organism = synthetic construct
SEQUENCE: 48
DIQVTQSPSS LSASVGDRVT ITCQASENIA NALAWYQQKP GKPPKFLIYG ASNLASGVPS    60
RFSGSGSGTD FTFTISSLQP EDIATYYCQQ AYYGNSFVEG TFGGGTKVEI K           111

SEQ ID NO: 49          moltype = AA  length = 111
FEATURE                Location/Qualifiers
REGION                 1..111
                       note = Synthetic
source                 1..111
                       mol_type = protein
                       organism = synthetic construct
SEQUENCE: 49
DIQMTQSPSS LSASVGDRVT ITCQASENIA NALAWYQQKP GKPPKFLIYG ASNLASGVPS    60
RFSGSGSGTD FTFTISSLQP EDIATYYCQQ AYYGNSFVEG TFGGGTKVEI K           111

SEQ ID NO: 50          moltype = AA  length = 111
FEATURE                Location/Qualifiers
REGION                 1..111
                       note = Synthetic
source                 1..111
                       mol_type = protein
                       organism = synthetic construct
SEQUENCE: 50
DIQVTQSPSS LSASVGDRVT ITCQASENIA NALAWYQQKP GKAPKFLIYG ASNLASGVPS    60
RFSGSGSGTD FTFTISSLQP EDIATYYCQQ AYYGNSFVEG TFGGGTKVEI K           111

SEQ ID NO: 51          moltype = AA  length = 111
FEATURE                Location/Qualifiers
REGION                 1..111
                       note = Synthetic
source                 1..111
                       mol_type = protein
                       organism = synthetic construct
SEQUENCE: 51
DIQVTQSPSS LSASVGDRVT ITCQASENIA NALAWYQQKP GKPPKLLIYG ASNLASGVPS    60
RFSGSGSGTD FTFTISSLQP EDIATYYCQQ AYYGNSFVEG TFGGGTKVEI K           111

SEQ ID NO: 52          moltype = AA  length = 111
FEATURE                Location/Qualifiers
REGION                 1..111
                       note = Synthetic
source                 1..111
                       mol_type = protein
                       organism = synthetic construct
SEQUENCE: 52
DIQMTQSPSS LSASVGDRVT ITCQASENIA NALAWYQQKP GKAPKLLIYG ASNLASGVPS    60
RFSGSGSGTD FTFTISSLQP EDIATYYCQQ AYYGNSFVEG TFGGGTKVEI K           111

SEQ ID NO: 53          moltype = AA  length = 330
FEATURE                Location/Qualifiers
REGION                 1..330
                       note = Synthetic
source                 1..330
                       mol_type = protein
                       organism = synthetic construct
SEQUENCE: 53
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 54          moltype = AA  length = 107
FEATURE                Location/Qualifiers
REGION                 1..107
                       note = Synthetic
source                 1..107
                       mol_type = protein
                       organism = synthetic construct
SEQUENCE: 54
```

```
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 55           moltype = AA   length = 449
FEATURE                 Location/Qualifiers
REGION                  1..449
                        note = Synthetic
source                  1..449
                        mol_type = protein
                        organism = synthetic construct
SEQUENCE: 55
EVQLLESGGG LVQPGGSLRL SCAASGIDLS TYAMGWVRQA PGKGLEWVGL IHRSGRTYYA    60
TWAKGRFTIS KDSSKNTLYL QMNSLRAEDT AVYYCTRSYP DYSATASIWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                   449

SEQ ID NO: 56           moltype = AA   length = 218
FEATURE                 Location/Qualifiers
REGION                  1..218
                        note = Synthetic
source                  1..218
                        mol_type = protein
                        organism = synthetic construct
SEQUENCE: 56
DIQVTQSPSS LSASVGDRVT ITCQASENIA NALAWYQQKP GKPPKFLIYG ASNLASGVPS    60
RFSGSGSGTD FTFTISSLQP EDIATYYCQQ AYYGNSFVEG TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 57           moltype = AA   length = 454
FEATURE                 Location/Qualifiers
REGION                  1..454
                        note = Synthetic
source                  1..454
                        mol_type = protein
                        organism = synthetic construct
SEQUENCE: 57
EVQLLESGGG LVQPGGSLRL SCAASGFSLS NYAMIWVRQA PGKGLEWVST ISLGGYTYYA    60
NWAKGRFTIS RDSSKTTVYL QMNSLRAEDT AVYFCARARW STDSAIYTYA FDPWGPGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SREEMTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                              454

SEQ ID NO: 58           moltype = AA   length = 217
FEATURE                 Location/Qualifiers
REGION                  1..217
                        note = Synthetic
source                  1..217
                        mol_type = protein
                        organism = synthetic construct
SEQUENCE: 58
DYQMTQSPSS LSASVGDRVT ITCQASQSIS SYLSWYQQKP GKAPKLLIYK ASTLASGVPS    60
RFSGSGSGTD FTLTISSLQP EDFATYYCQQ GYTSSNIDNI FGGGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                           217

SEQ ID NO: 59           moltype = AA   length = 330
FEATURE                 Location/Qualifiers
REGION                  1..330
                        note = Synthetic
source                  1..330
                        mol_type = protein
                        organism = synthetic construct
SEQUENCE: 59
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLAG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPEEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 60           moltype = AA   length = 449
```

```
FEATURE                 Location/Qualifiers
REGION                  1..449
                        note = Synthetic
source                  1..449
                        mol_type = protein
                        organism = synthetic construct
SEQUENCE: 60
EVQLLESGGG LVQPGGSLRL SCAASGIDLS TYAMGWVRQA PGKGLEWVGL IHRSGRTYYA    60
TWAKGRFTIS KDSSKNTLYL QMNSLRAEDT AVYYCTRSYP DYSATASIWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLAGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPEEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 61           moltype = AA  length = 454
FEATURE                 Location/Qualifiers
REGION                  1..454
                        note = Synthetic
source                  1..454
                        mol_type = protein
                        organism = synthetic construct
SEQUENCE: 61
EVQLLESGGG LVQPGGSLRL SCAASGFSLS NYAMIWVRQA PGKGLEWVST ISLGGYTYYA    60
NWAKGRFTIS RDSSKTTVYL QMNSLRAEDT AVYFCARARW STDSAIYTYA FDPWGPGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLAGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPEE KTISKAKGQP REPQVYTLPP   360
SREEMTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                              454

SEQ ID NO: 62           moltype = AA  length = 12
FEATURE                 Location/Qualifiers
REGION                  1..12
                        note = Synthetic
source                  1..12
                        mol_type = protein
                        organism = synthetic construct
SEQUENCE: 62
RSSKSVYSNY LS                                                       12

SEQ ID NO: 63           moltype = AA  length = 7
FEATURE                 Location/Qualifiers
REGION                  1..7
                        note = Synthetic
source                  1..7
                        mol_type = protein
                        organism = synthetic construct
SEQUENCE: 63
RASTLTP                                                              7

SEQ ID NO: 64           moltype = AA  length = 11
FEATURE                 Location/Qualifiers
REGION                  1..11
                        note = Synthetic
source                  1..11
                        mol_type = protein
                        organism = synthetic construct
SEQUENCE: 64
AGGYSSGSDN T                                                        11

SEQ ID NO: 65           moltype = AA  length = 5
FEATURE                 Location/Qualifiers
REGION                  1..5
                        note = Synthetic
source                  1..5
                        mol_type = protein
                        organism = synthetic construct
SEQUENCE: 65
EYSMA                                                                5

SEQ ID NO: 66           moltype = AA  length = 7
FEATURE                 Location/Qualifiers
REGION                  1..7
                        note = Synthetic
source                  1..7
                        mol_type = protein
```

```
                        organism = synthetic construct
SEQUENCE: 66
RIDLNEY                                                                   7

SEQ ID NO: 67           moltype = AA   length = 17
FEATURE                 Location/Qualifiers
REGION                  1..17
                        note = Synthetic
source                  1..17
                        mol_type = protein
                        organism = synthetic construct
SEQUENCE: 67
YIDAGSGSAY YASWAKG                                                        17

SEQ ID NO: 68           moltype = AA   length = 14
FEATURE                 Location/Qualifiers
REGION                  1..14
                        note = Synthetic
source                  1..14
                        mol_type = protein
                        organism = synthetic construct
SEQUENCE: 68
DVYPGYTTGT NLGL                                                           14

SEQ ID NO: 69           moltype = AA   length = 110
FEATURE                 Location/Qualifiers
REGION                  1..110
                        note = Synthetic
source                  1..110
                        mol_type = protein
                        organism = synthetic construct
SEQUENCE: 69
AAVLTQTPAS VSAAVGGTVS ISCRSSKSVY SNYLSWYQQK PGQPPKLLIY RASTLTPGVP         60
SRFKGSGSGT QFSLTIRDVQ SADAGSYYCA GGYSSGSDNT FGGGTKLEIK                   110

SEQ ID NO: 70           moltype = AA   length = 121
FEATURE                 Location/Qualifiers
REGION                  1..121
                        note = Synthetic
source                  1..121
                        mol_type = protein
                        organism = synthetic construct
SEQUENCE: 70
QSVKESGGRL VTPGGSLTLT CTVSRIDLNE YSMAWVRQAP GKGLEWIGYI DAGSGSAYYA         60
SWAKGRFTIS KTSSTTVDLE MTTLTTEDTA TYFCARDVYP GYTTGTNLGL WGPGTLVTVS        120
S                                                                       121

SEQ ID NO: 71           moltype = AA   length = 217
FEATURE                 Location/Qualifiers
REGION                  1..217
                        note = Synthetic
source                  1..217
                        mol_type = protein
                        organism = synthetic construct
SEQUENCE: 71
AAVLTQTPAS VSAAVGGTVS ISCRSSKSVY SNYLSWYQQK PGQPPKLLIY RASTLTPGVP         60
SRFKGSGSGT QFSLTIRDVQ SADAGSYYCA GGYSSGSDNT FGGGTKLEIK RADAAPTVSI        120
FPPSSEQLTS GGASVVCFLN NFYPKDINVK WKIDGSERQN GVLNSWTDQD SKDSTYSMSS        180
TLTLTKDEYE RHNSYTCEAT HKTSTSPIVK SFNRNEC                                217

SEQ ID NO: 72           moltype = AA   length = 451
FEATURE                 Location/Qualifiers
REGION                  1..451
                        note = Synthetic
source                  1..451
                        mol_type = protein
                        organism = synthetic construct
SEQUENCE: 72
QSVKESGGRL VTPGGSLTLT CTVSRIDLNE YSMAWVRQAP GKGLEWIGYI DAGSGSAYYA         60
SWAKGRFTIS KTSSTTVDLE MTTLTTEDTA TYFCARDVYP GYTTGTNLGL WGPGTLVTVS        120
SAKTTAPSVY PLAPVCGDTT GSSVTLGCLV KGYFPEPVTL TWNSGSLSSG VHTFPAVLQS        180
DLYTLSSSVT VTSSTWPSQS ITCNVAHPAS STKVDKKIEP RGPTIKPCPP CKCPAPNLLG        240
GPSVFIFPPK IKDVLMISLS PIVTCVVVDV SEDDPDVQIS WFVNNVEVHT AQTQTHREDY        300
NSTLRVVSAL PIQHQDWMSG KEFKCKVNNK DLPAPIERTI SKPKGSVRAP QVYVLPPPEE        360
EMTKKQVTLT CMVTDFMPED IYVEWTNNGK TELNYKNTEP VLDSDGSYFM YSKLRVEKKN        420
WVERNSYSCS VVHEGLHNHH TTKSFSRTPG K                                      451

SEQ ID NO: 73           moltype = AA   length = 11
FEATURE                 Location/Qualifiers
```

```
REGION                      1..11
                            note = Synthetic
source                      1..11
                            mol_type = protein
                            organism = synthetic construct
SEQUENCE: 73
QASQRIGNAL A                                                                    11

SEQ ID NO: 74               moltype = AA  length = 7
FEATURE                     Location/Qualifiers
REGION                      1..7
                            note = Synthetic
source                      1..7
                            mol_type = protein
                            organism = synthetic construct
SEQUENCE: 74
RASTLES                                                                         7

SEQ ID NO: 75               moltype = AA  length = 12
FEATURE                     Location/Qualifiers
REGION                      1..12
                            note = Synthetic
source                      1..12
                            mol_type = protein
                            organism = synthetic construct
SEQUENCE: 75
LGGYISIGNV YT                                                                   12

SEQ ID NO: 76               moltype = AA  length = 12
FEATURE                     Location/Qualifiers
REGION                      1..12
                            note = Synthetic
source                      1..12
                            mol_type = protein
                            organism = synthetic construct
SEQUENCE: 76
QSSKSVNNNN LA                                                                   12

SEQ ID NO: 77               moltype = AA  length = 7
FEATURE                     Location/Qualifiers
REGION                      1..7
                            note = Synthetic
source                      1..7
                            mol_type = protein
                            organism = synthetic construct
SEQUENCE: 77
FASALAS                                                                         7

SEQ ID NO: 78               moltype = AA  length = 12
FEATURE                     Location/Qualifiers
REGION                      1..12
                            note = Synthetic
source                      1..12
                            mol_type = protein
                            organism = synthetic construct
SEQUENCE: 78
QGAYSGGSDS YA                                                                   12

SEQ ID NO: 79               moltype = AA  length = 11
FEATURE                     Location/Qualifiers
REGION                      1..11
                            note = Synthetic
source                      1..11
                            mol_type = protein
                            organism = synthetic construct
SEQUENCE: 79
QASQSISNAL A                                                                    11

SEQ ID NO: 80               moltype = AA  length = 7
FEATURE                     Location/Qualifiers
REGION                      1..7
                            note = Synthetic
source                      1..7
                            mol_type = protein
                            organism = synthetic construct
SEQUENCE: 80
EVSKVAS                                                                         7

SEQ ID NO: 81               moltype = AA  length = 13
```

```
FEATURE                 Location/Qualifiers
REGION                  1..13
                        note = Synthetic
source                  1..13
                        mol_type = protein
                        organism = synthetic construct
SEQUENCE: 81
QSAYYGNSYV WGA                                                              13

SEQ ID NO: 82           moltype = AA   length = 6
FEATURE                 Location/Qualifiers
REGION                  1..6
                        note = Synthetic
source                  1..6
                        mol_type = protein
                        organism = synthetic construct
SEQUENCE: 82
SNYYMC                                                                       6

SEQ ID NO: 83           moltype = AA   length = 7
FEATURE                 Location/Qualifiers
REGION                  1..7
                        note = Synthetic
source                  1..7
                        mol_type = protein
                        organism = synthetic construct
SEQUENCE: 83
GFDFSSN                                                                      7

SEQ ID NO: 84           moltype = AA   length = 18
FEATURE                 Location/Qualifiers
REGION                  1..18
                        note = Synthetic
source                  1..18
                        mol_type = protein
                        organism = synthetic construct
SEQUENCE: 84
CIHISSVTNT WYASWATG                                                         18

SEQ ID NO: 85           moltype = AA   length = 11
FEATURE                 Location/Qualifiers
REGION                  1..11
                        note = Synthetic
source                  1..11
                        mol_type = protein
                        organism = synthetic construct
SEQUENCE: 85
VGNSDYRYFN L                                                                11

SEQ ID NO: 86           moltype = AA   length = 6
FEATURE                 Location/Qualifiers
REGION                  1..6
                        note = Synthetic
source                  1..6
                        mol_type = protein
                        organism = synthetic construct
SEQUENCE: 86
YGYDMC                                                                       6

SEQ ID NO: 87           moltype = AA   length = 7
FEATURE                 Location/Qualifiers
REGION                  1..7
                        note = Synthetic
source                  1..7
                        mol_type = protein
                        organism = synthetic construct
SEQUENCE: 87
GFSFSYG                                                                      7

SEQ ID NO: 88           moltype = AA   length = 18
FEATURE                 Location/Qualifiers
REGION                  1..18
                        note = Synthetic
source                  1..18
                        mol_type = protein
                        organism = synthetic construct
SEQUENCE: 88
CISAGSSDNT WYASWAKG                                                         18
```

```
SEQ ID NO: 89              moltype = AA   length = 4
FEATURE                    Location/Qualifiers
REGION                     1..4
                           note = Synthetic
source                     1..4
                           mol_type = protein
                           organism = synthetic construct
SEQUENCE: 89
YLGL                                                                  4

SEQ ID NO: 90              moltype = AA   length = 5
FEATURE                    Location/Qualifiers
REGION                     1..5
                           note = Synthetic
source                     1..5
                           mol_type = protein
                           organism = synthetic construct
SEQUENCE: 90
SYAMS                                                                 5

SEQ ID NO: 91              moltype = AA   length = 7
FEATURE                    Location/Qualifiers
REGION                     1..7
                           note = Synthetic
source                     1..7
                           mol_type = protein
                           organism = synthetic construct
SEQUENCE: 91
GFSLSSY                                                               7

SEQ ID NO: 92              moltype = AA   length = 16
FEATURE                    Location/Qualifiers
REGION                     1..16
                           note = Synthetic
source                     1..16
                           mol_type = protein
                           organism = synthetic construct
SEQUENCE: 92
VISASGRIIY ATWAKG                                                    16

SEQ ID NO: 93              moltype = AA   length = 11
FEATURE                    Location/Qualifiers
REGION                     1..11
                           note = Synthetic
source                     1..11
                           mol_type = protein
                           organism = synthetic construct
SEQUENCE: 93
GVPSYSLVMS D                                                         11

SEQ ID NO: 94              moltype = AA   length = 110
FEATURE                    Location/Qualifiers
REGION                     1..110
                           note = Synthetic
source                     1..110
                           mol_type = protein
                           organism = synthetic construct
SEQUENCE: 94
DIQMTQSPSS LSASVGDRVT ITCQASQRIG NALAWYQQKP GKPPKLLIYR ASTLESGVPS     60
RFSGSGSGTD FTLTISSLQP EDVATYYCLG GYISIGNVYT FGGGTKVEIK              110

SEQ ID NO: 95              moltype = AA   length = 122
FEATURE                    Location/Qualifiers
REGION                     1..122
                           note = Synthetic
source                     1..122
                           mol_type = protein
                           organism = synthetic construct
SEQUENCE: 95
EQQLVESAGG LVQPGGSLRL SCAASGFDFS SNYYMCWVRQ APGKGLEWIG CIHISSVTNT     60
WYASWATGRF TISKDTSSTT VYLQMISLKT EDTAVYFCTR VGNSDYRYFN LWGPGTLVTV    120
SS                                                                  122

SEQ ID NO: 96              moltype = AA   length = 111
FEATURE                    Location/Qualifiers
REGION                     1..111
                           note = Synthetic
source                     1..111
                           mol_type = protein
```

```
                         organism = synthetic construct
SEQUENCE: 96
EQVLTQSPGT LSLSPGERAT LSCQSSKSVN NNNLAWYQQK PGQPPRLLIY FASALASGVP   60
DRFSGSGSGT DFTLTISRLE PEDFAVYYCQ GAYSGGSDSY AFGGGTKVEI K           111

SEQ ID NO: 97           moltype = AA  length = 115
FEATURE                 Location/Qualifiers
REGION                  1..115
                        note = Synthetic
source                  1..115
                        mol_type = protein
                        organism = synthetic construct
SEQUENCE: 97
EQQLVESGGG VVQPGRSLRL SCAASGFSFS YGYDMCWVRQ APGKGLEWIA CISAGSSDNT   60
WYASWAKGRF TISKDTSKTT VYLQMNSLRA EDTAVYFCSR YLGLWGPGTL VTVSS        115

SEQ ID NO: 98           moltype = AA  length = 111
FEATURE                 Location/Qualifiers
REGION                  1..111
                        note = Synthetic
source                  1..111
                        mol_type = protein
                        organism = synthetic construct
SEQUENCE: 98
EPVMTQSPAT LSVSPGERAT LSCQASQSIS NALAWYQQKP GQPPRLLIYE VSKVASGVPA   60
RFSGSGSGTE FTLTISSLQS EDFAVYYCQS AYYGNSYVWG AFGQGTKVEI K            111

SEQ ID NO: 99           moltype = AA  length = 119
FEATURE                 Location/Qualifiers
REGION                  1..119
                        note = Synthetic
source                  1..119
                        mol_type = protein
                        organism = synthetic construct
SEQUENCE: 99
EQQLVESGGG LVQPGGSLRL SCAVSGFSLS SYAMSWVRQA PGKGLEWIGV ISASGRIIYA   60
TWAKGRFTIS KDSAKTSVYL QMNSLRDEDT AVYFCARGVP SYSLVMSDWG PGTTVTVSS    119

SEQ ID NO: 100          moltype = AA  length = 217
FEATURE                 Location/Qualifiers
REGION                  1..217
                        note = Synthetic
source                  1..217
                        mol_type = protein
                        organism = synthetic construct
SEQUENCE: 100
DIQMTQSPSS LSASVGDRVT ITCQASQRIG NALAWYQQKP GKPPKLLIYR ASTLESGVPS   60
RFSGSGSGTD FTLTISSLQP EDVATYYCLG GYISIGNVYT FGGGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 101          moltype = AA  length = 452
FEATURE                 Location/Qualifiers
REGION                  1..452
                        note = Synthetic
source                  1..452
                        mol_type = protein
                        organism = synthetic construct
SEQUENCE: 101
EQQLVESAGG LVQPGGSLRL SCAASGFDFS SNYYMCWVRQ APGKGLEWIG CIHISSVTNT   60
WYASWATGRF TISKDTSSTT VYLQMISLKT EDTAVYFCTR VGNSDYRYFN LWGPGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 102          moltype = AA  length = 218
FEATURE                 Location/Qualifiers
REGION                  1..218
                        note = Synthetic
source                  1..218
                        mol_type = protein
                        organism = synthetic construct
SEQUENCE: 102
EQVLTQSPGT LSLSPGERAT LSCQSSKSVN NNNLAWYQQK PGQPPRLLIY FASALASGVP   60
DRFSGSGSGT DFTLTISRLE PEDFAVYYCQ GAYSGGSDSY AFGGGTKVEI KRTVAAPSVF   120
IFPPSDEQLK SGTASVVCLL NNFYPREAKV QWKVDNALQS GNSQESVTEQ DSKDSTYSLS   180
```

```
STLTLSKADY EKHKVYACEV THQGLSSPVT KSFNRGEC                            218

SEQ ID NO: 103              moltype = AA  length = 445
FEATURE                     Location/Qualifiers
REGION                      1..445
                            note = Synthetic
source                      1..445
                            mol_type = protein
                            organism = synthetic construct
SEQUENCE: 103
EQQLVESGGG VVQPGRSLRL SCAASGFSFS YGYDMCWVRQ APGKGLEWIA CISAGSSDNT    60
WYASWAKGRF TISKDTSKTT VYLQMNSLRA EDTAVYFCSR YLGLWGPGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP ELLGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSREEMTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPGK                                         445

SEQ ID NO: 104              moltype = AA  length = 218
FEATURE                     Location/Qualifiers
REGION                      1..218
                            note = Synthetic
source                      1..218
                            mol_type = protein
                            organism = synthetic construct
SEQUENCE: 104
EPVMTQSPAT LSVSPGERAT LSCQASQSIS NALAWYQQKP GQPPRLLIYE VSKVASGVPA    60
RFSGSGSGTE FTLTISSLQS EDFAVYYCQS AYYGNSYVWG AFGQGTKVEI KRTVAAPSVF    120
IPPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 105              moltype = AA  length = 449
FEATURE                     Location/Qualifiers
REGION                      1..449
                            note = Synthetic
source                      1..449
                            mol_type = protein
                            organism = synthetic construct
SEQUENCE: 105
EQQLVESGGG LVQPGGSLRL SCAVSGFSLS SYAMSWVRQA PGKGLEWIGV ISASGRIIYA    60
TWAKGRFTIS KDSAKTSVYL QMNSLRDEDT AVYFCARGVP SYSLVMSDWG PGTTVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 106              moltype = AA  length = 355
FEATURE                     Location/Qualifiers
REGION                      1..355
                            note = misc_feature - human CCR8
source                      1..355
                            mol_type = protein
                            organism = Homo sapiens
SEQUENCE: 106
MDYTLDLSVT TVTDYYYPDI FSSPCDAELI QTNGKLLLAV FYCLLFVFSL LGNSLVILVL    60
VVCKKLRSIT DVYLLNLALS DLLFVFSFPF QTYYLLDQWV FGTVMCKVVS GFYYIGFYSS    120
MFFITLMSVD RYLAVVHAVY ALKVRTIRMG TTLCLAVWLT AIMATIPLLV FYQVASEDGV    180
LQCYSFYNQQ TLKWKIFTNF KMNILGLLIP FTIFMFCYIK ILHQLKRCQN HNKTKAIRLV    240
LIVVIASLLF WVPFNVVLFL TSLHSMHILD GCSISQQLTY ATHVTEIISF THCCVNPVIY    300
AFVGEKFKKH LSEIFQKSCS QIFNYLGRQM PRESCEKSSS CQQHSSRSSS VDYIL        355

SEQ ID NO: 107              moltype = AA  length = 355
FEATURE                     Location/Qualifiers
REGION                      1..355
                            note = misc_feature - cyno CCR8
source                      1..355
                            mol_type = protein
                            organism = Macaca fascicularis
SEQUENCE: 107
MDYTLDPSMT TMTDYYYPDS LSSPCDGELI QRNDKLLLAV FYCLLFVFSL LGNSLVILVL    60
VVCKKLRNIT DIYLLNLALS DLLFVFSFPF QTYYQLDQWV FGTVMCKVVS GFYYIGFYSS    120
MFFITLMSVD RYLAVVHAVY AIKVRTIRMG TTLSLVVWLT AIMATIPLLV FYQVASEDGV    180
LQCYSFYNQQ TLKWKIFTNF EMNILGLLIP FTIFMFCYIK ILHQLKRCQN HNKTKAIRLV    240
LIVVIASLLF WVPFNVVLFL TSLHSMHILD GCSISQQLNY ATHVTEIISF THCCVNPVIY    300
AFVGEKFKKH LSEIFQKSCS HIFIYLGRQM PRESCEKSSS CQQHSFRSSS IDYIL        355
```

| SEQ ID NO: 108 | moltype = AA length = 353 |
| --- | --- |
| FEATURE | Location/Qualifiers |
| REGION | 1..353 |
| | note = misc_feature - mouse CCR8 |
| source | 1..353 |
| | mol_type = protein |
| | organism = Mus musculus |

SEQUENCE: 108
```
MDYTMEPNVT MTDYYPDFFT APCDAEFLLR GSMLYLAILY CVLFVLGLLG NSLVILVLVG    60
CKKLRSITDI YLLNLAASDL LFVLSIPFQT HNLLDQWVFG TAMCKVVSGL YYIGFFSSMF   120
FITLMSVDRY LAIVHAVYAI KVRTASVGTA LSLTVWLAAV TATIPLMVFY QVASEDGMLQ   180
CFQFYEEQSL RWKLFTHFEI NALGLLLPFA ILLFCYVRIL QQLRGCLNHN RTRAIKLVLT   240
VVIVSLLFWV PFNVALFLTS LHDLHILDGC ATRQRLALAI HVTEVISFTH CCVNPVIYAF   300
IGEKFKKHLM DVFQKSCSHI FLYLGRQMPV GALERQLSSN QRSSHSSTLD DIL          353
```

| SEQ ID NO: 109 | moltype = AA length = 13 |
| --- | --- |
| FEATURE | Location/Qualifiers |
| REGION | 1..13 |
| | note = Synthetic |
| source | 1..13 |
| | mol_type = protein |
| | organism = synthetic construct |

SEQUENCE: 109
```
QCAYYGNSFV EGT                                                      13
```

| SEQ ID NO: 110 | moltype = AA length = 24 |
| --- | --- |
| FEATURE | Location/Qualifiers |
| REGION | 1..24 |
| | note = Synthetic |
| source | 1..24 |
| | mol_type = protein |
| | organism = synthetic construct |

SEQUENCE: 110
```
MDYTLDLSVT TVTDYYYPDI FSSP                                          24
```

| SEQ ID NO: 111 | moltype = AA length = 448 |
| --- | --- |
| FEATURE | Location/Qualifiers |
| REGION | 1..448 |
| | note = Synthetic |
| source | 1..448 |
| | mol_type = protein |
| | organism = synthetic construct |

SEQUENCE: 111
```
EVQLLESGGG LVQPGGSLRL SCAASGIDLS TYAMGWVRQA PGKGLEWVGL IHRSGRTYYA    60
TWAKGRFTIS KDSSKNTLYL QMNSLRAEDT AVYYCTRSYP DYSATASIWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448
```

| SEQ ID NO: 112 | moltype = AA length = 453 |
| --- | --- |
| FEATURE | Location/Qualifiers |
| REGION | 1..453 |
| | note = Synthetic |
| source | 1..453 |
| | mol_type = protein |
| | organism = synthetic construct |

SEQUENCE: 112
```
EVQLLESGGG LVQPGGSLRL SCAASGFSLS NYAMIWVRQA PGKGLEWVST ISLGGYTYYA    60
NWAKGRFTIS RDSSKTTVYL QMNSLRAEDT AVYFCARARW STDSAIYTYA FDPWGPGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SREEMTKNQV SLTCLVKGFY PSDIAVEWES NGQPENNYKT TPPVLDSDGS FFLYSKLTVD   420
KSRWQQGNVF SCSVMHEALH NHYTQKSLSL SPG                                453
```

| SEQ ID NO: 113 | moltype = AA length = 448 |
| --- | --- |
| FEATURE | Location/Qualifiers |
| REGION | 1..448 |
| | note = Synthetic |
| source | 1..448 |
| | mol_type = protein |
| | organism = synthetic construct |

SEQUENCE: 113
```
EVQLLESGGG LVQPGGSLRL SCAASGIDLS TYAMGWVRQA PGKGLEWVGL IHRSGRTYYA    60
TWAKGRFTIS KDSSKNTLYL QMNSLRAEDT AVYYCTRSYP DYSATASIWG QGTTVTVSSA   120
```

```
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLAGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPEEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 114          moltype = AA  length = 453
FEATURE                 Location/Qualifiers
REGION                  1..453
                        note = Synthetic
source                  1..453
                        mol_type = protein
                        organism = synthetic construct
SEQUENCE: 114
EVQLLESGGG LVQPGGSLRL SCAASGFSLS NYAMIWVRQA PGKGLEWVST ISLGGYTYYA    60
NWAKGRFTIS RDSSKTTVYL QMNSLRAEDT AVYFCARARW STDSAIYTYA FDPWGPGTLV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSNTKVDK KVEPKSCDKT HTCPPCPAPE    240
LLAGPSVFLF PPKPKDTLMI SRTPEVTCVV VDVSHEDPEV KFNWYVDGVE VHNAKTKPRE    300
EQYNSTYRVV SVLTVLHQDW LNGKEYKCKV SNKALPAPEE KTISKAKGQP REPQVYTLPP    360
SREEMTKNQV SLTCLVKGFY PSDIAVEWES NGQPENNYKT TPPVLDSDGS FFLYSKLTVD    420
KSRWQQGNVF SCSVMHEALH NHYTQKSLSL SPG                                453

SEQ ID NO: 115          moltype = AA  length = 451
FEATURE                 Location/Qualifiers
REGION                  1..451
                        note = Synthetic
source                  1..451
                        mol_type = protein
                        organism = synthetic construct
SEQUENCE: 115
EQQLVESAGG LVQPGGSLRL SCAASGFDFS SNYYMCWVRQ APGKGLEWIG CIHISSVTNT    60
WYASWATGRF TISKDTSSTT VYLQMISLKT EDTAVYFCTR VGNSDYRYFN LWGPGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP G                                  451

SEQ ID NO: 116          moltype = AA  length = 444
FEATURE                 Location/Qualifiers
REGION                  1..444
                        note = Synthetic
source                  1..444
                        mol_type = protein
                        organism = synthetic construct
SEQUENCE: 116
EQQLVESGGG VVQPGRSLRL SCAASGFSFS YGYDMCWVRQ APGKGLEWIA CISAGSSDNT    60
WYASWAKGRF TISKDTSKTT VYLQMNSLRA EDTAVYFCSR YLGLWGPGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP ELLGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSREEMTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPG                                          444

SEQ ID NO: 117          moltype = AA  length = 448
FEATURE                 Location/Qualifiers
REGION                  1..448
                        note = Synthetic
source                  1..448
                        mol_type = protein
                        organism = synthetic construct
SEQUENCE: 117
EQQLVESGGG LVQPGGSLRL SCAVSGFSLS SYAMSWVRQA PGKGLEWIGV ISASGRIIYA    60
TWAKGRFTIS KDSAKTSVYL QMNSLRDEDT AVYFCARGVP SYSLVMSDWG PGTTVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448
```